(12) United States Patent
Wu et al.

(10) Patent No.: US 8,586,040 B2
(45) Date of Patent: Nov. 19, 2013

(54) METHODS OF USING APOPTOTIC ANTI-IGE ANTIBODIES

(75) Inventors: Lawren Wu, Foster City, CA (US);
Mercedesz Balazs, Hayward, CA (US);
Hans Brightbill, San Francisco, CA (US); Andy Chan, Menlo Park, CA (US); Yvonne Chen, San Mateo, CA (US); Anan Chuntharapai, Colma, CA (US); Mark Dennis, San Carlos, CA (US); Terence Wong, Alameda, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/281,209

(22) Filed: Oct. 25, 2011

(65) Prior Publication Data
US 2012/0177635 A1 Jul. 12, 2012

Related U.S. Application Data

(62) Division of application No. 12/053,063, filed on Mar. 21, 2008, now Pat. No. 8,071,097.

(60) Provisional application No. 60/896,339, filed on Mar. 22, 2007.

(51) Int. Cl.
*A61K 39/00* (2006.01)

(52) U.S. Cl.
USPC .................. 424/139.1; 424/133.1; 424/144.1; 424/153.1; 424/805; 424/810

(58) Field of Classification Search
None
See application file for complete search history.

(56) References Cited

U.S. PATENT DOCUMENTS

| | | | |
|---|---|---|---|
| 4,714,759 A * | 12/1987 | Whitaker, Jr. | 424/179.1 |
| 5,079,344 A | 1/1992 | Chang et al. | |
| 5,089,603 A | 2/1992 | Chang | |
| 5,091,313 A | 2/1992 | Chang | |
| 5,231,026 A | 7/1993 | Chang | |
| 5,252,467 A | 10/1993 | Chang | |
| 5,254,671 A | 10/1993 | Chang | |
| 5,260,416 A | 11/1993 | Chang | |
| 5,274,075 A | 12/1993 | Chang | |
| 5,292,867 A | 3/1994 | Chang | |
| 5,310,875 A | 5/1994 | Chang | |
| 5,342,924 A | 8/1994 | Chang | |
| 5,362,643 A | 11/1994 | Chang | |
| 5,420,251 A | 5/1995 | Chang et al. | |
| 5,422,258 A | 6/1995 | Chang | |
| 5,428,133 A | 6/1995 | Chang | |
| 5,449,760 A | 9/1995 | Chang | |
| 5,484,907 A | 1/1996 | Chang et al. | |
| 5,514,776 A | 5/1996 | Chang | |
| 5,543,144 A | 8/1996 | Chang | |
| 5,614,611 A | 3/1997 | Chang | |
| 5,690,934 A | 11/1997 | Chang et al. | |
| 5,866,129 A | 2/1999 | Chang et al. | |
| 6,172,213 B1 | 1/2001 | Lowman et al. | |
| 8,071,097 B2 | 12/2011 | Wu et al. | |
| 2006/0122377 A1 | 6/2006 | Dennis | |

FOREIGN PATENT DOCUMENTS

| | | |
|---|---|---|
| WO | 89/06138 | 7/1989 |
| WO | 90/15614 | 12/1990 |
| WO | 91/11456 | 8/1991 |
| WO | 92/17207 | 10/1992 |
| WO | 96/12740 A1 | 5/1996 |
| WO | 99/01556 | 1/1999 |
| WO | 2004/070010 | 8/2004 |
| WO | 2004/070011 | 8/2004 |
| WO | WO 2007041171 A2 * | 4/2007 |

OTHER PUBLICATIONS

Anand, S. et al., "Multiple transcripts of the murine immunoglobulin ε membrane locus are generated by alternative splicing and differential usage of two polyadenylation sites" Molecular Immunology 34(2):175-183 (1997).
Austrian Search Report GCC/P/2008/10423, mailing date Sep. 9, 2011, pp. 1-14 (Sep. 9, 2011).
Batista, F. et al., "The two membrane isoforms of human IgE assemble into functionally distinct B cell antigen receptors" Journal of Experimental Medicine 184:2197-2205 (Dec. 1996).
Bozelka, B. et al., "IgE isotype suppression in anti-ε-treated mice" Immunology 46:527-532 (1982).
Casale, T. et al., "Use of an anti-IgE humanized monoclonal antibody in ragweed-induced allergic rhinitis" J. Allergy Clin. Immunol. 100(1):110-121 (Jul. 1997).
Chang, T.W., "Developing Antibodies for Targeting Immunoglobulin and Membrane-Bound Immunoglobulin E" Allergy and Asthma Proceedings: The Official Journal of Regional and State Allergy Societies 2006 27(2):S7-S14 (Mar. 2006).
Chang, Tse Wen et al., "Anti-IgE antibodies for the treatment of IgE-mediated allergic diseases" Advances in Immunol. 93:63-119 (2007).
Chen, H. Y. et al., "Generation and Characterization of Monoclonal Antibodies Against a Segment (epsilonm67) Uniquely Present in Membrane-Bound IgE" FASEB Journal 15(5):A1018 (Mar. 8, 2001).
Chen, H.Y. et al., "Monoclonal Antibodies Against the C(epsilon)mX Domain of Human Membrane-Bound IgE and Their Potential Use for Targeting IgE-Expressing B Cells" Int. Arch Allergy Immunology 128(4):315-324 (Aug. 2002).
Chen, Jiun-Bo et al., "Unique Epitopes on CεmX in IgE-B Cell Receptors Are Potentially Applicable for Targeting IgE-Committed B Cells" The Journal of Immunology 184:1748-1756 (Jan. 2010).
Chothia and Lesk, "Canonical structures for the hypervariable regions of immunoglobulins" J. Mol. Biol. 196:901-917 (1987).
Corne, J. et al., "The effect of intravenous administration of a chimeric anti-IgE antibody on serum IgE levels in atopic subjects: efficacy, safety and pharmacokinetics" J. Clin. Invest. 99(5):879-887 (Mar. 1997).

(Continued)

Primary Examiner — Michael Szperka

(57) ABSTRACT

The present application relates to apoptotic anti-IgE antibodies, nucleic acid encoding the same, therapeutic compositions thereof, and their use in the treatment of IgE-mediated disorders.

50 Claims, 103 Drawing Sheets

(56) References Cited

OTHER PUBLICATIONS

Crestani, E. et al., "In Vivo Association of Cytokine Production and IgE Levels in Infants and Adults" J Allergy Clin Immunol 113(2):S87 (Feb. 2004).

D'Amato, Gennaro "Role of anti-IgE monoclonal antibody (omalizumab in the treatment of bronchial asthma and allergic respiratory diseases" European Journal of Pharmacology 533:302-307 (Feb. 7, 2006).

Davis, F. et al., "An epitope on membrane-bound but not secreted IgE: implications in isotype-specific regulation" Bio/Technology 9:53-56 (Jan. 1991).

Feichtner, S. et al., "Targeting the Extracellular Membrane-Proximal Domain of Membrane-Bound IgE by Passive Immunization Blocks IgE Synthesis in Vivo" Journal of Immunology 180(8):5499-5505 (Apr. 15, 2008).

Haak-Frendscho et al., "Administration of an anti-IgE antibody inhibits CD23 expression and IgE production in vivo" Immunology 82:306-313 (1994).

Haba and Nisinoff, "Inhibition of IgE synthesis by anti-IgE: Role in long-term inhibition of IgE synthesis by neonatally administered soluble IgE" Proc. Natl. Acad. Sci. USA 87:3363-3367 (May 1990).

Haba and Nisonoff, "Effects of syngeneic anti-IgE antibodies on the development of IgE memory and on the secondary IgE response" J. Immunol. 152:51-57 (1994).

Haba and Nisonoff, "Role of antibody and T cells in the long-term inhibition of IgE synthesis" Proc. Natl. Acad. Sci. USA 91:604-608 (Jan. 1994).

Hamers-Casterman et al., "Naturally occurring antibodies devoid of light chains" Nature 363:446-448 (Jun. 3, 1993).

Heusser, Ch.H. et al., "New concepts of IgE regulation" Int. Arch. Allergy Appl. Immunol. 94:87-90 (1991).

Infuhr, D. et al., "Molecular and Cellular Targets of Anti-IgE Antibodies" Allergy 60(8):977-985 (Aug. 2005).

Johansson, S.G.O., "IgE in allergic diseases" Proc. roy. Soc. Med. 62:37-38 (975-976) (Sep. 1969).

Johnson and Wu Methods in Molecular Biology "The Kabat Database and a Bioinformatics Example" Lo ed., Totowa, NJ:Human Press, vol. 248:11-25 (2003).

Klubal, R. et al., "The high-affinity receptor for IgE is the predominant IgE-binding structure in lesional skin of atopic dermatitis patients" J. Invest. Dermatol. 108:336-342 (1997).

Niwa, Rinpei et al., "IgG subclass-independent improvement of antibody-dependent cellular cytotoxicity by fucose removal from Asn297-linked Oligosaccharides" Immunological Methods 306:151-160 (Aug. 10, 2005).

Peng, C. et al., "A new isoform of human membrane-bound IgE" J. Immunol. 148:129-136 (Jan. 1, 1992).

Poggianella, M. et al., "The Extracellular Membrane-Proximal Domain of Human Membrane IgE Controls Apoptotic Signaling of the B Cell Receptor in the Mature B Cell Line A20" Journal of Immunology 177(6):3597-3605 (Sep. 15, 2006).

Sheriff and Constantine, "Redefining the minimal antigen-binding fragment" Nature Struct Biol 3(9):733-736 (Sep. 1996).

Stampfli, M. et al., "Inhibition of human IgE synthesis by anti-IgE antibodies requires divalent recognition" Eur. J. of Immunol. 24:2161-2167 (1994).

Sun, L. K. et al., "Transfectomas expressing both secreted and membrane-bound forms of chimeric IgE with anti-viral specificity" J. Immunol. 146(1):199-205 (Jan. 1, 1991).

Terr, A.I., "The Atopic Diseases" Med. Immunol., Stites et al., 9th edition, Stamford, Connecticut:Appleton & Lange, Chapter 27, (1997).

Tumas, D.B. et al., "Anti-IgE Efficacy in Murine Asthma Models is Dependent on the Method of Allergen Sensitization" The Journal of Allergy and Clinical Immunology 107(6):1025-1033 (Jun. 2001).

Xu and Davis, "Diversity in the CDR3 region of $V_H$ is sufficient for most antibody specificities" Immunity 13:37-45 (Jul. 2000).

Benhamou et al., "Anti-immunoglobulins induce death by apoptosis in WEHI-231 B lymphoma cells" Eur. J. Immunol 20:1405-1407 (1990).

Chinn et al., "Antibody therapy of non-Hodgkin's B-cell lymphoma" Cancer Immunol Immunother 52:257-280 (2003).

Janeway, Jr. et al. ImmunoBiology: the immune system in health and disease 6th edition, New York:Garland Science,:352, 353, 401, 402 (2005).

Rituxan ® (Rituximab) Proposed Mechanism of Action, pp. 1-3 (Internet Retrieval Date Oct. 5, 2012).

Fundamental Immunology Paul, W. ed., Third edition, New York:Raven Press,:242 (1993).

Gama Sosa et al., "Animal transgenesis: an overview" Brain Struct Funct 214:91-109 (2010).

Janeway et al. Immunobiology Third edition,Garland Press,:3:1 - 3:11 (1997).

Kolb et al., "Insertion of a foreign gene into the Beta-casein locus by Cre-mediated site-specific recombination" Gene 227:21-31 (1999).

Kumar et al., "Understanding B-cell tolerance through the use of immunoglobulin transgenic models" Immunol Res 40:208-223 (2008).

Portolano et al., "Lack of promiscuity in autoantigen-specific H and L chain combinations as revealed by human H and L chain 'Roulette'" J Immunol 150(3):880-887 (Feb. 1993).

Qi et al., "A New Transgenic Rat Model of Hepatic Steatosis and the Metabolic Syndrome" Hypertension 45:1004-1011 (2005).

Ravirajan et al., "Transgenic models of tolerance and autoimmunity: with special reference to systemic lupus erythematosus" Lupus 11:843-849 (2002).

Ristevski, "Making Better Transgenic Models" Molecular Biotechnology 29:153-163 (2005).

Rudikoff et al., "Single amino acid substitution altering antigen-binding specificity" P Natl Acad Sci USA 79:1979-1983 (Mar. 1982).

Sigmund, Arterioscler Throm Vasc Biol 20:1425-1429 (2000).

Smith et al., "Gene Transfer in higher animals: theoretical considerations and key concepts" J Biotechnol 99(1):1-22 (2002).

Third Party Submission under 37 CFR 1.290 filed Oct. 23, 2012.

* cited by examiner

FIG. 1A

IgE/M1' Sequences

| | | | | |
|---|---|---|---|---|
| Human | 1 | ITLQSSCDGGHFPPTIQLLCLVSGYTPGTINTWLEDGQVMDVDLSTAST | CH2 | 50 |
| Rhesus | 1 | ITLQSSCDDDGHFPPTIQLLCLISGYTPGTINTWLENGQVMKVNSPTPPA | | 50 |
| Cyno | 1 | ITLQSSCDDDGHFPPTIQLLCLISGYTPGAINVTWLENGQVMKVNSPTPPA | | 50 |
| Human | 51 | TQEGELASTQSELTLSQKHWLSDRTYTCQVTYQGHTFEDSTKKCADSNPR | CH2 | 100 |
| Rhesus | 51 | TQEGELASTQSEFTLAQKHWLSDRTYTCQVTYQGTTYNDSTKKCADSNPR | | 100 |
| Cyno | 51 | TQEGELASTQSEFTLAQKHWLSDRTYTCQVTYQGTTYNDSTKKCANSNPR | | 100 |
| Human | 101 | GVSAYLSRPSPFDLFIRKSPTITCLVVDLAPSKGTVNLTWSRASGKPVNH | CH3 | 150 |
| Rhesus | 101 | GVSAYLSRPSPFDLFISKSPTITCLVVDLAPSKETVNLTWSRASGKPVPH | | 150 |
| Cyno | 101 | GVSAYLSRPSPFDLFISKSPTITCLVVDLAPSKETVNLTWSRASGKPVPH | | 150 |
| Human | 151 | STRKEEK-QRNGTLTVTSELPVGTRDWIEGETYQCRVTHPHLPRALMRST | CH3 | 199 |
| Rhesus | 151 | EPATEKKQQRNGTLTVTSILPVVTQDWIEGETYQCRVTHPHLPRALVRSM | | 200 |
| Cyno | 151 | EPATEKK-QRNGTLTVTSILPVVTQDWIEGETYQCRVTHPHLPRALVRSM | | 199 |
| Human | 200 | TKTSGPRAAPEVYAFATPEWPGSRDKRTLACLIQNFMPEDISVQWLHNEV | CH4 | 249 |
| Rhesus | 201 | TKTSGPRAAPEVYVFATPEKLESRDKRTLACLIQNFMPEDISVQWLHSDV | | 250 |
| Cyno | 200 | TKTSGPRAAPEVYVFATPEKLESRDKRTLACLIQNFMPEDISVQWLHSDV | | 249 |

```
Human  250  QLPDARHSETQPRKTKGSGFFVFSRLEVTRAEWEQKDEFICRAVHEAASP  299
Rhesus 251  QLPDARHSVTQPRKTKGSGFFVFSRLEVTKAEWEQKDEFICRAVHEAASP  300
Cyno   250  QLPDARHSVTQPRKTKGSGFFVFSRLEVTKAEWEQKDEFICRAVHEAASP  299
                                                               ┘ CH4

Human  300  SQTVQRAVSVNPGLAGGSAQSQRAPDRVLCHSGQQQGLPRAAGSVPHPR  349
Rhesus 301  SWIVQQAVSVNPGLAGGSAQSQRAPDRVLCHSEQQQGLPRAARGSVPDH   350
Cyno   300  SWIVQQAVSVNPGLAGGSAQSQRAPDRVLCHSEQQQGLPRAARGSVPDHR  349
            └─ CH4                                         └─ M1'

Human  350  CHCGAGRADWPGPPELDVCVEEAEGRAPWTWTGLCIFAALFLLSVSYSAA  399
Rhesus 351  CHCGAGRADWPGLPELDLCVEEAESVLWTWTGLCIFATLFLLSVSYSAA   400
Cyno   350  CHCGAGRADWPGLPELDLCVEEAESVLWTWTGLCIFATLFLLSVSYSAA   399
                       └─ M1'                        Transmembrane Domain Human  400  LTLLMVQRFLSATRQGRPQTSLDYTNVLQPHA  431
Rhesus 401  ITLLMVQRFLSATRQGRPQTSLDYTNVLQPHA  432
Cyno   400  ITLLMVQRFLSVTRQGRPQTSLDYTNILQPHA  431
            T.M.             Intracellular Domain
```

| FIG. 2A-1 | FIG. 2A-2 | FIG. 2A-3 | FIG. 2A-4 | FIG. 2A-5 | FIG. 2A-6 |
|---|---|---|---|---|---|
| FIG. 2B-1 | FIG. 2B-2 | FIG. 2B-3 | FIG. 2B-4 | FIG. 2B-5 | FIG. 2B-6 |
| FIG. 2C-1 | FIG. 2C-2 | FIG. 2C-3 | FIG. 2C-4 | FIG. 2C-5 | FIG. 2C-6 |

*FIG. 2*

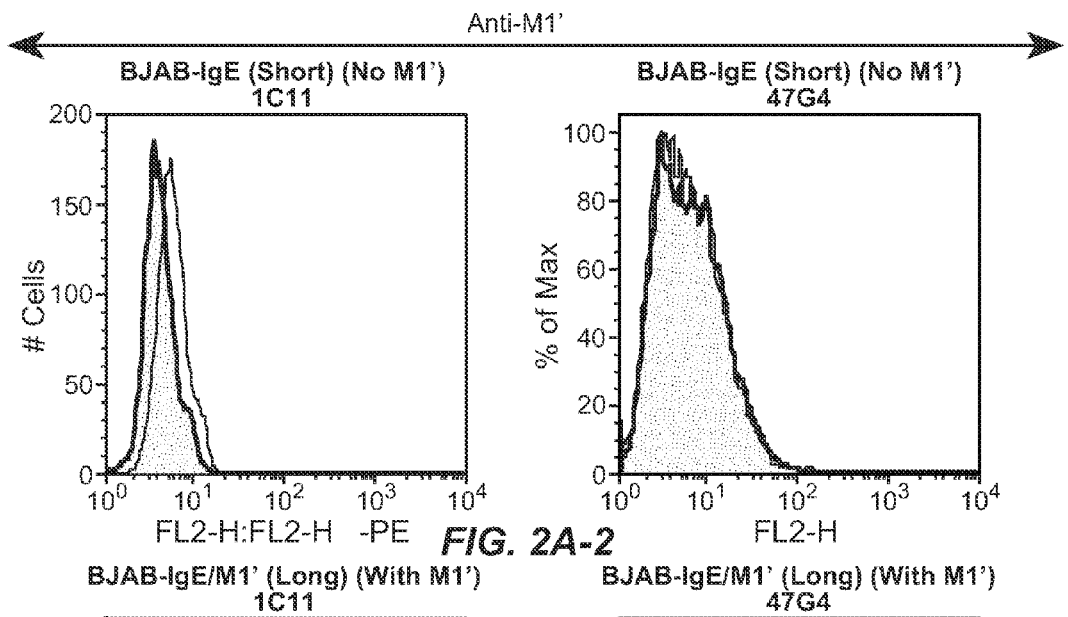
FIG. 2A-2
FIG. 2B-2
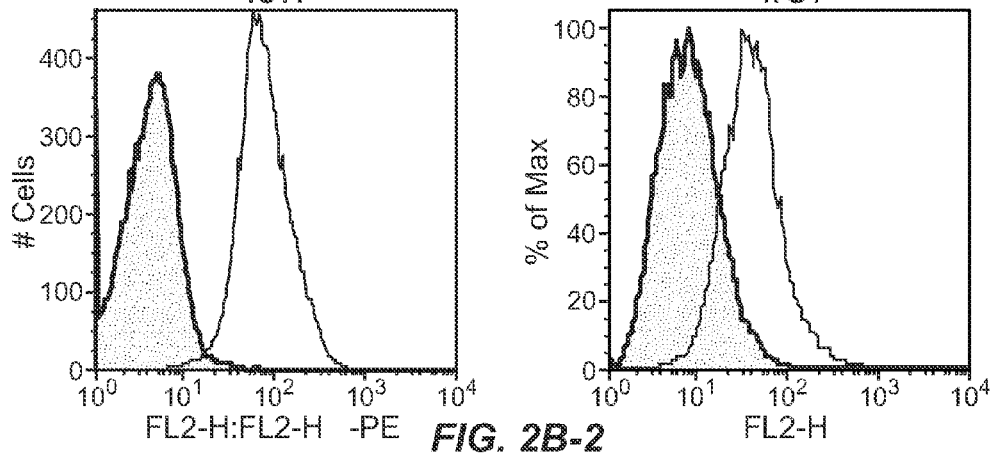
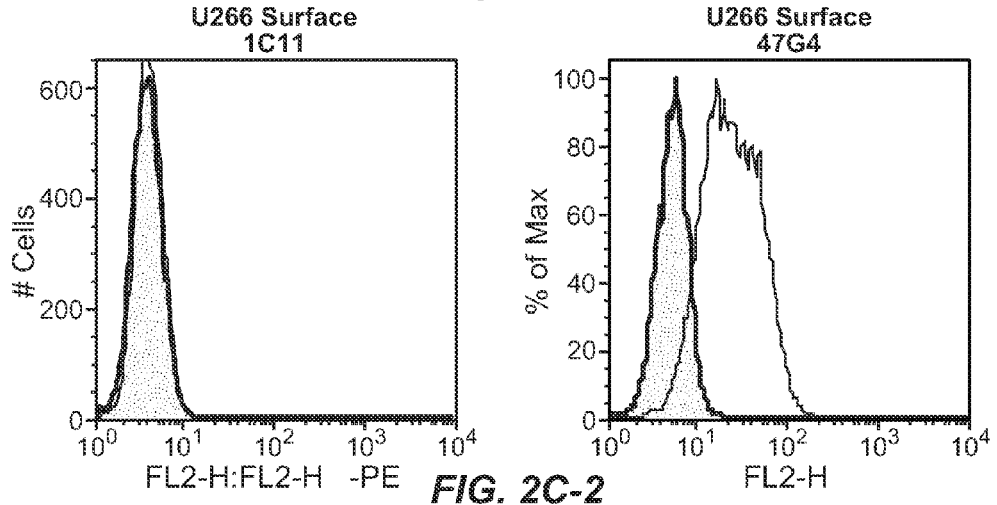
FIG. 2C-2

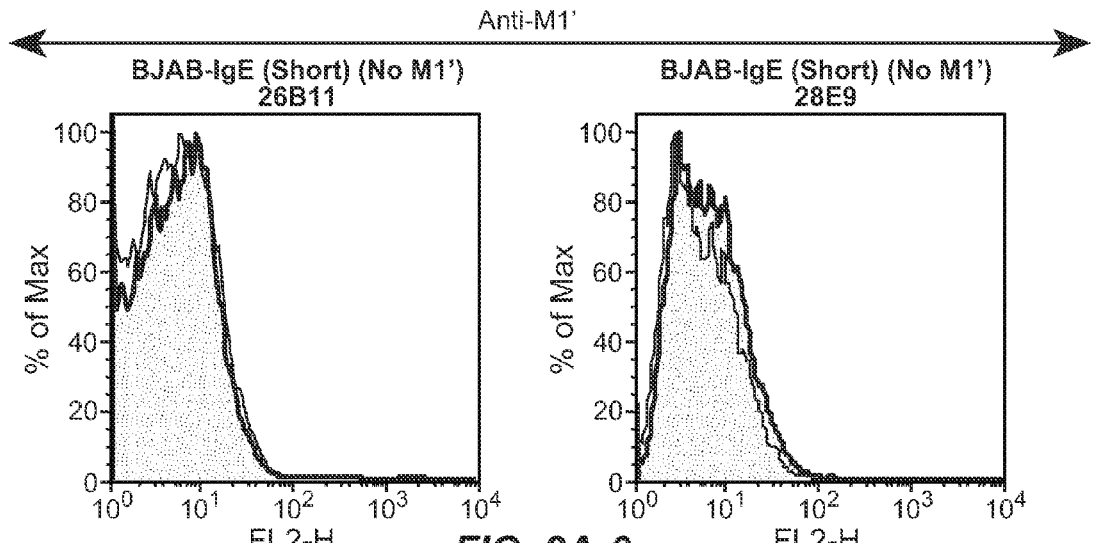
FIG. 2A-6
FIG. 2B-6
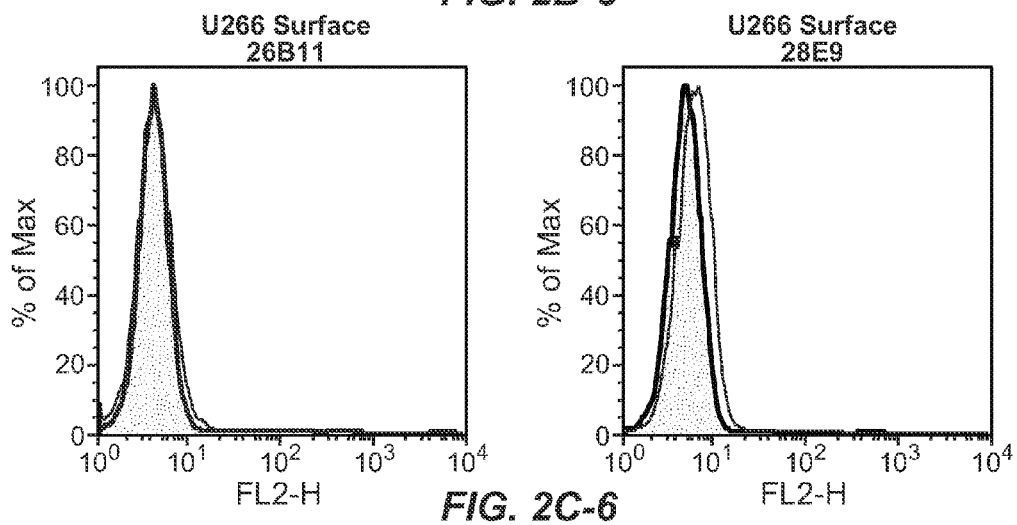
FIG. 2C-6

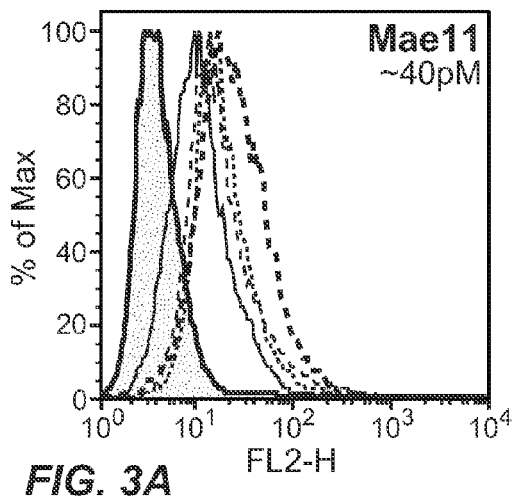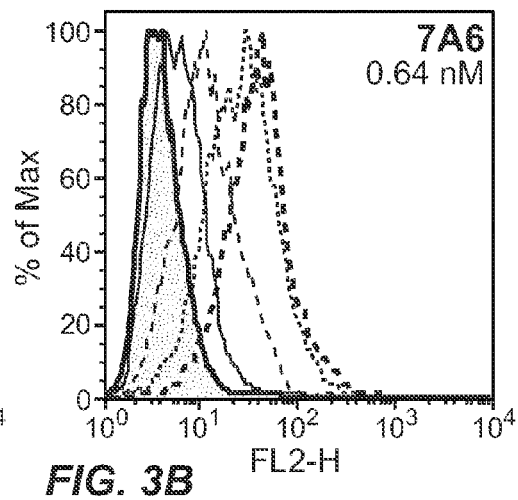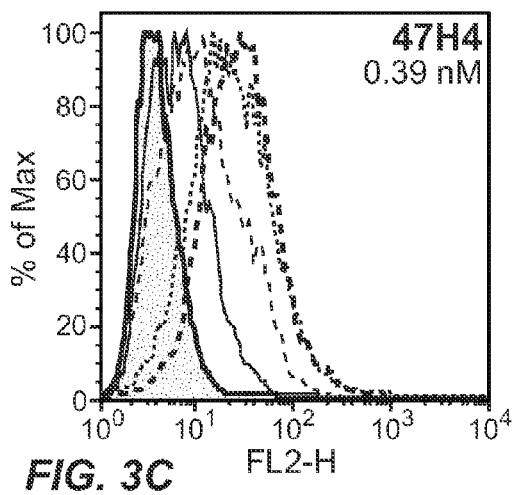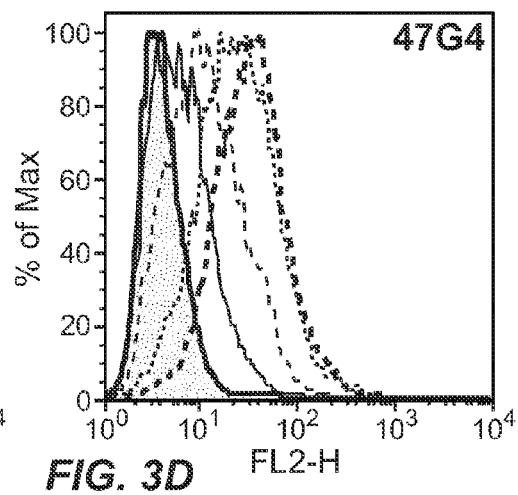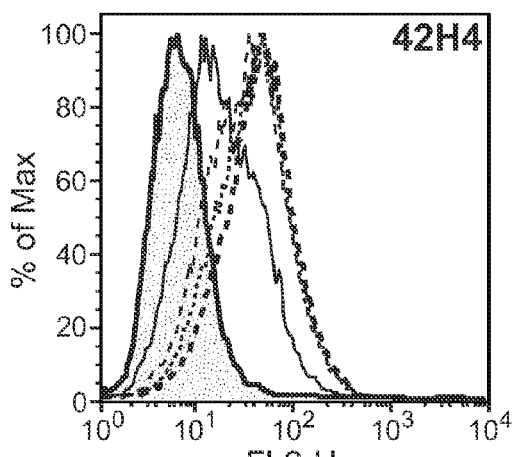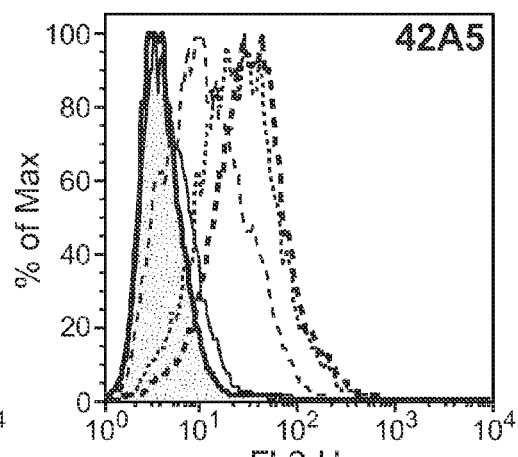

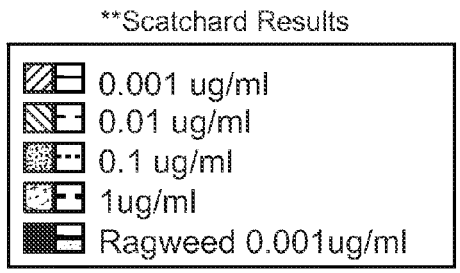
*FIG. 3M*
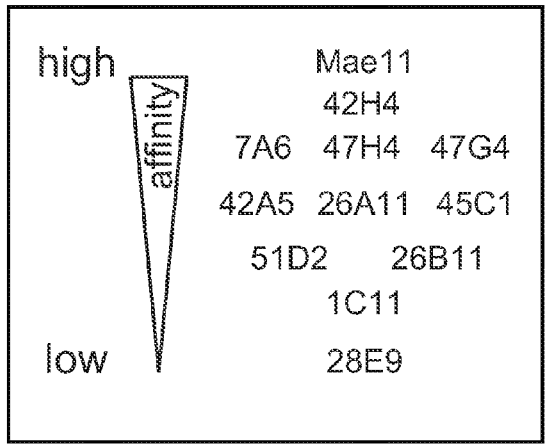
*FIG. 3N*
Humanized Anti-IgE/M1' Binding Affinities
| | Scatchard Human M1' (nM) | | | Scatchard Rhesus M1' (nM) | Scatchard Cyno M1' (nM) |
|---|---|---|---|---|---|
| | Measured | Mean | S.D. | | |
| 47H4 mIgG1 | | | | 0.77 | 0.97 |
| -exp. 1 | 0.74 0.83 | 0.79 | | | |
| -exp. 2 | 0.55 0.52 | 0.54 | | | |
| -exp. 3 | 0.47 0.30 | 0.39 | | | |
| Overall | | 0.57 | 0.190936 | | |
| 26A11 mIgG1 | | | | | |
| -exp. 1 | 1.68 2.59 | 2.14 | | | |
| -exp. 2 | 1.20 2.30 | 1.75 | | | |
| Overall | | 1.94 | 0.623772 | | |
| 7A6 mIgG1 | 0.64 | | | na | na |
*FIG. 3O*

|  | Scatchard Human M1' (nM) | Scatchard Rhesus M1' (nM) | Scatchard Cyno M1' (nM) |
|---|---|---|---|
| 47H4 v5 huIgG1 | 1.5 | 1.3 | 2.5 |
| 47H4 v2 huIgG1 | 0.54 | na | na |
| 47H4 v1 huIgG1 | 0.37 | na | na |
| 26A11 v6 huIgG1 | 1.85 | na | na |
| 26A11 v14 huIgG1 | 1.5 | na | na |
| 26A11 v1 huIgG1 | 1.06 | na | na |

*FIG. 3P*

| FIG. 4A-1 | FIG. 4A-2 | FIG. 4A-3 | FIG. 4A-4 | FIG. 4A-5 |
|---|---|---|---|---|
| FIG. 4A-6 | FIG. 4A-7 | FIG. 4A-8 | FIG. 4A-9 | FIG. 4A-10 |
| FIG. 4A-11 | FIG. 4A-12 | FIG. 4A-13 | FIG. 4A-14 | FIG. 4A-15 |
| FIG. 4A-16 | FIG. 4A-17 | FIG. 4A-18 | FIG. 4A-19 | FIG. 4A-20 |

*FIG. 4A*

Anti-IgE/M1' Antibody Epitope Binding/Blocking Studies

| 1° \ 2° Detection | 7A6 biotin | 47H4 alexa647 | 47G4 alexa647 | 42A5 mIgG1 | 42H4 mIgG1 | 1C11 biotin | 26A11 mIgG1/alexa647 | 51D2 mIgG2a | 45C1 mIgG2a | 28E9 mIgG1 | 26B11 mIgG1 |
|---|---|---|---|---|---|---|---|---|---|---|---|
| 7A6 mIgG1 | | | | | | | | | | | |
| 47H4* mIgG1 | Block | Block | Partial | | | Block | | Partial | Partial | | |
| 47G4* mIgG1 | Block | Block | Partial | Block | | Block | | Partial | Partial | | |
| 42A5* mIgG1 | Block | Block | Partial | | | Block | | Partial | Partial | | |
| 42H4* mIgG1 | Block | Block | Partial | | Block | Block | | Partial | Partial | | |
| 1C11 mIgG1 | | | | | | Block | | Block | Block | | |
| 26A11 mIgG1 | | | | | | Block | Block | Block | Block | | |
| 51D2 mIgG2a | | Partial | Partial | Partial | | Partial | slight | Block | Block | | |
| 45C1 mIgG2a | | Partial | Partial | | | | slight | Block | Block | | |
| 28E9* mIgG1 | slight | | | | | | | slight | | Block | |
| 26B11 mIgG1 | | | | | | | | slight | | | Block |

Legend: Block (1:1 Ratio); Partial Block (1:1); No Effect; Not Determined; * Bind U266

FIG. 4B

Anti-IgE/M1' Epitope Mapping

| | CH4 | M1' | | T.M. |
|---|---|---|---|---|
| | FTCRAVHEAASPSQTVQRAVSVNP | GLAGGSAQSQRAPDRVLCHSGQQQGLPRAAGGSVPHPRCHCGAGRADWPGPPE | | LDVCVEEAEGEAPWTWTGLCIFAALPL.. |
| 1 | ASPSQTVQRAVSVNP | | G    G    HPR   human | P |
| 2 | TVQRAVSVNP | GLAGG | E    DHH   Rhesus | L |
| 3 | | GLAGGSAQSQRAPDR | E    R    DHR   Cyno | L |
| 4 | | SAQSQRAPDRVLCHS | | |
| 5 | | RAPDRVLCHSGQQQG | | |
| 6 | | VLCHSGQQQGLPRAA | | |
| 7 | | GQQQGLPRAAGGSVP | | |
| 8 | | PRAAGGSVPHPRCH | | |
| 9 | | GGSVPHPRCHCGAGR | | |
| 10 | | HPRCHCGAGRADWPG | | |
| 11 | | CGAGRADWPGPPE | LD | |
| 12 | | ADWPGPPE | LDVCVEE | |
| 13 | | PPE | LDVCVEEAEGEA | |
| 14 | | | VCVEEAEGEAPWTWT | |
| 15 | | | AEGEAPWTWTGLCIF | |

M1' Peptides

FIG. 5A

Anti-IgE/M1' Epitope Mapping

|       | Peptide # | Peptide Sequence |
|-------|-----------|------------------|
| 47H4  | 4         | SAQSQRAPDRVLCHS  |
| 7A6   | 4         | SAQSQRAPDRVLCHS  |
|       | 5         | RAPDRVLCHSGQQQG  |
| 26A11 | 7         | GQQQGLPRAAGGSVP  |
|       | 8         | PRAAGGSVPHPRCH   |

*FIG. 5B*

Anti-IgE/M1' Epitope Mapping

|          | Peptide # | Peptide Sequence |
|----------|-----------|------------------|
| 47H4 v5  | 4         | SAQSQRAPDRVLCHS  |
| 7A6 v1   | 4         | SAQSQRAPDRVLCHS  |
|          | 5         | RAPDRVLCHSGQQQG  |
| 26A11 v6 | 7         | GQQQGLPRAAGGSVP  |
|          | 8         | PRAAGGSVPHPRCH   |

| Kabat# | 1 2 3 4 5 6 7 8 9 10 11 12 13 14 15 16 17 18 19 20 21 22 23 24 25 26 27 A B C D E F 28 29 30 31 32 33 34 35 36 37 |
|---|---|
| | Kabat - CDR L1 |
| | Chothia - CDR L1 |
| | Contact - CDR L1 |
| huKI | D I Q M T Q S P S S L S A S V G D R V T I T C — R A S Q — — — — S I S N Y L A W Y Q |
| mu7A6 | D I V M S Q S P S S L T V S V G E K V T L S C K S S Q T L L Y S T N Q K N Y L A W Y Q |
| hu7A6.v1 | D I Q M T Q S P S S L S A S V G D R V T I T C K S S Q T L L Y S T N Q K N Y L A W Y Q |

| Kabat# | 38 39 40 41 42 43 44 45 46 47 48 49 50 51 52 53 54 55 56 57 58 59 60 61 62 63 64 65 66 67 68 69 70 71 72 73 74 75 76 77 78 79 80 |
|---|---|
| | Kabat - CDR L2 |
| | Chothia - CDR L2 |
| | Contact - CDR L2 |
| huKI | Q K P G K A P K L L I Y A A S — — — S L E S G V P S R F S G S G S G T D F T L T I S S L Q P |
| mu7A6 | Q K P G Q S P K L L I Y W A S T R E S G V P D R F T G S G S G T D F T L T I S S V K A |
| hu7A6.v1 | Q K P G K A P K L L I Y W A S T R E S G V P S R F S G S G S G T D F T L T I S S L Q P |

| Kabat# | 81 82 83 84 85 86 87 88 89 90 91 92 93 94 95 A B C D E F 96 97 98 99 100 101 102 103 104 105 106 107 |
|---|---|
| | Kabat - CDR L3 |
| | Chothia - CDR L3 |
| | Contact - CDR L3 |
| huKI | E D F A T Y Y C Q Q Y N S L P — — — — W T F G Q G T K V E I K R |
| mu7A6 | E D F A V Y V C Q Q Y Y S Y P Y T F G G G T K V E I K R |
| hu7A6.v1 | E D F A T Y Y C Q Q Y Y S Y P Y T F G Q G T K V E I K R |

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| huKI | D | I | Q | M | T | Q | S | P | S | S | L | S | A | S | V | G | D | R | V | T | I | T | C | R | A | S | Q | | | | | | | S | I | S | N | Y | L | | | | |
| mu47H4 | D | I | V | L | T | Q | S | P | S | S | L | P | V | S | V | G | D | R | V | T | I | S | C | R | S | S | Q | | | | | | | S | L | V | H | N | | | | | | |
| hu47H4.v1,3 | D | I | Q | M | T | Q | S | P | S | S | L | S | A | S | V | G | D | R | V | T | I | T | C | R | A | S | Q | | | | | | | S | L | V | H | N | | | | | | |
| hu47H4.v2,4-6 | D | I | Q | M | T | Q | S | P | S | S | L | S | A | S | V | G | D | R | V | T | I | T | C | R | A | S | Q | | | | | | | N | T | Y | L | H | | | | | | |

Kabat - CDR L1 (positions 24–34)
Chothia - CDR L1 (positions 24–34)
Contact - CDR L1 (positions 30–36)

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| huKI | Q | K | P | G | K | A | P | K | L | L | I | Y | A | A | S | S | L | E | S | G | V | P | S | R | F | S | G | S | G | S | G | T | E | F | T | L | T | I | S | S | L | Q | P |
| mu47H4 | Q | K | P | G | Q | S | P | K | L | L | I | Y | K | V | S | N | R | F | S | G | V | P | D | R | F | S | G | S | G | S | G | T | D | F | T | L | K | I | S | R | V | E | A |
| hu47H4.v1-6 | Q | K | P | G | K | A | P | K | L | L | I | Y | K | V | S | N | R | F | S | G | V | P | S | R | F | S | G | S | G | S | G | T | E | F | T | L | T | I | S | S | L | Q | P |

Kabat - CDR L2
Chothia - CDR L2
Contact - CDR L2

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|---|
| huKI | E | D | F | A | T | Y | Y | C | Q | Q | Y | N | S | L | P | | | | | | | W | T | F | G | Q | G | T | K | V | E | I | K | R | |
| mu47H4 | E | D | L | G | V | Y | F | C | S | Q | S | T | H | V | P | | | | | | | W | T | F | G | G | G | T | K | V | E | I | K | R | |
| hu47H4.v1-6 | E | D | F | A | T | Y | Y | C | S | Q | S | T | H | V | P | | | | | | | W | T | F | G | Q | G | T | K | V | E | I | K | R | |

Kabat - CDR L3
Chothia - CDR L3
Contact - CDR L3

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | Chothia - CDR H1 | | | | | | | | | | Kabat - CDR H1 | | | | | |
| | | | | | | | | | | | | | | | | | | | | | | | | | | | | Contact - CDR H1 | | | | | | | | | | | | |
| humIII | E | V | Q | L | V | E | S | G | G | G | L | V | Q | P | G | G | S | L | R | L | S | C | A | A | S | G | F | T | F | S | S | Y | A | M | S | W | V | R | Q | A | P |
| mu26A11 | E | V | Q | L | Q | Q | S | G | P | E | L | K | K | P | G | E | S | V | K | M | S | C | K | A | S | G | Y | T | F | T | T | D | Y | Y | M | W | V | K | Q | A | P |
| hu26A11.v1-3,13,14 | E | V | Q | L | V | E | S | G | G | G | L | V | Q | P | G | G | S | L | R | L | S | C | A | A | S | G | Y | T | F | T | T | D | Y | Y | M | W | V | R | Q | A | P |
| hu26A11.v4-6,15,16 | E | V | Q | L | V | E | S | G | G | G | L | V | Q | P | G | G | S | L | R | L | S | C | A | A | S | G | Y | T | F | T | T | D | Y | Y | I | W | V | R | Q | A | P |

| Kabat# | 42 | 43 | 44 | 45 | 46 | 47 | 48 | 49 | 50 | 51 | 52 | a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | Chothia - CDR H2 | | | | | | | | | | | | | | | | | | | | | | | | | | | | | | | |
| | | | | | | | | | | | | | | Kabat - CDR H2 | | | | | | | | | | | | | | | | | | | | | | | | | |
| | | | | | | | Contact - CDR H2 | | | | | | | | | | | | | | | | | | | | | | | | | | | | | | | | | |
| humIII | G | K | G | L | E | W | V | S | V | I | S | G | D | G | G | S | T | Y | Y | A | D | S | V | K | G | R | F | T | I | S | R | D | N | S | K | N | T | L | Y | L |
| mu26A11 | G | K | S | L | E | W | I | G | D | I | N | P | N | N | G | G | T | S | Y | N | Q | K | F | K | G | K | A | T | L | T | V | D | K | S | S | S | T | A | Y | L |
| hu26A11.v1-16 | G | K | G | L | E | W | V | G | D | I | N | P | N | N | G | G | T | S | Y | N | Q | K | F | K | G | R | F | T | I | S | A | D | T | S | K | N | T | A | Y | L |

| Kabat# | 81 | 82 | A | B | C | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | Kabat - CDR H3 | | | | | | | | | | |
| | | | | | | | | | | | | | | | | | | | | | | | | | | | Chothia - CDR H3 | | | | | | | | | |
| | | | | | | | | | | | | | | | | | | Contact - CDR H3 | | | | | | | | | | | | | | | | | | |
| humIII | Q | M | N | S | L | R | A | E | D | T | A | V | Y | Y | C | A | R | | | | | | | F | D | Y | W | G | Q | G | T | L | V | T | V | S | S |
| mu26A11 | Q | L | N | S | L | T | S | E | D | S | A | V | Y | Y | C | A | S | | | | | | | K | A | Y | W | G | Q | G | T | L | V | T | V | S | S |
| hu26A11.v1-16 | Q | M | N | S | L | R | A | E | D | T | A | V | Y | Y | C | A | S | | | | | | | K | A | Y | W | G | Q | G | T | L | V | T | V | S | S |

| Kabat# | 1 2 3 4 5 6 7 8 9 10 11 12 13 14 15 16 17 18 19 20 21 22 23 24 25 26 27 28 29 30 31 32 33 34 35 A B 36 37 38 39 40 41 |
|---|---|
| | Chothia - CDR H1 / Kabat - CDR H1 |
| | Contact - CDR H1 |
| humIII | E V Q L V E S G G G L V Q P G G S L R L S C A A S G F T F S S Y A M S W V R Q A P |
| mu7A6 | Q V Q L Q Q S G A E L V R P G A S V T L S C K A S G Y T F T D Y E M H W V K Q T P |
| hu7A6.v1 | E V Q L V E S G G G L V Q P G G S L R L S C A A S G Y T F T D Y E M H W V R Q A P |

| Kabat# | 42 43 44 45 46 47 48 49 50 51 52 a b c 53 54 55 56 57 58 59 60 61 62 63 64 65 66 67 68 69 70 71 72 73 74 75 76 77 78 79 80 |
|---|---|
| | Kabat - CDR H2 |
| | Chothia - CDR H2 |
| | Contact - CDR H2 |
| humIII | G K G L E W V S V I S G D G S T Y Y A D S V K G R F T I S R D N S K N T L Y L |
| mu7A6 | V H G L E W I G A I D P E T G G T A Y N Q K F K G K A T L T A D K S S N T A Y M |
| hu7A6.v1 | G K G L E W V G A I D P E T G G T A Y N Q K F K G R F T I S A D K S K N T A Y L |

| Kabat# | 81 82 A B C 83 84 85 86 87 88 89 90 91 92 93 94 95 96 97 98 99 100 A B C D ... K 101 102 103 104 105 106 107 108 109 110 111 112 113 |
|---|---|
| | Kabat - CDR H3 |
| | Chothia - CDR H3 |
| | Contact - CDR H3 |
| humIII | Q M N S L R A E D T A V Y Y C A R ... ... ... ... ... ... ... ... ... ... W G Q G T L V T V S S |
| mu7A6 | Q I E S L T S E D S A V Y Y C T R L R P H Y D Y D N A M D S W G Q G T S V T V S S |
| hu7A6.v1 | Q M N S L R A E D T A V Y Y C T R L R P H Y D Y D N A M D S W G Q G T L V T V S S |

| Kabat# | 1 2 3 4 5 6 7 8 9 10 11 12 13 14 15 16 17 18 19 20 21 22 23 24 25 26 27 28 29 30 31 32 33 34 35 A B 36 37 38 39 40 41 |
|---|---|
| | Chothia - CDR H1 / Kabat - CDR H1 / Contact - CDR H1 |
| humIII | E V Q L V E S G G G L V Q P G G S L R L S C A A S G F T F S S Y A M S W V R Q A P |
| mu47H4 | E V K L V E S G G G L V Q P G G S R K L S C A A S G F T F S D Y G M A W V R Q A P |
| hu47H4.v1,2,6 | E V Q L V E S G G G L V Q P G G S L R L S C A A S G F T F S D Y G M A W V R Q A P |
| hu47H4.v3-5 | E V Q L V E S G G G L V Q P G G S L R L S C A A S G F T F S D Y I W V R Q A P |

| Kabat# | 42 43 44 45 46 47 48 49 50 51 52 a b c 53 54 55 56 57 58 59 60 61 62 63 64 65 66 67 68 69 70 71 72 73 74 75 76 77 78 79 80 |
|---|---|
| | Chothia - CDR H2 / Kabat - CDR H2 / Contact - CDR H2 |
| humIII | G K G L E W V S S V I S G D G G S T Y Y A D S V K G R F T I S R D N S K N T L Y L |
| mu47H4 | G K G P E W V A A F I S D L A Y T I Y Y A D T V T G K R F T I S R E N A K N T L Y L |
| hu47H4.v1-16 | G K G L E W V A A F I S D L A Y T I Y Y A D T V T G R F T I S R D N S K N T L Y L |

| Kabat# | 81 82 A B C 83 84 85 86 87 88 89 90 91 92 93 94 95 96 97 98 99 K 101 102 103 104 105 106 107 108 109 110 111 112 113 |
|---|---|
| | Kabat - CDR H3 / Chothia - CDR H3 / Contact - CDR H3 |
| humIII | Q M N S L R A E D T A V Y Y C A R . . . . . . . . . . D Y W G Q G T L V T V S S |
| mu47H4 | E M S S L R S E D T A L Y Y C A R G A R D N W D A M D Y W G Q G T S V T V S S |
| hu47H4.v1,2,5 | Q M N S L R A E D T A V Y Y C A R A R D N W D A M D Y W G Q G T L V T V S S |
| hu47H4.v3,4,6 | Q M N S L R A E D T A V Y Y C A R A R D N W D A L M D Y W G Q G T L V T V S S |

*FIG. 6F*

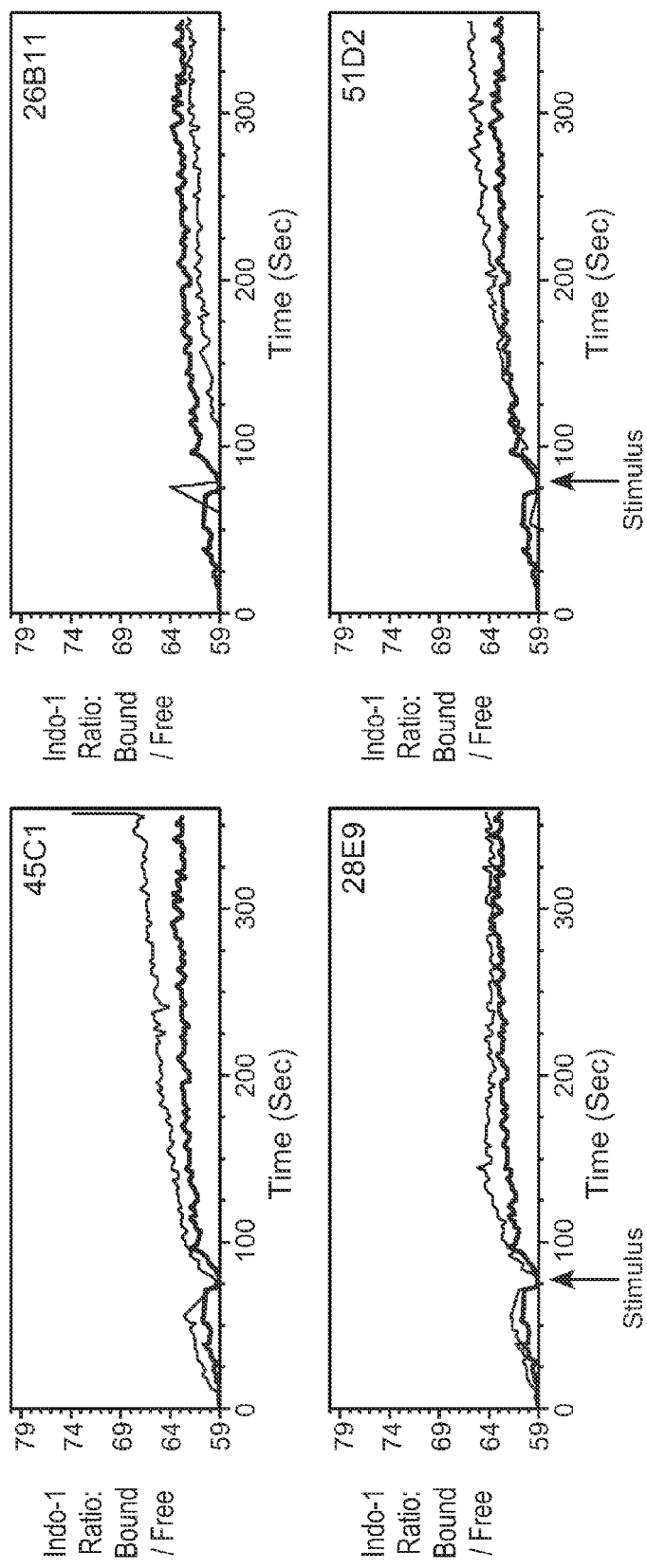

7A6

7A6 HC mIgG1

*QVQLQQSGAELVRPGASVTLSCKAS<u>GYTFIDYEMH</u>WVKQTPVHGLEWIG<u>AIDPETGTTAYNQKF
KGK</u>ATLTAAKSSSTAYMELRSLTSEDSAVYYC<u>TRLRPHYDYDNAMDS</u>WGQGTTLTVSSASTKGP
 // SVYPLAPGSAAQTNSMVTLGCLVKGYFPEPVTVTWNSGSLSSGVHTFPAVLQSDLYTLSS
SVTVPSSTWPSETVTCNVAHPASSTKVDKKIVPRDCGCKPCICTVPEVSSVFIFPPKPKDVLTI
TLTPKVTCVVVDISKDDPEVQFSWFVDDVEVHTAQTQPREEQFNSTFRSVSELPIMHQDWLNGK
EFKCRVNSAAFPAPIEKTISKTKGRPKAPQVYTIPPPKEQMAKDKVSLTCMITDFFPEDITVEW
QWNGQPAENYKNTQPIMDTDGSYFVYSKLNVQKSNWEAGNTFTCSVLHEGLHNHHTEKSLSHSP
GK*

7A6 LC mkappa

*DIVMSQSPSSLTVSVGEKVTL<u>SCKSSQTLLYSTNQKNYLA</u>WYQQKPGQSPKLLIY<u>WASTRESG</u>V
PDRFTGSGSGTDFTLTISSVKAEDLAVYYC<u>QQYYSYPYT</u>FGGGT // KVEIKRADAAPTVSIF
PPSSEQLTSGGASVVCFLNNFYPKDINVKWKIDGSERQNGVLNSWTDQDSKDSTYSMSSTLTLT
KDEYERHNSYTCEATHKTSTSPIVKSFNRNEC*

47H4 HC mIgG1

*EVKLVESGGGLVQPGGSRKLSCAAS<u>GFTFSDYGMA</u>WVRQAPGKGPEWVA<u>FISDLAYTIYYADTV
TG</u>RFTISRENAKNTLYLEMSSLRSEDTALYYC<u>ARDNWDAMDY</u>WGQGTSVTVSSAKTTPP // S
SVYPLAPGSAAQTNSMVTLGCLVKGYFPEPVTVTWNSGSLSSGVHTFPAVLQSDLYTLSSSVTV
PSSTWPSETVTCNVAHPASSTKVDKKIVPRDCGCKPCICTVPEVSSVFIFPPKPKDVLTITLTP
KVTCVVVDISKDDPEVQFSWFVDDVEVHTAQTQPREEQFNSTFRSVSELPIMHQDWLNGKEFKC
RVNSAAFPAPIEKTISKTKGRPKAPQVYTIPPPKEQMAKDKVSLTCMITDFFPEDITVEWQWNG
QPAENYKNTQPIMDTDGSYFVYSKLNVQKSNWEAGNTFTCSVLHEGLHNHHTEKSLSHSPGK*

47H4 LC mkappa

*DIVLTQTPLSLPVSLGDQASISC<u>RSSQSLVHNNGNTYLH</u>WYLQKPGQSPKLLIY<u>KVSNRFS</u>GVP
DRFSGSGSGTDFTLKISRLEAEDLGVYFC<u>SQNTLVPWT</u>FGGGT // KVEIKRADAAPTVSIFP
PSSEQLTSGGASVVCFLNNFYPKDINVKWKIDGSERQNGVLNSWTDQDSKDSTYSMSSTLTLTK
DEYERHNSYTCEATHKTSTSPIVKSFNRNEC*

26A11 HC mIgG1

*EVQLQQSGPELVKPGASVKMSCKAS<u>GYTFTDYYMM</u>WVKQSHGKSLEWIG<u>DINPNNYDTSYNQKF</u>*
*<u>KG</u>KATLTVDKSSSTAYIQLNSLTSEDSAVYYCAS<u>KAY</u>WGQGTLVTVSAASTTPP* // SVYPLA
PGSAAQTNSMVTLGCLVKGYFPEPVTVTWNSGSLSSGVHTFPAVLQSDLYTLSSSVTVPSSTWP
SETVTCNVAHPASSTKVDKKIVPRDCGCKPCICTVPEVSSVFIFPPKPKDVLTITLTPKVTCVV
VDISKDDPEVQFSWFVDDVEVHTAQTQPREEQFNSTFRSVSELPIMHQDWLNGKEFKCRVNSAA
FPAPIEKTISKTKGRPKAPQVYTIPPPKEQMAKDKVSLTCMITDFFPEDITVEWQWNGQPAENY
KNTQPIMDTDGSYFVYSKLNVQKSNWEAGNTFTCSVLHEGLHNHHTEKSLSHSPGK

26A11 LC mkappa

*DIQMTQTTSSLSASLGDRVTITC<u>RSSQDISNSLNW</u>YQQKPDGPVKLLIY<u>STSRLHS</u>GVPSRFSG*
*SGSGTDYSLTISNLEQEDLATYFC<u>QQGHTLPWT</u>FGGGT* // KVEIKRADAAPTVSIFPPSSEQ
LTSGGASVVCFLNNFYPKDINVKWKIDGSERQNGVLNSWTDQDSKDSTYSMSSTLTLTKDEYER
HNSYTCEATHKTSTSPIVKSFNRNEC

45C1 HC mIgG2a

*QIQLVQSGPELKKPGETVKISCKASGYTFTNYGMNWVKQAPGKGLKWMGWINTYTGEPTYVDDF*
*KGRFAFSLETSASTAYLQINNLKNEDMATYFCARGIYYDNDDIYWGQGTILTVSSAKTTAP* //
SVYPLAPVCGDTTGSSVTLGCLVKGYFPEPVTLTWNSGSLSSGVHTFPAVLQSDLYTLSSSVTV
TSSTWPSQSITCNVAHPASSTKVDKKIEPRGPTIKPCPPCKCPAPNLLGGPSVFIFPPKIKDVL
MISLSPIVTCVVVDVSEDDPDVQISWFVNNVEVHTAQTQTHREDYNSTLRVVSALPIQHQDWMS
GKEFKCKVNNKDLPAPIERTISKPKGSVRAPQVYVLPPPEEEMTKKQVTLTCMVTDFMPEDIYV
EWTNNGKTELNYKNTEPVLDSDGSYFMYSKLRVEKKNWVERNSYSCSVVHEGLHNHHTTKSFSR
TPGK

45C1 LC mkappa

*DIVMTQTPLTLSVTIGQPASISCKSSQSLLDSDGKTYLNWLLQRPGQSPKRLIYLVSKLDSGVP*
*DRFTGSGSGTDFTLKISRVEAEDLGVYYCWQGTHFPHTFGGGT* // KVEIKRADAAPTVSIFP
PSSEQLTSGGASVVCFLNNFYPKDINVKWKIDGSERQNGVLNSWTDQDSKDSTYSMSSTLTLTK
DEYERHNSYTCEATHKTSTSPIVKSFNRNEC

28E9 HC mIgG1

EVKLVESEGGLVQPGGSLRLSCATSGFTFTDYYMSWVRQPPGKPLEWLGFISNKLNGYTTEYSS
SVQGRFTISRDDSQSILYLQMNTLRPEDSAAYYCARDMVPYYYALDYWGQGTSVAVSSAKTTPP
 // SVYPLAPGSAAQTNSMVTLGCLVKGYFPEPVTVTWNSGSLSSGVHTFPAVLQSDLYTLSS
SVTVPSSTWPSETVTCNVAHPASSTKVDKKIVPRDCGCKPCICTVPEVSSVFIFPPKPKDVLTI
TLTPKVTCVVVDISKDDPEVQFSWFVDDVEVHTAQTQPREEQFNSTFRSVSELPIMHQDWLNGK
EFKCRVNSAAFPAPIEKTISKTKGRPKAPQVYTIPPPKEQMAKDKVSLTCMITDFFPEDITVEW
QWNGQPAENYKNTQPIMDTDGSYFVYSKLNVQKSNWEAGNTFTCSVLHEGLHNHHTEKSLSHSP
GK

28E9 LC mkappa

DIQMTQSPASLSVSVGETVTFTCRTSENIYTYLAWIQQKQGKSPQLLVYNAQILAEGVPSRFSG
SGSGSQFSLQINSLQPEDFGYYYCQHHYGTPFTFGSGT // KVEIKRADAAPTVSIFPPSSEQ
LTSGGASVVCFLNNFYPKDINVKWKIDGSERQNGVLNSWTDQDSKDSTYSMSSTLTLTKDEYER
HNSYTCEATHKTSTSPIVKSFNRNEC

1C11 HC mIgG1

QVQLQQSGAELVRPGASVTLSCKASGYTFTDFEMHWVKQTPVHGLEWIGAIAPETGTSAYNQKF
RGKATLTADISSSTAYMDLRSLTSEDSAVYYCTIYYAAPWFAYWGQGTLVTVSSASTKGP //
SVYPLAPGSAAQTNSMVTLGCLVKGYFPEPVTVTWNSGSLSSGVHTFPAVLQSDLYTLSSSVTV
PSSTWPSETVTCNVAHPASSTKVDKKIVPRDCGCKPCICTVPEVSSVFIFPPKPKDVLTITLTP
KVTCVVVDISKDDPEVQFSWFVDDVEVHTAQTQPREEQFNSTFRSVSELPIMHQDWLNGKEFKC
RVNSAAFPAPIEKTISKTKGRPKAPQVYTIPPPKEQMAKDKVSLTCMITDFFPEDITVEWQWNG
QPAENYKNTQPIMDTDGSYFVYSKLNVQKSNWEAGNTFTCSVLHEGLHNHHTEKSLSHSPGK

1C11 LC mkappa

DIVMSQSPSSLAVSVGEKVTMSCKSSQSLLYSSNQKNYLAWYQQKPGQSPKLLIYWASTRESGV
PDRFTGSGSVTDFPLTISSVKAEDLAVYYCQQYYSYPYTFGGGT // KVEIKRADAAPTVSIF
PPSSEQLTSGGASVVCFLNNFYPKDINVKWKIDGSERQNGVLNSWTDQDSKDSTYSMSSTLTLT
KDEYERHNSYTCEATHKTSTSPIVKSFNRNEC

*FIG. 11F*

Effect of Anti-M1' on Serum IgE

| #07-0377 | Total IgE (ng/ml) | | | |
|---|---|---|---|---|
| Group | Mean | S.D. | % Change | p-value |
| gp120 mIgG1 | 3606.0 | 1385.3 | na | na |
| 47H4 mIgG1 | 589.2 | 91.8 | -83.7% | <0.0001 |
| 26A11 mIgG1 | 838.42 | 224.8 | -76.7% | <0.0001 |
| 7A6 mIgG1 | 1248.33 | 360.4 | -65.4% | <0.0001 |

*FIG. 12C*

Effect of Anti-IgE/M1' on IgE-producing Cells

| #07-0377 | #Elispots/Spleen (%) | | | |
|---|---|---|---|---|
| Group | Mean | S.D. | % Change | p-value |
| gp120 mIgG1 | 0.0103 | 0.0040 | na | na |
| 47H4 mIgG1 | 0.0032 | 0.0020 | -68.9% | 0.0003 |
| 26A11 mIgG1 | 0.0068 | 0.0040 | -34.0% | 0.0815 |
| 7A6 mIgG1 | 0.0083 | 0.0030 | -19.4% | 0.4518 |

*FIG. 12E*

Effect of Anti-IgE/M1' on Total Plasma Cells

| #07-0377 | % total PC | | | |
|---|---|---|---|---|
| Group | Mean | S.D. | % Change | p-value |
| gp120 mIgG1 | 4.24 | 1.52 | na | na |
| 47H4 mIgG1 | 4.20 | 1.30 | -1% | 1.0000 |
| 26A11 mIgG1 | 6.18 | 4.51 | +45.8% | 0.2667 |
| 7A6 mIgG1 | 4.6 | 1.28 | +8.5% | 0.9835 |

*FIG. 12I*

Effect of Anti-IgE/M1' on Other Serum Immunoglobulins

| #07-0377 | huIgG1 | | | | huIgG2 | | | |
|---|---|---|---|---|---|---|---|---|
| Group | Mean | S.D. | % Change | p-value | Mean | S.D. | % Change | p-value |
| gp120 mIgG1 | 1936.8 | 512.2 | na | na | 149.4 | 41.5 | na | na |
| 47H4 mIgG1 | 1540.8 | 269.1 | -20.4 | 0.1265 | 115.4 | 22.7 | -22.8 | 0.0504 |
| 26A11 mIgG1 | 2028.7 | 567 | +4.7 | 0.9278 | 136.4 | 33.8 | -8.7 | 0.6399 |
| 7A6 mIgG1 | 1406.8 | 341 | -27.4 | 0.0210 | 121.8 | 24.2 | -18.5 | 0.1125 |

| #07-0377 | huIgG3 | | | | huIgG4 | | | |
|---|---|---|---|---|---|---|---|---|
| Group | Mean | S.D. | % Change | p-value | Mean | S.D. | % Change | p-value |
| gp120 mIgG1 | 71.1 | 22.7 | na | na | 55.7 | 11.8 | na | na |
| 47H4 mIgG1 | 46.8 | 11.9 | -34.2 | 0.0143 | 40.5 | 5.8 | -27.3 | 0.0071 |
| 26A11 mIgG1 | 75.4 | 20.2 | +6.0 | 0.9013 | 53 | 14 | -4.8 | 0.8799 |
| 7A6 mIgG1 | 47.9 | 17 | -32.6 | 0.0138 | 39.7 | 8.4 | -28.7 | 0.0031 |

| #07-0377 | huIgM | | | | huIgA | | | |
|---|---|---|---|---|---|---|---|---|
| Group | Mean | S.D. | % Change | p-value | Mean | S.D. | % Change | p-value |
| gp120 mIgG1 | 236.9 | 51.7 | na | na | 15.7 | 4.2 | na | na |
| 47H4 mIgG1 | 184.8 | 33.8 | -22 | 0.0321 | 13.7 | 3.3 | -12.7 | 0.5443 |
| 26A11 mIgG1 | 205.2 | 50 | -13.4 | 0.2375 | 15.6 | 5 | -0.6 | +1.0 |
| 7A6 mIgG1 | 180.2 | 39.2 | -23.9 | 0.0131 | 13.4 | 2.9 | -14.6 | 0.3992 |

*FIG. 12G*

Effect of 47H4 v5 on Other Serum Immunoglobulins

| Group | huIgG1 | | | | huIg2 | | | |
|---|---|---|---|---|---|---|---|---|
| | Mean | S.D. | % Change | p-value | Mean | S.D. | % Change | p-value |
| Herceptin huIgG1 | 1304.8 | 221 | na | na | 142.2 | 20.5 | na | na |
| 47H4 v5 huIgG1 | 1165.2 | 232.4 | -10.7 | 0.1545 | 130.7 | 34.7 | -8.1 | 0.3357 |

| Group | huIg3 | | | | huIgG4 | | | |
|---|---|---|---|---|---|---|---|---|
| | Mean | S.D. | % Change | p-value | Mean | S.D. | % Change | p-value |
| Herceptin huIgG1 | 27.9 | 9.5 | na | na | 20.5 | 8.9 | na | na |
| 47H4 v5 huIgG1 | 23.6 | 6.9 | -15.4 | 0.2331 | 19.7 | 6.3 | -3.9 | 0.808 |

| Group | huIgA | | | | huIgM | | | |
|---|---|---|---|---|---|---|---|---|
| | Mean | S.D. | % Change | p-value | Mean | S.D. | % Change | p-value |
| Herceptin huIgG1 | 17.7 | 4.3 | na | na | 296.1 | 64.6 | na | na |
| 47H4 v5 huIgG1 | 16.7 | 2.6 | -5.6 | 0.5243 | 290.3 | 111.7 | -2 | 0.8791 |

*FIG. 13F*

Effect of 47H4 v5 on Total Plasma Cells

| Group | Total PC % | | | |
|---|---|---|---|---|
| | Mean | S.D. | % Change | p-value |
| Herceptin huIgG1 | 1.2% | 0.46% | na | na |
| 47H4 v5 huIgG1 | 1.6% | 1.2% | +33.3% | 0.2132 |

*FIG. 13H*

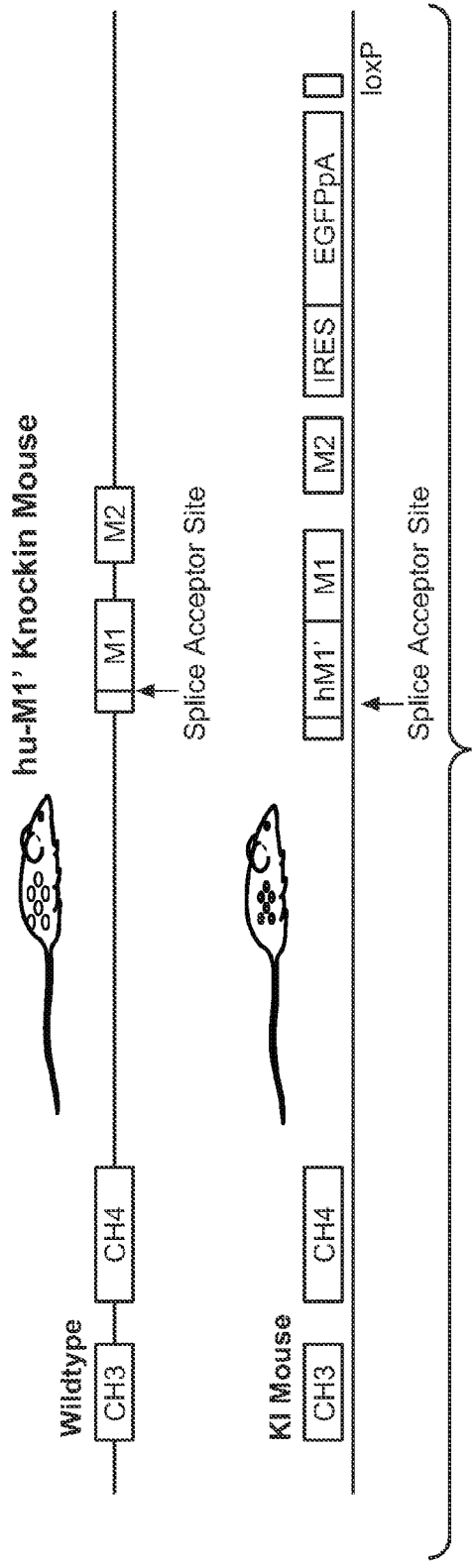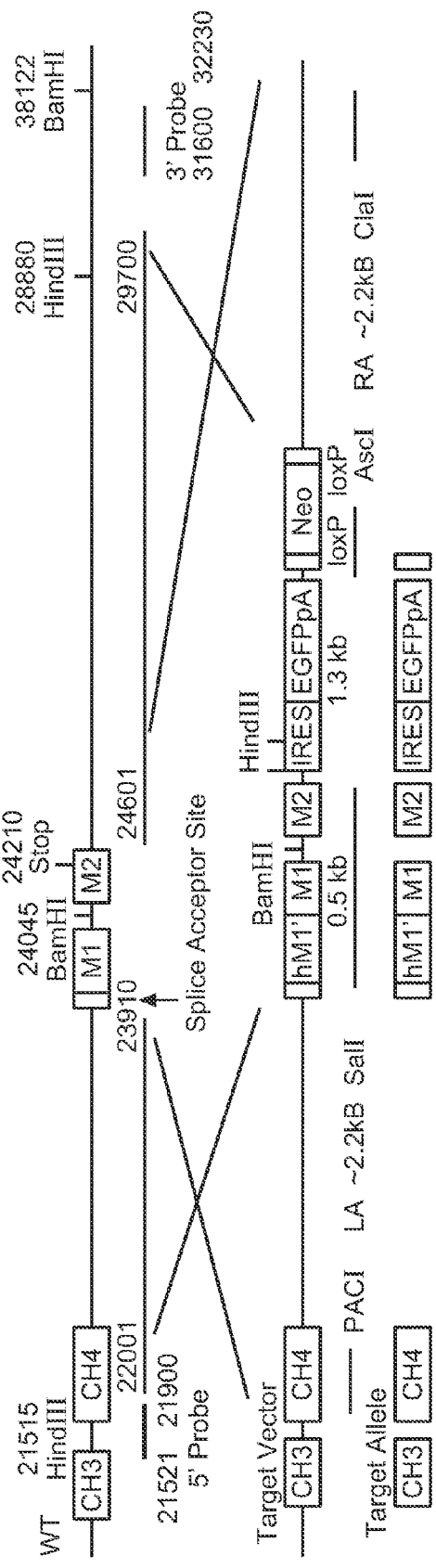
FIG. 14A
FIG. 14B

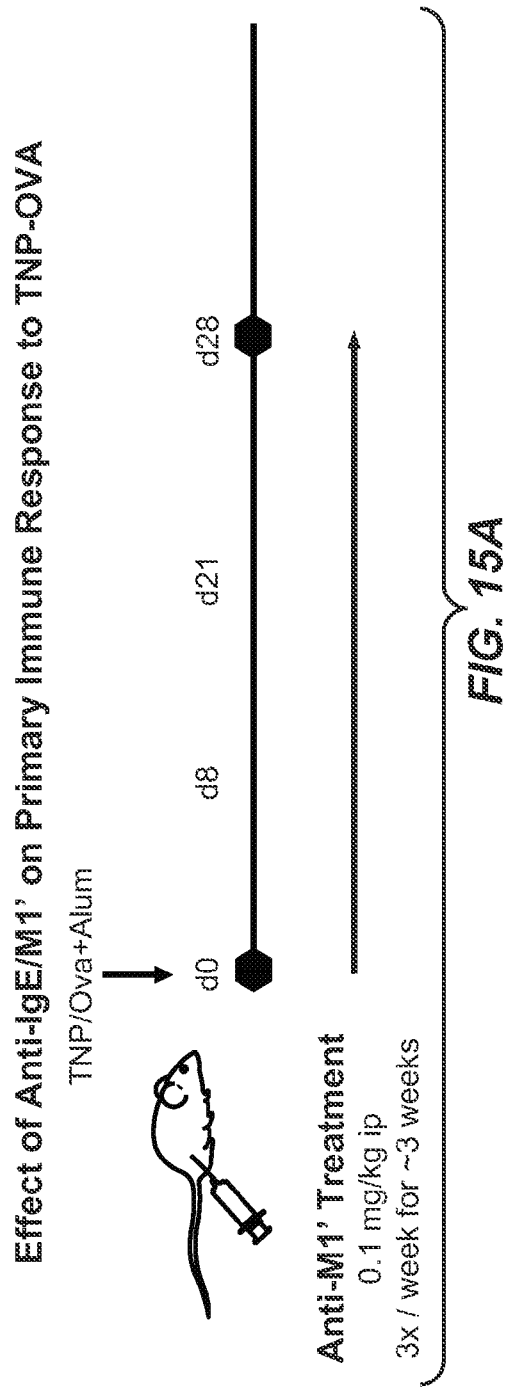

Effect of Anti-IgE/M1' on IgE Levels Primary Immune Response to TNP-OVA

| #07-0234 F | mIgE Day 8 | | | mIgE Day 14 | | |
|---|---|---|---|---|---|---|
| Group | Mean | S.D. | % Change | p-value | Mean | S.D. | % Change | p-value |
| gp120 mIgG1 | 19.3 | 17.8 | na | na | 25 | 36.8 | na | na |
| 47H4 mIgG1 | 2.8 | 1.4 | -97.5% | <0.0001 | 2.6 | 1.4 | -98.7% | 0.0033 |
| Un-immunized | <2.3 | 0 | -100.0% | 0.0015 | <2.3 | 0 | -100% | 0.0490 |

*FIG. 15E*

Effect of Anti-IgE/M1' on Levels of IgG1 in Primary Immune Response to TNP-OVA

| | mIgG1 Day 8 | | | | mIgG1 Day 14 | | | |
|---|---|---|---|---|---|---|---|---|
| Group | Mean | S.D. | % Change | p-value | Mean | S.D. | % Change | p-value |
| gp120 mIgG1 | 3467.1 | 2841.7 | na | na | 40592.8 | 32951.3 | na | na |
| 47H4 mIgG1 | 2393.3 | 2049.5 | -31.1% | 0.1835 | 25363.4 | 11750.8 | -37.5% | 0.0407 |
| Un-immunized | 3.4 | 5.1 | -100% | 0.0010 | 11.4 | 21.8 | -100% | 0.0001 |

*FIG. 15I*

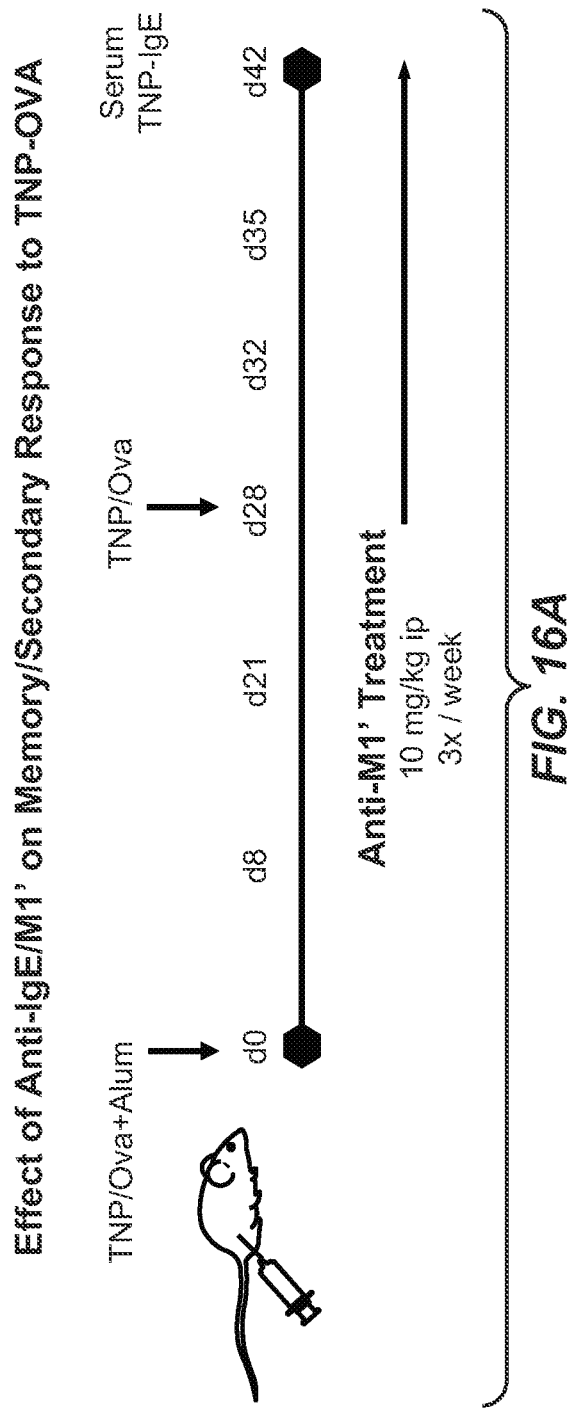

Effect of Anti-IgE/M1' on IgE Levels in Memory Immune Response to TNP-OVA

07-0234 B

| Group | TNP-OVA IgE (ng/ml) Day 32 | | | | TNP-OVA IgE (ng/ml) Day 35 | | | |
|---|---|---|---|---|---|---|---|---|
| | Mean | S.D. | % Change | p-value | Mean | S.D. | % Change | p-value |
| gp120 mIgG1 | 87.3 | 35.3 | na | na | 52.3 | 24 | na | na |
| 47H4 mIgG1 | 38.5 | 40 | -59.1% | 0.0066 | 9.7 | 11.6 | -89.5% | <0.0001 |
| 26A11 mIgG1 | 25.3 | 12.5 | -75.1% | 0.001 | 7.8 | 5.8 | -93.3% | <0.0001 |
| Un-immunized | <4.69 | 0.0 | -100% | <0.0001 | <4.69 | 0.0 | -100.0% | <0.0001 |

FIG. 16D

Effect of Anti-IgE/M1' on IgE in TNP-OVA-Induced Memory/Secondary Response

| Group | AUC: TNP-OVA IgE (ng/ml) | | | | Average Daily TNP-OVA IgE | | | |
|---|---|---|---|---|---|---|---|---|
| | Mean | S.D. | % Change | p-value | Mean | S.D. | % Change | p-value |
| gp120 mIgG1 | 770 | 316.4 | na | na | 36.7 | 15.1 | na | na |
| 47H4 mIgG1 | 271 | 208.5 | -74.3% | 0.0001 | 12.9 | 9.9 | -74.3% | 0.0001 |
| 26A11 mIgG1 | 214 | 61.6 | -83.5% | <0.0001 | 10.2 | 2.9 | -83.4% | <0.0001 |
| Un-immunized | 98.4 | 0.0 | -100% | <0.0001 | <4.69 | 0.0 | -100% | <0.0001 |

FIG. 16H

Effect of Anti-IgE/M1' on IgG1 in TNP-OVA-Induced Memory/Secondary Response

| | TNP-OVA mIgG1 (µg/ml) Day 28 | | | | TNP-OVA mIgG1 (µg/ml) Day 35 | | | |
|---|---|---|---|---|---|---|---|---|
| Group | Mean | S.D. | % Change | p-value | Mean | S.D. | % Change | p-value |
| gp120 mIgG1 | 107 | 64.7 | na | na | 139 | 92.7 | na | na |
| 47H4 mIgG1 | 91.7 | 56.3 | -14.3% | 0.8966 | 149 | 73.8 | +7.2% | 0.9879 |
| 26A11 mIgG1 | 61.7 | 48.3 | -42.3% | 0.2544 | 99.3 | 84.4 | -28.6% | 0.6294 |
| Un-immunized | <0.00078 | 0.0 | -100% | 0.0024* | <0.00078 | 0.0 | -100% | 0.006* |

FIG. 16K

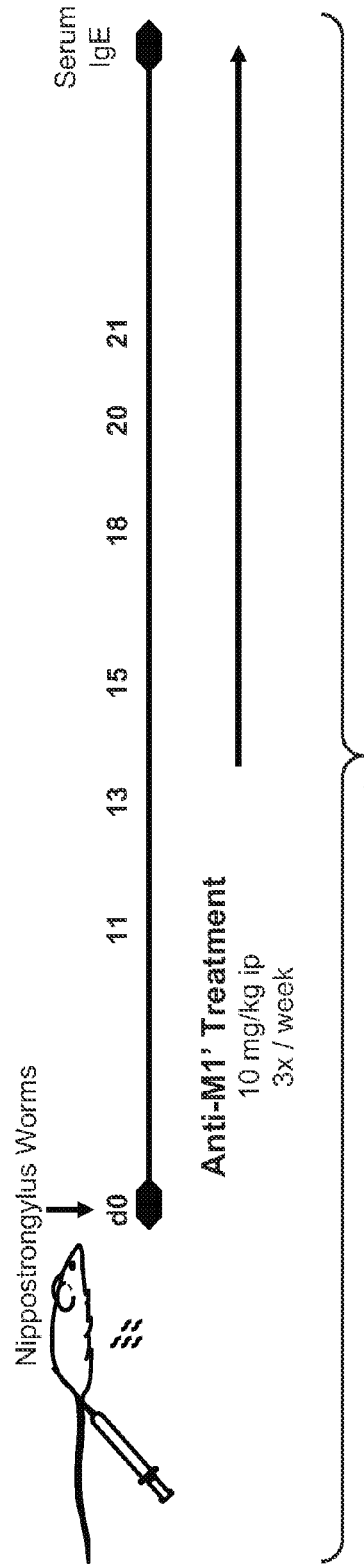

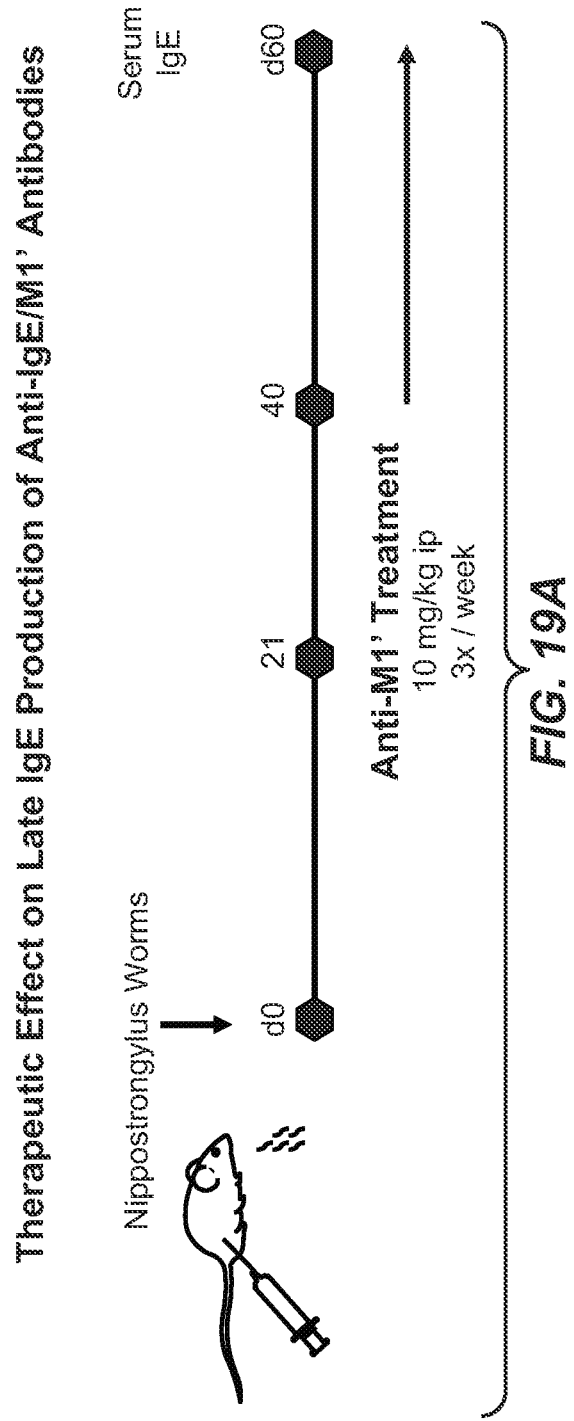

METHODS OF USING APOPTOTIC ANTI-IGE ANTIBODIES

RELATION BACK

This application is a division of U.S. Ser. No. 12/053,063, filed Mar. 21, 2008, now allowed, which claims priority under 35 U.S.C. §119(e) to U.S. Ser. No. 60/896,339, filed Mar. 22, 2007.

BACKGROUND OF THE INVENTION

1. Field of the Invention

This invention relates to apoptotic anti-IgE antibodies, nucleic acid encoding the same, therapeutic compositions thereof, and their use in the treatment of IgE-mediated disorders.

2. Description of the Related Art

Allergy refers to certain diseases in which immune responses to environmental antigens cause tissue inflammation and organ dysfunction. The clinical features of each allergic disease reflect the immunologically induced inflammatory response in the organ or tissue involved. These features are generally independent of the chemical or physical properties of the antigen. The diversity of allergic responses arises from the involvement of different immunological effector pathways, each of which generates a unique pattern of inflammation.

Allergy is common throughout the world. The predilection for specific diseases, however, varies among different age groups, sexes and races. The prevalence of sensitivity to specific allergens is determined both by genetic predilection and by the geographic and cultural factors that are responsible for exposure to the allergen. A clinical state of allergy affects only some individuals who encounter each allergen. The occurrence of allergic disease on exposure to an allergen requires not only prior "sensitization" but also other factors that determine the localization of the reaction to a particular organ.

A biological process that precedes the disease of allergy upon allergen exposure allergen is induces an immune response known as "sensitization" or the sensitization phase. Once sensitization occurs, an individual does not become symptomatic until there is a subsequent exposure to the allergen. The effect of sensitization is also known as immune memory.

One of the primary pathways by which in inflammation is induced is through the immunoglobulin E (IgE). IgE plays a central role in allergies by virtue of their role as allergen receptors on the surface of mast cells and basophils. IgE antibodies are fixed to the surface of mast cells and basophils at the Fc portion of the molecule to a high affinity cell surface receptor, called FcεRI. The allergic reaction is initiated when the polyvalent allergen molecule binds to antibodies that are occupying these receptors. The result is a bridging of the FcεRI, which in turn signals intracellularly causing the release and activation of mediators of inflammation: histamine, leukotrienes, chemotactic factors, platelet-activating factor, and proteinases. These activated mediators act locally and cause increased vascular permeability, vasodilation, smooth muscle contraction and mucous gland secretion. Such events are termed clinically the immediate or early phase, and occur within the first 15-30 minutes following allergen exposure. Over the succeeding 12 hours there is progressive tissue infiltration of inflammatory cells, proceeding from neutrophils to eosinophils to mononuclear cells in response to other chemical mediators not quite fully understood. This period of time 6-12 hours after allergen exposure is designated the late phase and is characterized by clinical manifestations of cellular inflammation. Given that late phase reactions, especially in the lung, occur in the absence of early phase reactions, it is still not entirely understood if the late phase reaction is necessarily IgE mediated.

IgE exists in a membrane bound form and in a secreted form. These distinct forms appear to be splice variants. Previous approaches to achieve therapeutic effect by down regulating IgE targeting primarily the secreted form (e.g., XOLAIR® omalizumab), so as prevent or disarm further "arming" of the immune system. The secreted form of IgE is a shorter form, essentially the Fc region ends at the CH4 domain (FIG. 1), whereas the longer form includes additional C-terminal residues including the peptides encoded by the exons known as M1/M1' and M2. While some have reported two distinct forms of membrane bound IgE, both with and without a 52 amino acid segment known as M1' [Batista et al., *J. Exp. Med.* 184: 2197-2205 (1996)], Applicants were unable to verify that any membrane bound form lacks this M1' segment. Conventional therapy with anti-IgE antibodies, which bind to the secreted form of IgE, results in reduction of free serum, but not total serum IgE. Casale et al., *J. Allergy Clin. Immunol.* 100 (1): 110-121 (1997).

It has further been noted that in the absence of antigen signal, B-cell receptors (i.e., immunoglobulins) that are cross-linked are prone to apoptosis. Surprisingly, Applicants have found that targeting the M1' segment of IgE with anti-IgE antibodies can result in inducing apoptosis of the B-cell. As the progeny of activated B-cells can result in plasma cells that make and secrete the secreted form of IgE, the depletion of the IgE-producing B-cell through apoptosis offers a novel therapeutic approach to the treatment of allergy.

SUMMARY OF THE INVENTION

The present invention provides for apoptotic anti-IgE antibodies, or functional fragments thereof, and for their use in the treatment of IgE-mediated disorders. The invention further provides for compositions and methods of inhibiting IgE production and secretion from B-cells. The invention further provides compositions and methods of specifically depleting IgE-producing B-cells, and lowering total serum IgE.

In one embodiment, the invention provides for an anti-IgE/M1' antibody that specifically binds the M1' segment of IgE and which induces apoptosis in IgE-expressing B-cells. In a specific aspect, the antibody specifically depletes IgE-producing B-cells. In another specific aspect, the antibody reduces total serum IgE. In yet another specific aspect, the antibody reduces both total serum and free serum IgE. In a further specific aspect, the serum IgE is allergen-specific. In a still further specific aspect, the antibody binds to IgE that is human, rhesus monkey and cynomolgus monkey in origin. In a still further specific aspect, the antibody is chimeric. In a still further specific aspect, the antibody is humanized. In a still further aspect, the antibody is human.

In another embodiment, the invention provides for an anti-IgE/M1' antibody that specifically binds to any one of the M1' epitopes corresponding to the peptides identified in FIG. 5. In a specific aspect, the antibody specifically binds to the same epitope as the one bound by an antibody selected from the group consisting of: 47H4, 7A6, 26A11, 47H4v5, 7A6v1 and 26A11v6. In another specific aspect, the antibody binds to an epitope corresponding to a peptide selected from the group consisting of: peptide 4 (SEQ ID NO:8), peptide 5 (SEQ ID NO:9), peptide 7 (SEQ ID NO:11) or peptide 8 (SEQ ID NO:12). In yet another specific aspect, the antibody binds to peptide 4 (SEQ ID NO:8).

In yet another embodiment, the invention provides for an M1' epitope of IgE selected from the group consisting of: peptide 4 (SEQ ID NO:8), peptide 5 (SEQ ID NO:9), peptide 7 (SEQ ID NO:11) or peptide 8 (SEQ ID NO:12). In a specific aspect, the M1' peptide is peptide 4 (SEQ ID NO:8).

In a further embodiment, the invention provides for an anti-IgE antibody that specifically binds to an M1' segment of IgE with a Scatchard binding affinity to human IgE is equivalent to that of the murine anti-IgE/M1' antibody 47H4 or humanized variant thereof. In a specific aspect, the affinity is equivalent to the binding affinity of 47H5. In another specific aspect, the affinity is between 0.30 and 0.83 nm. In yet another specific aspect, the affinity is equivalent to the binding affinity of 47H4v5. In a further specific aspect, the affinity is about 1.5 nm.

In a still further embodiment, the invention provides for an anti-IgE/M1' antibody comprising the heavy chain and light chain HVRs of the antibody appearing in any of FIGS. 6A-6F and FIGS. 20-25. In a specific aspect, the antibody further comprises the variable regions of the heavy and light chains of the antibody sequences appearing in any of FIGS. 6A-6F and FIGS. 20-25. In another specific aspect, the antibody comprises the full length heavy and light chains of the antibodies appearing in any of FIGS. 6A-6F. In yet another specific aspect, the heavy and light chains of the antibody sequences appear in any of FIGS. 6A-6F. In a further specific aspect, the antibody is selected from group consisting of: 26A11, 26A11 v1-16, 7A6, 7A6v1, 47H4, 47H4v1-6. In a still further specific aspect, the antibody is 47H4v5. In a still further specific aspect, the antibody is afucosylated.

In a still further embodiment, the invention provides for a composition comprising an anti-IgE/M1' antibody comprising the heavy chain and light chain HVRs of the antibody appearing in any of FIGS. 6A-6F in combination with at least one pharmaceutically acceptable carrier. In a specific aspect, the antibody is selected from the group consisting of: 26A11, 26A11v1-16, 7A6, 7A6v1, 47H4, 47H4v1-6. In another specific aspect, the antibody is 47H4v5. In yet another specific aspect, the antibody is afucosylated.

In a still further embodiment, the invention provides for a composition comprising an anti-IgE/M1' antibody comprising the heavy chain and light chain HVRs of the antibody appearing in any of FIGS. 8-13 in combination with one or more drugs selected from the group consisting of: anti-IgE antibody, antihistamine, bronchodilator, glucocorticoid, NSAID, TNF-antagonist, integrin antagonist, immunosuppressive agent, IL-4 antagonist, IL-13 antagonist, dual IL-4/IL-13 antagonist, DMARD, antibody that binds to a B-cell surface marker and BAFF antagonist. In a specific aspect, the composition further comprises at least one pharmaceutically acceptable carrier.

In a still further embodiment, the invention provides for isolated nucleic acid encoding the heavy chain HVRs of the anti-IgE/M1' antibody appearing in any of FIGS. 6A-6F. In a specific aspect, the isolated nucleic acid further comprises nucleic acid encoding the light chain HVRs of the antibody appearing in any of FIGS. 6A-6F. In another specific aspect, the antibody is chimeric. In yet another specific aspect, the antibody is humanized. In a further aspect, the antibody is human. In a still further specific aspect, the antibody is selected from group consisting of: 26A11, 26A11 v1-16, 7A6, 7A6v1, 47H4, 47H4v1-6. In a still further specific aspect, the antibody is 47H4v5. In a still further specific aspect, the antibody is afucosylated. In a still further aspect, the nucleic acid further comprises a vector suitable for expression of the nucleic acid. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

In a still further embodiment, the invention provides for a process of making an anti-IgE/M1' antibody, or functional fragment thereof, that specifically binds to an M1' segment of IgE, comprising culturing a host cell containing nucleic acid encoding such antibody or fragment in a form suitable for expression, under conditions suitable to produce such antibody or fragment, and recovering the antibody or fragment.

In a still further embodiment, the invention provides an article of manufacture comprising a container enclosing a composition disclosed herein and a package insert indicating use for the treatment of an IgE-mediated disorder. In a specific aspect, the article of manufacture is a vial. In another specific aspect, the article of manufacture is a pre-filled syringe. In yet another specific aspect, the pre-filled syringe is further contained within an injection device. In a further specific aspect, the injection device is an auto-injector.

In a still further embodiment, the invention provides for a method of specifically depleting IgE-producing B-cells comprising administering a therapeutically effective amount of an anti-IgE/M1' antibody that specifically binds to the M1' segment of IgE and induces apoptosis in IgE-expressing B-cells. In a specific aspect, the antibody comprises the heavy and light chain HVRs of the antibody appearing in any of FIGS. 6A-6F. In another specific aspect, the method reduces total serum IgE. In yet another specific aspect, the method reduces both free serum and total serum IgE. In a further specific aspect, the serum IgE is allergen-specific. In a still further specific aspect, the antibody is selected from group consisting of: 26A11, 26A11 v1-16, 7A6, 7A6v1, 47H4, 47H4v1-6. In a still further specific aspect, the antibody is 47H4v5. In a still further specific aspect, the antibody has ADCC activity.

In a still further embodiment, the invention provides for a method of treating an IgE-mediated disorder comprising administering a therapeutically effective amount of an anti-IgE/M1' antibody that that specifically binds to the M1' segment of IgE and induces apoptosis in IgE-expressing B-cells. In a specific aspect, the antibody specifically depletes IgE-producing B-cells. In another specific aspect, the antibody reduces total serum IgE. In yet another specific aspect, the antibody reduces both total and free IgE. In a further specific aspect, the serum IgE is allergen-specific. In a still further specific aspect, the antibody comprises the heavy and light chain HVRs of the antibody appearing in any of FIGS. 6A-6F. In a still further specific aspect, the antibody is selected from the group consisting of: 26A11, 26A11 v1-16, 7A6, 7A6v1, 47H4, 47H4v1-6. In a further specific aspect, the antibody is 47H4v5. In a still further specific aspect, the antibody has ADCC activity. In a still further specific aspect, the IgE-mediated disorder is selected from the group consisting of: allergic rhinitis, asthma (e.g., allergic asthma and non-allergic asthma), atopic dermatitis, allergic gastroenteropathy, hypersensitivity (e.g., anaphylaxis, urticaria, food allergies etc.), allergic bronchopulmonary aspergillosis, parasitic diseases, interstitial cystitis, hyper-IgE syndrome, ataxia-telangiectasia, Wiskott-Aldrich syndrome, athymic lymphoplasia, IgE myeloma and graft-versus-host reaction. In yet a still further specific aspect, the IgE-mediated disorder is food allergy, anaphylaxis, contact dermatitis and allergic purpura.

In a still further embodiment, the invention provides for a method of treating an IgE-mediated disorder comprising administering a composition comprising a therapeutically effective amount of an anti-IgE/M1' antibody that specifically binds to the M1' segment of IgE and induces apoptosis in IgE-expressing B-cells in combination with a therapeutically effective amount of at least one drug selected from the group consisting of: anti-IgE antibody, antihistamine, bronchodilator, glucocorticoid, NSAID, decongestant, cough suppressant, analgesic, TNF-antagonist, integrin antagonist, immunosuppressive agent, IL-4 antagonist, IL-13 antagonist, dual IL-4/IL-13 antagonist, DMARD, antibody that binds to a B-cell surface marker and BAFF antagonist. In a specific aspect, the antibody specifically depletes IgE-producing B-cells. In another specific aspect, the antibody reduces total serum IgE. In yet another specific aspect, the antibody reduces both total and free IgE. In a further specific aspect, the serum IgE is allergen-specific. In a still further specific aspect, the antibody comprises the heavy and light chain HVRs of the antibody appearing in any of FIGS. 6A-6F. In a still further specific aspect, the antibody is selected from group consisting of: 26A11, 26A11v1-16, 7A6, 7A6v1, 47H4, 47H4v1-6. In a still further specific aspect, the antibody is 47H4v5. In a still further specific aspect, the antibody has ADCC activity.

In a still further embodiment, the invention provides for a method of treating an IgE-mediated disorder comprising a combined treatment regimen of administering a therapeutically effective amount of an anti-IgE/M1' antibody that specifically binds to the M1' segment of IgE and induces apoptosis in IgE-expressing B-cells, prior to, simultaneous with or after the administration of a known method of treatment for allergic disorders. In a specific aspect, the combination comprises the administration of an anti-IgE antibody, antihistamine, a bronchodilator, a glucocorticoid, a non-steroidal anti-inflammatory drug, an immunosuppressant, IL-4 antagonist, IL-13 antagonist, dual IL-4/IL-13 antagonist, a decongestant, a cough suppressant or an analgesic. In another specific aspect, the anti-IgE/M1' antibody is administered in combination with a treatment regimen of allergen densitization. In a specific aspect, the antibody specifically depletes IgE-producing B-cells. In another specific aspect, the antibody reduces total serum IgE. In yet another specific aspect, the antibody reduces both total and free IgE. In a further specific aspect, the serum IgE is allergen-specific. In a still further specific aspect, the antibody comprises the heavy and light chain HVRs of the antibody appearing in any of FIGS. 6A-6F. In a still further specific aspect, the antibody is selected from group consisting of: 26A11, 26A11 v1-16, 7A6, 7A6v1, 47H4, 47H4v1-6. In a still further specific aspect, the antibody is 47H4v5. In a still further specific aspect, the antibody has ADCC activity.

In a still further embodiment, the invention provides for a method of preventing allergen-induced IgE production, comprising administering a therapeutically effective amount of an anti-IgE/M1' antibody that specifically binds to the M1' segment of IgE and induces apoptosis in IgE-expressing B-cells. In a specific aspect, the antibody comprises the heavy and light chain HVRs of the antibody appearing in any of FIGS. 6A-6F. In another specific aspect, the method specifically depletes IgE-producing B-cells. In yet another specific aspect, the method reduces total serum IgE. In a further another specific aspect, the method reduces both free serum and total serum IgE. In a still further specific aspect, the serum IgE is allergen-specific. In a still further specific aspect, the antibody is selected from group consisting of: 26A11, 26A11v1-16, 7A6, 7A6v1, 47H4, 47H4v1-6. In a still further specific aspect, the antibody is 47H4v5. In a still further specific aspect, the antibody has ADCC activity.

In a still further embodiment, the invention provides for a method of reducing the allergen-induced IgE production, comprising administering a therapeutically effective amount of an anti-IgE/M1' antibody that specifically binds to the M1' segment of IgE and induces apoptosis in IgE-expressing B-cells. In a specific aspect, the antibody comprises the heavy and light chain HVRs of the antibody appearing in any of FIGS. 6A-6F. In another specific aspect, the method specifically depletes IgE-producing B-cells. In yet another specific aspect, the method reduces total serum IgE. In a further specific aspect, the method reduces both free serum and total serum IgE. In a still further specific aspect, the serum IgE is allergen-specific. In a still further specific aspect, the antibody is selected from group consisting of: 26A11, 26A11 v1-16, 7A6, 7A6v1, 47H4, 47H4v1-6. In a still further specific aspect, the antibody is 47H4v5. In a still further specific aspect, the antibody has ADCC activity.

In a still further embodiment, the invention provides for a composition useful for any of the previously described methods.

In a still further embodiment, the invention provides for the use of a composition for any of the previously described methods.

In a still further embodiment, the invention provides a murine hybridoma deposited at the ATCC on Mar. 21, 2007 with a designation selected from the group consisting of: 7A6.18, 1C11.10.20, 47G4.6.2, 47H4.12.10, 42H4.6.9, 42A5.20.11, 26A11.6.5, 51D2.22.15, 45C1.6.14, 26B11.3.12, 28E9.12.9. In a specific aspect, the invention provides for an antibody secreted by the deposited hybridoma.

In a still further embodiment, the invention provides for a transgenic animal that expresses the human M1' segment of IgE.

BRIEF DESCRIPTION OF THE DRAWINGS

FIGS. 1A-B is an alignment of selected constant chain regions of IgE of the human (SEQ ID NO:1, rhesus monkey (SEQ ID NO:2) and cynomolgous monkey (SEQ ID NO:3). Shown are the approximate locations of the CH2, CH3, CH4, M1', transmembrane and intracellular domains.

FIGS. 2A-2C are FACS Scatchard plots showing the specificity of the various anti-M1' antibodies. FIG. 2A-1 to 2A-6 shows binding against the short form of IgE (missing M1'), while FIGS. 2B-1 to 2B-6 show binding against the long form (with M1'). FIGS. 2C-1 to 2C-6 show binding against IgE expressed by U266 cell line. The shaded curve shows fluorescence intensive of control Ab, while unshaded curve shows relative fluorescence of the tested antibody. FIG. 2D shows that 47H4 binds to human, rhesus, and cyno IgE/M1', but not to IgE lacking M1'. FIG. 2E shows that 47H4 bound to U266, while 26A11 and 7A6 do not. FIG. 2F shows that 47H4 and 7A6 bind both Rhesus and Cyno M1', whereas 26A11 binds only Rhesus. FIG. 2G shows that all three humanized variants 47H4v5, 26A11v6 and 7A6v1 are specific for IgE-M1', but not IgE lacking M1'. FIG. 2H shows that variants 47H4v5 and 26A11v6 (but not 7A6v1) bind U266. FIG. 2I shows that 47H4v5 and 7A6v1 bind rhesus and cyno M1', whereas 26A11v6 only binds rhesus M1'.

FIGS. 3A-L are FACS plots showing the relative binding affinity affinities of the various anti-M1' antibodies using the serial dilutions indicated in FIG. 3M. FIG. 3N shows the relative affinities for each antibody. FIG. 3O summarizes the affinities of the murine antibodies 47H4, 26A11 and 7A6 as measured by Scatchard analysis against human, Rhesus and Cyno M1'. Unless otherwise indicated, numbers reported are mean averages. FIG. 3P summarizes the affinities of the indicated humanized variants of antibodies 47H4 and 26A11 as measured by Scatchard analysis against human, Rhesus and Cyno M1'.

FIGS. 4A-D show a relative binding/blocking study of the anti-M1' antibodies. FIGS. 4A-1 to 4A-20 are FACS plots showing antibodies that blocked or partially blocked binding. FIG. 4B is a two dimensional plot showing the relative ability to block binding of the other antibodies (partially or fully using a 1:1 molar ratio). FIG. 4C is a two dimensional plot that is more focused on the specifically indicated antibodies and in which the blocking study was repeated with a molar ratio of 10:1. FIG. 4D is a schematic that shows the groupings resulting from epitope binding/blocking studies.

FIGS. 5A-C show epitope binding studies performed using 47H4, 7A6 and 26A11. FIG. 5A shows the M1' segment including adjacent N- and C-terminal residues (SEQ ID NO:3), and M1' peptides 1-5, (SEQ ID NOS:5-19), respectively, used to determine epitope binding. FIGS. 5B and 5D show that parent murine antibodies 47H4 binds peptide 4, 7A6 binds peptides 4 and 5 and 26A11 binds peptides 7 and 8. FIGS. 5C and 5E show that humanized variants 47H4v5 binds peptide 4, while 7A67v1 binds peptides 4 and 5, and 26A11v6 binds peptides 7 and 8, thereby retaining the epitope specificities of the parent murine antibodies.

FIGS. 6A-F show the variable light and heavy chain sequences of murine antibody 26A11, 7A6 and 47H4 and various humanized variants thereof. Positions are numbered according to Kabat and hypervariable regions that were grafted to the variable consensus network (Kappa I for light, subgroup III for heavy chain) are boxed. FIG. 6A shows, relative to human kappa I light chain (SEQ ID NO:20), the variable light chain of 26A11 (SEQ ID NO:21) and humanized variants 1,4 (SEQ ID NO:22), variants 2,5 (SEQ ID NO:23), variants 3,6 (SEQ ID NO:24), variants 13,15 (SEQ ID NO:25) and variants 14,16 (SEQ ID NO:26). FIG. 6B shows, relative to human kappa I light chain (SEQ ID NO:20), the variable light chain of 7A6 (SEQ ID NO:27) and humanized variant 1 (SEQ ID NO:28). FIG. 6C shows, relative to human kappa I light chain (SEQ ID NO:20), the variable light chain of 47H4 (SEQ ID NO:29) and humanized variants 1,3 (SEQ ID NO:30) and variants 2, 4-6 (SEQ ID NO:31). FIG. 6D shows, relative to human III heavy chain (SEQ ID NO:32), the variable heavy chain of 26A11 (SEQ ID NO:33) and humanized variants 1-3, 13, 14 (SEQ ID NO:34) and variants 4-6, 15, 16 (SEQ ID NO:35). FIG. 6E shows, relative to human heavy chain (SEQ ID NO:34), the variable heavy chain of 7A6 (SEQ ID NO:36) and humanized variant 1 (SEQ ID NO:37). FIG. 6F shows, relative to human III heavy chain (SEQ ID NO:32), the variable heavy chain of 47H4 (SEQ ID NO:38), and humanized variants 1,2 (SEQ ID NO:39), variants 3-4 (SEQ ID NO:40), variant 5 (SEQ ID NO:41) and variant 6 (SEQ ID NO:42).

FIG. 7A is a FACS plot showing essentially that IgM is expressed at a higher level than IgE. FIG. 7B shows the effect of crosslinking anti-IgM [F(ab')$_2$] antibodies and application of camptothecin, in inducing apoptosis, respectively. Cells staining positive for annexin, but negative for PI are dying, while cells staining positive for both annexin and PI are dead. FIG. 7C is a graphical depiction of the total observed apoptosis, in which the light bar shows the cells annexin-(+) and PI-(−), while the dark bar shows annexin-(+) and PI-(+). FIGS. 7D-7G are graphical representations of anti-M1'-induced apoptosis at concentrations of 25, 10, 1, 0.1, 0.01 and 0.001 µg/ml. FIG. 7D shows the results of application of the M1' antibodies of the epitope group A1, including 7A6, 47H4, 47G4, 42A5, 42H4 (along with controls MAE-11 and GP120) without crosslinking FIG. 7E shows the results of application of M1' antibodies of the epitope group A2, including 1C11, 26A11, 51D2, 45C1) and epitope group B/C, including 26B11 and 28E9 without crosslinking. FIG. 7F shows epitope group A1 with crosslinking, and FIG. 7G shows epitope group A2 and B/C with crosslinking.

FIG. 8A shows that humanized variants 47H4v5, 26A11v6 and 7A6v1 induce apoptosis in the range of 30-40% at the higher concentration levels (i.e., 10-25 µg/ml 47H4 and 26A11 variants, 1, 10 and 25 µg 7A6 variant). FIG. 8B shows the apoptotic activity of the same antibody on IgE-M1' transfected Daudi cells that that are treated in the presence of goat anti-human IgG F(ab')2 cross-linking antibody. All antibodies induced maximum apoptotic levels of 70-90%, with some decrease in apoptotic activity at high concentrations (e.g., 47H4-v1, -v2, 26A11-v1, -v14).

FIG. 9A is the control showing the effect of anti-IgM and MAE11, while FIG. 9B1-B2 show the effect of the application of the indicated murine anti-M1' antibodies.

FIG. 10 shows the ability of humanized anti-IgE/M1' antibody 47H4 v5 wt and afucosylated variant to induce ADCC. While the wt and afucosylated variants induce similar maximal cytotoxicity, the afucosylated variant ("AF") was more potent than the wildtype form (EC50 AF≈0.83 nM, EC50 wt≈6.6 nM).

FIG. 11A-11F are full length sequences of the heavy and light chains of murine anti-IgE/M1' antibodies. The variable regions are shown in italics, while the HVRs (hypervariable regions) are underlined. FIG. 11A shows the heavy and light chains of the murine antibody 7A6 (SEQ ID NOS: 43 and 44), respectively. FIG. 11B shows the heavy and light chains of the murine antibody 47H4 (SEQ ID NOS: 45 and 46), respectively. FIG. 11C shows the heavy and light chains of the murine antibody 26A11 (SEQ ID NOS: 47 and 48), respectively. FIG. 11D shows the heavy and light chains of the murine antibody 45C1 (SEQ ID NOS: 49 and 50), respectively. FIG. 11E shows the heavy and light chains of the murine antibody 28E9 (SEQ ID NOS: 51 and 52), respectively. FIG. 11F shows the heavy and light chains of the murine antibody 1C11 (SEQ ID NOS: 53 and 54), respectively.

FIGS. 12A-I demonstrate the ability of the murine anti-IgE/M1' antibodies to inhibit the production of serum IgE and IgE producing plasma cells in an atopic hu-SCID model. FIG. 12A is a graphical depiction of the experimental design. FIGS. 12B-C show that treatment with the murine anti-IgE/M1' antibodies reduced IgE levels by 65-84%. FIGS. 12D-E show the reduction of IgE-producing cells in vivo was 19-69%. FIGS. 12F-G show that the levels of other immunoglobulins (e.g., IgG1-4, IgA, IgM) were relatively unaffected. FIGS. 12H-I show that no reduction in the total number of plasma cells of the spleen was observed.

FIGS. 13A-H show the effect of the humanized variant 47H4v5 on immunoglobulin levels in the atopic hu-SCID model. FIG. 13A is a graphical depiction of the experimental design. FIGS. 13B-D show that serum IgE was reduced by 79%, and that IgE-producing plasma cells were reduced by 75%. FIGS. 13E-F show no reduction in levels of other serum immunoglobulins. FIGS. 13G-H show no reduction in total plasma cell levels, thus demonstrating that 47H4 specifically reduces IgE-producing plasma cells, which are a very small proportion of total plasma cells.

FIGS. 14A-D illustrate the generation of huM1' knock-in mice. FIG. 14A shows the location of the M1' exon on the mouse IgE locus. FIG. 14B shows a schematic of the recombination in the mouse IgE locus resulting in the creation of the target allele. FIG. 14C shows PCR genotyping of a 668 bp band in wt mice and a 457 bp band in the M1' knock-ins. FIG. 14D shows a Southern Blot in which a 7.4 kB HindIII fragment in wt mice, becomes a 3 kB fragment in hu-M1' knock-ins, and a 14.1 kB BamHI fragment becomes an 18.1 fragment in the hu-M1' knockin allele. Both wildtype and heterozygous mice are shown.

FIGS. 15A-I show the ability of the anti-IgE/M1' antibodies to prevent the generation of IgE in a primary immune response. FIG. 15A is schematic showing the timeline of the experimental design, including administration of TNP/OVA and anti-IgE/M1' antibodies. FIG. 15B is a graph of antigen-specific IgE levels over time and shows that while antigen-specific IgE levels in control animals (i.e., gp120) reached peak levels between days 8 and 14, anti-IgE/M1' prevented any increase, and measured antigen-specific IgE levels were not significantly different from unimmunized mice. FIGS. 15C-D show that anti-IgE/M1' treatment prevented the increase in antigen-specific serum IgE on days 8 and 14, respectively, and was not statistically different from unimmunized mice (FIG. 15E). FIGS. 15F-I show that levels of antigen-specific IgG1 were not significantly affected by anti-IgE/M1' through the 28 days of the experiment (except for a modest difference at day 14).

FIGS. 16A-K show the ability of the anti-IgE/M1' antibodies to prevent the generation of antigen-specific IgE in a memory or secondary immune response. FIG. 16A is a schematic showing the timelines of secondary boost of TNP-OVA and administration of anti-IgE/M1' antibodies, which was first administered on day 28. FIG. 16B is a graph of antigen-specific IgE levels over time and shows that secondary IgE response to TNP-OVA boost on day 28 is more rapid, peaking after 4 days rather than 8-9 days in the primary response. FIGS. 16C-D show that antigen-specific IgE levels in anti-IgE/M1' treated animals were significantly reduced compared to isotype control, 59-65% by day 32 and 90-93 by day 35. FIG. 16E shows that by day 42 (12 days initial administration of anti-IgE), antigen-specific IgE levels were reduced to a level not statistically different from naïve control mice. FIGS. 16F-H show that between days 28 and 49, the administration of anti-IgE/M1' reduced serum IgE levels by 74-84%, and the average daily level of antigen-specific IgE was also reduced by 74-83%. FIGS. 16I-K show that levels of antigen-specific IgG1 were not significantly affected by anti-IgE/M1'.

FIG. 17A is a schematic showing the experimental design. Animals were treated three times per week starting on day 0 through day 21. FIG. 17B shows IgE levels over time in response to NB infection with anti-IgE/M1' and control antibodies. FIGS. 17C-D show that at day 15, anti-IgE/M1' treated animals had reduced serum IgE levels not statistically significant from uninfected mice.

FIGS. 18A-I illustrate the ability of the anti-IgE/M1' antibodies to thereby therapeutically treat peak IgE response to *Nippostrongylus brasiliensis* ("NB") infection. FIG. 18A is a schematic showing the experimental design. Animals were treated three times per week between days 11 and 21. FIG. 18B shows IgE levels over time in response to NB infection with anti-IgE/M1' and control antibodies. FIG. 18C-D show that anti-IgE/M1' reduced serum IgE levels by 82-89% within four days of treatment. FIG. 18E shows that by day 21 IgE levels in anti-IgE/M1' treated animals by 97-98%, and reached levels not statistically significant from the uninfected control group. FIGS. 18F-G shows that IgE-producing plasma cells (as quantitated by Elispot) in the lymph nodes and spleen were reduced by 88-94% and 57-66%, respectively. FIGS. 18H-I show that total plasma cells (CD138+) in both lymph node and spleen increased in all treatment groups compared with uninfected mice, and that treatment with anti-IgE/M1' did not significantly change the total number of plasma cells in either organ. These results demonstrate the ability of anti-IgE/M1' antibodies to reduce serum IgE levels by depleting IgE producing cells in vivo.

FIGS. 19A-G illustrate the ability of the anti-IgE/M1' antibodies to therapeutically treat IgE response occurring late in an infection cycle to *Nippostrongylus brasiliensis* ("NB") infection. FIG. 19A is a schematic showing the experimental design in which animals were treated three times per week starting at day 40. FIG. 19B shows that peak IgE production occurred around day 15 and that all anti-IgE/M1' antibodies reduced serum IgE. FIG. 19C-D shows that anti-IgE/M1' antibody shows a significant reduction in both absolute and normalized IgE levels, respectively, relative to commencement of treatment. FIGS. 19E-G show that anti-IgE/M1' treatment significantly reduced serum IgE levels, compared to the anti-gp120 mIgG1 isotype control between days 48 and 55,

DETAILED DESCRIPTION OF THE PREFERRED EMBODIMENT

Figures 1, 2A:
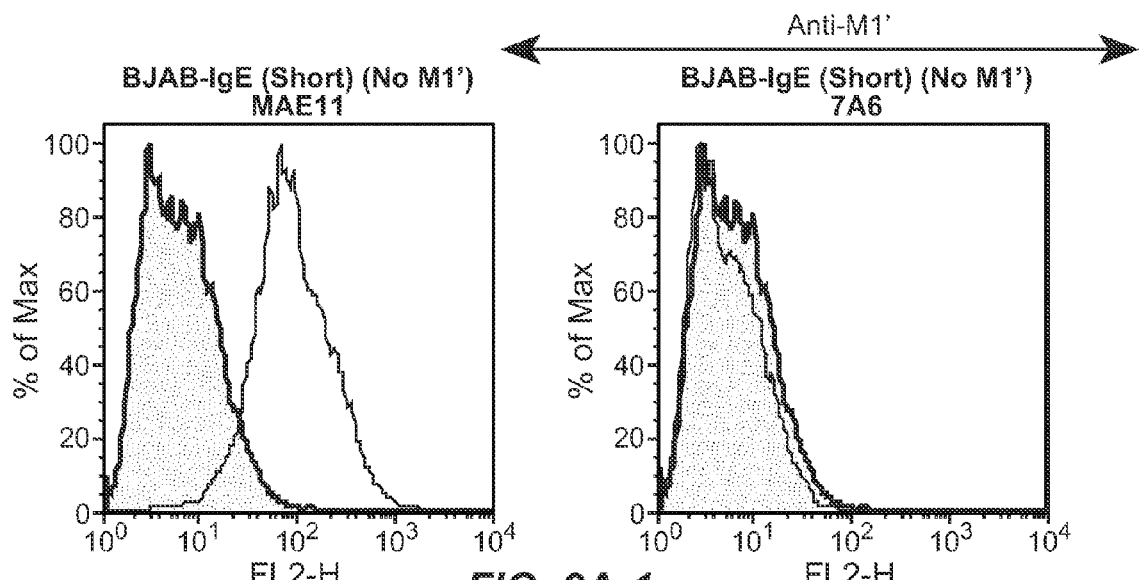
Figures 1, 2B:
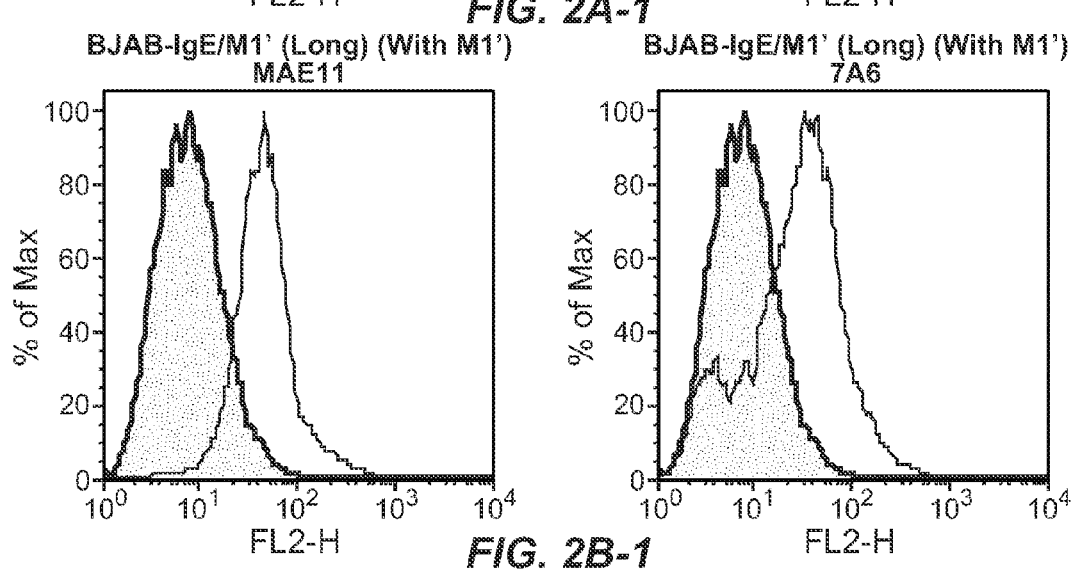

All references mentioned herein are specifically incorporated by reference.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds 1987, and periodic updates); *PCR: The Polymerase Chain Reaction*, (Mullis et al., ed., 1994); *A Practical Guide to Molecular Cloning* (Perbal Bernard V., 1988); *Phage Display: A Laboratory Manual* (Barbas et al., 2001).

Lymphocyte Development and Activation

The two major types of lymphocytes in humans are T (thymus-derived) and B (bone marrow derived. These cells are derived from hematopoietic stem cells in the bone marrow and fetal liver that have committed to the lymphoid development pathway. The progeny of these stem cells follow divergent pathways to mature into either B or T lymphocytes. Human B-lymphocyte development takes place entirely within the bone marrow. T cell, on the other hand, develop from immature precursors that leave the marrow and travel through bloodstream to the thymus, where they proliferate and differentiate into mature T lymphocytes.

Mature lymphocytes that emerge from the thymus or bone marrow are in a quiescent, or "resting" state, i.e., they are mitotically inactive. When dispersed into the bloodstream, these "naïve" or "virgin" lymphocytes, travel into various secondary or peripheral lymphoid organs, such as the spleen, lymph nodes or tonsils. Most virgin lymphocytes have an inherently short life span and die without a few days after leaving the marrow or thymus. However, if such a cell receives signals that indicate the presence of an antigen, they may activate and undergo successive rounds of cell division. Some of the resulting progeny cells then revert to the resting state to become memory lymphocytes—B and T cells that are essentially primed for the next encounter with the stimulating allergen. The other progeny of activated virgin lymphocytes are effector cells, which survive for only a few days, but carry out specific defensive activities.

Lymphocyte activation refers to an ordered series of events through which a resting lymphocyte passes as it is stimulated to divide and produce progeny, some of which become effector cells. A full response includes both the induction of cell proliferation (mitogenesis) and the expression of immunologic functions. Lymphocytes become activated when specific ligands bind to receptors on their surfaces. The ligands are different for T cells and B cells, but the resulting intracellular physiological mechanisms are similar.

While foreign antigens themselves can induce lymphocyte activation, especially large polymeric antigens that cross-linking surface immunoglobulins on B-cells, or other glycoproteins on T-cells. However, most antigens are not polymeric and even when binding directly to the B-cell in large numbers fail to result in activation. B cells are activated by these more common antigens when they are co-stimulated with nearly activated helper T-lymphocytes. Such stimulation may occur from lymphokines secreted by the T-cell, but is transmitted most efficiently by direct contact of the B cell with T-cell surface proteins that interact with certain B-cell surface receptors to generate a secondary signal.

B-Cells

The defining feature of B-cells is the ability to synthesize immunoglobulins. Immunoglobulins (Ig) are an extremely diverse family of proteins made up of related types of polypeptides called heavy chains and light chains. Each Ig binds specifically with high affinity to its own specific antigen. Mature B cells can express immunoglobulin in two different forms, each of which serve unique functions. In resting B lymphocytes (virgin or memory) immunoglobulins are expressed only on the cell surface, where they act essentially as membrane-bound receptor for specific antigens. In contrast, B cell effector cells (plasma cells) secrete immunoglobulin into the surrounding milieu. Such secreted immunoglobulin retain the ability to recognize and bind (vis-à-vis the membrane-bound form on resting B-cells), and are typically referred to as antibodies.

When an activated B-lymphocyte divides, some of it progeny become memory B cells, while the remainder differentiate into plasma cells. As plasma cells have a relatively short life span, unless new plasma cells are produced, the population soon dies out and immunoglobulins are no longer secreted. As a result, activation of B cells typically results in a transient wave of proliferation, followed by a burst of antibody secretion that increases and then subsides over several days or a few weeks. B-cells are the primary cell type involved in humoral immunity, or the protective effect mediated through tissue fluids. Because the anti-IgE/M1' antibodies of the invention actually deplete B-cells, including memory B-cells, they can be used to "reset" memory. Thus the effect of this could be that the B-cell component that is driving the allergic response in individuals can be attenuation if not eliminated.

T-Cells

T lymphocytes do not express immunoglobulins, but, instead detect the presence of foreign substances by way of surface proteins called T-cell receptors. These receptors recognize antigens by either direct contact or through influencing the activity of other immune cells. Together with macrophages, T cells are the primary cell type involved in the cell-mediated immunity.

Unlike B-cells, T-cells can detect foreign substances only in specific contexts. In particular, T-lymphocytes will recognize a foreign protein only if it first cleaved into small peptides, which are then displayed on the surface of a second host cell, called an antigen-presenting cell (APC). May types of host cells can present antigens under some conditions but certain types are more specifically adapted for this purpose and are particularly important in controlling T-cell activity, and include macrophages and other B-cells. Antigen presentation depends in part on specific proteins, called major histocompatibility complex (MHC) proteins, on the surface of the presenting cells. Thus, to stimulate cell-mediated immunity, foreign peptides must be presented to T-cells in combination with MHC peptides, and this combination must be recognized by a T-cell receptor.

There are two significant T-cell subsets: cytotoxic T lymphocytes ($T_c$ cells or CTLs) and helper T cells ($T_H$) cells, which can roughly be identified on the basis of cell surface expression of the marker CD8 and CD4. Tc cells are important in viral defense, and can kill viruses directly by recognizing certain cell surface expressed viral peptides. $T_H$ cells promote proliferation, maturation and immunologic function of other cell types, e.g., lymphokine secretion to control activities of B cells, macrophages and cytotoxic T cells. Both virgin and memory T-lymphocytes ordinarily remain in the resting state, and in this state they do not exhibit significant helper or cytotoxic activity. When activated, these cells undergo several rounds of mitotic division to produce daughter cells. Some of these daughter cells return to the resting state as memory cells, but others become effector cells that actively express helper of cytotoxic activity. These daughter cells resemble their parents: CD4+ cells can only product CD4+ progeny, while CD8+ cells yield only CD8+ progeny. Effector T-cells express cell surface markers that are not expressed on resting T-cells, such as CD25, CD28, CD29, CD40L, transferrin receptors and class II MHC proteins. When the activating stimuli is withdrawn, cytotoxic or helper activity gradually subsides over a period of several days as the effector cells either die or revert to the resting state.

Similar to B-cell activation, T-lymphocyte responses to most antigens also require two types of simultaneous stimuli. The first is the antigen, which if appropriately displayed by MHC proteins on an antigen-presenting cell, can be recognized and bound by T-cell receptors. While this antigen-MHC complex does send a signal to the cell interior, it is usually insufficient to result in T-cell activation. Full activation, such as occurs with helper T-cells, requires costimulation with other specific ligands called costimulators that are expressed on the surface of the antigen-presenting cell. Activation of a cytotoxic T cell, on the other hand, generally requires IL-2, a cytokine secreted by activated helper T cells.

The Immune Response

The three primary functional properties of the mammalian immune system distinguishing it from the other body's defenses include: (1) specificity—the ability to recognize and respond or not to respond individually among a vast number of target molecules, (2) discrimination—the ability to determine self from non-self so as to peacefully coexist with all the innumerable proteins and other organic material, yet still respond vigorously against foreign material that is introduced to the body, and (3) memory—the ability to be molded by experience such that subsequent encounters with a particular foreign pathogen will provoke a more rapid and vigorous response than what occurred at the initial encounter. Because the IgE antagonists of the invention induce apoptosis in IgE-bearing B-cells, they are expected to attenuate or even erase immune memory to particular antigens. This is expected to be of particular benefit when vigorous immune response to common allergens is pathological, such as is the case with atopic disorders.

Virgin lymphocytes are continually released from the primary lymphoid organs into the periphery, each carrying surface receptors that enable antigen binding. Antigen binding in B cells is mediated through surface-bound immunoglobulins, whereas in T-cells it is mediated by T-cell receptors. When virgin lymphocytes are not activated, they die within a few days after entering the periphery. Those that are activated survive and proliferate, yielding daughter cells that may then undergo further cycles of activation and proliferation. The speed and intensity of response to a given antigen is determined largely by clonal selection: the larger the population daughter cells or clones specific to a particular antigen, the greater the number of cell that can recognize and participate in the immune response. Every immune response is complex and intricately regulated sequence of events involving several cell types. It is triggered when an immunogen enters the body and encounters a specialized class of cells called antigen-presenting cells (APCs). These APCs capture a minute amount of the immunogen and display it in a form that can be recognized by antigen-specific helper T-lymphocytes. The helper T cells then become activated and, in turn, promote activation of other classes of lymphocytes, such as B cells or cytotoxic T cells. The activated lymphocytes then proliferate and carry out their specific effector functions. At each stage in this process, the lymphocytes and APCs communicate with one another through direct contact or by secreting regulatory cytokines.

Exogenous antigens that are captured by an APC undergo a series of alterations called antigen processing. Such processing, especially of proteinaceous immunogens involves denaturation and partial proteolytic digestions, so that the immunogen is cleaved into short peptides. A limited number of the resulting peptides then associated non-covalently with class II MHC proteins and are transported to the APC surface, a process known as antigen presentation. A CD4+ helper T lymphocyte that comes into direct contact with an APC may become activated, but it will do so only if it expressed a T-cell receptor protein that can recognize and bind the particular peptide-MHC complex presented by the APC.

Helper T ($T_H$) cells are the principal orchestrators of the immune response because they are needed for activation of the two other lymphatic effector cells: cytotoxic T (Tc) cells and antibody secreting plasma cells. $T_H$ activation occurs early in an immune response and requires at least two signals. One signal is provided by binding of the T-cell antigen receptor to the antigenic peptide-MHC complex on the APC surface that is transmitted through the CD3 protein complex, while the second, costimulatory signal through the APC is thought to result from binding of a separate signal-transmitting protein on the T-cell surface with a specific ligand on the APC. One known such interaction is the T-cell protein CD28 and the family of APC surface proteins known as B7. Other surface proteins pairs may also mediate costimulation.

Together, the two signals induce the helper T cell to begin secreting a cytokine known as interleukin-2 (IL-2) and also to begin expressing specific high affinity IL-2 receptors on its surface. IL-2 is a highly potent mitogenic factor for T-lymphocytes and is essential for the proliferative response of activated T-cells. The effect of IL-2 on the cell from which it is secreted—a phenomenon known as an autocrine effect. It has further been shown that even if a T-cell has received both signals, it will not proliferate if its own surface IL-2 receptors are blocked. IL-2 can also act on cells in the immediate vicinity, in a so-called paracrine effect. This effect is especially important to activate Tc cells, which generally do not produce enough IL-2 to stimulate their own proliferation. In addition to IL-2, activated $T_H$ cells secrete other cytokines and promote the growth, differentiation, and functions of B-cells, macrophages and other cell types.

The contact between and APC and an antigen-specific $T_H$ cell also has effect on the APC—one of the most important of which is the release of IL-1. This cytokine is believed to act in an autocrine manner to increase surface expression of class II MHC proteins and of various adhesion molecules thereby strengthening binding of the $T_H$ cell and enhancing antigen presentation. At the same time, IL-1 functions in a paracrine manner on the TH cell to promote IL-2 secretion and IL-2 receptor expression.

During activation of $T_H$ cells in the manner previously described, some B-cells may also have been engaging the immunogen through their antigen receptors, which are membrane-bound forms of the antibodies that they will later secrete. Unlike T-cells, B-cells recognize an immunogen in its free, unprocessed form. Specific antigen binding provides one type of signal that can lead to B-cell activation. A second type is provided by activated $T_H$ cells, which express proteins that help activate the B cell by binding to non-immunoglobulin receptors on its surface. These $T_H$-derived signals, which act on any B cell regardless of its antigen specificity, are known as helper factors. These helper factors include IL-2, IL-4 and IL-6. However, help is more efficiently achieved through cell-cell contact, which allows proteins on the T-cell surface to directly contact those on the B cell. The most effect form of contact-mediated help occurs when a protein called CD40 ligand (CD40L), which is expressed on TH cells only after they become activated, binds to a protein called CD40 on B cells. In a process known as by-stander activation, contact with an activated B cell can even be sufficient to activate resting B cells even though its surface immunoglobulins have not engaged in antigen.

Tc lymphocytes function to eradicate cells that express foreign antigens on their surfaces, such as virus-infected host cells. Most Tc cells express CD8 rather than CD4 and hence recognize antigens in association with class I rather than class II MHC proteins. When a somatic cell is infected by a virus, some immunogenic viral proteins may undergo processing within the cell, and the resulting peptides may then appear as surface complexes with class I MHC molecules. These peptide-MHC complexes may then be recognized by the T-cell receptor of an antigen-specific clone, providing one of two signals necessary for Tc-cell activation. This first signal alone induces high-affinity IL-2 receptors on the Tc cell. The second signal is furnished by IL-2 secreted from a nearby activated $T_H$ lymphocyte. On receiving both signals, the activated Tc cell acquires cytotoxic activity, enabling it to kill the cell to which it is bound, as well as any other cells bearing the same peptide-MHC class I complexes. In some cases, killing occurs because the Tc releases specific toxins onto the target cell; in others, the Tc induces the target cell to commit suicide by apoptosis. The activate Tc cell also proliferates, giving rise to additional Tc cells with the same antigen specificity.

The IgE/Mast Cell/Mediatory Pathway.

IgE antibodies are fixed to the surface of mast cells and basophils at the Fc portion of the molecule to a high affinity cell surface receptor, called FcεRI. The allergic reaction is initiated when the polyvalent allergen molecule binds to antibodies that are occupying these receptors. The result is a bridging of the FcεRI, which in turn signals intracellularly causing the release and activation of mediators of inflammation: histamine, leukotrienes, chemotactic factors, platelet-activating factor, and proteinases. These activated mediators act locally and cause increased vascular permeability, vasodilation, smooth muscle contraction and mucous gland secretion. Such events are termed clinically the immediate or early phase, and occur within the first 15-30 minutes following allergen exposure. Over the succeeding 12 hours there is progressive tissue infiltration of inflammatory cells, proceeding from neutrophils to eosinophils to mononuclear cells in response to other chemical mediators not quite fully understood. This period of time 6-12 hours after allergen exposure is designated the late phase and is characterized by clinical manifestations of cellular inflammation. Given that late phase reactions, especially in the lung occur in the absence of early phase reactions, there is still not entirely understood if the late phase reaction is necessarily IgE mediated.

This mechanism is primarily responsible for the anaphylaxis, urticaria and the atopic diseases such as allergic rhinitis, allergic asthma, atopic dermatitis and allergic gastroenteropathy.

The Effector T-Lymphocyte/Lymphokine Pathway

Certain allergic diseases are mediated by allergen reaction with the effector T-lymphocyte sensitized to the specific allergen from a prior exposure. When allergen is encountered, CD4+ T-cells become activated to generate lymphokines, which results over the period of several days with the accumulation of mononuclear cell infiltrate.

I. Definitions

An "allergen" or "immunogen" is any molecule that can trigger an immune response. As used herein, the term covers either the antigenic molecule itself, or its source, such as pollen grain, animal dander, insect venom or food product. This is contrasted with the term antigen, which refers to a molecule can be specifically recognized by an immunoglobulin or T-cell receptor. Any foreign substance capable of inducing an immune response is a potential allergen. Many different chemicals of both natural and synthetic origin are known to be allergenic. Complex natural organic chemicals, especially proteins, are likely to cause antibody-mediated allergy, whereas simple organic compounds, inorganic chemicals, and metals more preferentially cause T-cell mediated allergy. In some cases, the same allergen may be responsible for more than one type of allergy. Exposure to the allergen may be through inhalation, injection, injection, or skin contact.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2, IgG3, IgG4, IgA1 and IgA2.

An "isolated" antibody is one that has been identified, separated and/or recovered from a component of its production environment (E.g., naturally or recombinantly). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature*, 256: 495-97 (1975); Hongo et al., *Hybridoma*, 14 (3): 253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Mono-* clonal Antibodies, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., Proc. Natl. Acad. Sci. USA 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147 (1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. Immunity 13:37-45 (2000); Johnson and Wu in Methods in Molecular Biology 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., Nature 363:446-448 (1993) and Sheriff et al., Nature Struct. Biol. 3:733-736 (1996).

A number of HVR delineations are in use and are encompassed herein. The HVRs that are Kabat complementarity-determining regions (CDRs) are based on sequence variability and are the most commonly used (Kabat et al., supra). Chothia refers instead to the location of the structural loops (Chothia and Lesk J. Mol. Biol. 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L34 | L30-L36 |
| L2 | L50-L56 | L50-L56 | L50-L56 | L46-L55 |
| L3 | L89-L97 | L89-L97 | L91-L96 | L89-L96 |
| H1 | H31-H35B | H26-H35B | H26-H32 | H30-H35B (Kabat Numbering) |

| Loop | Kabat | AbM | Chothia | Contact |
|------|-------|-----|---------|---------|
| H1 | H31-H35 | H26-H35 | H26-H32 | H30-H35 (Chothia Numbering) |
| H2 | H50-H65 | H50-H58 | H53-H56 | H47-H58 |
| H3 | H95-H102 | H95-H102 | H95-H102 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 47-65 (a preferred embodiment) (H2), and 93-102 (H3) in the VH. The variable-domain residues are numbered according to Kabat et al., supra, for each of these extended-HVR definitions.

"Framework" or "FR" residues are those variable-domain residues other than the HVR residues as herein defined.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

An "acceptor human framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, Md. (1991). In one embodiment, for the VL, the subgroup is subgroup kappa I as in Kabat et al., supra. In one embodiment, for the VH, the subgroup is subgroup III as in Kabat et al., supra.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences: EVQLVESGGGLVQPGGSL-RLSCAAS (H1) (SEQ ID NO:55), WVRQAPGKGLEWVA (SEQ ID NO:56)(H2), RFTISRDDSKNTLYLQMNSL-RAEDTAVYYCAR (SEQ ID NO:57)(H3), WGQGTLVTVSS (SEQ ID NO:58)(H4).

A "VL subgroup I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: DIQMTQSPSSLSASVGDRVTITC (SEQ ID NO:59)(L1), WYQQKPGKAPKLLIY (SEQ ID NO: 60) (L2), GVPSRFSGSGSGTDFTLTISSLQPEDFA-TYYC (SEQ ID NO:61)(L3), FGQGTKVEIKR (SEQ ID NO:62)(L4).

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154 (7):3310-9 (1995); and Hawkins et al, *J. Mol. Biol.* 226:889-896 (1992).

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the M1' specific antibodies of the present invention are specific to the M1' extracellular segment of IgE found on IgE bound on B-cells, but which is not present on secreted IgE.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. The apoptotic anti-IgE antibodies of the invention block the activity of IgE in mediating immune response in a manner so as reduce both free serum and total serum IgE.

Antibodies that "induce apoptosis" or are "apoptotic" are those that induce programmed cell death as determined by standard apoptosis assays, such as binding of annexin V, fragmentation of DNA, cell shrinkage, dilation of endoplasmic reticulum, cell fragmentation, and/or formation of membrane vesicles (called apoptotic bodies). For example, the apoptotic activity of the anti-IgE antibodies of the present invention can be showed by staining cells with surface bound IgE with annexin V.

The term "total serum IgE" refers to a total amount of IgE present in a sample, including both free or unbound, as well as IgE that is complexed with a binding partner (E.g., anti-IgE antibody, IgE-bearing B-cell). "Free serum IgE" refers to IgE that is not bound to a binding partner.

The term "allergen-specific IgE" refers to IgE that is specific to a particular antigen, resulting from an initial exposure to allergen in a process known as allergy sensitization, and which binds the surface of mast cells and basophils and which can result in the activation of mast cells and basophils upon subsequent exposure to the same allergen. Several mitogenic factors in viruses (e.g., Cytomegalovirus—CMV), bacteria (e.g., *Staphylococcus*), helminths (e.g., *Ascaris, Schistosoma*) and adjuvant factors in air pollution (e.g., cigarette smoke, and diesel exhaust) stimulate the production of IgE molecules without initiating any allergen specific IgE-sensitization. Thus, because IgE levels may elevate in a manner that does not necessarily predispose the host to become more susceptible to an IgE-mediated disorder, allergen-specific IgE levels are sometimes used in clinical evaluations.

The term "specifically deplete IgE-producing B-cells" means the ability to specifically reduce the population of or effectiveness of B-cells that specifically secrete IgE (i.e., plasma cells), but that does not significantly affect the population or effectiveness of B-cells that secrete other immunoglobulins, such as IgG1, IgG2, IgG3, IgG4, IgA and IgM.

The term "solid phase" describes a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody—dependent cell-mediated cytotoxicity (ADCC); phagocytosis; down regulation of cell surface receptors (e.g., B cell receptors); and B cell activation.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2, IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (HIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.).

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils, with PBMCs and MNK cells being preferred. The effector cells may be isolated from a native source, e.g., blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed.

Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

The N-glycosylation site in IgG is at Asn297 in the CH2 domain. The present invention also provides compositions of a CD20-binding, humanized antibody having a Fc region, wherein about 80-100% (and preferably about 90-99%) of the antibody in the composition comprises a mature core carbohydrate structure which lacks fucose, attached to the Fc region of the glycoprotein. Such compositions were demonstrated herein to exhibit a surprising improvement in binding to FcγRIIIA (F158), which is not as effective as FcγRIIIA (V158) in interacting with human IgG. Thus, the compositions herein are anticipated to be superior to previously described anti-CD20 antibody compositions, especially for therapy of human patients who express FcγRIIIA (F158). FcγRIIIA (F158) is more common than FcγRIIIA (V158) in normal, healthy African Americans and Caucasians. See Lehrnbecher et al. *Blood* 94:4220 (1999). The present application further demonstrates the synergistic increase in FcγRI11 binding and/or ADCC function that results from combining the glycosylation variations herein with amino acid sequence modification(s) in the Fc region of the glycoprotein.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen-binding assay (RIA) performed with the Fab version of an antibody of interest and its antigen as described by the following assay. Solution-binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, microtiter plates (DYNEX Technologies, Inc.) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ surfactant in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, the Kd is measured by using surface-plasmon resonance assays using a BIACORE®-2000 or a BIACORE®-3000 instrument (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 µl/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^1s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

An "on-rate," "rate of association," "association rate," or "$k_{on}$" according to this invention can also be determined as described above using a BIACORE®-2000 or a BIACORE®-3000 system (BIAcore, Inc., Piscataway, N.J.).

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, authored by Genentech, Inc. The source code of ALIGN-2 has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described in the immediately preceding paragraph using the ALIGN-2 computer program.

An "isolated" nucleic acid molecule encoding the antibodies herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "epitope tagged" when used herein refers to a chimeric polypeptide comprising a polypeptide or antibody described herein fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesion") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and C3 regions of an IgG1 molecule. For the production of immunoglobulin fusions see also U.S. Pat. No. 5,428,130 issued Jun. 27, 1995. For example, useful immunoadhesins as second medicaments useful for combination therapy herein include polypeptides that comprise the BLyS-binding portions of a BLyS receptor without the transmembrane of BR3, TACI or BCMA is fused to a constant domain of an immunoglobulin sequence.

A "fusion protein" and a "fusion polypeptide" refer to a polypeptide having two portions covalently linked together, where each of the portions is a polypeptide having a different properly. The property may be a biological property, such as activity in vitro or in vivo. The property may also be simple chemical or physical property, such as binding to a target molecule, catalysis of a reaction, etc. The two portions may be linked directly by a single peptide bond or through a peptide linker will be in reading frame with each other.

A "stable" formulation is one in which the protein therein essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation during storage can be used as an indicator of protein stability. Thus, a "stable" formulation may be one wherein less than about 10% and preferably less than about 5% of the protein are present as an aggregate in the formulation. In other embodiments, any increase in aggregate formation during storage of the formulation can be determined.

A "reconstituted" formulation is one which has been prepared by dissolving a lyophilized protein or antibody formulation in a diluent such that the protein is dispersed throughout. The reconstituted formulation is suitable for administration (e.g. parenteral administration) to a patient to be treated with the protein of interest and, in certain embodiments of the invention, may be one which is suitable for subcutaneous administration.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present invention are hypertonic as a result of the addition of salt and/or buffer.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

A "pharmaceutically acceptable acid" includes inorganic and organic acids which are non toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cycloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo[2.2.2]-oct-2-ene-1-carboxylic, glucoheptonic, 4,4'-methylenebis-3-(hydroxy-2-ene-1-carboxylic acid), hydroxynapthoic.

"Pharmaceutically-acceptable bases" include inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amines, substituted amines, cyclic amines and basic ion exchange resins, [e.g., $N(R')_4^+$ (where R' is independently H or $C_{1-4}$ alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Additional pharmaceutically acceptable acids and bases useable with the present invention include those which are derived from the amino acids, for example, histidine, glycine, phenylalanine, aspartic acid, glutamic acid, lysine and asparagine.

"Pharmaceutically acceptable" buffers and salts include those derived from both acid and base addition salts of the above indicated acids and bases. Specific buffers and/or salts include histidine, succinate and acetate.

A "pharmaceutically acceptable sugar" is a molecule which, when combined with a protein of interest, significantly prevents or reduces chemical and/or physical instability of the protein upon storage. When the formulation is intended to be lyophilized and then reconstituted, "pharmaceutically acceptable sugars" may also be known as a "lyoprotectant". Exemplary sugars and their corresponding sugar alcohols include: an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; PLURONICS®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose. Pharmaceutically acceptable sugars are added to the formulation in a "protecting amount" (e.g. pre-lyophilization) which means that the protein essentially retains its physical and chemical stability and integrity during storage (e.g., after reconstitution and storage).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

"Treatment" refers to clinical intervention designed to alter the natural course of the individual or cell being treated, and can be performed either for prophylaxis or during the course of clinical pathology. Desirable effects of treatment include preventing occurrence or recurrence of disease, preventing metastasis, decreasing the rate of disease progression, ameliorating or palliating the disease state, and remission or improved prognosis. In some embodiments, antibodies of the invention are used to delay development of a disease or disorder. A subject is successfully "treated", for example, using the apoptotic anti-IgE antibodies of the invention if one or more symptoms associated with an IgE-mediated disorder is mitigated.

An "effective amount" refers to at least an amount effective, at dosages and for periods of time necessary, to achieve the desired or indicated effect, including a therapeutic or prophylactic result.

A "therapeutically effective amount" is at least the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in subjects prior to or at the earlier stage of disease, the prophylactically effective amount can be less than the therapeutically effective amount.

"Chronic" administration refers to administration of the medicament(s) in a continuous as opposed to acute mode, so as to main the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, horses, rabbits, cattle, pigs, hamsters, gerbils, mice, ferrets, rats, cats, etc. Preferably, the mammal is human.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

A "sterile" formulation is aseptic or free from all living microorganisms and their spores.

The term "about" as used herein refers to the usual error range for the respective value readily known to the skilled person in this technical field.

An "antihistamine" as used herein is an agent that antagonizes the physiological effect of histamine. The binding of histamine to its receptors, $H_1$ and $H_2$ results in the characteristic allergic symptoms and effects or itching, redness, swelling etc. Many antihistamines act by blocking the binding of histamine to its receptors, H1, H2; however others are believed to operate by inhibiting the release of histamine. Examples of antihistamines are chlorpheniramine, diphenhydramine, promethazine, cromolyn sodium, astemizole, azatadine maleate, bropheniramine maleate, carbinoxamine maleate, cetirizine hydrochloride, clemastine fumarate, cyproheptadine hydrochloride, dexbrompheniramine maleate, dexchlorpheniramine maleate, dimenhydrinate, diphenhydramine hydrochloride, doxylamine succinate, fexofenadine hydrochloride, terphenadine hydrochloride, hydroxyzine hydrochloride, loratidine, meclizine hydrochloride, tripelannamine citrate, tripelennamine hydrochloride, triprolidine hydrochloride.

A "bronchodilator" as used herein, describes agents that antagonize or reverse bronchoconstriction, a physiological event that occurs typically in early phase asthmatic reactions resulting in decreased lung capacity and shortness of breath. Example bronchodilators include epinephrine, a broad acting alpha and beta-adrenergic, and the beta-adrenergics, albuterol, pirbuterol, metaproterenol, salmeterol, and isoetharine. Bronchodilation can also be achieved through administration of xanthines, including aminophylline and theophylline.

A "glucocorticoid" as used herein describes steroidal based agents having anti-inflammatory activity. Glucocorticoids are commonly used to attenuate late phase asthmatic reaction. Example glucocorticoids include prednisone, beclomethasone dipropionate, triamcinolone acetonide, flunisolide, betamethasone, budesonide, dexamethasone, desamehasone tramcinolone, fludrocortisone acetate, flunisolide, fluticasone propionate, hydrocortisone, prednisolone [including methylprednisolone (e.g., SOLU-MEDROL® methlprednisolone sodium succinate)], and triamcinolone.

A "non-steroidal anti-inflammatory drug" or "NSAID", as used herein describes agents having anti-inflammatory activity that are not steroidal based. Example NSAID's include acematacin, acetaminophen, aspirin, azapropazone, benorylate, bromfenac sodium, cyclooxygenase (COX)-2 inhibitors such as GR 253035, MK966, celecoxib (CELEBREX®; 4-(5-(4-methylphenyl)-3-(trifluoromethyl)-1H-pyrazol-1-yl) benzene-sulfonamide) and valdecoxib (BEXTRA®), diclofenac, diclofenac retard, diclofenac sodium, diflunisal, etodolac, fenbufen, fenoprofen calcium, flurbiprofen, ibuprofen, ibuprofen retard, indomethacin, ketoprofen, meclofenamate sodium, mefenamic acid, meloxicam (MOBIC®), nabumetone, naproxen, naproxen sodium, oxyphenbutazone, phenylbutzone, piroxicam, sulindac, tenoxicam, tiaprofenic acid, tolmetin, tolmetin sodium, including salts and derivatives thereof, etc.

The term "IgE-mediated disorders" includes atopic disorders, which are characterized by a general inherited propensity to respond immunologically to many common naturally occurring inhaled and ingested antigens and the continual production of IgE antibodies. Specific atopic disorders include allergic asthma, allergic rhinitis (conjunctivitis), atopic dermatitis, food allergy, anaphylaxis, contact dermatitis, allergic gastroenteropathy, allergic bronchopulmonary aspergillosis and allergic purpura (Henoch-Schönlein). Atopic patients often have multiple allergies, meaning that they have IgE antibodies to, and symptoms from, many environmental allergens, including seasonal, perennial and occupational allergens. Example seasonal allergens include pollens (e.g., grass, tree, rye, timothy, ragweed), while example perennial allergens include fungi (e.g., molds, mold spores), feathers, animal (e.g., pet or other animal dander) and insect (e.g., dust mite) debris. Example occupational allergens also include animal (e.g. mice) and plant antigens as well as drugs, detergents, metals and immunoenhancers such as isocyanates. Non-antigen specific stimuli that can result in an IgE-mediated reaction include infection, irritants such as smoke, combustion fumes, diesel exhaust particles and sulphur dioxide, exercise, cold and emotional stress. Specific hypersensitivity reactions in atopic and nonatopic individuals with a certain genetic background may result from exposure to proteins in foods (e.g., legumes, peanuts), venom (e.g., insect, snake), vaccines, hormones, antiserum, enzymes, latex, antibiotics, muscle relaxants, vitamins, cytotoxins, opiates, and polysaccharides such as dextrin, iron dextran and polygeline.

Other disorders associated with elevated IgE levels, that appear to be IgE-mediated and are treatable with the formulations of this present invention include: ataxia-telangiectasia, Churg-Strauss Syndrome, eczema, enteritis, gastroenteropathy, graft-versus-host reaction, hyper-IgE (Job's) syndrome, hypersensitivity (e.g., anaphylactic hypersensitivity, candidiasis, vasculitis), IgE myeloma, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis, parasitic diseases (e.g., trypanosomiasis), hypersensitivity vasculitis, urticaria and Wiskott-Aldrich syndrome.

Additionally, disorders that may be treatable by lowering IgE levels, regardless of whether the disorders themselves are associated with elevated IgE, and thus should be considered within the scope of "IgE-mediated disorder" include: Addison's disease (chronic adrenocortical insufficiency), alopecia, hereditary angioedema, anigioedema (Bannister's disease, angioneurotic edema), ankylosing spondylitis, aplastic anemia, arteritis, amyloidosis, immune disorders, such as autoimmune hemolytic anemia, autoimmune oophoritis, autoimmune orchitis, autoimmune polyendocrine failure, autoimmune hemolytic anemia, autoimmunocytopenia, autoimmune glomerulonephritis, Behcet's disease, bronchitis, Buerger's disease, bullous pemphigoid, Caplan's syndrome (rheumatoid pneumoconiosis), carditis, celiac sprue, Chediak-Higashi syndrome, chronic obstructive lung Disease (COPD), Cogan-Reese syndrome (iridocorneal endothelial syndrome), CREST syndrome, dermatitis herpetiformis (Duhring's disease), diabetes mellitus, eosinophilic fasciitis, eosinophilic nephritis, episcleritis, extrinsic allergic alveolitis, familial paroxysmal polyserositis, Felty's syndrome, fibrosing alveolitis, glomerulonephritis, Goodpasture's syndrome, granulocytopenia, granuloma, granulomatosis, granuloma myositis, Graves' disease, Guillain-Barre syndrome (polyneuritis), Hashimoto's thyroiditis (lymphadenoid goiter), hemochromatosis, histocytosis, hypereosinophilic syndrome, irritable bowel syndrome, juvenile arthritis, keratitis, leprosy, lupus erythematosus, Lyell's disease, Lyme disease, mixed connective tissue disease, mononeuritis, mononeuritis multiplex, Muckle-Wells syndrome, mucocutaneous lymphoid syndrome (Kawasaki's disease), multicentric reticulohistiocystosis, multiple sclerosis, myasthenia gravis, mycosis fungoides, panninculitis, pemphigoid, pemphigus, pericarditis, polyneuritis, polyarteritis nodoas, psoriasis, psoriatic arthritis, pulmonary arthritis, pulmonary adenomatosis, pulmonary fibrosis, relapsing polychondritis, rheumatic fever, rheumatoid arthritis, rhinosinusitis (sinusitis), sarcoidosis, scleritis, sclerosing cholangitis, serum sickness, Sezary syndrome, Sjögren's syndrome, Stevens-Johnson syndrome, systemic mastocytosis, transplant rejection, thrombocytopenic purpura, thymic alymphoplasia, uveitis, vitiligo, Wegener's granulomatosis.

An "autoimmune disorder" herein is a disease or disorder arising from and directed against an individual's own tissues or organs or a co-segregation or manifestation thereof or resulting condition therefrom. In many of these autoimmune and inflammatory disorders, a number of clinical and laboratory markers may exist, including, but not limited to, hyper-gammaglobulinemia, high levels of autoantibodies, antigen-antibody complex deposits in tissues, benefit from corticosteroid or immunosuppressive treatments, and lymphoid cell, aggregates in affected tissues. Without being limited to any one theory regarding B-cell mediated autoimmune disorder, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases.

"Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis (RA), polymyositis, etc.). Preferred such diseases include autoimmune rheumatologic disorders (such as, for example, RA, Sjögren's syndrome, scleroderma, lupus such as SLE and lupus nephritis, polymyositis-dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, RA, ulcerative colitis, ANCA-associated vasculitis, lupus, multiple sclerosis, Sjögren's syndrome, Graves' disease, IDDM, pernicious anemia, thyroiditis, and glomerulonephritis.

The term "cytotoxic agent" as used herein refers to a substance that inhibits or prevents the function of cells and/or causes destruction of cells. The term includes radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), and toxins such as small-molecule toxins or enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (see, e.g., Nicolaou et al., Angew. Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chlorambucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX®); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

A "growth-inhibitory agent" refers to a compound or composition that inhibits growth of a cell, which growth depends on receptor activation either in vitro or in vivo. Thus, the growth-inhibitory agent includes one that significantly reduces the percentage of receptor-dependent cells in S phase. Examples of growth-inhibitory agents include agents that block cell-cycle progression (at a place other than S phase), such as agents that induce G1 arrest and M-phase arrest. Classical M-phase blockers include the vincas and vinca alkaloids (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The *Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb).

The term "cytokine" is a generic term for proteins released by one cell population that act on another cell as intercellular mediators. Examples of such cytokines are lymphokines, monokines; interleukins (ILs) such as IL-1, IL-1α, IL-2, IL-3, IL-4, IL-5, IL-6, IL-7, IL-8, IL-9, IL-11, IL-12, IL-13, IL-15, including PROLEUKIN® rIL-2; a tumor-necrosis factor such as TNF-α or TNF-β; and other polypeptide factors including LIF and kit ligand (KL). As used herein, the term cytokine includes proteins from natural sources or from recombinant cell culture and biologically active equivalents of the native-sequence cytokines, including synthetically produced small-molecule entities and pharmaceutically acceptable derivatives and salts thereof.

The term "hormone" refers to polypeptide hormones, which are generally secreted by glandular organs with ducts. Included among the hormones are, for example, growth hormone such as human growth hormone, N-methionyl human growth hormone, and bovine growth hormone; parathyroid hormone; thyroxine; insulin; proinsulin; relaxin; estradiol; hormone-replacement therapy; androgens such as calusterone, dromostanolone propionate, epitiostanol, mepitiostane, or testolactone; prorelaxin; glycoprotein hormones such as follicle stimulating hormone (FSH), thyroid stimulating hormone (TSH), and luteinizing hormone (LH); prolactin, placental lactogen, mouse gonadotropin-associated peptide, gonadotropin-releasing hormone; inhibin; activin; mullerian-inhibiting substance; and thrombopoietin. As used herein, the term hormone includes proteins from natural sources or from recombinant cell culture and biologically active equivalents of the native-sequence hormone, including synthetically produced small-molecule entities and pharmaceutically acceptable derivatives and salts thereof.

The term "growth factor" refers to proteins that promote growth, and include, for example, hepatic growth factor; fibroblast growth factor; vascular endothelial growth factor; nerve growth factors such as NGF-β; platelet-derived growth factor; transforming growth factors (TGFs) such as TGF-α and TGF-β; insulin-like growth factor-I and -II; erythropoietin (EPO); osteoinductive factors; interferons such as interferon-α, β, and -γ; and colony stimulating factors (CSFs) such as macrophage-CSF (M-CSF); granulocyte-macrophage-CSF (GM-CSF); and granulocyte-CSF (G-CSF). As used herein, the term growth factor includes proteins from natural sources or from recombinant cell culture and biologically active equivalents of the native-sequence growth factor, including synthetically produced small-molecule entities and pharmaceutically acceptable derivatives and salts thereof.

The term "integrin" refers to a receptor protein that allows cells both to bind to and to respond to the extracellular matrix and is involved in a variety of cellular functions such as wound healing, cell differentiation, homing of tumor cells and apoptosis. They are part of a large family of cell adhesion receptors that are involved in cell-extracellular matrix and cell-cell interactions. Functional integrins consist of two transmembrane glycoprotein subunits, called alpha and beta, that are non-covalently bound. The alpha subunits all share some homology to each other, as do the beta subunits. The receptors always contain one alpha chain and one beta chain. Examples include Alpha6beta1, Alpha3beta1, Alpha7beta1, LFA-1 etc. As used herein, the term "integrin" includes proteins from natural sources or from recombinant cell culture and biologically active equivalents of the native-sequence integrin, including synthetically produced small-molecule entities and pharmaceutically acceptable derivatives and salts thereof.

A "TNF antagonist" is defined herein as a molecule that decreases, blocks, inhibits, abrogates, or interferes with TNFα activity in vitro, in situ, and/or preferably in vivo. A suitable TNF antagonist can also decrease block, abrogate, interfere, prevent and/or inhibit TNF RNA, DNA or protein synthesis, TNFα release, TNFα receptor signaling, membrane TNFα cleavage, TNFα activity, TNFα production and/or synthesis. Such TNF antagonists include, but are not limited to, anti-TNFα antibodies, antigen-binding fragments thereof, specified mutants or domains thereof that bind specifically to TNFα that, upon binding to TNFα, destroy or deplete cells expressing the TNFα in a mammal and/or interferes with one or more functions of those cells, a soluble TNF receptor (e.g., p55, p70 or p85) or fragment, fusion polypeptides thereof, a small-molecule TNF antagonist, e.g., TNF binding protein I or II (TBP-I or TBP-II), nerelimonmab, CDP-571, infliximab, enteracept (ENBREL™), adalimulab (HUMIRA™), CDP-571, CDP-870, afelimomab, lenercept, and the like), antigen-binding fragments thereof, and receptor molecules that bind specifically to TNFα; compounds that prevent and/or inhibit TNFα synthesis, TNFα release or its action on target cells, such as thalidomide, tenidap, phosphodiesterase inhibitors (e.g, pentoxifylline and rolipram), A2b adenosine receptor agonists and A2b adenosine receptor enhancers; compounds that prevent and/or inhibit TNFα receptor signalling, such as mitogen activated protein (MAP) kinase inhibitors; compounds that block and/or inhibit membrane TNFα cleavage, such as metalloproteinase inhibitors; compounds that block and/or inhibit TNFα activity, such as angiotensin converting enzyme (ACE) inhibitors (e.g., captopril); and compounds that block and/or inhibit TNFα production and/or synthesis, such as MAP kinase inhibitors. The preferred antagonist comprises an antibody.

"Tumor necrosis factor-alpha", TNF-alpha", or "TNFα" refers to a human TNFα molecule comprising the amino acid sequence of Pennica et al., *Nature,* 312:721 (1984) or Aggarwal et al., *JBC,* 260:2345 (1985). A "TNFα inhibitor" herein is an agent that inhibits, to some extent, a biological function of TNFα, generally through binding to TNFα and neutralizing its activity. Examples of TNFα inhibitors herein include etanercept (ENBREL®), infliximab (REMICADE®), and adalimumab (HUMIRA™).

Examples of "integrin antagonists or antibodies" herein include an LFA-1 antibody, such as efalizumab (RAPTIVA®) commercially available from Genentech, or an alpha 4 integrin antibody such as natalizumab (ANTEGREN®) available from Biogen, or diazacyclic phenylalanine derivatives (WO 2003/89410), phenylalanine derivatives (WO 2003/70709, WO 2002/28830, WO 2002/16329 and WO 2003/53926), phenylpropionic acid derivatives (WO 2003/10135), enamine derivatives (WO 2001/79173), propanoic acid derivatives (WO 2000/37444), alkanoic acid derivatives (WO 2000/32575), substituted phenyl derivatives (U.S. Pat. Nos. 6,677,339 and 6,348,463), aromatic amine derivatives (U.S. Pat. No. 6,369,229), ADAM disintegrin domain polypeptides (US2002/0042368), antibodies to alphavbeta3 integrin (EP 633945), aza-bridged bicyclic amino acid derivatives (WO 2002/02556), etc.

The term "immunosuppressive agent" refers to a substance that acts to suppress or mask the immune system of the subject being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); trocade (Ro32-355); a peripheral sigma receptor antagonist such as ISR-31747; alkylating agents such as cyclophosphamide; bromocriptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, rimexolone, and dexamethasone; dihydrofolate reductase inhibitors such as methotrexate (oral or subcutaneous); anti-malarial agents such as chloroquine and hydroxychloroquine; sulfasalazine; leflunomide; cytokine release inhibitors such as SB-210396 and SB-217969 monoclonal antibodies and a MHC II antagonist such as ZD2315; a PG1 receptor antagonist such as ZD4953; a VLA4 adhesion blocker such as ZD7349; anti-cytokine or anti-cytokine receptor antibodies including anti-interferon-alpha, -beta, or -gamma antibodies, anti-TNF-α antibodies (infliximab (REMICADE®) or adalimumab), anti-TNF-α immunoadhesin (etanercept), anti-TNF-beta antibodies, interleukin-1 (IL-1) blockers such as recombinant HuIL-1Ra and IL-1B inhibitor, anti-interleukin-2 (IL-2) antibodies and anti-IL-2 receptor antibodies; IL-2 fusion toxin; anti-L3T4 antibodies; leflunomide; heterologous anti-lymphocyte globulin; OPC-14597; NISV (immune response modifier); an essential fatty acid such as gammalinolenic acid or eicosapentaenoic acid; CD-4 blockers, pan-T antibodies, preferably anti-CD3 or anti-CD4/CD4a antibodies; co-stimulatory modifier (e.g., CTLA4-Fc fusion, also known as ABATACEPT™; anti-interleukin-6 (IL-6) receptor antibodies and antagonists; anti-LFA-1 antibodies, including anti-CD11a and anti-CD18 antibodies; soluble peptide containing a LFA-3 binding domain (WO 1990/08187); streptokinase; IL-10; anti-IL-4 antagonists, anti-IL-13 antagonists and bispecific anti-IL-4/IL-13 antagonist antibodies, transforming growth factor-beta (TGF-beta); streptodornase; RNA or DNA from the host; FK506; RS-61443; enlimomab; CDP-855; PNP inhibitor; CH-3298; GW353430; 4162W94, chlorambucil; deoxyspergualin; rapamycin; T-cell receptor (U.S. Pat. No. 5,114,721); T-cell receptor fragments (Offner et al., *Science,* 251: 430-2 (1991); WO 1990/11294; Janeway, *Nature,* 341: 482-483 (1989); and WO 1991/01133); BAFF antagonists such as BAFF antibodies and BR3 antibodies; zTNF4 antagonists (Mackay and Mackay, *Trends Immunol.,* 23:113-5 (2002)); biologic agents that interfere with T-cell helper signals, such as anti-CD40 receptor or anti-CD40 ligand (CD154), including blocking antibodies to CD40-CD40 ligand (e.g., Durie et al., *Science,* 261: 1328-30 (1993); Mohan et al., *J. Immunol.,* 154: 1470-80 (1995)) and CTLA4-Ig (Finck et al., *Science,* 265: 1225-7 (1994)); and T-cell receptor antibodies (EP 340, 109) such as T10B9. Some preferred immunosuppressive agents herein include cyclophosphamide, chlorambucil, azathioprine, leflunomide, MMF, or methotrexate (MTX).

"Disease-modifying anti-rheumatic drugs" or "DMARDs" include, e.g., chloroquine, hydroxycloroquine, myocrisin, auranofin, sulfasalazine, methotrexate, leflunomide, etanercept, infliximab (and oral and subcutaneous MTX), azathioprine, D-penicilamine, gold salts (oral), gold salts (intramuscular), minocycline, cyclosporine, e.g., cyclosporine A and topical cyclosporine, staphylococcal protein A (Goodyear and Silverman, *J. Exp. Med.*, 197:1125-39 (2003)), including salts and derivatives thereof, etc.

A "B cell" is a lymphocyte that matures within the bone marrow, and includes a naïve B cell, memory B cell, or effector B cell (plasma cells). The B cell herein may be normal or non-malignant.

A "B-cell surface marker" or "B-cell surface antigen" herein is an antigen expressed on the surface of a B cell that can be targeted with an antagonist that binds thereto. Exemplary B-cell surface markers include the CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86 leukocyte surface markers (for descriptions, see *The Leukocyte Antigen Facts Book*, 2nd Edition. 1997, ed. Barclay et al. Academic Press, Harcourt Brace & Co., New York). Other B-cell surface markers include RP105, FcRH2, B-cell CR2, CCR6, P2X5, HLA-DOB, CXCR5, FCER2, BR3, Btig, NAG14, SLGC16270, FcRH1, IRTA2, ATWD578, FcRH3, IRTA1, FcRH6, BCMA, and 239287. The preferred B-cell surface marker is preferentially expressed on B cells compared to other non-B-cell tissues of a mammal and may be expressed on both precursor and mature B cells. The most preferred such markers are CD20 and CD22.

The "CD20" antigen, or "CD20," is an about 35-kDa, non-glycosylated phosphoprotein found on the surface of greater than 90% of B cells from peripheral blood or lymphoid organs. CD20 is present on both normal B cells as well as malignant B cells, but is not expressed on stem cells. Other names for CD20 in the literature include "B-lymphocyte-restricted antigen" and "Bp35". The CD20 antigen is described in Clark et al., *Proc. Natl. Acad. Sci. (USA)* 82:1766 (1985), for example.

The "CD22" antigen, or "CD22," also known as BL-CAM or Lyb8, is a type 1 integral membrane glycoprotein with molecular weight of about 130 (reduced) to 140 kD (unreduced). It is expressed in both the cytoplasm and cell membrane of B-lymphocytes. CD22 antigen appears early in B-cell lymphocyte differentiation at approximately the same stage as the CD19 antigen. Unlike other B-cell markers, CD22 membrane expression is limited to the late differentiation stages comprised between mature B cells (CD22+) and plasma cells (CD22−). The CD22 antigen is described, for example, in Wilson et al., *J. Exp. Med.* 173:137 (1991) and Wilson et al., *J. Immunol.* 150:5013 (1993).

An "antibody that binds to a B-cell surface marker" is a molecule that, upon binding to a B-cell surface marker, destroys or depletes B cells in a mammal and/or interferes with one or more B-cell functions, e.g. by reducing or preventing a humoral response elicited by the B cell. The antibody preferably is able to deplete B cells (i.e. reduce circulating B-cell levels) in a mammal treated therewith. Such depletion may be achieved via various mechanisms such antibody-dependent cell-mediated cytotoxicity (ADCC) and/or complement-dependent cytotoxicity (CDC), inhibition of B-cell proliferation and/or induction of B-cell death (e.g. via apoptosis).

Examples of CD20 antibodies include: "C2B8," which is now called "rituximab" ("RITUXAN®") (U.S. Pat. No. 5,736,137); the yttrium-[90]-labelled 2B8 murine antibody designated "Y2B8" or "Ibritumomab Tiuxetan" (ZEVALIN®) commercially available from IDEC Pharmaceuticals, Inc. (U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine I131 tositumomab" antibody (BEXXAR™) commercially available from Corixa (see, also, U.S. Pat. No. 5,595,721); murine monoclonal antibody "1F5" (Press et al. *Blood* 69(2):584-591 (1987) and variants thereof including "framework patched" or humanized 1F5 (WO 2003/002607, Leung, S.; ATCC deposit HB-96450); murine 2H7 and chimeric 2H7 antibody (U.S. Pat. No. 5,677,180); a humanized 2H7 (WO 2004/056312 (Lowman et al.) and as set forth below); HUMAX-CD20™ fully human, high-affinity antibody targeted at the CD20 molecule in the cell membrane of B-cells (Genmab, Denmark; see, for example, Glennie and van de Winkel, *Drug Discovery Today* 8: 503-510 (2003) and Cragg et al., *Blood* 101: 1045-1052 (2003)); the human monoclonal antibodies set forth in WO04/035607 (Teeling et al.); AME-133™ antibodies (Applied Molecular Evolution); A20 antibody or variants thereof such as chimeric or humanized A20 antibody (cA20, hA20, respectively) (US 2003/0219433, Immunomedics); and monoclonal antibodies L27, G28-2, 93-1B3, B-C1 or NU-B2 available from the International Leukocyte Typing Workshop (Valentine et al., In: Leukocyte Typing III (McMichael, Ed., p. 440, Oxford University Press (1987)). The preferred CD20 antibodies herein are chimeric, humanized, or human CD20 antibodies, more preferably rituximab, a humanized 2H7, chimeric or humanized A20 antibody (Immunomedics), and HUMAX-CD20™ human CD20 antibody (Genmab).

The terms "rituximab" or "RITUXAN®" herein refer to the genetically engineered chimeric murine/human monoclonal antibody directed against the CD20 antigen and designated "C2B8" in U.S. Pat. No. 5,736,137, including fragments thereof that retain the ability to bind CD20.

Purely for the purposes herein and unless indicated otherwise, a "humanized 2H7" refers to a humanized CD20 antibody, or an antigen-binding fragment thereof, wherein the antibody is effective to deplete primate B cells in vivo. The antibody includes those set forth in US 2006/0062787 and the figures thereof, and including version 114, the sequences of which are provided in US 2006/0188495. See also US 2006/0034835 and US 2006/0024300. In a summary of various preferred embodiments of the invention, the V region of variants based on 2H7 version 16 as disclosed in US 2006/0062787 will have the amino acid sequences of v16 except at the positions of amino acid substitutions that are indicated in the table below. Unless otherwise indicated, the 2H7 variants will have the same L chain as that of v16.

| 2H7 version | Heavy chain ($V_H$) changes | Light chain ($V_L$) changes | Fc changes |
|---|---|---|---|
| 16 | — | — | — |
| 31 | — | — | S298A, E333A, K334A |
| 73 | N100A | M32L | |
| 75 | N100A | M32L | S298A, E333A, K334A |
| 96 | D56A, N100A | S92A | |
| 114 | D56A, N100A | M32L, S92A | S298A, E333A, K334A |
| 115 | D56A, N100A | M32L, S92A | S298A, E333A, K334A, E356D, M358L |
| 116 | D56A, N100A | M32L, S92A | S298A, K334A, K322A |
| 138 | D56A, N100A | M32L, S92A | S298A, E333A, K334A, K326A |
| 477 | D56A, N100A | M32L, S92A | S298A, E333A, K334A, K326A, N434W |
| 375 | — | — | K334L |

One preferred humanized 2H7 is an intact antibody or antibody fragment having the sequence of version 16. Another preferred humanized 2H7 has the sequences of version 114.

"BAFF antagonists" are any molecules that block the activity of BAFF or BR3. They include immunoadhesins comprising a portion of BR3, TACI or BCMA that binds BAFF, or variants thereof that bind BAFF. In other aspects, the BAFF antagonist is a BAFF antibody. A "BAFF antibody" is an antibody that binds BAFF, and preferably binds BAFF within a region of human BAFF comprising residues 162-275 of human BAFF. In another aspect, the BAFF antagonist is a BR3 antibody. A "BR3 antibody" is an antibody that binds BR3, and preferably binds BR3 within a region of human BR3 comprising residues 23-38 of human BR3. The sequences of human BAFF and human BR3 are found, e.g., in US 2006/0062787. Other examples of BAFF-binding polypeptides or BAFF antibodies can be found in, e.g., WO 2002/092620, WO 2003/014294, Gordon et al., *Biochemistry* 42(20):5977-83 (2003), Kelley et al., *J. Biol. Chem.* 279: 16727-35 (2004), WO 1998/18921, WO 2001/12812, WO 2000/68378 and WO 2000/40716.

"Anti-IgE antibody" includes any antibody that binds specifically to IgE in a manner so as to not induce cross-linking when IgE is bound to the high affinity receptor on mast cells and basophils. Exemplary antibodies include the antibodies of the invention as well as rhuMabE25 (E25, XOLAIR®), E26, E27, as well as CGP-5101 (Hu-901) and the HA antibody. The amino acid sequences of the heavy and light chain variable domains of the humanized anti-IgE antibodies E25, E26 and E27 are disclosed, for example in U.S. Pat. No. 6,172,213 and WO99/01556. The CGP-5101 (Hu-901) antibody is described in Come et al., (1997) J. Clin. Invest. 99(5): 879-887, WO 92/17207 and ATCC Dep. Nos. BRL-10706, BRL-11130, BRL-11131, BRL-11132 and BRL-11133. The HA antibody is described in U.S. Ser. No. 60/444,229, WO2004/070011 and WO2004/070010.

II. Modes for Carrying out the Invention

A. Recombinant Preparation

The invention also provides an isolated nucleic acid encoding apoptotic anti-IgE antibodies, vectors and host cells comprising such nucleic acid, and recombinant techniques for the production of the antibody.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide proves that are capable of binding specifically to genes encoding the heavy and light chains of the antibody). Many vectors are available. The vector components generally include, but are not limited to, one or more of the following, a signal sequence, an origin of replication, one or more marker genes, and enhancer element, a promoter, and a transcription termination sequence.

(1) Signal Sequence Component

The anti-IgE antibodies of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native mammalian signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, factor leader (including *Saccharomyces* and *Kluyveromyces*-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the IgE binding antibody.

(2) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(3) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the IgE binding antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding IgE binding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics,* 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of *Kluyveromyces* yeasts. Alternatively, an expression system for large-scale production of recombinant calf chymosin was reported for *K. lactis.* Van den Berg, *Bio/Technology,* 8:135 (1990). Stable multi-copy expression vectors for secretion of mature recombinant human serum albumin by industrial strains of *Kluyveromyces* have also been disclosed. Fleer et al., *Bio/Technology,* 9:968-975 (1991).

(4) Promoter Component

Expression and cloning vectors usually contain a promoter that is recognized by the host organism and is operably linked to the nucleic acid encoding the IgE binding antibody. Promoters suitable for use with prokaryotic hosts include the phoA promoter, -lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the IgE binding antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phos-phate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

IgE binding antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

(5) Enhancer Element Component

Transcription of a DNA encoding the IgE binding antibody of this invention by higher eukaryotes is often increased by inserting an enhancer sequence into the vector. Many enhancer sequences are now known from mammalian genes (globin, elastase, albumin, -fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the IgE binding antibody-encoding sequence, but is preferably located at a site 5' from the promoter.

(6) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding IgE binding antibody. One useful transcription termination component is the bovine growth hormone polyadenylation region. See WO94/11026 and the expression vector disclosed therein.

(7) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia,* e.g., *E. coli, Enterobacter, Erwinia, Klebsiella, Proteus, Salmonella,* e.g., *Salmonella typhimurium, Serratia,* e.g., *Serratia marcescans,* and *Shigella,* as well as Bacilli such as *B. subtilis* and *B. licheniformis* (e.g., *B. licheniformis* 41P disclosed in DD 266,710 published 12 Apr. 1989), *Pseudomonas* such as *P. aeruginosa,* and *Streptomyces.* One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for IgE binding antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crasser; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated IgE binding antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for IgE binding antibody production and cultured in conventional nutrient media modified as appropriate for inducing promoters, selecting transformants, or amplifying the genes encoding the desired sequences.

(8) Culturing the Host Cells

The host cells used to produce the IgE binding antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(9) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human 1, 2, or 4 heavy chains (Lindmark et al., *J. Immunol. Meth.* 62:1-13 (1983)). Protein G is recommended for all mouse isotypes and for human 3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification.

Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

B. Antibody Preparation

1) Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysien residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the antigen, immunogenic conjugates, or derivatives by combining, e.g., 100 μg or 5 μg or the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

2) Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986).

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, *J. Immunol.*, 133: 3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130:151-188 (1992).

In a further embodiment, antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3) Humanized Antibodies.

The antibodies of the invention may further comprise humanized or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domain, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332:323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.*, 151:2296 (1993); Chothia et al., *J. Mol. Biol.*, 196:901 (1987). Another method uses a particular framework derived from the consensus sequence of all human antibodies of a particular subgroup of light or heavy chains. The same framework may be used for several different humanized antibodies. Carter et al., *Proc. Natl. Acad. Sci. USA*, 89:4285 (1992); Presta et al., *J. Immunol.*, 151:2623 (1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Various forms of the humanized antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

4) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); U.S. Pat. No. 5,591,669 and WO 97/17852.

Alternatively, phage display technology can be used to produce human antibodies and antibody fragments in vitro, from immunoglobulin variable (V) domain gene repertoires from unimmunized donors. McCafferty et al., *Nature* 348: 552-553 (1990); Hoogenboom and Winter, *J. Mol. Biol.* 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., *Curr. Opin Struct. Biol.* 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also, U.S. Pat. Nos. 5,565,332 and 5,573,905.

The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., *J. Immunol.* 147(1): 86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368: 812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

Finally, human antibodies may also be generated in vitro by activated B cells (see U.S. Pat. Nos. 5,567,610 and 5,229, 275).

5) Antibody Fragments

In certain circumstances there are advantages to using antibody fragments, rather than whole antibodies. Smaller fragment sizes allow for rapid clearance, and may lead to improved access to solid tumors.

Various techniques have been developed for the production of antibody fragments. Traditionally, these fragments were derived via proteolytic digestion of intact antibodies (see, e.g., Morimoto et al., *J Biochem Biophys. Method.* 24:107-117 (1992); and Brennan et al., *Science* 229:81 (1985)). However, these fragments can now be produced directly by recombinant host cells. Fab, Fv and scFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ with increase in vivo half-life is described in U.S. Pat. No. 5,869,046. In other embodiments, the antibody of choice is a single chain Fv fragment (scFv). See WO 93/16185; U.S. Pat. No. 5,571,894 and U.S. Pat. No. 5,587,458. The antibody fragment may also be a "linear antibody", e.g., as described in U.S. Pat. No. 5,641,870. Such linear antibody fragments may be monospecific or bispecific.

6) Antibody Dependent Enzyme-Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO 81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to convert it into its more active, cytotoxic form.

Enzymes that are useful in the method of this invention include, but are not limited to, glycosidase, glucose oxidase, human lysozyme, human glucuronidase, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anticancer drug 5-fluorouracil; proteases, such as serratia protease, thermolysin, subtilisin, carboxypeptidases (e.g., carboxypeptidase G2 and carboxypeptidase A) and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes" can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The above enzymes can be covalently bound to the polypeptide or antibodies described herein by techniques well known in the art such as the use of the heterobifunctional cross-linking agents discussed above. Alternatively, fusion proteins comprising at least the antigen binding region of the antibody of the invention linked to at least a functionally active portion of an enzyme of the invention can be constructed using recombinant DNA techniques well known in the art (see, e.g. Neuberger et al., *Nature* 312: 604-608 (1984)).

7) Bispecific and Polyspecific Antibodies

Bispecific antibodies (BsAbs) are antibodies that have binding specificities for at least two different epitopes, including those on the same or another protein. Alternatively, one arm can be armed to bind to the target antigen, and another arm can be combined with an arm that binds to a triggering molecule on a leukocyte such as a T-cell receptor molecule (e.g., CD3), or Fc receptors for IgG (FcγR) such as FcγRI (CD64), FcγRII (CD32) and FcγRIII (CD16), so as to focus and localize cellular defense mechanisms to the target antigen-expressing cell. Such antibodies can be derived from full length antibodies or antibody fragments (e.g. F(ab')$_2$ bispecific antibodies).

Bispecific antibodies may also be used to localize cytotoxic agents to cells which express the target antigen. Such antibodies possess one arm that binds the desired antigen and another arm that binds the cytotoxic agent (e.g., saporin, anti-interferon-a, vinca alkoloid, ricin A chain, methotrexate or radioactive isotope hapten). Examples of known bispecific antibodies include anti-ErbB2/anti-FcgRIII (WO 96/16673), anti-ErbB2/anti-FcgRI (U.S. Pat. No. 5,837,234), anti-ErbB2/anti-CD3 (U.S. Pat. No. 5,821,337).

Methods for making bispecific antibodies are known in the art. Traditional production of full length bispecific antibodies is based on the coexpression of two immunoglobulin heavy-chain/light chain pairs, where the two chains have different specificities. Millstein et al., *Nature,* 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecules provides for an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA*, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147: 60 (1991).

Exemplary bispecific antibodies may bind to two different epitopes on a given molecule. Alternatively, an anti-protein arm may be combined with an arm which binds to a triggering molecule on a leukocyte such as a T-cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

8) Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and N2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

9) Heteroconjugate Antibodies

Heteroconjugate antibodies are also within the scope of the present invention. Heteroconjugate antibodies are composed of two covalently joined antibodies. For example, one of the antibodies in the heteroconjugate can be coupled to avidin, the other to biotin. Such antibodies have, for example, been proposed to target immune system cells to unwanted cells, U.S. Pat. No. 4,676,980, and for treatment of HIV infection. WO 91/00360, WO 92/200373 and EP 0308936. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

10) Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced antitumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

11) Immunoconjugates

The invention also pertains to immunoconjugates or antibody-drug conjugates (ADC), comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate). Such ADC must show an acceptable safety profile.

The use of ADCs for the local delivery of cytotoxic or cytostatic agents, e.g., drugs to kill or inhibit tumor cells in the treatment of cancer [Syrigos and Epenetos, *Anticancer Research* 19: 605-14 (1999); Niculeascu-Duvaz and Springer, *Adv. Drug Del. Rev.* 26: 151-72 (1997); U.S. Pat. No. 4,975,278] theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., *Lancet*, 603-05 (1986); Thorpe, (1985) *Antibody Carriers Of Cytotoxic Agents In Cancer Therapy: A Review*, in *Monoclonal Antibodies '84: Biological And Clinical Applications*, A. Pinchera et al. (eds), pp. 475-506). Maximal efficacy with minimal toxicity is sought thereby. Both polyclonal antibodies and monoclonal antibodies have been reported as useful in these strategies (Rowland et al., *Cancer Immunol. Immunother.* 21:183-87 (1986)). Drugs used in these methods include daunomycin, doxorubicin, methotrexate, and vindesine. Toxins used in antibody-toxin conjugates include bacterial toxins such as diphtheria toxin, plant toxins such as ricin, small molecule toxins such as geldanamycin (Mandler et al. *J. Nat. Cancer Inst.* 92(19):1573-81 (2000); Mandler et al., *Bioorganic & Med. Chem. Letters* 10:1025-28 (2000); Mandler et al. *Bioconjugate Chem.* 13: 786-91 (2002)), maytansinoids (EP 1391213; Liu et al., *Proc. Natl. Acad. Sci. USA* 93: 8618-23 (1996)), and calicheamicin (Lode et al., *Cancer Res.* 58:2928 (1998); and Hinman et al., *Cancer Res.* 53:3336-42 (1993)). The toxins may exert their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Chemotherapeutic agents useful in the generation of such immunoconjugates have been described above, and include BCNU, streptozoicin, vincristine, vinblastine, adriamycin and 5-fluorouracil.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triamine-pentaacetic acid (MX-DTPA) is an exemplary chelating agent for conjugation of radionucleotide to the antibody. See, for example, WO 1994/11026.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al., *Cancer Res.* 52:127-131 (1992)) may be used.

Additionally, the small molecule toxins such as calicheamicin, maytansine (U.S. Pat. No. 5,208,020), trichothene and CC1065 are also contemplated as conjugatable toxins for use with the inventive formulation. In one embodiment, the full length antibody or antigen binding fragments thereof can be conjugated to one or more maytansinoid molecules (e.g., about 1 to about 10 maytansinoid molecules per antibody molecule). Maytansinoids are mitotic inhibitors which act by inhibiting tubulin polymerization. Maytansinoids, isolated from natural sources or prepared synthetically, including maytansine, maytansinal and derivatives and analogues thereof have been described, see e.g., U.S. Pat. No. 5,208,020 and references cited therein (see col. 2, line 53 to col. 3, line 10) and U.S. Pat. Nos. 3,896,111 and 4,151,042. Methods of preparing antibody-maytansinoid conjugates are also described in U.S. Pat. No. 5,208,020. In a preferred embodiment, a maytansinoid is linked to the antibody via a disulfide or other sulfur-containing linker group. Maytansine may, for example, be converted to May-SS-Me, which may be reduced to May-SH3 and reacted with modified antibody to generate a maytansinoid-antibody immunoconjugate. Chari et al., *Cancer Res.* 52: 127-131 (1992). The antibody can be modified by known methods and the antibody containing free or protected thiol groups is then reacted with a disulfide containing maytansinoid to produce the conjugate. The cytotoxicity of the antibody-maytansinoid conjugate can be measured in vitro or in vivo by known methods and the $IC_{50}$ determined.

Calicheamicin is another immunoconjugate of interest. The calicheamicin family of antibiotics are capable of producing double-stranded DNA breaks at sub-picomolar concentrations. Structural analogues of calicheamicin which may be used include, but are not limited to, $\gamma_1^1$, $\alpha_2^1$, $\alpha_3^1$, N-aceytl-$\gamma_1^1$, PSAG and $\theta_1^1$ (Hinman et al., *Cancer Res.* 53:3336-3342 (1993) and Lode et al., *Cancer Res.* 58:2925-2928 (1998)). Other anti-tumor drugs that the antibody can be conjugated to include QFA which is an antifolate. Both calicheamicin and QFA have intracellular sites of actions and do not readily cross the plasma membrane. Therefore, cellular uptake of these agents through antibody mediated internalization greatly enhances their cytotoxic effects.

Immunoconjugates formed between an antibody and a compound with nucleolytic activity (e.g., a ribonuclease or DNA endonuclease such as deoxyribonuclease, DNase) are also contemplated.

In the ADCs of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

$$Ab\text{-}(L\text{-}D)_p \qquad \text{Formula I}$$

Nucleophilic groups on antibodies include, but are not limited to: (i) N-terminal amine groups, (ii) side-chain amine groups, e.g. lysine, (iii) side-chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

ADCs of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups that may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Domen et al., *J. Chromatog.*, 510: 293-302 (1990)). In another embodiment, proteins containing N-terminal serine or threonine residues can react with sodium meta-periodate, resulting in production of an aldehyde in place of the first amino acid (Geoghegan and Stroh, *Bioconjugate Chem.* 3:138-46 (1992); U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide that does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

The ADCs herein are optionally prepared with cross-linker reagents: BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), which are commercially available (e.g., Pierce Biotechnology, Inc., Rockford, Ill.).

The antibody may also be conjugated to a highly radioactive atom. A variety of radionuclides are available for the production of radioconjugated antibodies. Examples include $At^{211}$, $Bi^{212}$, $I^{131}$, $In^{131}$, $Y^{90}$, $Re^{186}$, $Re^{188}$, $Sm^{153}$, $P^{32}$ and $Pb^{212}$ and radioactive isotopes of Lu. When the conjugate is used for diagnosis, it may comprise a radioactive atom for scintigraphic studies, for example $Tc^{99}$ or $I^{123}$, or a spin label for nuclear magnetic resonance (nmr) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such $Tc^{99}$ or $I^{123}$, $Re^{186}$, $Re^{188}$ and $In^{111}$ can be attached via a cysteine residue in the peptide. Yttrium-90 can be attached via a lysine residue. The IODOGEN® method can be used to incorporate iodine-123, Fraker et al., *Biohem. Biophys. Res. Commun.* 80:49-57 (1978). Other methods of conjugating radionuclides are described in "Monoclonal Antibodies in Immunoscintigraphy," (Chatal, CRC Press 1989).

Alternatively, a fusion protein comprising the antibody and the cytotoxic agent may be made by recombinant techniques or peptide synthesis. The length of DNA may comprise respective regions encoding the two portions of the conjugate either adjacent to one another or separated by a region encoding a linker peptide which does not destroy the desired properties of the conjugate.

In another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

12) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table A below under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

Amino Acid Substitutions

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |

TABLE A-continued

Amino Acid Substitutions

| Original Residue | Exemplary Substitutions | Preferred Substitutions |
| --- | --- | --- |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | Ala | ala |
| Ser (S) | Thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and IgE. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-IgE antibody.

13) Other Antibody Modifications

The antibodies of the present invention can be further modified to contain additional nonproteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy*, 20th Ed., Alfonso Gennaro, Ed., Philadelphia College of Pharmacy and Science (2000).

C. Pharmaceutical Formulations

Therapeutic formulations are prepared for storage by mixing the active ingredient having the desired degree of purity with optional pharmaceutically acceptable carriers, excipients or stabilizers (*Remington: The Science and Practice of Pharmacy*, 20th Ed., Lippincott Williams & Wiklins, Pub., Gennaro Ed., Philadelphia, Pa. 2000). Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

When the therapeutic agent is an antibody fragment, the smallest inhibitory fragment which specifically binds to the binding domain of the target protein is preferred. For example, based upon the variable region sequences of an antibody, antibody fragments or even peptide molecules can be designed which retain the ability to bind the target protein sequence. Such peptides can be synthesized chemically and/or produced by recombinant DNA technology (see, e.g., Marasco et al., *Proc. Natl. Acad. Sci. USA* 90: 7889-7893 [1993]).

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition, supra.

Stability of the proteins and antibodies described herein may be enhanced through the use of non-toxic "water-soluble polyvalent metal salts". Examples include $Ca^{2+}$, $Mg^{2+}$, $Zn^{2+}$, $Fe^{2+}$, $Fe^{3+}$, $Cu^{2\pm}$, $Sn^{2+}$, $Sn^{4+}$, $Al^{2+}$ and $Al^{3+}$. Example anions that can form water soluble salts with the above polyvalent metal cations include those formed from inorganic acids and/or organic acids. Such water-soluble salts have a solubility in water (at 20° C.) of at least about 20 mg/ml, alternatively at least about 100 mg/ml, alternatively at least about 200 mg/ml.

Suitable inorganic acids that can be used to form the "water soluble polyvalent metal salts" include hydrochloric, acetic, sulfuric, nitric, thiocyanic and phosphoric acid. Suitable organic acids that can be used include aliphatic carboxylic acid and aromatic acids. Aliphatic acids within this definition may be defined as saturated or unsaturated $C_{2-9}$ carboxylic acids (e.g., aliphatic mono-, di- and tri-carboxylic acids). For example, exemplary monocarboxylic acids within this definition include the saturated $C_{2-9}$ monocarboxylic acids acetic, proprionic, butyric, valeric, caproic, enanthic, caprylic pelargonic and capryonic, and the unsaturated $C_{2-9}$ monocarboxylic acids acrylic, propriolic methacrylic, crotonic and isocrotonic acids. Exemplary dicarboxylic acids include the saturated $C_{2-9}$ dicarboxylic acids malonic, succinic, glutaric, adipic and pimelic, while unsaturated $C_{2-9}$ dicarboxylic acids include maleic, fumaric, citraconic and mesaconic acids. Exemplary tricarboxylic acids include the saturated $C_{2-9}$ tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated polypeptides of this invention include, for example: (1) the inorganic acid metal salts of halides (e.g., zinc chloride, calcium chloride), sulfates, nitrates, phosphates and thiocyanates; (2) the aliphatic carboxylic acid metal salts (e.g., calcium acetate, zinc acetate, calcium proprionate, zinc glycolate, calcium lactate, zinc lactate and zinc tartrate); and (3) the aromatic carboxylic acid metal salts of benzoates (e.g., zinc benzoate) and salicylates.

D. Methods of Treatment:

For the prevention or treatment of disease, the appropriate dosage of an active agent, will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

A preferred method of treatment is the treatment of IgE-mediated disorders. IgE mediated disorders includes atopic disorders, which are characterized by an inherited propensity to respond immunologically to many common naturally occurring inhaled and ingested antigens and the continual production of IgE antibodies. Specific atopic disorders include allergic asthma, allergic rhinitis, atopic dermatitis and allergic gastroenteropathy. Atopic patients often have multiple allergies, meaning that they have IgE antibodies to, and symptoms from, many environmental allergens, including pollens, fungi (e.g., molds), animal and insect debris and certain foods.

However disorders associated with elevated IgE levels are not limited to those with an inherited (atopic) etiology. Other disorders associated with elevated IgE levels, that appear to be IgE-mediated and are treatable with the formulations of this present invention include hypersensitivity (e.g., anaphylactic hypersensitivity), eczema, urticaria, allergic bronchopulmonary aspergillosis, parasitic diseases, hyper-IgE syndrome, ataxia-telangiectasia, Wiskott-Aldrich syndrome, thymic alymphoplasia, IgE myeloma and graft-versus-host reaction.

Allergic rhinitis, also known as allergic rhinoconjunctivitis or hay fever, is the most common manifestation of an atopic reaction to inhaled allergens, the severity and duration of which is often correlative with the intensity and length of exposure to the allergen. It is a chronic disease, which may first appear at any age, but the onset is usually during childhood or adolescence. A typical attack consists of profuse watery rhinorrhea, paroxysmal sneezing, nasal obstruction and itching of the nose and palate. Postnasal mucus drainage also causes sore throat, throat clearing and cough. There can also be symptoms of allergic blepharoconjunctivitis, with intense itching of the conjunctivae and eyelids, redness, tearing, and photophobia. Severe attacks are often accompanied by systemic malaise, weakness, fatigue, and sometimes, muscle soreness after intense periods of sneezing.

Asthma, also known as reversible obstructive airway disease, is characterized by hyperresponsiveness of the tracheobronchial tree to respiratory irritants and bronchoconstrictor chemicals, producing attacks of wheezing, dyspnea, chest tightness, and cough that are reversible spontaneously or with treatment. It is a chronic disease involving the entire airway, but varies in severity from occasional mild transient episodes to severe, chronic, life-threatening bronchial obstruction. Asthma and atopy may coexist, but only about half of asthmatics are also atopic, and an even smaller percentage of atopic patients also have asthma. However, atopy and asthma are not entirely independent in that asthma occurs more frequently among atopic than amongst nonatopic individuals, especially during childhood. Asthma has further been historically broken down into two subgroups, extrinsic asthma and intrinsic asthma.

Extrinsic asthma, also known as allergic, atopic or immunologic asthma, is descriptive of patients that generally develop asthma early in life, usually during infancy or childhood. Other manifestations of atopy, including eczema or allergic rhinitis often coexist. Asthmatic attacks can occur during pollen seasons, in the presence of animals, or on exposure to house dust, feather pillows, or other allergens. Skin tests show positive wheal-and-flare reactions to the causative allergens. Interestingly, total serum IgE concentrations are frequently elevated, but are sometimes normal.

Intrinsic asthma, also known as nonallergic or idopathic asthma, typically first occurs during adult life, after an apparent respiratory infection. Symptoms include chronic or recurrent bronchial obstruction unrelated to pollen seasons or exposure to other allergens. Skin tests are negative to the usual atopic allergens, serum IgE concentration is normal. Additional symptoms include sputum blood and eosinophilia. Other schemes for classifying asthma into subgroups, like aspirin-sensitive, exercise-induced, infectious and psychologic merely define external triggering factors that affect certain patients more so than others.

Finally, it is important to note that while some classifications have historically associated only allergic asthma with IgE dependency, there is now strong statistically significant data showing a correlation between IgE and asthma (both allergic and non-allergic). Chapter 27, "The Atopic Diseases", A. I. Terr in Medical Immunology, 9th Ed., Simon and Schuster, Stites et al, Ed. (1997). As a result, the term "IgE-mediated disorders", for purposes of this patent application, includes both allergic and non-allergic asthma.

Physical signs of an asthma attack include tachypnea, audible wheezing, and use of the accessory muscles of respiration. Rapid pulse and elevated blood pressure are also typically present, as are elevated levels of eosinophils in the peripheral blood and nasal secretions. Pulmonary functions show a decrease in flow rates and 1 second forced expiratory volume ($FEV_1$). The total lung capacity and functional residual capacity are typically normal or slightly increased, but may be decreased with extreme bronchospasm.

The pathology of asthma can be distinguished by early phase and late phase reactions. The early phase is characterized by smooth muscle contraction, edema and hypersecretion, while the late phase reactions are characterized by cellular inflammation. Asthma can be induced by various nonspecific triggers including infections (e.g., viral respiratory infections), physiologic factors (e.g., exercise, hyperventilation, deep breathing, psychologic factors), atmospheric factors (e.g., sulfur dioxide, ammonia, cold air, ozone, distilled water vapor), ingestants (e.g., propranolol, aspirin, nonsteroidal anti-inflammatory drugs), experimental inhalants (e.g., hypertonic solutions, citric acid, histamine, methacholine, prostaglandin $F_{2\alpha}$) and occupational inhalants (e.g., isocyanates). Various additional occupational or environmental allergens that cause allergic asthma can include animal products, insect dusts, sea creatures, plant products, fruits, seeds, leaves and pollens, organic dyes and inks, microbial agents, enzymes, therapeutic agents, sterilizing agents, and inorganic and organic chemicals.

Atopic dermatitis, also known as eczema, neurodermatitis, atopic eczema or Besnier's prurigo, is common chronic skin disorder specific to a subset of patients with the familial and immunologic features of atopy. The essential feature is a pruritic dermal inflammatory response, which induces a characteristic symmetrically distributed skin eruption with predilection for certain sites. There is also frequent overproduction of IgE by B lymphocytes. While atopic dermatitis is classified as a cutaneous form of atopy because it is associated with allergic rhinitis and asthma and high IgE levels, the severity of the dermatitis, however, does not always correlate with exposure to allergens on skin testing, and desensitization (unlike other allergic diseases) is not effective treatment. While high serum IgE is confirmatory of a diagnosis of allergic asthma, normal levels do not preclude it. Onset of the disease can occur at any age, and lesions begin acutely with erythematous edematous papule or plaque with scaling. Itching leads to weeping and crusting, then to chronic lichenification. On the cellular level, acute lesion is edemous and the dermis is infiltrated with mononuclear cells, CD4 lymphocytes. Neutrophils, eosinophils, plasma cells and basophils are rare, but degranulated mast cells are present. Chronic lesions feature epidermal hyperplasia, hyperkeratosis and parakeratosis, and the dermis is infiltrated with mononuclear cells, Langerhans' cells and mast cells. There may also be focal areas of fibrosis, including involvement of the perineurium of small nerves.

Allergic gastroenteropathy, also known as eosinophilic gastroenteropathy, is an unusual atopic manifestation in which multiple IgE food sensitivities are associated with a local gastrointestinal tract mucosal reaction. It is rare in adults, but more common, but transient, in infants. The condition results when ingested food allergens react with local IgE antibodies in the jejunal mucosa liberate mast cell mediators, resulting in gastrointestinal symptoms shortly after the meal. Continued exposure produced chronic inflammation, resulting in gastrointestinal protein loss and hypoproteinemic edema. Blood loss through the inflamed intestinal mucosa may be significant enough to cause iron deficiency anemia. The allergic reaction occurs locally in the upper gastrointestinal mucosa following allergen exposure, but resolves with allergen avoidance.

Anaphylaxis and urticaria are clearly IgE-mediated, but they lack genetic determinants, and have no predilection for atopic individuals. Anaphylaxis is an acute, generalized allergic reaction with simultaneous involvement of several organ systems, usually cardiovascular, respiratory, cutaneous and gastrointestinal. The reaction is immunologically mediated, and it occurs on exposure to an allergen to which the subject has been previously sensitized. Urticaria and angioedema refers to the physical swelling, erythema and itching resulting from histamine stimulated receptor in superficial cutaneous blood vessels, and is the hallmark cutaneous feature of systemic anaphylaxis. Systemic anaphylaxis is the occurrence of an IgE-mediated reaction simultaneously in multiple organs resulting from drug, insect venom or food. It is caused suddenly by allergen induced, mast cell loaded IgE, resulting in profound and life-threatening alteration in the functioning of various vital organs. Vascular collapse, acute airway obstruction, cutaneous vasodilation and edema, and gastrointestinal and genitourinary muscle spasm occur almost simultaneously, although not always to the same degree.

The pathology of anaphylaxis includes angioedema and hyperinflated lungs, with mucous plugging of airways and focal atelectasis. On a cellular level, the lungs appear similarly as during an acute asthma attack, with hypersecretion of bronchial submucosal glands, mucosal and submucosal edema, peribronchial vascular congestion and eosinophilia in the bronchial walls. Pulmonary edema and hemorrhage may be present. Bronchial muscle spasm, hyperinflation, and even rupture of alveoli may also be present. Important features of human anaphylaxis include edema, vascular congestion, and eosinophilia in the lamina propria of the larynx, trachea, epiglottis and hypopharynx.

Exposure to the allergen may be through ingestion, injection, inhalation or contact with skin or mucous membrane. The reaction begins within seconds or minutes after exposure to the allergen. There may be an initial fright or sense of impending doom, followed rapidly by symptoms in one or more target organ systems: cardiovascular, respiratory, cutaneous or gastrointestinal.

The allergens responsible for anaphylaxis differ from those commonly associated with atopy. Foods, drugs, insect venoms or latex are the common sources. Food allergens includes those found in crustaceans, mollusks (e.g., lobster, shrimp, crab), fish, legumes (e.g., peanuts, peas, beans, licorice), seeds (e.g. sesame, cottonseed, caraway, mustard, flaxseed, sunflower), nuts, berries, egg whites, buckwheat and milk. Drug allergens include those found in heterologous proteins and polypeptides, polysaccharides and haptenic drugs. Insect allergens include Hymenoptera insects, including the honeybee, yellow jacket, hornet, wasp and fire ant.

While epinephrine is the typical treatment for anaphylaxis, antihistamine or other histamine blockers are typically prescribed for less severe urticaria or angioedemic reaction.

E. Combination Therapies

The method of the invention can be combined with known methods of treatment for IgE-mediated disorder, either as combined or additional treatment steps or as additional components of a therapeutic formulation.

For example, antihistamines, especially non-sedating antihistamines may be administered before, prior to, or commensurate with the anti-IgE antibodies of the invention. Suitable antihistamines include those of the alkylamine (e.g., chlorpheniramine), ethanolamine (e.g., diphenhydramine) and phenothiazine (e.g., promethazine). While many antihistamines antagonize the pharmacological effects of histamine by blocking its receptor sites on the effector cells, other common antihistamine drugs operate by blocking histamine release from mast cells that have been sensitized and armed with allergen-specific IgE (e.g., cromolyn sodium). Example antihistamines include astemizole, azatadine maleate, bropheniramine maleate, carbinoxamine maleate, cetirizine hydrochloride, clemastine fumarate, cyproheptadine hydrochloride, dexbrompheniramine maleate, dexchlorpheniramine maleate, dimenhydrinate, diphenhydramine hydrochloride, doxylamine succinate, fexofendadine hydrochloride, terphenadine hydrochloride, hydroxyzine hydrochloride, loratidine, meclizine hydrochloride, tripelannamine citrate, tripelennamine hydrochloride, triprolidine hydrochloride.

Particular symptoms of IgE-mediated disorders (e.g., early phase reactions) can be ameliorated with sympathomimetics or drugs having bronchodialator effect. Epinephrine is a broad acting alpha and beta-adrenergic often administered subcutaneously in a dose of 0.2-0.5 mL of 1:100 aqueous solution. A longer acting form of epinephrine (i.e., terbutaline) in 1:200 suspension is also used when a longer duration effect is desired. Suitable additional beta-adrenergics include albuterol, pirbuterol, metaproterenol, salmeterol, isoetharine and formeterol for administration nasally (e.g., hand-held nebulizer, intermittent positive-pressure breathing device, or metered-dose pressurized inhalers) or orally.

Bronchodilation can also be achieved through administration of xanthines, especially when they are administered in combination with the above sympathomimetic drugs. Example xanthines include aminophylline (iv. 250-500 mg) and theophylline (oral, 10-20 μg/ml serum concentration).

Other symptoms from various IgE-mediated disorders (e.g., late phase reactions) can be attenuated by treatment with glucocorticoids or other drugs having anti-inflammatory effects. Prednisone (30-60 mg daily) is administered systemically for severe attacks, while beclomethasone dipropionate, triamcinolone acetonide and flunisolide are administered in aerosolized form as long-term maintenance therapy. Additional corticosteroids that have anti-inflammatory effects include: betamethasone, budesonide, dexamethasone, fludrocortisone acetate, flunisolide, fluticasone propionate, hydrocortisone, methylprednisolone, prednisolone, prednisone, triamcinolone.

Non-steroidal anti-inflammatory drugs that may also be used in combination with the therapeutic methods of the invention include, acetaminophen, aspirin, bromfenac sodium, diclofenac sodium, diflunisal, etodolac, fenoprofen calcium, flurbiprofen, ibuprofen, indomethacin, ketoprofen, meclofenamate sodium, mefenamic acid, nabumetone, naproxen, naproxen sodium, oxyphenbutazone, phenylbutzone, piroxicam, sulindac, tolmetin sodium.

Additionally, the maximum therapeutic benefit may also be achieved with the administration of decongestants (e.g., phenylephrine, phenylpropanolamine, pseudoephadrin), cough suppressants (e.g., dextromethorphan, codeine, or hydrocodone) or analgesic (e.g., acetaminophen, aspirin).

Allergen desensitization is a treatment form in which allergens are injected into the patient for the purpose or reducing or eliminating the allergic response. It is also known as allergen immunotherapy, hyposensitization or allergy injection therapy. It is often used in combination with other allergy treatments, but not often as a primary treatment. It has been successfully employed when allergen avoidance is impossible. A typical allergen desensitization treatment incorporates subcutaneous injection of sterile allergen in increasing doses once or twice a week until a dose is achieved that produces a transient small local area of inflammation at the injection site. The dose is then given on a maintenance schedule once every 2-4 weeks. Allergic desensitization is most often used in the treatment of allergic asthma and allergic rhinitis, although it has had success in treating anaphylaxis. Desensitization has also been effectively used through the use of adjuvants, such as incomplete Freund's adjuvant, which is an emulsion of aqueous antigen in mineral oil. The physiological effect creates an insoluble liquid depot from which droplets of allergen are gradually released. Another form of allergen desensitization is to polymerize monomeric allergens with glutaraldehyde to create a molecule with relatively low allergenicity (i.e., causes allergic response), while retaining an effective degree of immunogenicity.

F. Pharmaceutical Dosages:

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the polypeptides or antibodies described herein are used, normal dosage amounts may vary from about 10 ng/kg up to about 100 mg/kg of mammal body weight or more per day, preferably about 1 mg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is within the scope of the invention that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

G. Administration of the Formulation

The formulations of the present invention, including but not limited to reconstituted formulations, are administered to a mammal in need of treatment with the protein, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In preferred embodiments, the formulations are administered to the mammal by subcutaneous (i.e. beneath the skin) administration. For such purposes, the formulation may be injected using a syringe. However, other devices for administration of the formulation are available such as injection devices (e.g. the INJECT-EASE™ and GENJECT™ devices); injector pens (such as the GENPEN™); auto-injector devices, needleless devices (e.g. MEDIJECTOR™ and BIOJECTOR™); and subcutaneous patch delivery systems.

In a specific embodiment, the present invention is directed to kits for a single dose-administration unit. Such kits comprise a container of an aqueous formulation of therapeutic protein or antibody, including both single or multi-chambered pre-filled syringes. Exemplary pre-filled syringes are available from Vetter GmbH, Ravensburg, Germany.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. The protein is suitably administered to the patient at one time or over a series of treatments and may be administered to the patient at any time from diagnosis onwards. The protein may be administered as the sole treatment or in conjunction with other drugs or therapies useful in treating the condition in question.

Where the protein of choice is an antibody, from about 0.1-20 mg/kg is an initial candidate dosage for administration to the patient, whether, for example, by one or more separate administrations. However, other dosage regimens may be useful. The progress of this therapy is easily monitored by conventional techniques.

Uses for an anti-IgE formulation (e.g., rhuMAbE-25, rhMAbE-26, Hu-901) include the treatment or prophylaxis of IgE-mediated allergic diseases, parasitic infections, interstitial cystitis and asthma, for example. Depending on the disease or disorder to be treated, a therapeutically effective amount (e.g. from about 1-15 mg/kg) of the anti-IgE antibody is administered to the patient.

H. Articles of Manufacture

In another embodiment of the invention, an article of manufacture is provided which contains the formulation and preferably provides instructions for its use. The article of manufacture comprises a container. Suitable containers include, for example, bottles, vials (e.g. dual chamber vials), syringes (such as single or dual chamber syringes) and test tubes. The container may be formed from a variety of materials such as glass or plastic. The container holds the formulation. The label, which is on, or associated with the container may indicate directions for reconstitution and/or use. The label may further indicate that the formulation is useful or intended for subcutaneous administration. The container holding the formulation may be a multi-use vial, which allows for repeat administrations (e.g. from 2-6 administrations) of the reconstituted formulation. The article of manufacture may further comprise a second container comprising a suitable diluent (e.g. BWFI). Upon mixing of the diluent and the lyophilized formulation, the final protein concentration in the reconstituted formulation will generally be at least 50 mg/ml. The article of manufacture may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All citations throughout the disclosure are hereby expressly incorporated by reference.

In another embodiment, the invention provides for an article of manufacture comprising the formulations described herein for administration in an auto-injector device. An auto-injector can be described as an injection device that upon activation, will deliver its contents without additional necessary action from the patient or administrator. They are particularly suited for self-medication of therapeutic formulations when the delivery rate must be constant and the time of delivery is greater than a few moments.

EXAMPLE 1

Isolation of Primate IgE

Human IgE was cloned from the human IgE myeloma cell line U266 (ATCC, Manassas, Va., TIB #196). Rhesus and cyno IgE sequences were determined by cloning and sequencing the IgE from cDNA derived from rhesus and cyno peripheral blood mononuclear cells that had been stimulated to generated IgE-switched cells (PBMC). Forward and reverse primers (shown below) were designed from the human IgE sequences. An upstream forward primer was designed just upstream of the CH2 domain. The reverse primer was designed at the end of the transmembrane domain. Rhesus and Cyno PBMC was obtained from the California National Primate Research Center (Davis, Calif.). 5×10[6] PBMC were cultured with IL-4 (100 ng/ml) and CD40L (3 µg/ml) (R&D Systems, Minneapolis, Minn., #204-IL and #617-CL respectively) for 4 days. Cells were then harvested, RNA was prepared (RNeasy Mini Kit, #74106, Qiagen, Valencia, Calif.), and cDNA made using BD Sprint Powerscript oligo dT priming kit (BD Biosciences, San Jose, Calif., #639558). RT-PCR was then performed [94° C. 2 minutes; 94° C. 15 seconds; 60° C. 30 seconds; 68° C. 2 minutes; 30 cycles; 68° C. 10 minutes]. Taq polymerase was added (10 minutes 72° C.) after the indicated cycles to add A overhangs for TA cloning (Invitrogen, Carlsbad, Calif., #45-0641). PCR products were cloned by TOPO-TA cloning and clones were then sequence verified (Genentech, Inc.). Human, Rhesus and Cyno sequences were aligned using in house analysis programs (Genentech, Inc.). The following homologies are for sequences between the CH2 and transmembrane domains. Between Rhesus (432 amino acids) and Cyno (431 amino acids) there were 6 differences which is approximately 98.6% homology. Between human and Rhesus there were 53 differences equaling 87.7% homology. Human and Cyno there was 56 differences equaling 87% homology (See FIG. 1).

Primers Used for Cloning:
Forward primers upstream of CH2 sequence:

(SEQ ID NO: 63)
5'-ccgcccaccgtgaagatcttacagtc

Reverse primer at the end of the transmembrane domain:

(SEQ ID NO: 64)
5'-cggctcgagactaggcgtggggctggaggacgttg

EXAMPLE 2

Isolation of Anti-IgE/M1' Abs

Generation of the CH3-CH4-M1'/Fc Fusion Protein

The human IgE CH3-CH4-M1'/Fc fusion protein was generated by PCR amplification of the human IgE CH3-CH4-M1' domains, plus an additional 15 amino acids immediately downstream of the M1' domain from cDNA prepared from U266 cells (ATTC Manassas, Va., TIB#196). RNA was prepared from U266 cells (RNeasy Mini Kit, #74106, Qiagen, Valencia, Calif.) and cDNA made using BD Sprint Powerscript oligo dT priming (BD Biosciences, San Jose, Calif., #639558). RT-PCR was performed, and the PCR product cloned by TOPO-TA cloning (Invitrogen, Carlsbad, Calif., #45-0641). An N-terminal signal sequence was added by PCR mutagenesis for expression in mammalian cells, and the signal sequence+CH3+CH4+M1'+15 amino acids was cloned into an expression vector (pRK huIgG1 Fc; Genentech) to generated a C-terminal fusion with the human IgG1 Fc region. The sequence of the final protein, including signal sequence and human IgG1 Fc is as follows:

(SEQ ID NO: 65)
MGWSCIILFLVATATGVHSTKKCADSNPRGVSAYLSRPSPFDLFIRKSPT

ITCLVVDLAPSKGTVNLTWSRASGKPVNHSTRKEEKQRNGTLTVTSTLPV

GTRDWIEGETYQCRVTHPHLPRALMRSTTKTSGPRAAPEVYAFATPEWPG

SRDKRTLACLIQNFMPEDISVQWLHNEVQLPDARHSTTQPRKTKGSGFFV

FSRLEVTRAEWEQKDEFICRAVHEAASPSQTVQRAVSVNPGLAGGSAQSQ

RAPDRVLCHSGQQQGLPRAAGGSVPHPRCHCGAGRADWPGPPELDVCVEE

AEGEAPWRAQVTDKAAHYTLCPPCPAPELLGGPSVFLFPPKPKDTLMISR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFF

LYSKLTVDKSRWQQGNVFSCSVMHEALHNHYTQKSLSLSPGK

The protein was produced by transient transfection of CHO cells (Genentech), and protein was purified from cell culture supernatant using standard Protein A sepharose column chromatography techniques.

Immunization and Creation of Hybridomas

A panel of pan-specific antibodies that selectively bind the M1' portion of human IgE-M1' were generated using the CH3-CH4-M1'/Fc protein. Each hind footpad of a BALB/c mouse was injected with 1 µg CH3-CH4-M1'/Fc resuspended in monophosphoryl-lipid A and trehalose dicorynomycolate (MPL™+TDM) adjuvant (Corixa, Hamilton, Mont.) at 3- to 4-day intervals. Serum was taken after 8 boosts and titered by enzyme-linked immunosorbant assay (ELISA) and fluorescence-activated cell sorting and flow cytometry (FACS screening, see next section) to ensure that the mouse had a good immune response to CH3-CH4-M1'/Fc. Three days after the final boost, popliteal node cells were fused with the mouse myeloma cell line P3X63Ag.U.1 (see, for example, Chuntharapai et al., 1997, *Methods Enzymol.* 288:15-27). Fused hybridoma cells were selected from unfused popliteal node or myeloma cells using hypoxanthin-aminopterin-thymidine (HAT) selection in Medium D from the ClonaCell® hybridoma selection kit (StemCell Technologies, Inc., Vancouver, BC, Canada), resulting the generation of 4224 clones.

Screening for Pan-Specific Anti-Human M1' Antibodies

Hybridoma clones generated as previously described were screened for production of monoclonal antibodies binding to the M1' region of the CH3-CH4-M1'/Fc protein, the M1' region of human IgE-M1' stably expressed on the surface of the A20 mouse B-cell lymphoma cell line (IgE-M1'/A20), and the M1' region of human IgE-M1' stably expressed on the surface of the BJAB human B-cell lymphoma cell line (IgE-M1'/BJAB). Negative controls included human CD-4/Fc, human IgE stably expressed on the surface of the A20 mouse B-cell lymphoma cell line (IgE/A20), A20 mouse B-cell lymphoma cell line (A20), human IgE stably expressed on the surface of the BJAB human B-cell lymphoma cell line (IgE/BJAB), and BJAB human B-cell lymphoma cell line (BJAB).

ELISA Screening

To screen the 4224 clones, enzyme-linked immunosorbant assay (ELISA) was performed generally as described in Baker et al., 2002, *Trends Biotechnol.*, 20:149-156. Assays were performed in both 384- and 96-well plates. Briefly, a 384- (or a 96-) well plate was coated with 50 µl of goat anti-human IgG Fc (MP Biomedicals, Irvine, Calif.) at a concentration of 2 µg/ml in coating buffer (0.05 M carbonate buffer, pH 9.6), sealed, and stored overnight at 4° C. After removing the coating solution, 80 µl (or 200 µl for a 96-well plate) of assay/blocking solution containing 0.5% bovine serum albumin and 0.05% Tween®-20 in PBS (pH 7.4) (ELISA diluent) was added to each well, and plates were incubated at room temperature for one hour with agitation. Wells were then washed three times with 100 µl (or 300 µl for a 96-well plate) 0.05% Tween®-20 in PBS (wash buffer).

After the washing step, 50 µl (or 100 µl for a 96-well plate) of antigen solution containing 0.4 µg/ml of CH3-CH4-M1'/Fc or human CD-4/Fc in ELISA diluent was added to each well, and plates were incubated at room temperature for one hour with agitation. The wells were washed three times with wash buffer as before. Supernatant from individual hybridoma clones was added such that one well with CH3-CH4-M1'/Fc and one well with human CD-4/Fc each received 50 µl (or 100 µl for a 96-well plate) of supernatant from a single hybridoma clone. Plates were incubated at room temperature for one hour with agitation, and the wells were washed three times with wash buffer as before.

After washing, 50 µl (or 100 µl for a 96-well plate) of a 1:1000 dilution of sheep anti-mouse IgG coupled to horseradish peroxidase (no cross-reactivity to human IgG (MP Biomedicals)) in ELISA diluent was added to each well. Plates were incubated at room temperature for one hour with agitation, washed three times with wash buffer as before, and patted dry. Wells were developed by adding 50 µl (or 100 µl for a 96-well plate) of tetramethylbenzidine (TMB) microwell peroxidase substrate (BioFX Laboratories, Owing Mills, Md., catalog #TMBW-0100-01) to each well and incubating at room temperature for 5-10 minutes or until a good color change was observed. Development was stopped by adding 50 µl (or 100 µl for a 96-well plate) of TMB Stop Solution (BioFX Laboratories catalog #BSTP-0100-01) to each well. Plates were analyzed with a Sunrise plate reader (Tecan US, Inc., Research Triangle Park, N.C.) at 650 nm.

Prebleed and polysera were used as controls. Prebleed samples contained mouse sera prior to immunization, and polysera samples contained mouse anti-sera obtained after 10 immunizations.

FACS Screening

To screen 3221 clones generated in Example 1, fluorescence-activated cell sorting (FACS) was performed using IgE-M1'/A20 and IgE-M1'/BJAB cell lines. IgE/A20, IgE/BJAB, A20, and BJAB cell lines served as negative controls. Cells were resuspended and centrifuged at 500 g for 5 minutes at 4° C. Media was aspirated and cells were resuspended in 4° C. FACSFlow (BD Biosciences, San Jose, Calif.) buffer with 1% fetal bovine serum (cell staining buffer). Cells were centrifuged as before, media aspirated, and cells were resuspended at 2×10$^6$ cells/ml of cell staining buffer at 4° C. Cells were added to 96-well round bottom plates at 50 µl/well (1×10$^5$ cells/well), and 100 µl of supernatant from individual hybridoma clones was added to each well such that each hybridoma supernatant was incubated with one well containing each cell line. The plate was incubated on ice for 30 minutes. The plate was centrifuged at 500 g for 5 minutes at 4° C. and supernatants were aspirated. Each well was resuspended in 200 µl cell staining buffer at 4° C., and the plates were centrifuged as before. Cell staining buffer was aspirated.

After the washing step, cells in each well were resuspended in 100 µl of a 1:1000 dilution of goat anti-mouse IgG Fc coupled to R-phycoerythrin (Jackson Immunoresearch, West Grove, Pa.) in cell staining buffer at 4° C., and plates were incubated in the dark on ice for 30 minutes. The plate was centrifuged at 500 g for 5 minutes at 4° C. and supernatants were aspirated. Each well was resuspended in 200 µl cell staining buffer at 4° C., and the plates were centrifuged as before. Cell staining buffer was aspirated. Cells in each well were resuspended in 200 µl cell staining buffer at 4° C. and transferred to 1.2 ml micro titertubes (Quality Scientific Plastics, Petaluma, Calif.). FACS was performed on a FACScan or FACSCalibur (BD Biosciences).

N-Terminal Sequencing/Isolation of RNA/Sequencing and Cloning

The antibodies were purified from the supernatant of anti-IgE/M1' hybridomas, and were analyzed for N-terminal sequencing for clonality determination in phosphate buffered saline. Each antibody was separated on a Precast 4-20% Tris HCl SDS-PAGE (Invitrogen, Carlsbad, Calif.) under reducing condition. The resolved heavy chain (HC) and light chain (LC) were each subjected to N-terminal sequencing using a Procise 494 N-terminal sequencer (Applied Biosystems, Foster City, Calif.) using the 20-min cycle as described by Henzel et al. *Analytical Biochemistry* 267, 148-160 (1999). The first 25 residues were sequenced to establish monoclonality. When the HC or LC chain of the Ab was blocked with a pyroglutamyl group that made the N-terminal amino acid inaccessible to Edman sequencing, removal of the blocking group was performed prior to sequencing. The pyroglutamyl group was removed with the pyroglutamate aminopeptidase enzyme (PGAP, Sigma, St Louis, Mo.) using the protocol described by Pham et al. *Electrophoresis* 2005, 26 4243-4251.

The sequence of the heavy chain (HC) and light chain (LC) Mr antibodies 7A6, 1C11, 47H4, 26A11, 45C1 and 28E9 were determined to be the following:

```
7A6
                                         (SEQ ID NO: 66)
    HC         QVQLQQSGAELVRPGASVTLSCKAS (SEQ ID NO: 67)
    LC         DIVMSQSPSSLTVSVGEKVTLSCKS

1C11
                                         (SEQ ID NO: 68)
    HC         QVQLQQSGAELVRPGASVTLSCKAS (SEQ ID NO: 69)
    LC         DIVMSQSPSSLAVSVGEKVTMSCKS

47H4
                                         (SEQ ID NO: 70)
    HC         EVKLVESGGGLVQPGGSRKLSCAAS (SEQ ID NO: 71)
    LC         DVVLTQTPLSLPVSLGDQASI

26A11
                                         (SEQ ID NO: 72)
    HC         EVQLQQSGPELVKPGASVKMSCKAS (SEQ ID NO: 73)
    LC         DIQMTQTTSSLSASLGDRVTITCRS

45C1
                                         (SEQ ID NO: 74)
    HC         QIQLVQSGPELKKPGETVK (SEQ ID NO: 75)
    LC         DVVMTQTPLTLSVTIGQPASISCK

28E9
                                         (SEQ ID NO: 76)
    HC         EVKLVESGGGLVQPGGSLRLSCATS (SEQ ID NO: 77)
    LC         DIQMTQSPASLSVSVGETVTFTCR
```

In order to determine the full length sequences, 5' degenerate primers were designed from the N terminal amino acid sequences and known Ig gene segments, and PCR was performed with degenerate downstream heavy and light chain conserved sequences.
Forward Primers

```
7A6
HC FOR.BsiWI
                                          (SEQ ID NO: 78)
5'-tcgacgtacgctcaggttcagctgcagcaatctggggctgagctgg LC FOR.EcoRV
                                          (SEQ ID NO: 79)
5'-gatcgatatcgtgatgtcccagtctcctcctccctaac 1C11
HC FOR.BsiWI
                                          (SEQ ID NO: 80)
5'-tcgacgtacgctcaggttcaattgcagcagtctggggctgagctgg LC FOR.EcoRV
                                          (SEQ ID NO: 81)
5'-gatcgatatcgtaatgtctcagtctccttcctccctagc 47H4
HC 9.1HCF.BsiWI
                                          (SEQ ID NO: 82)
5'-tcgacgtacgctgaggtgaagttggtggagtctggggaggcttag LC 47H4LCF.EcoRV
                                          (SEQ ID NO: 83)
5'-gatcgatatcgtgctgactcagactccactctccctgcc 26A11
HC C7F7HCF.BsiWI
                                          (SEQ ID NO: 84)
5'-tcgacgtacgctgaggtccagctccagcagtctggacctgagc LC 2B4LCF.EcoRV
                                          (SEQ ID NO: 85)
5'-gatcgatatccagatgacccaaactacatcctccctg 45C1
HC 2G6HCF.BsiWI
                                          (SEQ ID NO: 86)
5'-tcgacgtacgctcagatccagttggtgcagtctggacctgagctg LC 9C10LCF.EcoRV
                                          (SEQ ID NO: 87)
5'-gatcgatatcgtgatgacgcagactccactcactttgtcgg 28E9
HC 9.1HCFBsiWI
                                          (SEQ ID NO: 88)
5'-tcgacgtacgctgaggtgaagctggtggagtctgaaggaggcttgg LC 5E10.LCF.EcoRV
                                          (SEQ ID NO: 89)
5'-gatcgatatccagatgacccagtctccagcctccctatc
```

Reverse Primers

```
Heavy Chain Primer (HCR)
                                          (SEQ ID NO: 90)
5'-ctggacagggatccagagttccaggtcactgtcactggctcaggg Light Chain Primer (LCR)
                                          (SEQ ID NO: 91)
5'-ctgtaggtgctgtctttgctgtcctgatcagtccaactg
```

RNA was harvested from anti-IgE/M1' hybridomas (RNeasy Mini Kit, #74106, Qiagen, Valencia, Calif.) and cDNA was prepared using BD Sprint Powerscript oligo dT priming kit (BD Biosciences, San Jose, Calif., #639558). PCR was performed using the above primers and PCR products were cloned using the TOPO-TA kit (Invitrogen, Carlsbad, Calif., #45-0641). PCR was done using Platinum Pfx High Fidelity Polymerase (Invitrogen, Carlsbad, Calif., #11708-039) with PCR conditions [94° C. 2 minutes; 94° C. 15 seconds; 60° C. 30 seconds; 68° C. 2 minutes; 30 cycles; 68° C. 10 minutes]. Clones were screened for inserts and multiple clones were sequenced (Genentech, Inc.) to verify original anti-IgE/M1' heavy chain and light chain gene sequence.

Anti-M1' antibody variable domains were subcloned into expression vectors with different Fc regions to generate chimeric antibodies with different species and/or isotype Fc's. Primers were designed to clone the variable domain (CDR+framework) into mouse IgG2a, mouse IgG2a-DANA, and human IgG1 Fc regions.

Primers were designed to incorporate restriction sites with heavy and light chain sequence. Heavy chains were cloned using BsiWI and ApaI. Light chains were cloned using EcoRV and KpnI. New PCR products were then digested and ligated into mIgG2a (LPG10), mIgG2a-DANA (pErk-E27DANA), or huIgG1 for heavy chain, or mKappa (LPG2) or huKappa expression vectors (Genentech, Inc.). Final clones were sequence verified (Genentech, Inc.).

3' primers and forward and reverse primer combinations for cloning of Variable CDR sequences are as follows:
Reverse Primers

```
7A6
                                          (SEQ ID NO: 92)
HC REV.ApaI
5'-accgatgggcccttggtggaggctgaagagactgtgag (SEQ ID NO: 93)
LC REV.KpnI
5'-ccttggtaccccctccgaacgtgtacggatagctataatattg 1C11
                                          (SEQ ID NO: 94)
HC REV.ApaI
5'-gaccgatgggcccttggtggaggctgaggagactgtg (SEQ ID NO: 95)
LC REV.KpnI
5'-ccttggtaccccctccgaacgtgtacggatagctataa 47H4
                                          (SEQ ID NO: 96)
HC 47H4HCR.ApaI
5'-tgggcccttggtggaggctgaggagacggtgactgag (SEQ ID NO: 97)
LC 47H4LCR.KpnI
5'-ttccaacttggtacctccacc 26A11
                                          (SEQ ID NO: 98)
HC 7G8HCR.ApaI
5'-gaccgatgggcccttggtggargctgcagagacagtgaccagag (SEQ ID NO: 99)
LC 47H4LCR.KpnI
5'-ttccaacttggtacctccacc 45C1
                                          (SEQ ID NO: 100)
HC 45C1HCR.ApaI
5'-cgatgggcccttggtggargckgaggagacggtgagaatg (SEQ ID NO: 101)
LC 5C2LCR.KpnI
5'-agcttggtaccccctccg 28E9
                                          (SEQ ID NO: 102)
HC 28E9.HC.REV.ApaI
5'-cgatgggcccttggtggaggctgaggagacggcgactgag (SEQ ID NO: 103)
LC 1D5.2LCR, KpnI
5'-ttccaacttggtacccgagccg
```

Primer Combinations:

|       |     | Forward         |   | Reverse        |
|-------|-----|-----------------|---|----------------|
| 7A6:  | HC  | 7A6.FOR.BsiWI   | — | 7A6.REV.ApaI   |
|       | LC  | 7A6.FOR.EcoRV   | — | 7A6.REV.KpnI   |
| 1C11: | HC  | 1C11.FOR.BsiWI  | — | 1C11.REV.ApaI  |
|       | LC  | 1C11.FOR.EcoRV  | — | 1C11.REV.KpnI  |
| 47H4: | HC  | 9.1.HCF.BsiWI---|   | 7H4HCR.ApaI    |
|       | LC* | 47H4.LCF.EcoRV  | — | 47H4.LCR.KpnI  |
| 26A11 | HC  | C7F7.HCF.BsiWI  | — | 7G8.HCR.ApaI   |
|       | LC  | 2B4.LCF.EcoRV   | — | 47H4.LCR.KpnI  |
| 45C1  | HC  | 2G6.HCF.BsiWI   | — | 45C1.HCR.ApaI  |
|       | LC  | 9C10.LCF.EcoRV  | — | 5C2.LCR.KpnI   |
| 28E9  | HC  | 9.1.HCF.BsiWI   | — | 28E9.HCR.ApaI  |
|       | LC  | 5E10.LCF.EcoRV  | — | 1D52.LCR.KpnI  |

The 47H4 light chain had an internal KpnI site that precluded direct cloning into the mKappa and huKappa expression vectors. The internal KpnI site was mutated using the Quick Change XL Site Directed Mutagenesis Kit (Stratagene, Cedar Creek, Tex., #200517-5) [95° C. 1 minute; 95° C. 50 seconds; 60° C. 50 seconds; 68° C. 4.5 minutes; 68° C. 7 minutes]. Primers were designed according to requirements of the kit to mutate a single nucleotide within the KpnI site that did not change the amino acid sequence. TAC was mutated to TAT which conserved the tyrosine (Y) at that position. Final clones were sequence verified (Genentech, Inc.).

Primers Used for Mutagenesis were:

```
FOR
                                       (SEQ ID NO: 104)
5'-cc tat tta cat tgg tat ctg cag aag cca ggc c REV
                                       (SEQ ID NO: 105)
5'-ggc ctg gct tct gca gat acc aat gta aat agg
```

EXAMPLE 2A

Humanization of Anti-IgE/M1' Antibodies

This example describes the humanization of the murine anti-IgE/M1' antibodies 26A11, 7A6 and 47H4.

Materials and Methods

The M1' domain of membrane associated human IgE was expressed as an Fc fusion in CHO cells and purified by conventional means. Hybridomas expressing the antibodies 26A11, 7A6 and 47H4 were obtained by immunizing mice with the recombinant M1'-Fc fusion protein and identified by ELISA using plates coated with M1'-Fc. Functional antibodies were identified by their ability to bind to M1' expressing cells and promote apoptosis.

Cloning of murine 26A11, 7A6 and 47H4 variable domains—Total RNA was extracted from hybridoma cells producing 26A11, 7A6 or 47H4 using standard methods. The variable light (VL) and variable heavy (VH) domains were amplified using RT-PCR with degenerate primers to the heavy and light chains. The forward primers were specific for the N-terminal amino acid sequence of the VL and VH regions. Respectively, the LC and HC reverse primers were designed to anneal to a region in the constant light (CL) and constant heavy domain 1 (CH1), which are highly conserved across species. The polynucleotide sequence of the inserts was determined using routine sequencing methods. The 26A11, 7A6 and 47H4 VL and VH amino acid sequences are shown in FIGS. 6A and 6D, 6B and 6E, and 6C and 6F, respectively.

Direct hypervariable region grafts onto the acceptor human consensus framework—The phagemid used for this work is a monovalent Fab-g3 display vector and consists of 2 open reading frames under control of a single phoA promoter. The first open reading frame consists of the stE signal sequence fused to the VL and CH1 domains of the acceptor light chain and the second consists of the stII signal sequence fused to the VH and CH1 domains of the acceptor heavy chain followed by the minor phage coat protein P3.

The VL and VH domains from murine 26A11, 7A6 or 47H4 antibodies (mu26A11, mu7A6 or mu47H4) were aligned with the human VL kappa I (huKI) and human VH subgroup III (huIII) consensus sequences. To make the CDR grafts, hypervariable regions from mu26A11, mu7A6 or mu47H4 were grafted into the huKI and huIII consensus acceptor frameworks to generate the direct CDR-graft (26A11.v1, 7A6.v1 or 47H4.v1) (FIGS. 6A-6F). In the VL domain the following regions were grafted to the human consensus acceptor: positions 24-34 (L1), 50-56 (L2) and 89-97 (L3). In the VH domain, positions 26-35 (H1), 49-65 (H2) and 94-102 (H3) were grafted. MacCallum et al. [MacCallum et al. *J. Mol. Biol.* 262: 732-745 (1996))]have analyzed antibody and antigen complex crystal structures and found position 49 and 94 of the heavy chain to be part of the contact region thus it seems reasonable to include these positions in the definition of CDR-H2 and CDR-H3 when humanizing antibodies.

Humanized anti-IgE/M1' antibodies 26A11.v1, 7A6.v1 and 47H4.v1 were generated as IgG antibodies by Kunkel mutagenesis of LC and HC expression vectors using separate oligonucleotides for each hypervariable region. Amino acid changes to increase stability were also made using Kunkel mutagenesis. Kunkel et al., *J. Biol. Chem.* 263(29): 14784-14789 (1988). Correct clones were identified by DNA sequencing.

IgG Production—For screening purposes, IgG variants were initially produced in 293 cells. Vectors coding for VL and VH (25 µg) were transfected into 293 cells using the FuGene system. 500 µl of FuGene was mixed with 4.5 ml of DMEM media containing no FBS and incubated at room temperature for 5 min. Each chain (25 µg) was added to this mixture and incubated at room temperature for 20 min and then transferred to five T-150 flasks for transfection overnight at 37° C. in 5% $CO_2$. The following day the media containing the transfection mixture is removed and replaced with 23 ml PS04 media with 0.1 ml/L trace elements (A0934) and 10 mg/L insulin (A0940). Cells were incubated for an additional 5 days after which the media was harvested at 1000 rpm for 5 min and sterile filtered using a 0.22 µm low protein-binding filter. Samples could be stored at 4° C. after addition of 2.5 ml 0.1% PMSF for every 125 ml of media.

Affinity determinations—Affinity determinations were performed by Scatchard analysis, a cell binding ELISA and by surface plasmon resonance using a BIAcore™-2000 or A100. Scatchard analysis—Daudi-human, Rhesus and Cyno IgE/M1' cells were prepared for binding in cold Binding buffer composed of base media, with 10 mM HEPES pH 7.4, and 2% FBS as well as 40 ug/ml human IgG. Cells are diluted to concentration of $1.7 \times 10^6$ cells/ml, and kept on ice until they are added to the assay. The proteins/antibodies are iodinated with Iodogen method. Various concentrations of cold protein are prepared in triplicate, using a 1:2 dilution starting with the saturation concentration and ending at a concentration of zero, with a total of 14 concentrations. Hot protein of a single concentration is added to all dilutions to compete with the cold protein. Lastly the cells are added to the hot and cold protein mixture, 250,000 cells per sample were used. Assay is kept at 4° C. for 4 hours, shaking. Each sample is then collected and filtered on membrane, washed at least 3 times with binding buffer, allowed to dry and then counted for 1 minute using Perkin Elmer Wizard 1470 Auto Gamma Counter.

Competitive electrochemilluminescent cell binding assay—Relative binding affinities of humanized variants were measured using a competitive electrochemilluminescent cell binding assay. Transfected BJAB cells expressing IgE-M1' (BJAB-IgE/M1') (long) or control transfected cells not expressing M1' (BJAB-IgE) (short) were washed with phosphate-buffered saline (PBS) and seeded at 25,000 cells/well in 25 µl PBS on 96-well MULTI-ARRAY High Bind plates (Meso Scale Discovery). Cells were incubated on the plates for one hour at room temperature to allow cell attachment to the wells. To block non-specific binding, 25 µl of 30% FBS in PBS was added to each well. The plates were then incubated at room temperature for 30 minutes with mild shaking. Blocking solution was decanted and serial dilutions of humanized variants (0.022-1333 nM) supplemented with a fixed amount of biotinylated anti-IgE M1' antibody (33.3 nM 26A11 or 47H4) in 25 µl PBS containing 2% FBS (assay buffer) were added. After one hour incubation at room temperature with mild agitation, the plates were washed three times with PBS (300 µl/well), using a microplate washer (ELx405 Select, Bio-Tek Instruments, Inc., Winooski, Vt.). Bound antibodies were detected by adding 25 µl of 0.25 µg/ml ruthenium-labeled streptavidin in assay buffer. After a one hour incubation at room temperature, plates were washed and Tris-based Read Buffer T (1×, without surfactant) (Meso Scale Discovery) was added (150 µl/well). Electrochemilluminescent signals were recorded using Sector Imager 6000 reader (Meso Scale Discovery).

Biacore 2000—Two orientations were used; either M1'-Fc or a particular antibody variant were immobilized (approximately 100 RU, in 10 mM Sodium Acetate pH 4.8 on a CM5 sensor chip) and the corresponding ligand (antibody variant or M1'Fc, respectively) served as the analyte (injected at a flow rate of 30 µL/min, using a 2-fold serial dilution of 0.5 to 1000 nM in PBST). Each sample was analyzed with 3-minute association and 10-minute disassociation. After each injection the chip was regenerated using 10 mM Glycine pH 1.7. Biacore A-100—M1'—was immobilized (approximately 100 RU, in 10 mM Sodium Acetate pH 4.8 on a CM-5 sensor chip) and the antibody variant served as the analyte (injected at a flow rate of 30 µL/min, using a 2-fold serial dilution of 0.5 to 1000 nM in PBST). Each sample was analyzed with 5-minute association and 5-minute disassociation. After each injection the chip was regenerated using 10 mM Glycine pH 1.7.

Binding response was corrected by subtracting a control flow cell from 18F7 variant IgG flow cells. A 1:1 Languir model of simultaneous fitting of $k_{on}$ and $k_{off}$ was used for kinetics analysis.

Results and Discussion

CDR grafts of 26A11, 7A6 and 47H4—The human acceptor framework used for humanization is based on the consensus human kappa I VL domain and the consensus human subgroup III VH domain. The VL and VH domains of mu26A11, mu7A6 and mu47H4 were aligned with the human kappa I and subgroup III domains; each complementarity determining region (CDR) was identified and grafted into the human acceptor framework to generate a CDR graft that could be expressed as an IgG (FIGS. 6A-6F).

Affinity Evaluation—26A11.v1, 7A6.v1 and 47H4.v1 were evaluated using a cell binding ELISA and by surface plasmon resonance (Table 1). These assays indicated that the CDR grafts had affinities very similar to their respective hybridoma antibodies.

Figures 1, 4A:
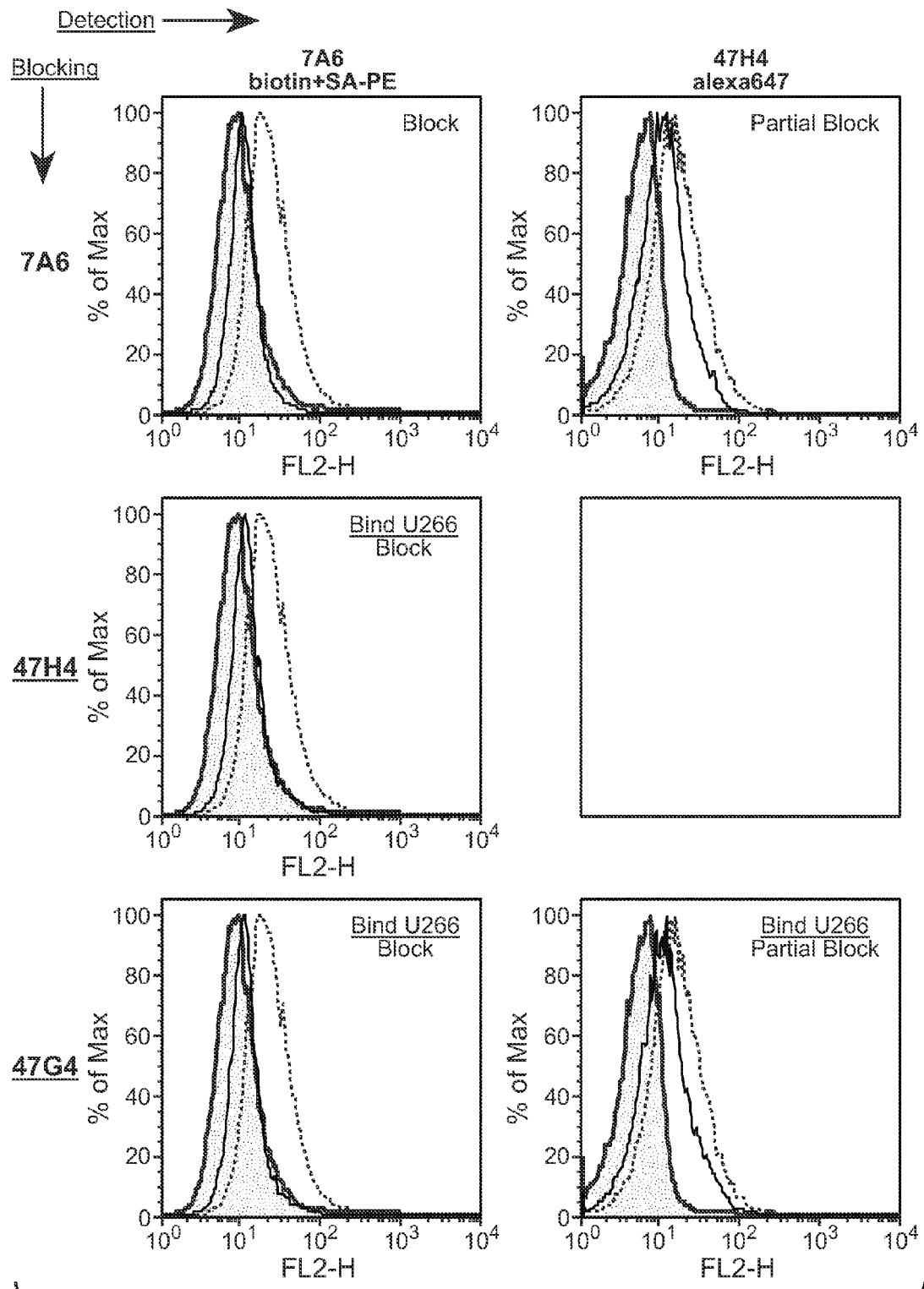
Figures 2, 4A:
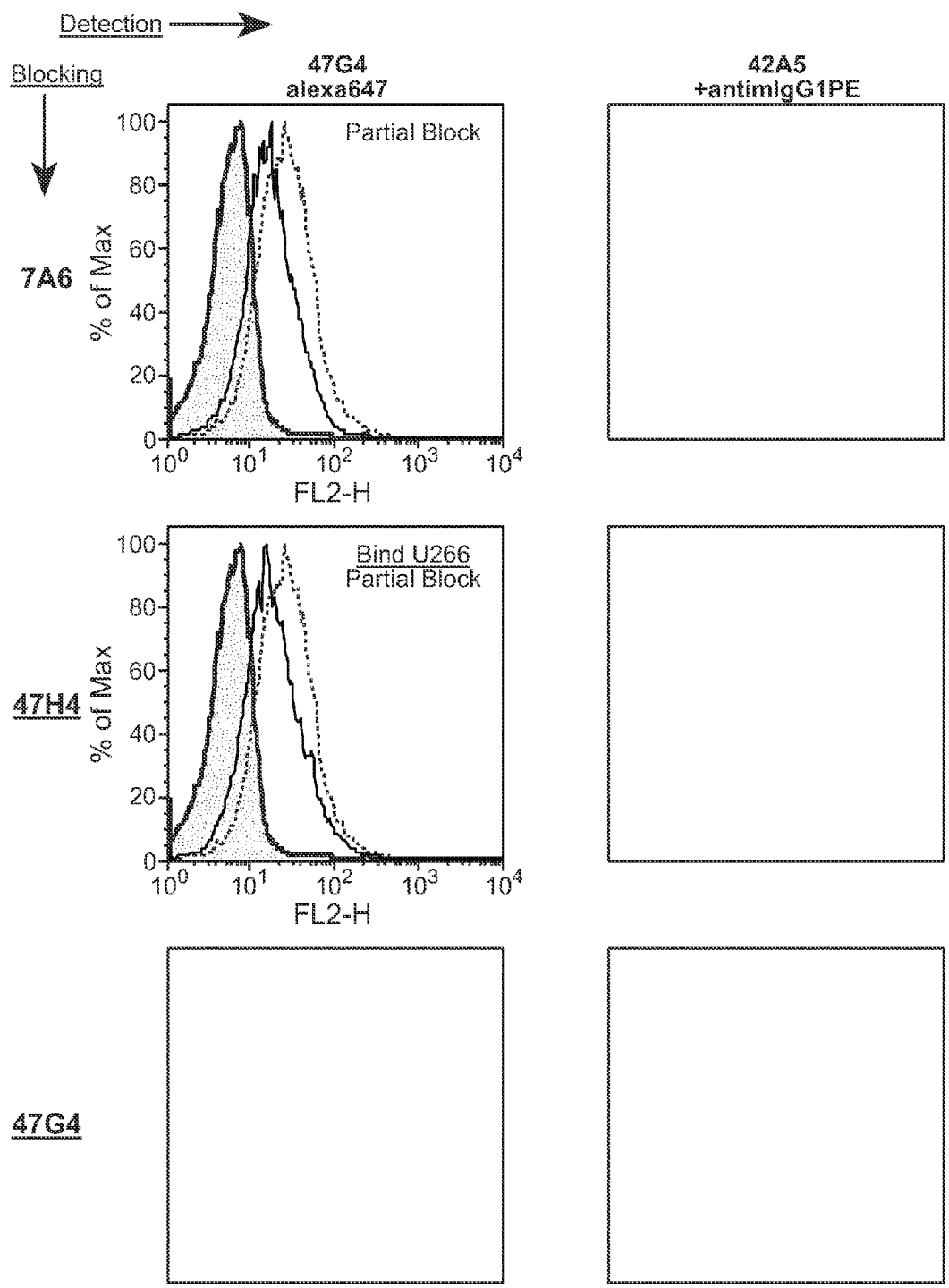
Figures 3, 4A:
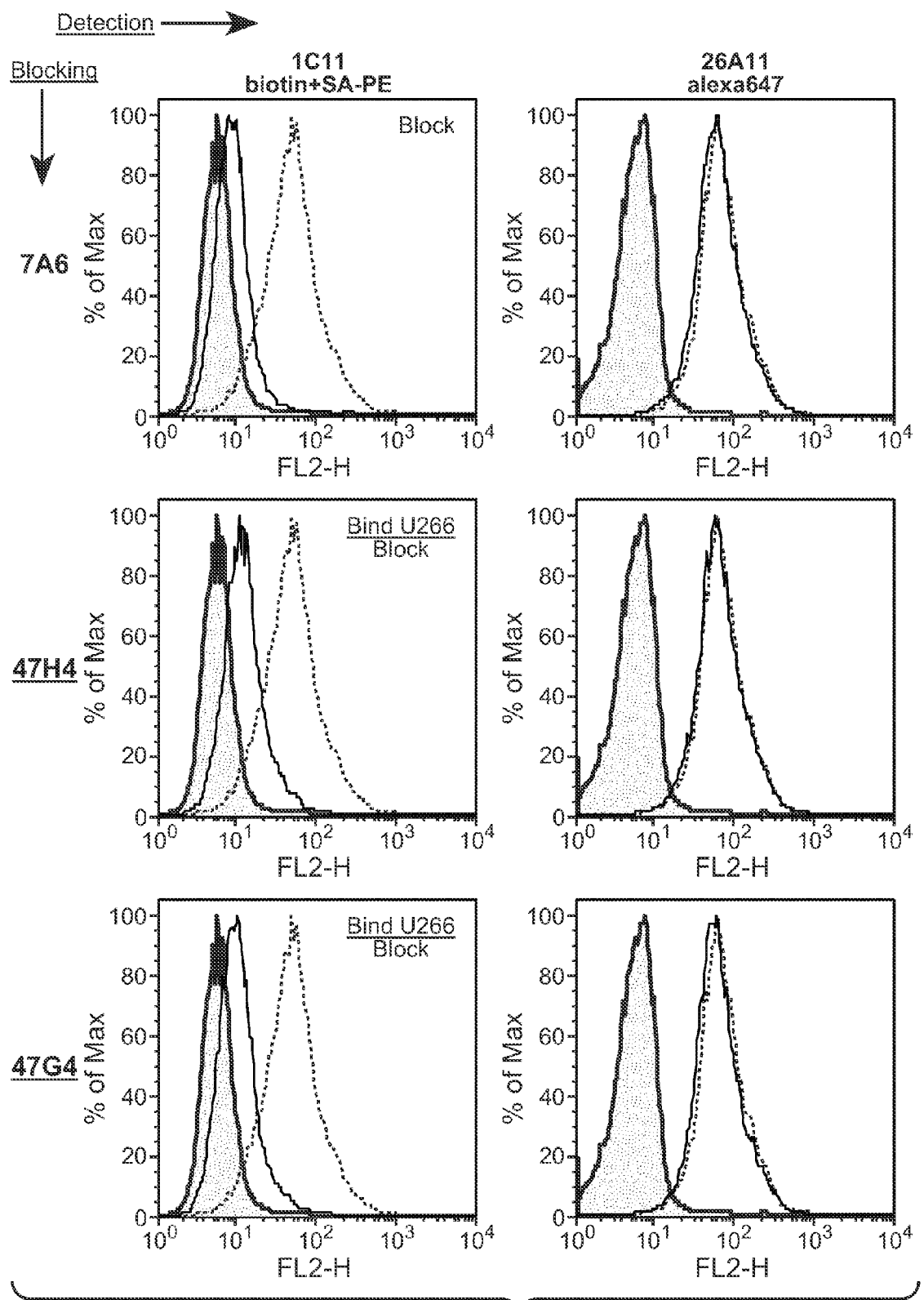
Figures 4, 4A:
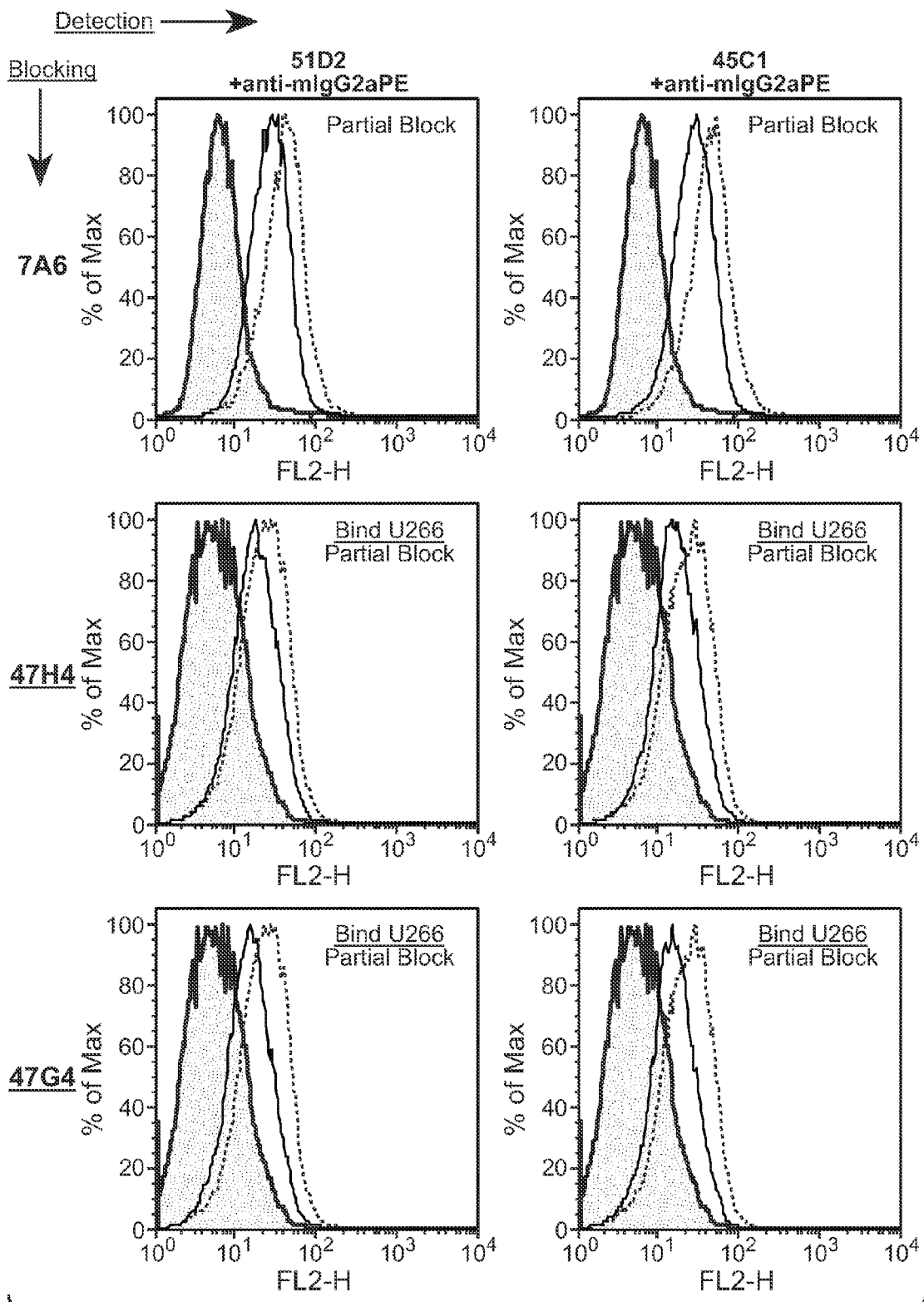
Figures 4, 4A, 5:
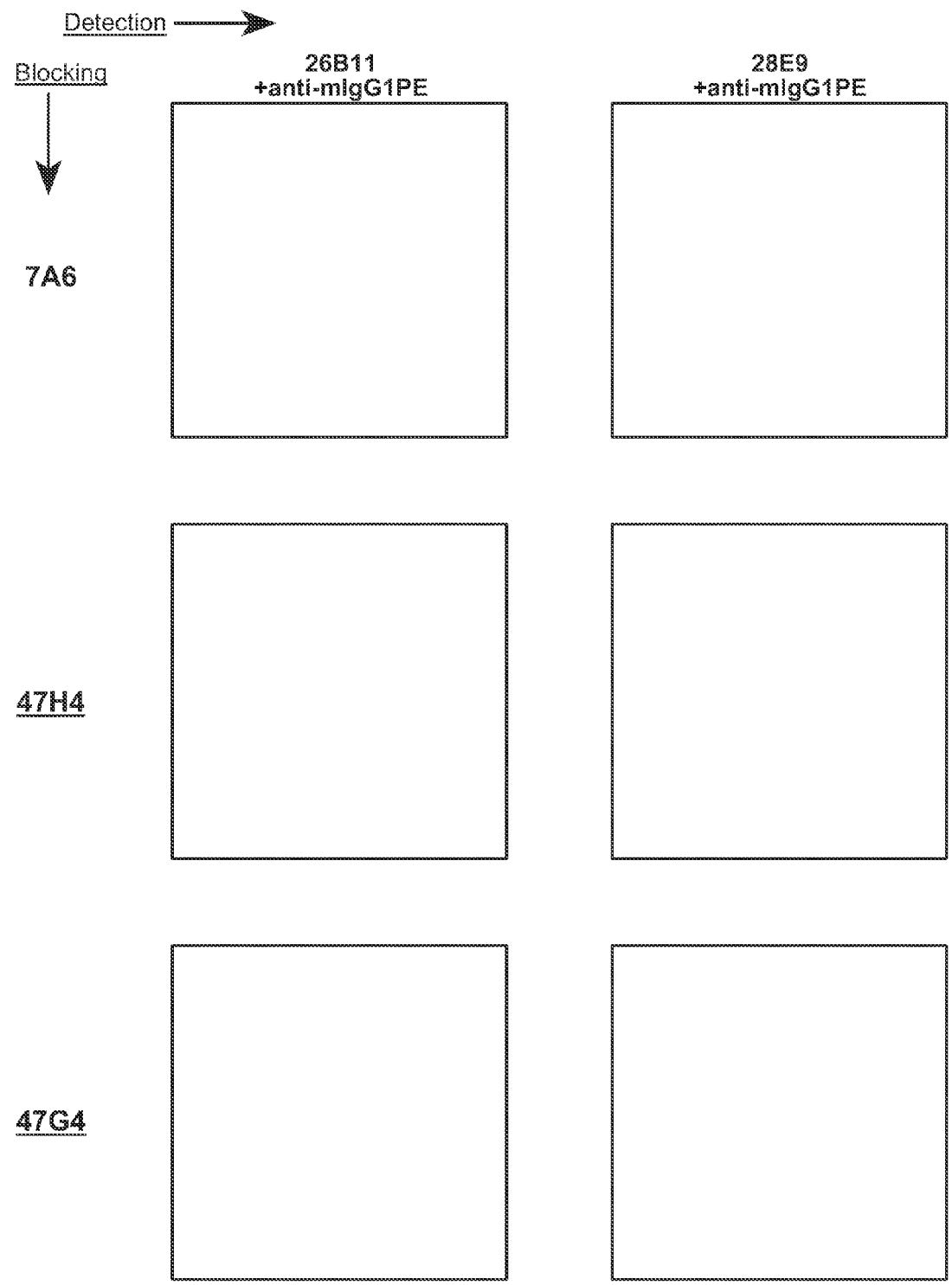
Figures 4, 4A, 5, 6:
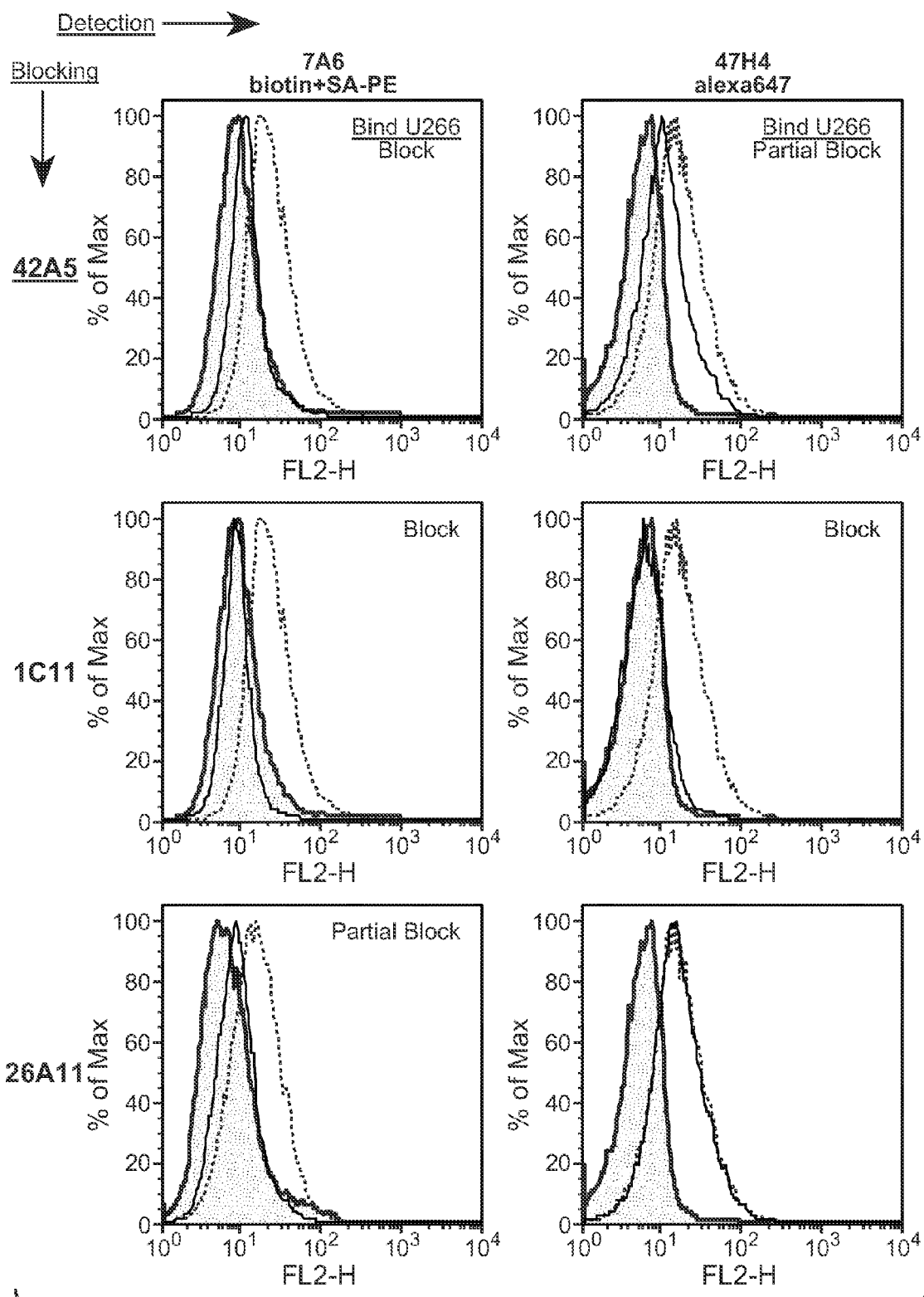
Figures 4, 4A, 5, 6, 7:
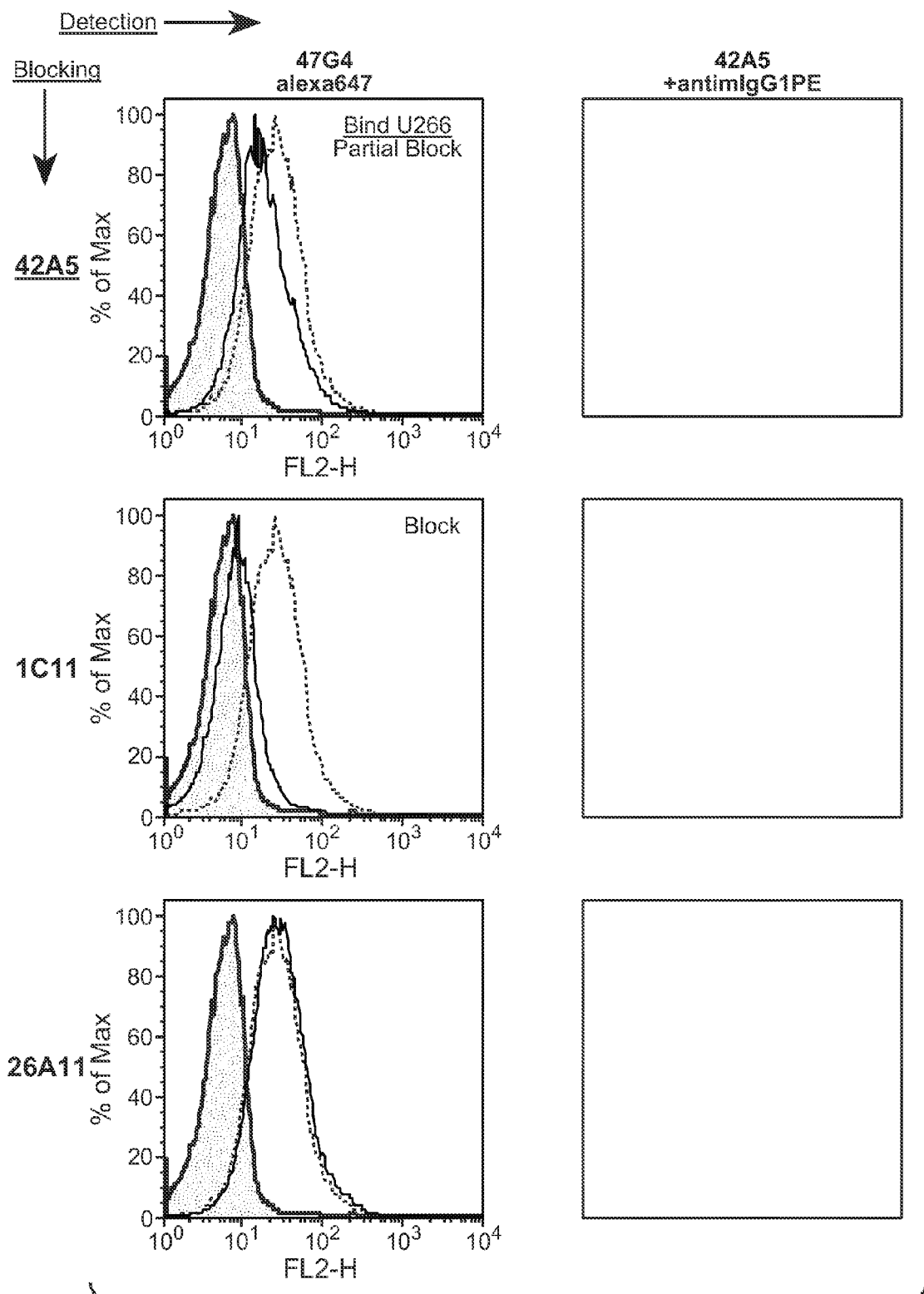
Figures 4, 4A, 5, 6, 7, 8:
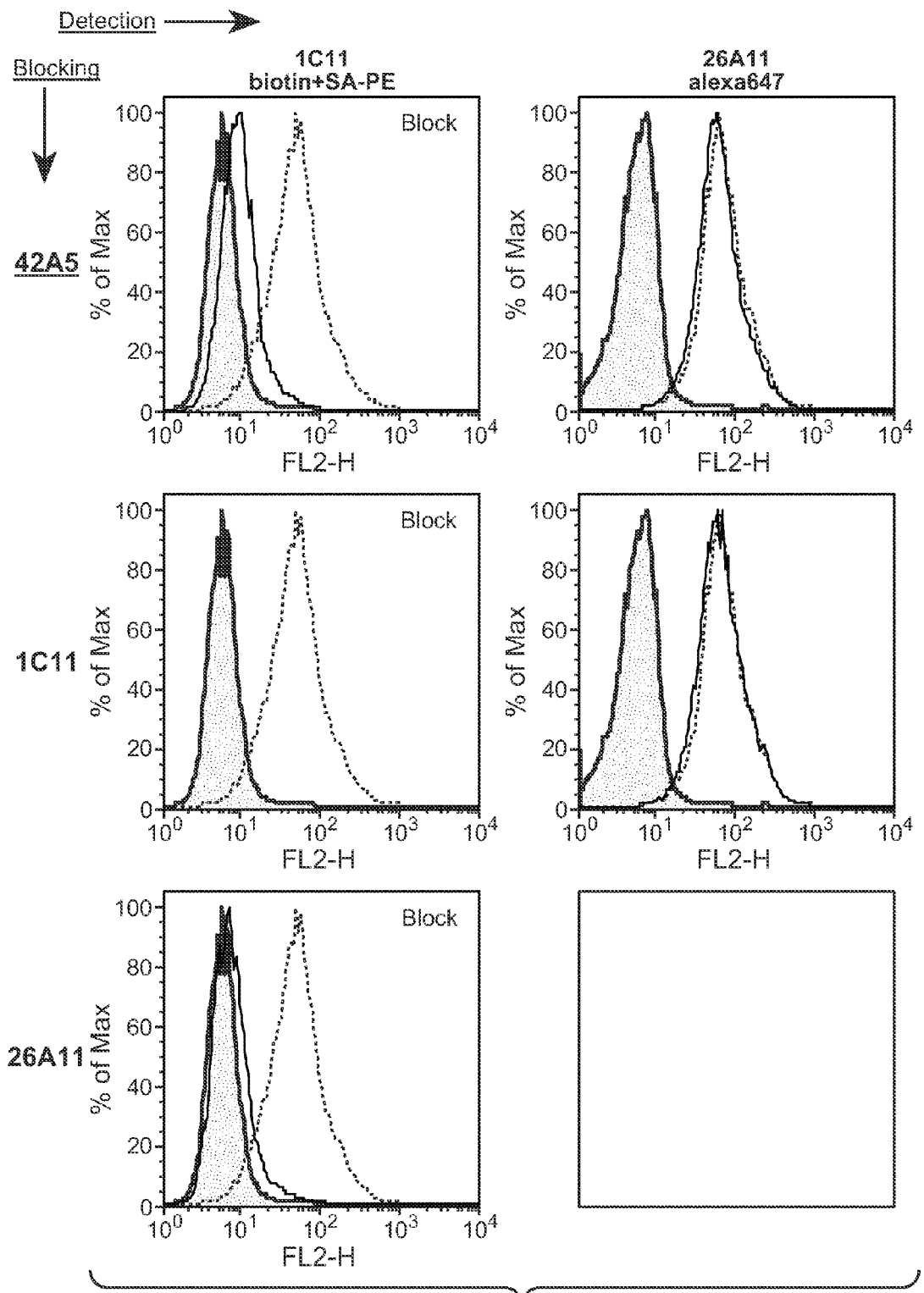
Figures 4, 4A, 5, 6, 7, 8, 9:
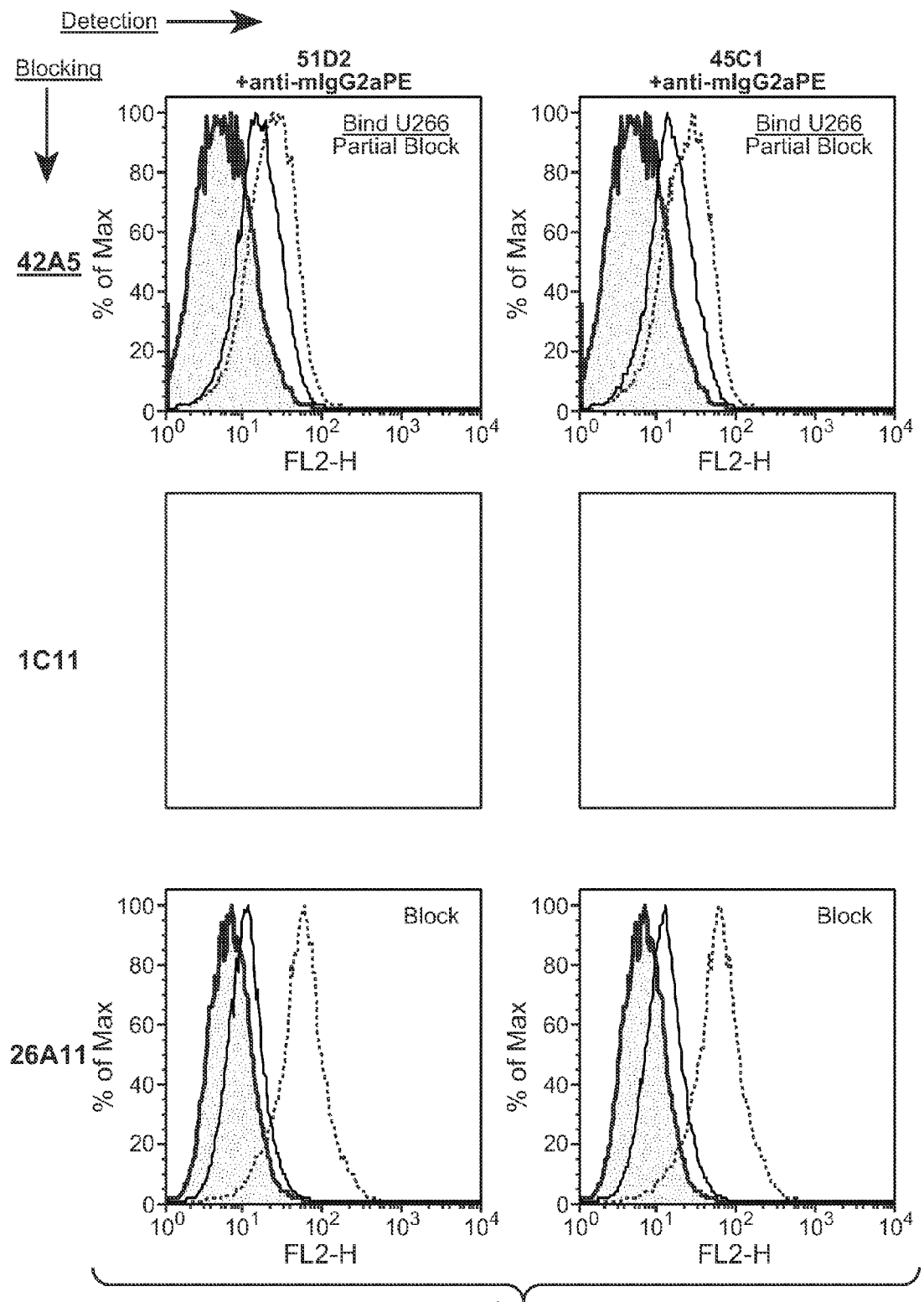
Figure 6A:
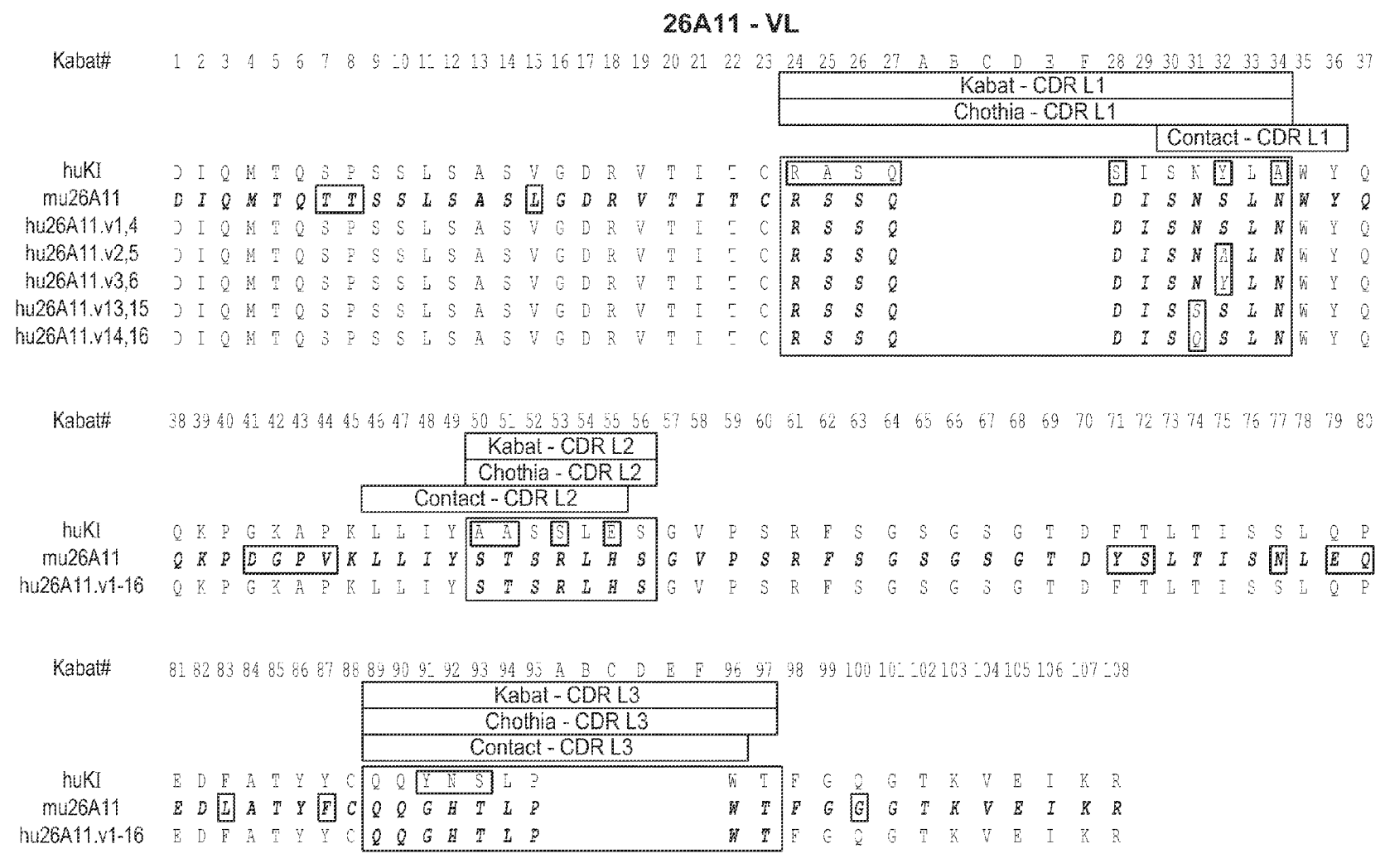

Elimination of potential deamidation and iso-aspartic acid forming sites in CDR-L1 of 26A11 and 47H4—To avoid potential manufacturing issues, potential iso-aspartic acid forming sites $Asn_{28}$-$Gly_{29}$ in CDR-L1 of 47H4.v1 and $Asn_{31}$-$Ser_{32}$ in CDR-L1 of 26A11.v1 were eliminated by sampling residues found in other antibodies at these positions (FIGS. 6A, 6C, Table I). Changing $Gly_{29}$ to $Ala_{29}$ in CDR-L1 of 47H4.v1 (47H4.v2 and 47H4.v5), and $Ser_{32}$ to $Tyr_{32}$ in CDR-L1 of 26A11 (26A11.v3 and 26A11.v6) or $Ala_{32}$ (26A11.v2 or 26A11.v5) were found to be a suitable replacements. In addition, changing $Asn_{31}$ to either $Ser_{31}$ (26A11.v13 or 26A11.v15) or $Gln_{31}$ (26A11.v14 or 26A11.v16) also served to eliminate potential deamidation and iso-aspartic acid formation and provided candidates with affinities similar to their respective hybridoma antibodies.

Potential oxidation of $Met_{34}$ in CDR-H1 of either 26A11.v1 or 47H4.v1 was avoided by changing this residue to $Ile_{34}$ in both antibodies without affecting M1' binding.

EXAMPLE 3

Specificity of Anti-M1' Abs

The specificity of anti-IgE/M1' antibody clones was tested on human B cell line BJAB (ATCC Manassas, Va., #HB-136) transfected with IgE with the M1' sequence ("long form") or IgE lacking the M1' sequence ("short form"). IgE BJAB cell lines were generated by retroviral transduction of BJAB cells using a pMSCV expression vector (Washington University, St. Louis, Mo.). cDNA of the full length heavy and light chains of human IgE B cell receptor were obtained from the human IgE myeloma cell line U266 (ATCC, Manassas, Va., TIB#196) and were subcloned into the retroviral vector in combination with an IRES (Internal Ribosomal Entry Sequence) to allow for bicistronic co-transfection and co-expression of the antibody heavy and light chains. Further description of the method of retroviral transduction is provided below.

PG13 packaging cells (ATCC CRL-10686) were seeded on a 10 cm tissue culture plate at $2\times10^6$ cells per plate (DMEM high glucose, 10% FBS, penicillin, streptomycin, 2 mM L-glutamine) for 24 hours. Cells were transfected with pMSCV DNA constructs using FuGENE 6 and cultured for 2 days at 37° C., 5% CO2. Cell culture supernatant containing retroviral particles was harvested and filtered through a 0.4 micron filter. Sterile protamine sulfate was added to a final concentration of 10 μg/ml, and 4 ml of supernatant was used to infect approximately $1\times10^6$ BJAB cells by spin infection at 32° C. for 90 minutes, followed by continued culture in retroviral supernatant for 3-4 hours at 37° C. in 5% $CO_2$. Infected BJAB cells were recovered, transferred to RPMI cell culture medium (RPMI, 10% FBS (Hyclone, Logun, Utah, #SH30071.03), penicillin, streptomycin, 2 mM L-glutamine), and expanded for sorting. Positively transfected cells were identified by flow cytometry using MAE11 (Genentech) anti-human IgE antibody to detect surface IgE.

Anti-IgE/M1' antibodies are specific for the long form and not the short form of membrane IgE, as determined by flow cytometry staining of BJAB IgE short and long form cell lines. Anti-human IgE (Mae11) antibody (Genentech, Inc.)

was used as a positive control for its ability to bind both the long and short form of IgE. Anti-gp120 mIgG1 or anti-ragweed mIgG2a antibodies were used as isotype controls (Genentech, Inc).

BJAB cells are grown in RPMI 10% FBS (Hyclone, Logun, Utah, #SH30071.03), Penicillin/Streptomycin, 2 mM L-Glutamine (Genentech, Inc.). 0.5×10$^6$ BJAB-Long or BJAB-short cells were blocked with mouse (10 µl) (VWR, #RLD108-0100) and human serum (10 µl) (Sigma, St. Louis, Mo., #S-2257) for 15 minutes on ice in 100 µl of FACs Wash Buffer (2% FBS in 1×PBS (Genentech, Inc.). Cells were then stained with 1 µg/ml of each anti-M1' antibody for another 20 minutes on ice and then washed with 1 ml of FACs wash buffer and centrifuged at 1200 rpm for 5 minutes. Cells were resuspended in 100 µl of FACs Wash Buffer and then stained with goat anti-mouse IgG-PE (5 µl) (Caltag/Invitrogen, Carlsbad, Calif., #M30004-4) on ice for 20 minutes. Cells were washed as before and resuspended in 1 ml of FACs wash buffer for analysis on the FACs Calibur machine (BD, Inc, Franklin Lakes, N.J.). All antibodies tested were specific for the long form of IgE and did not bind BJAB-IgE/short cells above isotype control.

Figures 1, 2C:
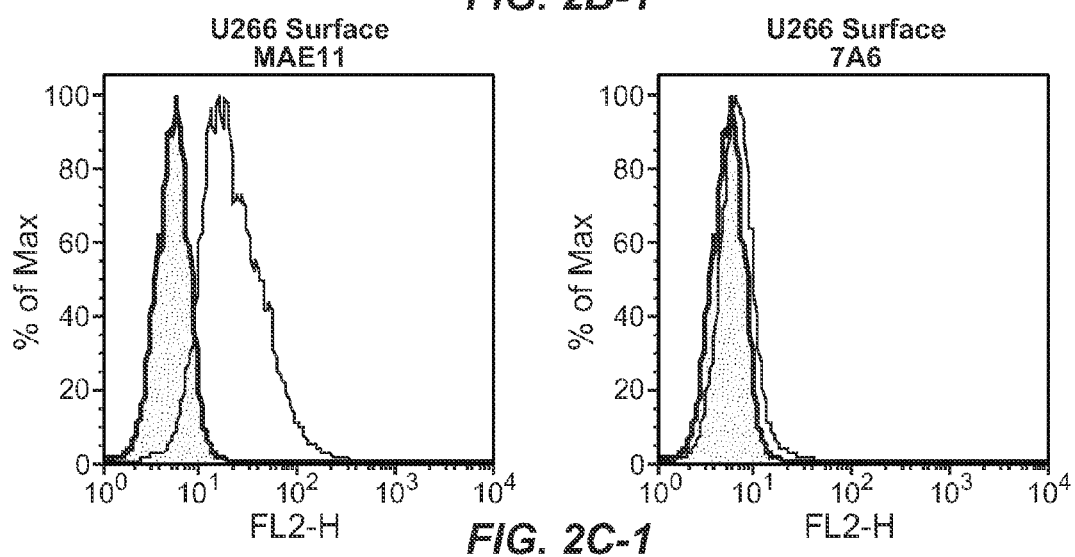

We observed a wide range of relative affinities based on staining intensities. We also assessed anti-M1' antibody binding to the U266 cell line (ATCC, Manassas, Va., #TIB196) which naturally expresses a low level of human IgE containing M1' on the cell surface. U266 cells are maintained at high density (1-2×10$^6$/ml) in hybridoma medium [RPMI 1640, 15% Fetal bovine serum, 2 mM L-glutamine, 10 mM HEPES, 4.5 g/L glucose, 1.5 g/L bicarbonate]. U266 cells were stained with anti-M1' antibodies at 1 µg/ml. 47H4, 47G4 and 42A5 stained U266 at levels similar to Mae11. Antibodies 42H4, 45C1 and 28E9 stained U266 at very low levels. 7A6, 1C11, 26A11, 51D2, and 26B11 did not stain U266. (FIG. 2C)

EXAMPLE 3A

Murine Anti-IgE/M1' Binding Specificity

Figures 2, 2A, 3:
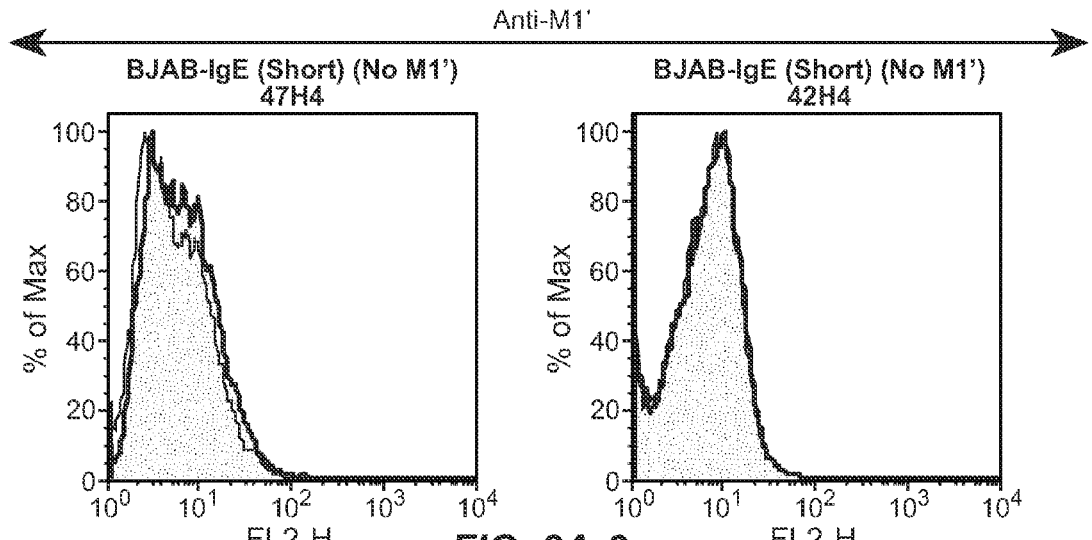
Figures 2, 2B, 3:
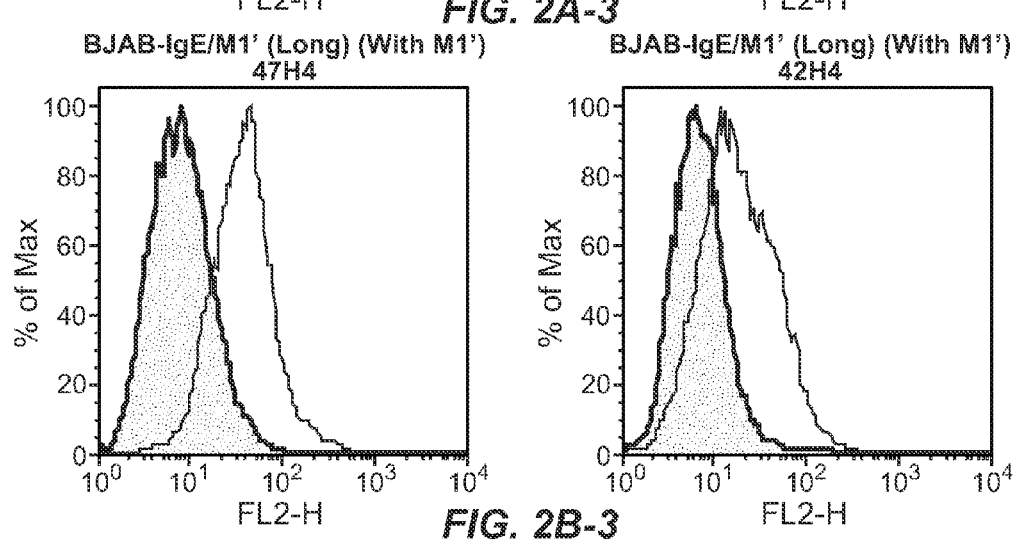
Figures 2, 2C, 3:
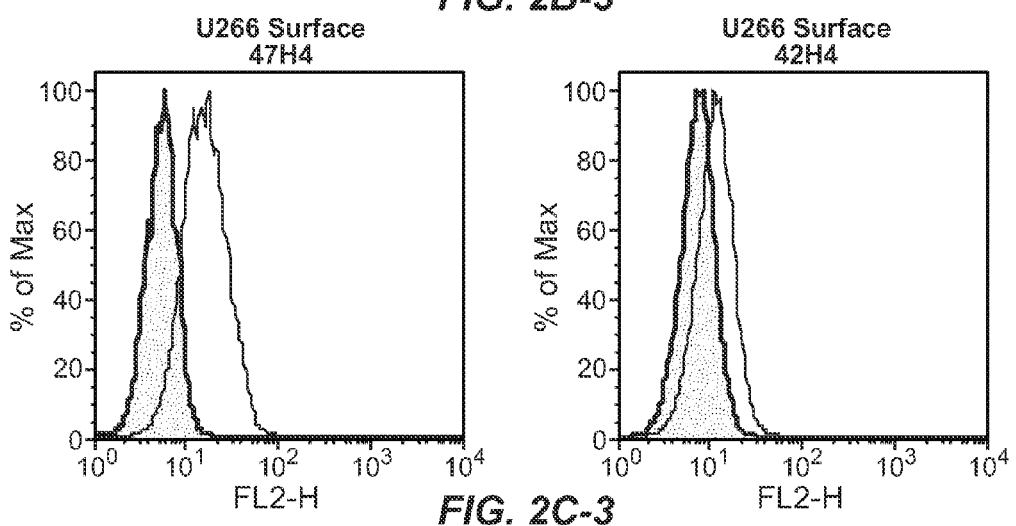
Figures 2, 2A, 3, 4:
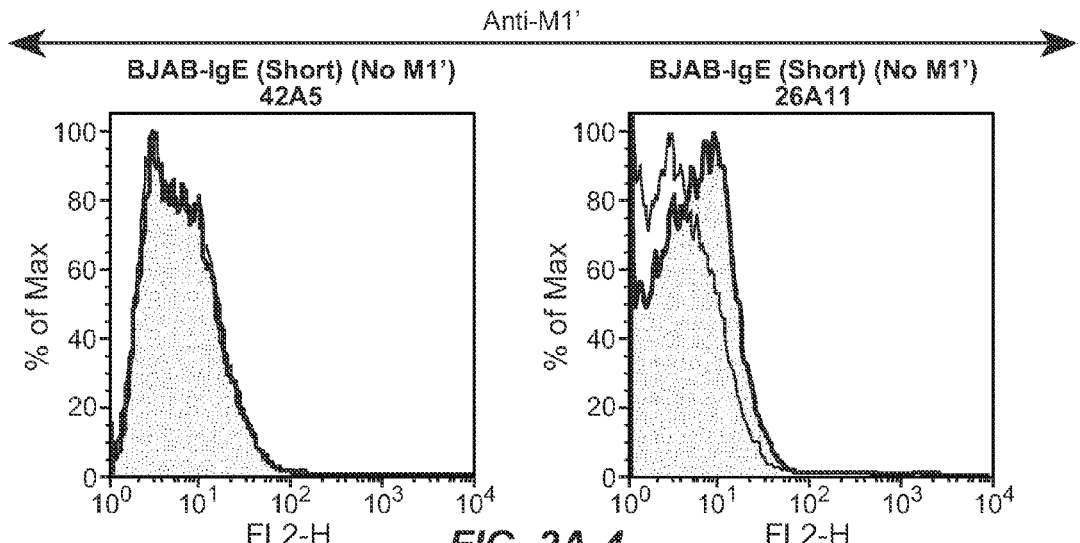
Figures 2, 2B, 3, 4:
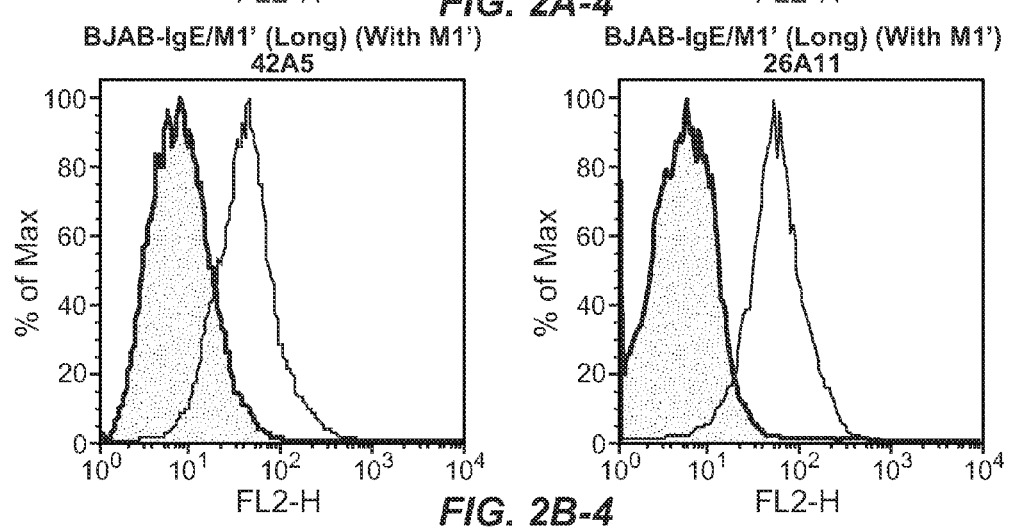
Figures 2, 2C, 3, 4:
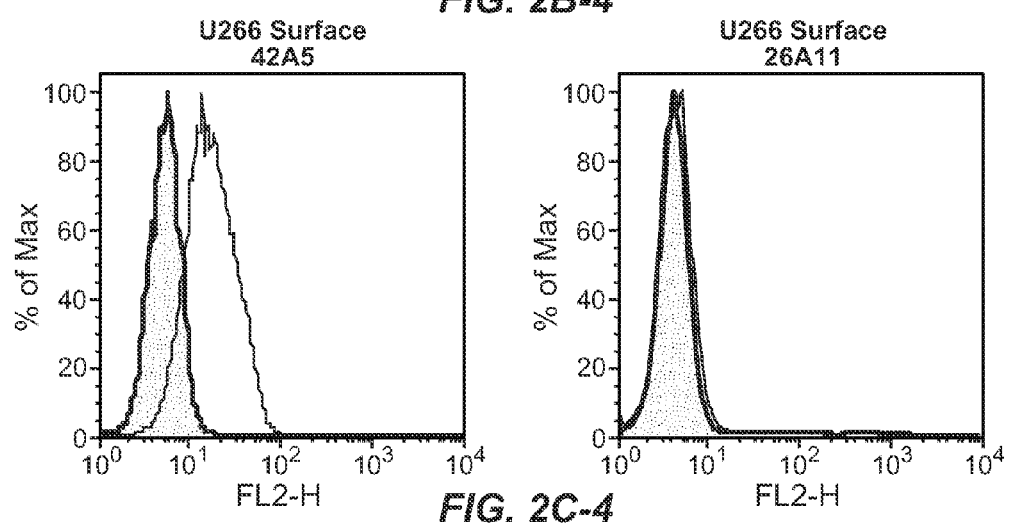
Figures 2, 2A, 3, 4, 5:
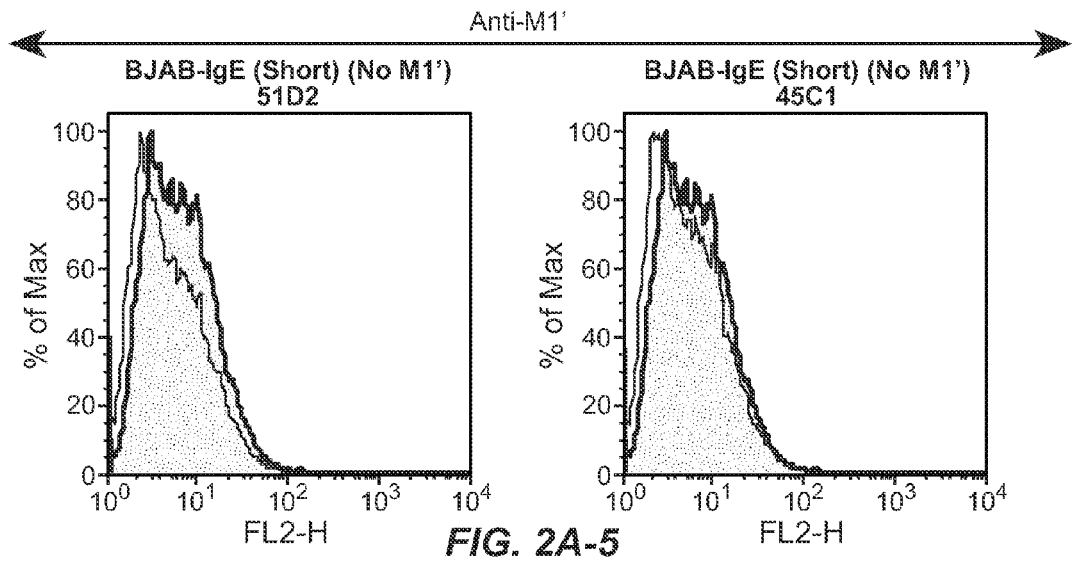
Figures 2, 2B, 3, 4, 5:
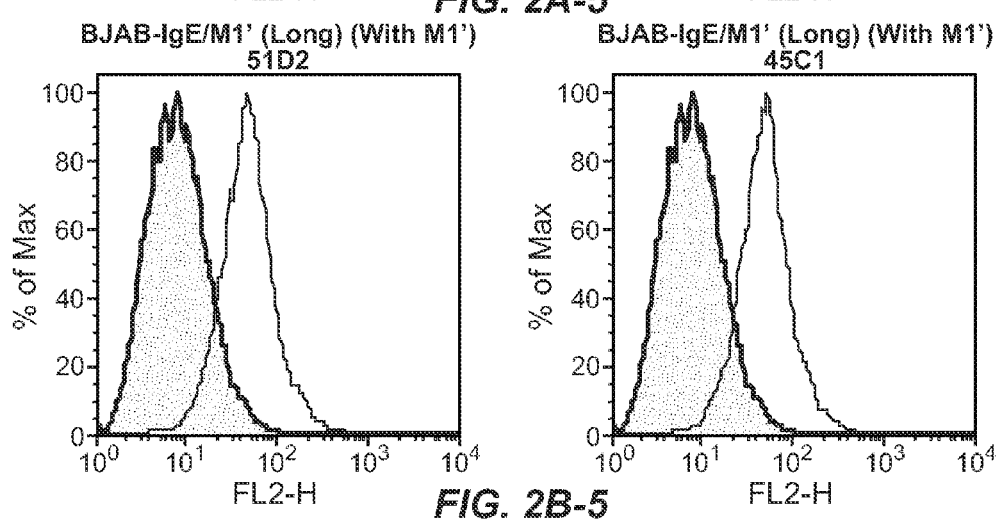
Figures 2, 2C, 3, 4, 5:
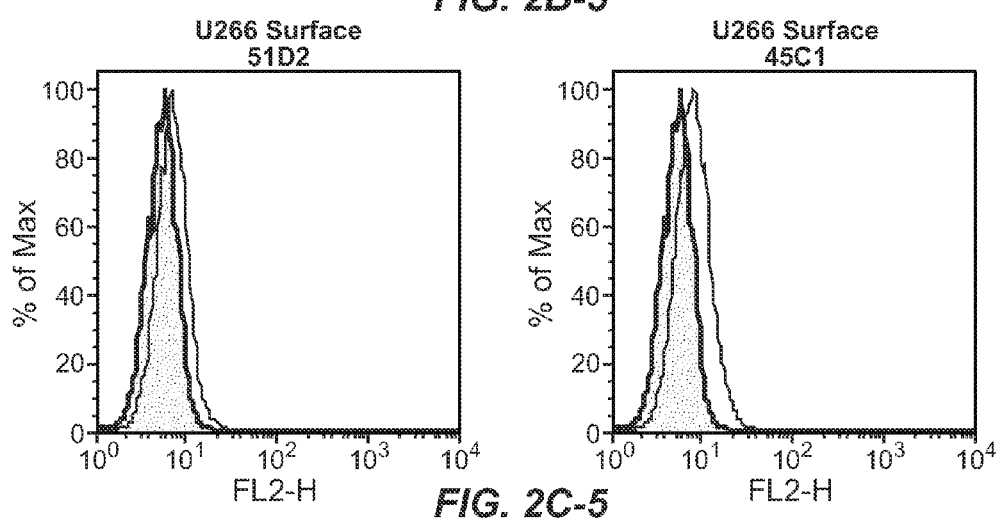
Figure 2D:
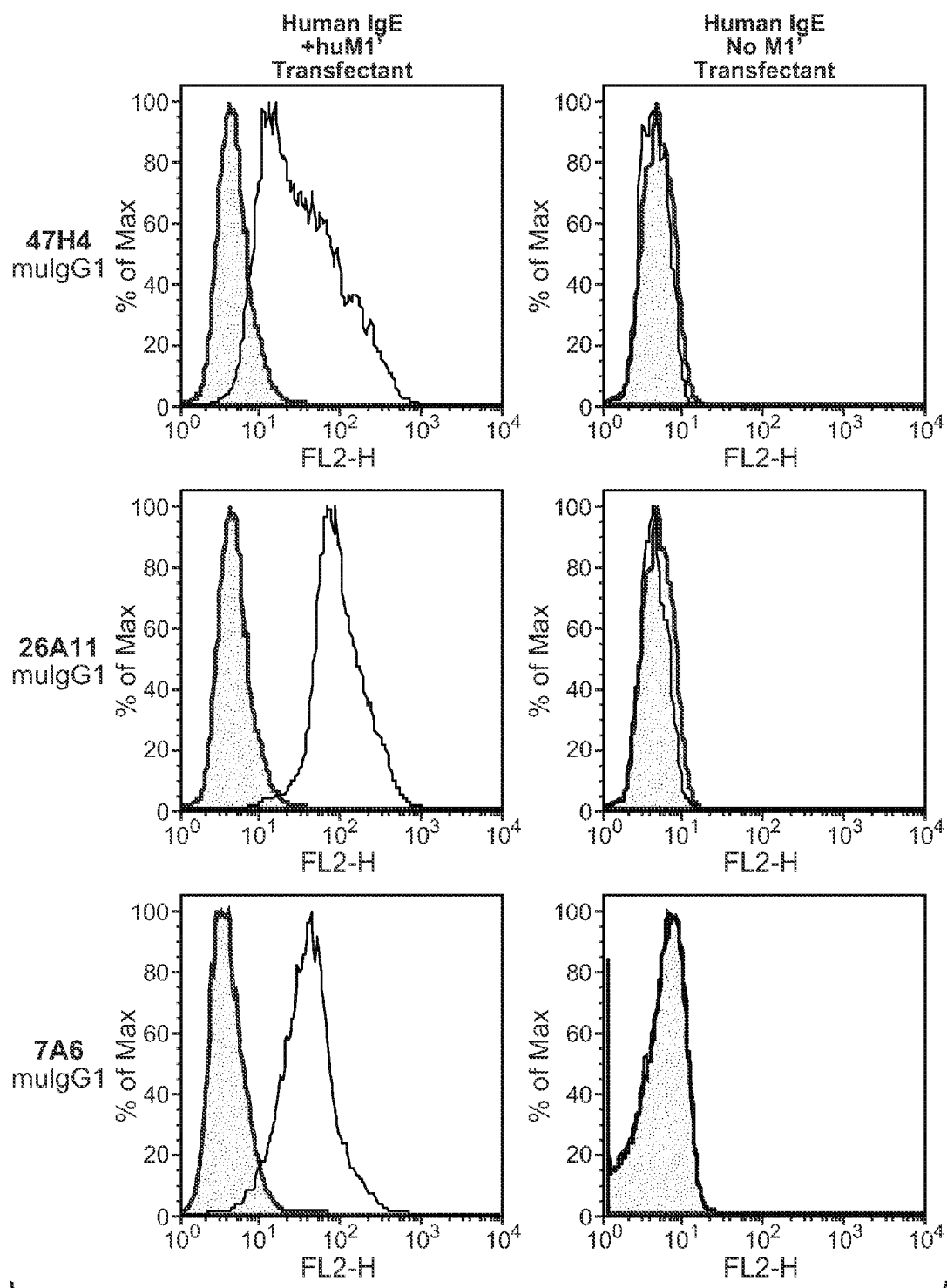
FIGS. 2D-F show the binding specificities of the murine anti-IgE/M1' antibodies 47H4, 26A11 and 7A6.
Figure 2E:
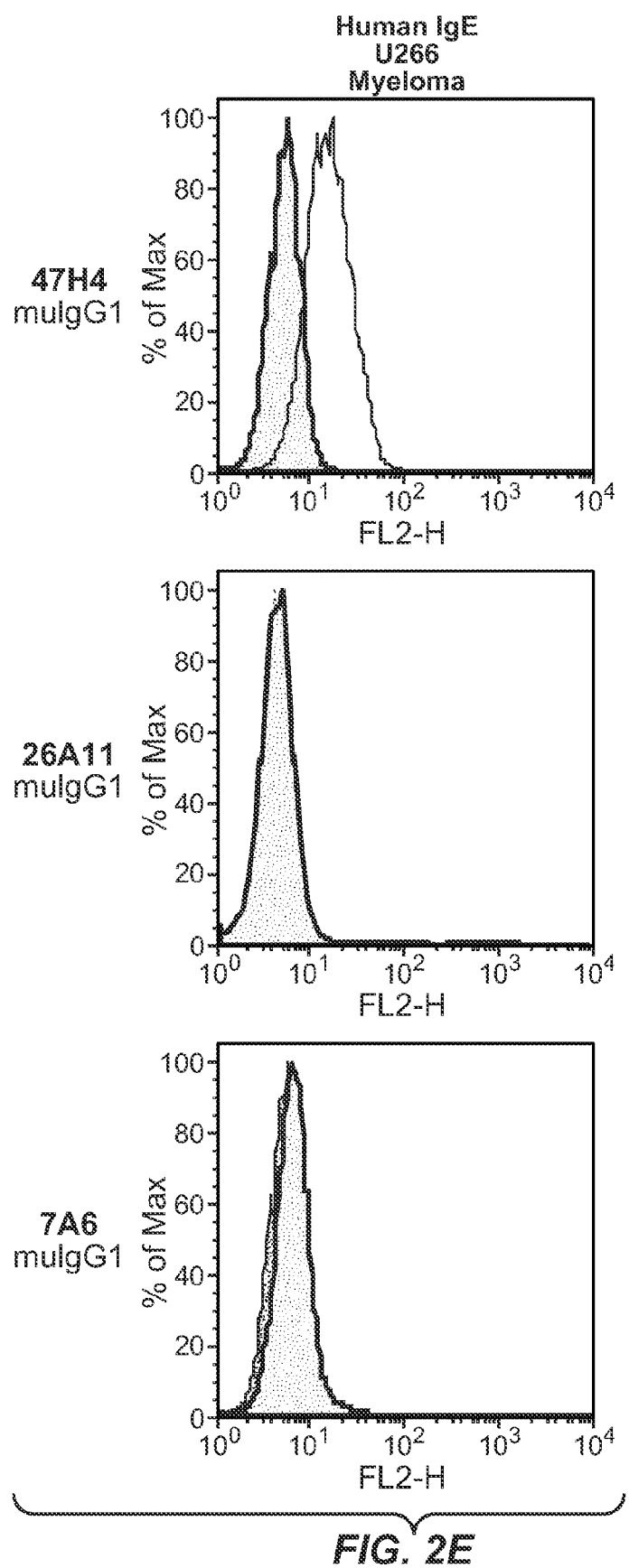
Figure 2F:
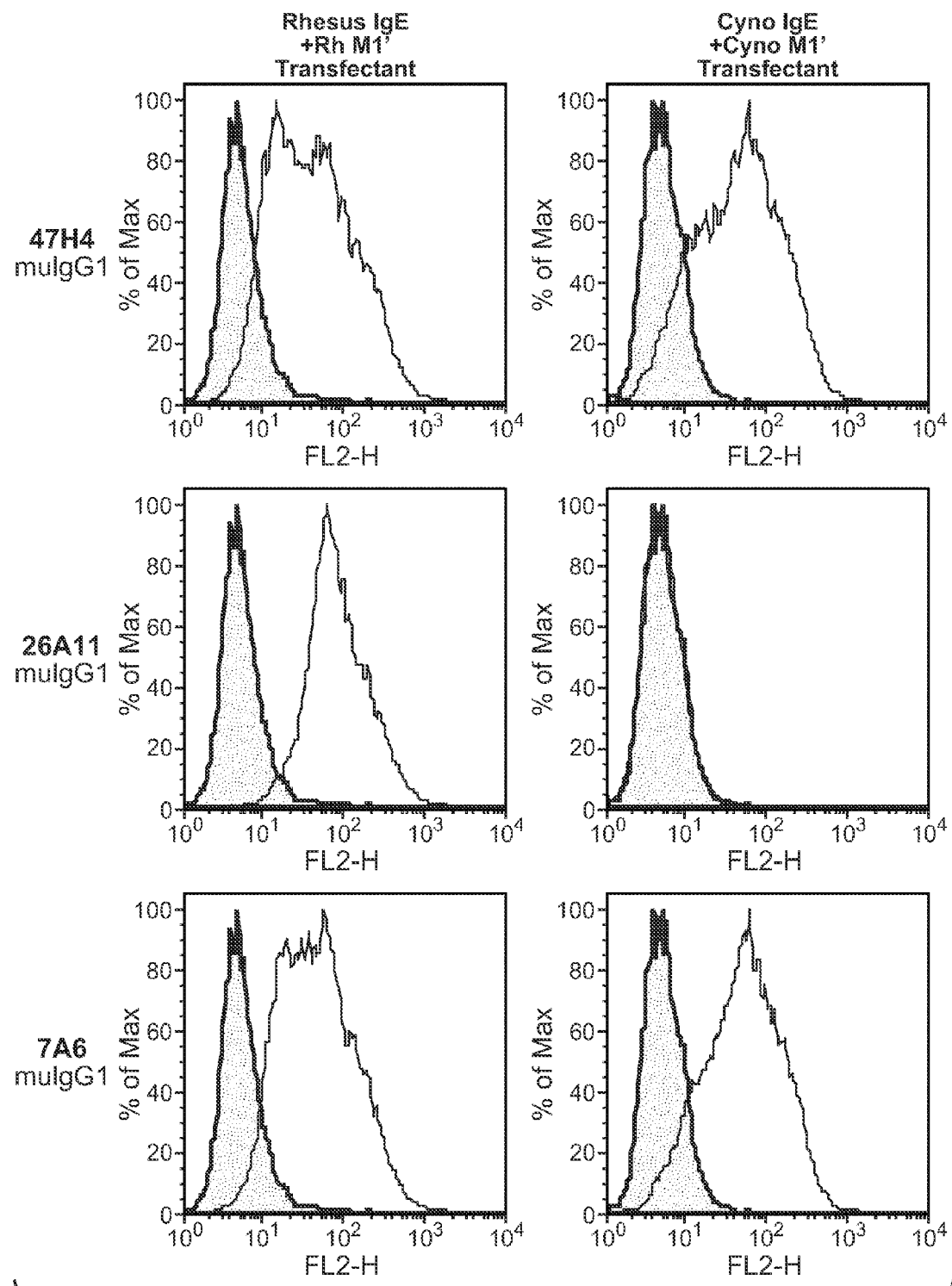

FIGS. 2D-F show the binding of murine anti-IgE/M1' antibodies 47H4, 26A11 and 7A6 to a collection of cell lines that express human Rhesus or Cyno IgE/M1'.

The specificity of anti-IgE/M1' antibody clones was tested on the human B cell line BJAB (ATCC Manassas, Va., #HB-136) and Daudi (ATCC #CCL-213) infected by retrovirus to express the long form of IgE with the M1' sequence or the short form of IgE lacking the M1' sequence. BJAB cells are grown in RPMI 10% FBS (Hyclone, Logun, Utah, #SH30071.03), Penicillin/Streptomycin, 2 mM L-Glutamine (Genentech, Inc.). 0.5×10$^6$ BJAB-Long or BJAB-short cells were blocked with mouse (10 µl) (VWR, #RLD108-0100) and human serum (10 µl) (Sigma, St. Louis, Mo., #S-2257) for 15 minutes on ice in 100 µl of FACs Wash Buffer (2% FBS in 1×PBS (Genentech, Inc.)). Cells were then stained with 1 µg/ml of each anti-M1' antibody for another 20 minutes on ice and then washed with 1 ml of FACs wash buffer and centrifuged at 1200 rpm for 5 minutes. Cells were resuspended in 100 µl of FACs Wash Buffer and then stained with goat anti-mouse IgG-PE (5 µl) (Caltag/Invitrogen, Carlsbad, Calif., #M30004-4) on ice for 20 minutes. Cells were washed as before and resuspended in 1 ml of FACs wash buffer for analysis on the FACs Calibur machine (BD, Inc, Franklin Lakes, N.J.). All antibodies tested were specific for the long form of IgE and did not bind BJAB-IgE/short cells above isotype control. We observed a wide range of relative affinities based on staining intensities.

The specificity of anti-IgE/M1' antibody clones was tested on the human B cell line Daudi infected by retrovirus to express membrane IgE with the M1' sequence (long form) or a membrane IgE lacking the M1' sequence (short form). Anti-IgE/M1' antibodies (47H4, 26A11, 7A6) are specific for the long form and not the short form (FIG. 2D). An anti-gp120 mIgG1 antibody was used an isotype control (Genentech, Inc).

The human B cell line Daudi was transduced with the retrovirus containing the human IgE/primate M1' cassette for either rhesus or cyno or the human IgE/M1'. Following transduction cells expressing human, rhesus, or cyno IgE/M1' were sorted by FACs sorter to >98% purity over the course of 3-4 sorts.

FIG. 2F demonstrates the ability of anti-IgE/M1' antibodies to bind Rhesus and Cyno M1'. 47H4 and 7A6 bind both Rhesus and Cyno M1', whereas 26A11 binds only Rhesus M1'.

In addition to the Daudi transfectant cell lines, we assessed anti-IgE/M1' antibody binding to U266, a human IgE myeloma cell line (ATCC, Manassas, Va., #TIB 196). U266 cells are maintained at high density (1-2×10$^6$/ml) in hybridoma medium [RPMI 1640, 15% Fetal bovine serum, 2 mM L-glutamine, 10 mM HEPES, 4.5 g/L glucose, 1.5 g/L bicarbonate]. U266 cells were stained with anti-M1' antibodies at 1 µg/ml. anti-IgE/M1' antibody 47H4 bound U266 while 26A11 and 7A6 did not (FIG. 2E).

EXAMPLE 3B

Humanized Anti-IgE/M1' Binding Specificity

Example 3B shows the binding of humanized anti-IgE/M1' antibodies to a collection of cell liens that express human, rhesus or cyno IgE/M1'.

Figure 2G:
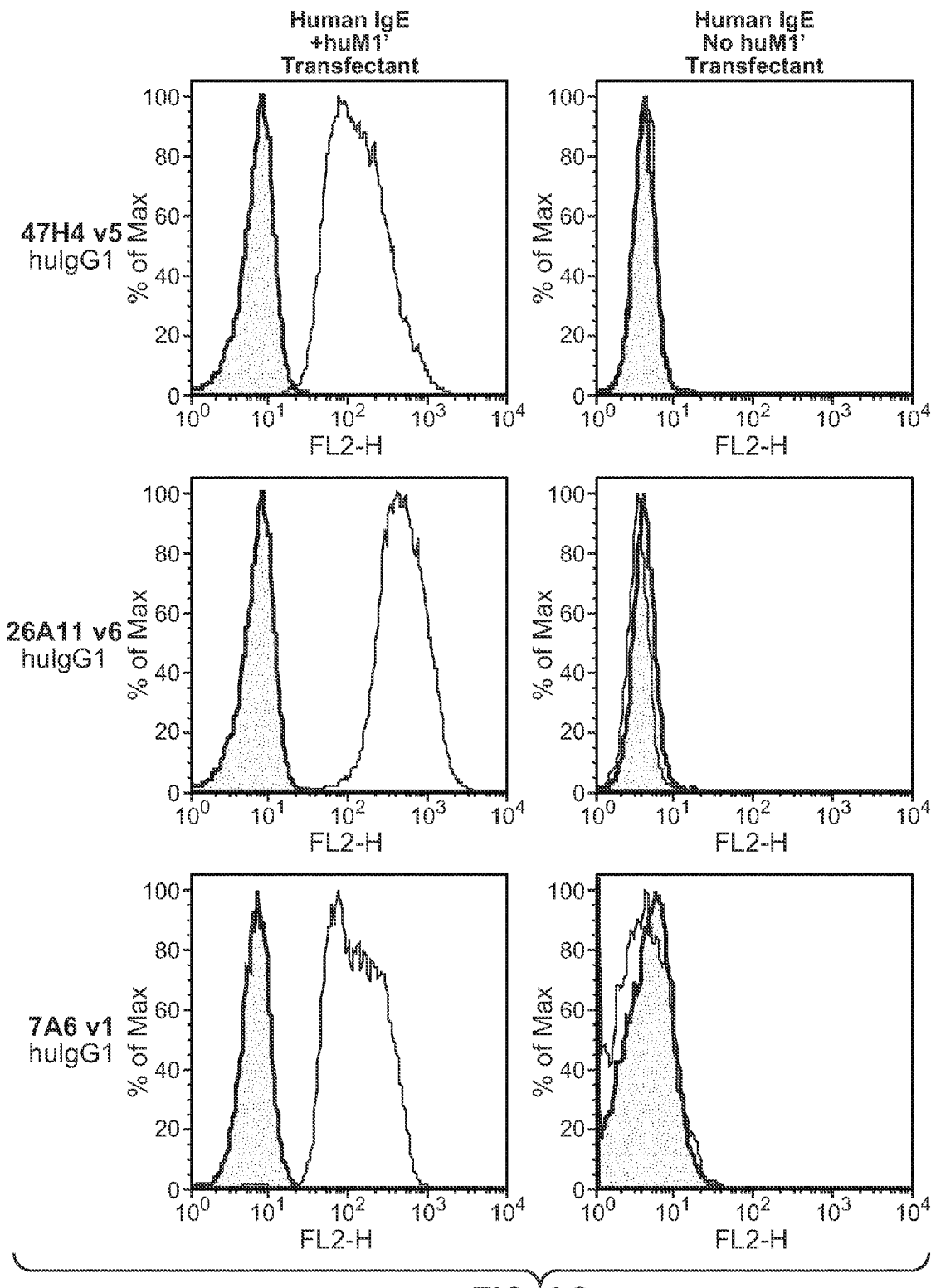
FIGS. 2G-I show the binding specificities of the humanized anti-IgE/M1' antibodies 47H5 v.5, 26A11 v6 and 7A6 v1.
Figure 2H:
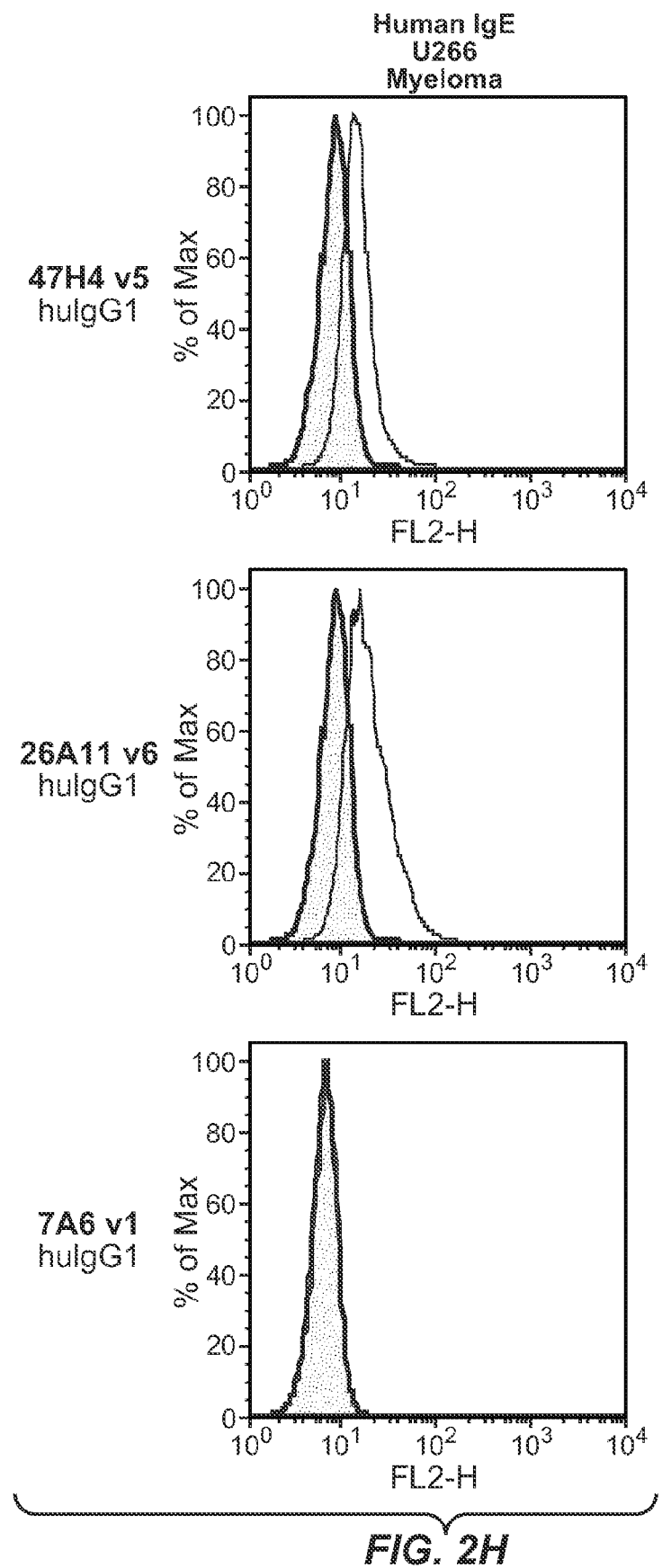

Using the same Daudi or BJAB human B cell lines overexpressing human, rhesus and cyno M1' discussed in Example 3A, the specificity of humanized anti-IgE/M1' antibody clones was tested on the human B cell line Daudi infected by retrovirus to express the long form of IgE with the M1' sequence or the short form of IgE lacking the M1' sequence. Humanized anti-IgE/M1' antibodies (47H4v5, 26A11v6, 7A6v1) are specific for the long form and not the short form (no M1') [FIG. 2G]. HERCEPTIN® anti-Her2 MAb huIgG1 was used as an isotype control (Genentech, Inc.). In addition, humanized anti-IgE/M1' antibodies (47H4v5 and 26A11v6) bind to U266 cell lines (FIG. 2H).

Figure 2I:
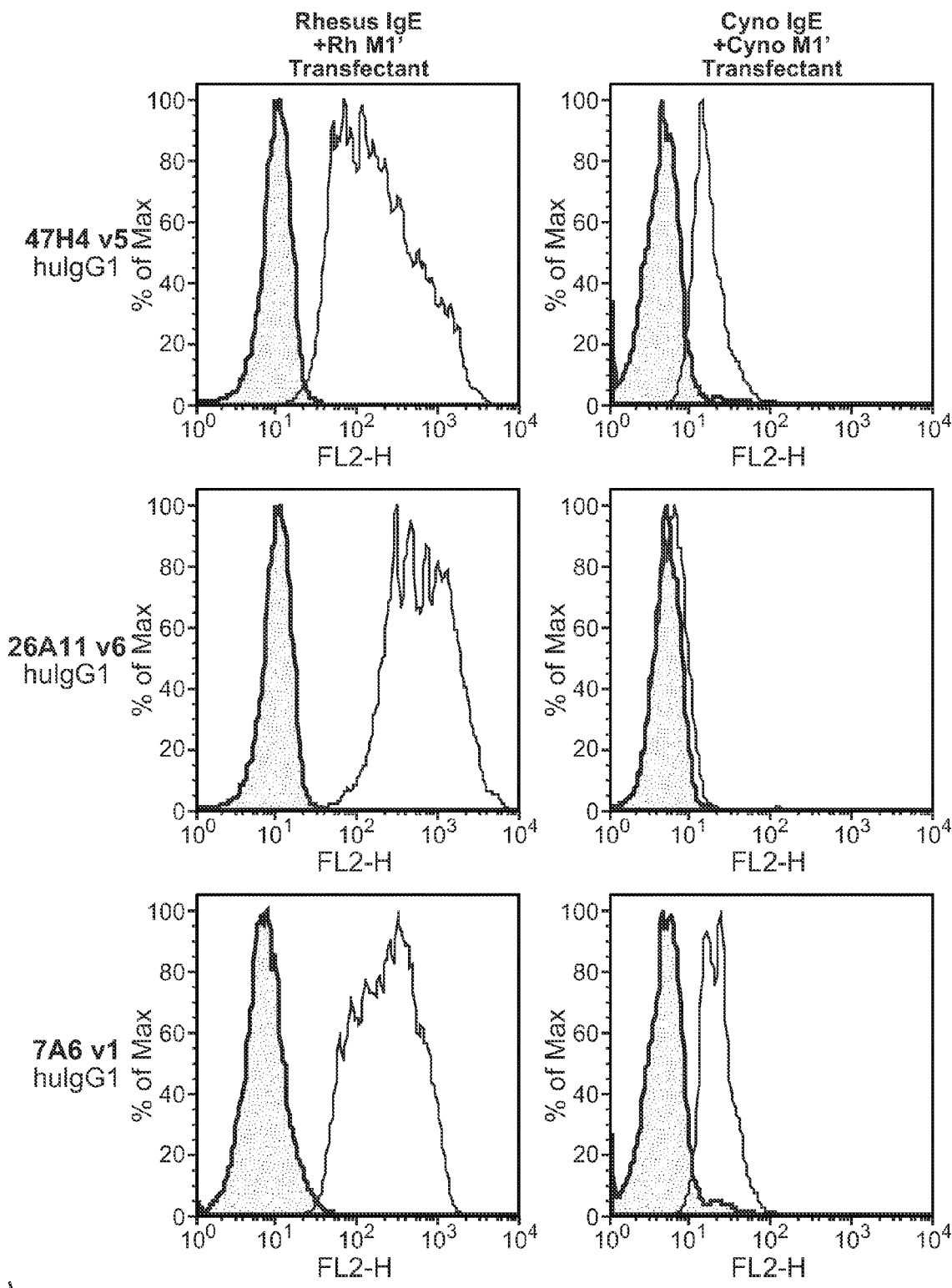
Figure 3G:
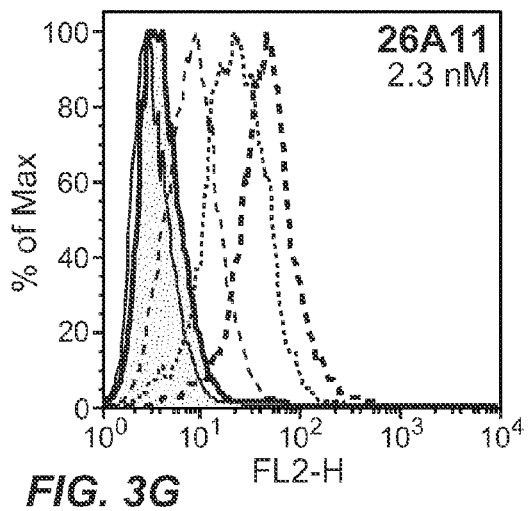
Figure 3H:
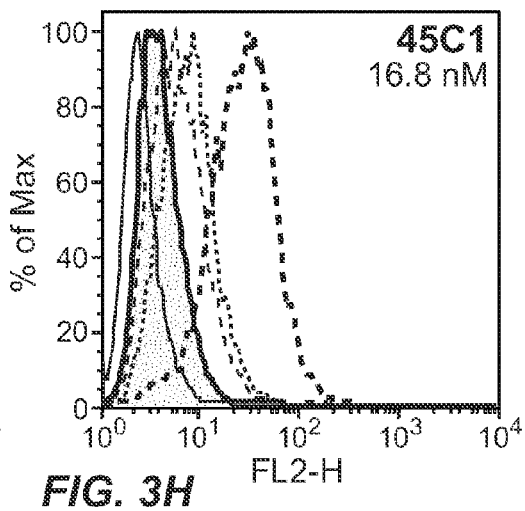
Figure 3I:
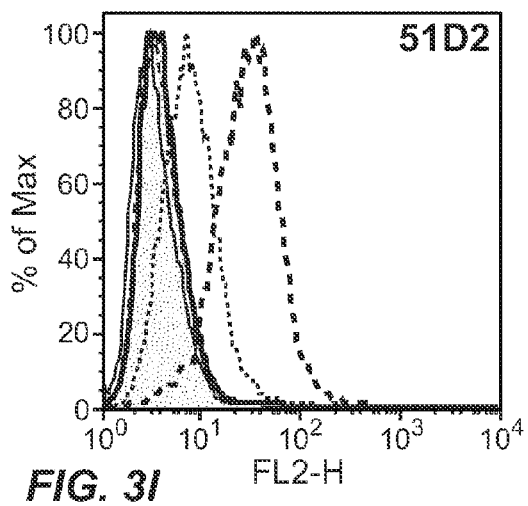
Figure 3J:
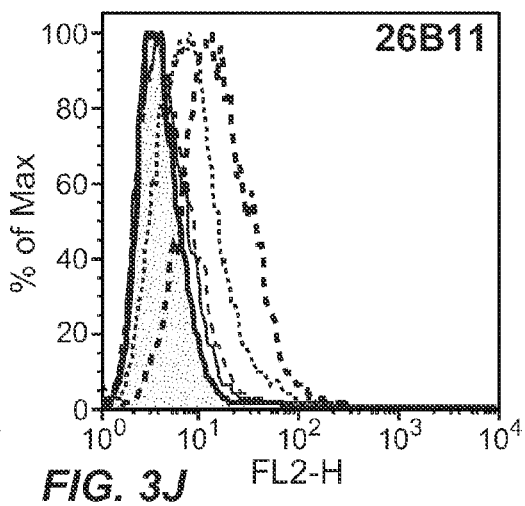
Figure 3K:
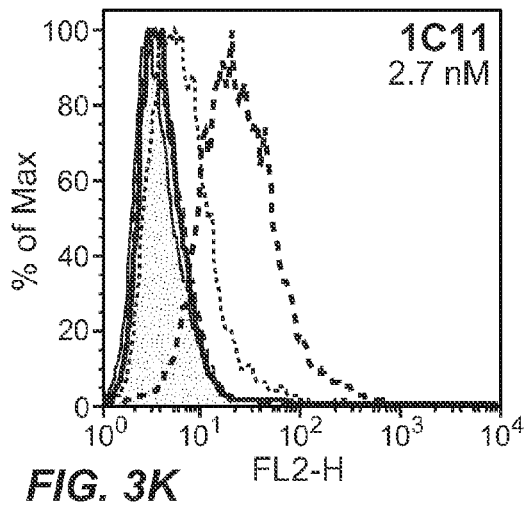
Figure 3L:
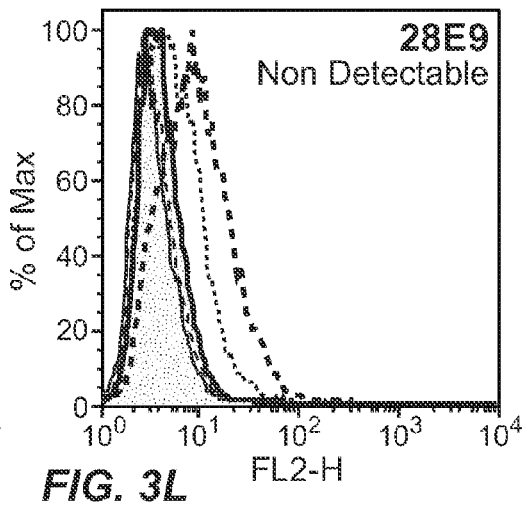

FIG. 2I shows the ability of humanized anti-IgE/M1' antibodies to bind both rhesus and cyno M1'. The antibodies 47H4v5 and 7A6v1 bind both rhesus and cyno M1', whereas 26A11v6 only binds only rhesus M1'.

EXAMPLE 4

Relative Binding Affinity of Anti-M1' Antibodies

We observed a wide range of anti-IgE/M1' antibody binding intensities at 1 mg/ml. To assess the relative affinities of these antibodies for the IgE-long receptor, we stained BJAB-Long cells with a dilution series of anti-M1' antibody (1, 0.1, 0.01, 0.001 µg/ml). BJAB-Long cells were blocked with mouse and human serum (10 µl) for 20 minutes on ice. Cells were stained with the appropriate amount of anti M1'-antibody, or anti-gp120 mIgG1 or anti-ragweed mIgG2a isotype controls for another 20 minutes. Cells were then washed in FACs wash buffer (1 ml), centrifuged (1200 rpm for 5 minutes) and then resuspended in 100 µl of FACs Wash buffer with goat anti-mouse IgG-PE antibody (5 μl) (CALTAG/Invitrogen, Carlsbad, Calif. #M30004-4) for detection. Cells were washed again as above and then analyzed on a FACs Calibur machine (BD, Inc, Franklin Lakes, N.J.). Voltage settings were based on the 0.001 μg/ml isotype control. From these results anti-IgE/M1' antibody candidates were ranked according to relative binding affinity:

42H4>7A6, 47H4, 47G4>42A5, 26A11, 45C1>51D2, 26B11>1C11>28E9

In addition to relative affinity determinations by antibody titration and FACs detection, we also determined affinities of selected anti-M1' antibodies to BJAB cell lines expressing IgE long form using Scatchard analysis. BJAB-Long cells were prepared for binding in cold Binding buffer composed of base media, with 10 mM HEPES pH 7.4, and 2% FBS as well as 40 μg/ml human IgG. Cells were diluted to a concentration of $1.7\times10^6$ cells/ml, and kept on ice until added to the assay. The antibodies were iodinated with Iodogen method. Various concentrations of unlabelled antibody were prepared in triplicate, using a 1:2 dilution starting with the saturation concentration and ending at a concentration of zero, with a total of 14 concentrations. Iodinated antibody of a single concentration was added to all dilutions of the competitor unlabelled antibody. Lastly 250,000 BJAB-Long cells were added to each mixture of iodinated and unlabelled antibody. The samples were incubated at 4° C. for 4 hours, shaking. Each sample was then collected and filtered on a membrane, washed at least 3 times with binding buffer, allowed to dry and then measured for 1 minute using a Perkin Elmer Wizard 1470 Auto Gamma Counter.

EXAMPLE 4A

Scatchard Affinity of Murine Anti-IgE/M1' Antibodies

The BJAB or Daudi cells expressing various forms of IgE with or without M1' (Human, Rhesus, Cyno) were prepared for binding in cold Binding buffer composed of base media, with 10 mM HEPES pH 7.4, and 2% FBS as well as 40 ug/ml human IgG. Cells are diluted to concentration of $1.7\times10^6$ cells/ml, and kept on ice until they are added to the assay. The proteins/antibodies are iodinated with the Iodogen method. Various concentrations of cold protein are prepared in triplicate, using a 1:2 dilution starting with the saturation concentration and ending at a concentration of zero, with a total of 14 concentrations. Hot protein of a single concentration is added to all dilutions compete with the cold protein. Lastly the cells are added to the hot and cold protein mixture, 250,000 cells per sample were used. Assay is kept at 4° C. for 4 hours, shaking. Each sample is then collected and filtered on membrane, washed at least 3 times with binding buffer, allowed to dry and then counted for 1 minute using Perkin Elmer Wizard 1470 Auto Gamma Counter.

FIG. 3O summarizes the affinities of murine anti-M1' antibodies measured by Scatchard analysis. Murine antibody 47H4 mIgG1 bound human, Rhesus, Cyno M1' with affinities of 0.79, 0.77 and 0.97 nM, respectively. Murine antibodies 26A 11 mIgG1 and 7A6 mIgG1 bound human M1' with affinities of 2.3 and 0.64 nM, respectively.

FIG. 3P summarizes the binding affinities of humanized anti-IgE/M1' antibodies to human, rhesus and cyno M1'. Humanized antibody 47H4v5 huIgG1 bound human, rhesus and cyno M1' with affinities of 1.5, 1.3 and 2.5 nm, respectively. Humanized antibodies 47H4 v2, 47H4 v1, 26A11 v6, 26A11 v14 and 26A11 v1 bound human M1' with affinities of 0.54, 0.37, 1.85, 1.5 and 1.06, respectively.

EXAMPLE 5

Anti-IgE/M1' Epitope Binding/Blocking Studies

Blocking studies were performed between anti-IgE/M1' antibody candidates to determine overlapping or distinct binding epitopes. When the blocking and detecting antibodies were of different isotype (i.e., IgG1 vs. IgG2a), these isotype differences were exploited to determine the extent of blocking by detecting with an isotype-specific secondary antibody (CALTAG/Invitrogen, Carlsbad, Calif., Goat anti-mouse IgG1-PE #32004, or Goat anti-mouse IgG2a #M32204). When the blocking and binding antibody antibodies were of the same isotypes, the antibodies were conjugated to Biotin (Pierce, Rockford, Ill., EZ-link-sulfo-NHS-LC-Biotin #CAS 127062-220) and detected with Streptavidin-PE (BD #554061), or conjugated to Alexa-647 (Molecular Probes/Invitrogen, Carlsbad, Calif., #A20173). Initially blocking and detection antibodies were used at a 1:1 ratio (10 μg/ml) (FIGS. 4A-4B). Antibody combinations that initially gave no block or only partial block were further tested using a 10:1 blocking to detection antibody ratio. BJAB-Long cells were blocked with mouse and human serum (as described above), and then stained with the blocking antibody (10 μg/ml) in FACs Wash Buffer (2% FBS/1×PBS) for 20 minutes on ice. Cells were washed in FACs Wash Buffer and then stained with the detection antibody at the 1:1 (10 μg/ml) or 10:1 ratio (1 μg/ml) for 20 minutes on ice. Cells were washed again as above and then analyzed on a FACS Calibur machine (BD, Inc, Franklin Lakes, N.J.). Stained cells were compared to an isotype control antibody either anti-gp120 mIgG1 (Genentech, Inc.) or anti-Ragweed mIgG2a (Genentech, Inc.) (FIG. 4C). For comparison, complete blocking was determined by staining with the same antibody unconjugated when possible.

The blocking studies revealed three major binding groups A and B and C. Group A was further divided into two groups A1 (47H4, 47G4, 42H4, 42A5), and A2 (45C1, 51D2, 26A11) based on partial overlapping epitopes (FIG. 4D). Group C (26B11) had very little overlap with other antibody candidates. Three candidates overlapped more broadly than the others. 1C11 appeared to have overlapping binding with group A1 and A2, and was only partially blocked by group B (28E9). 7A6 primarily belongs to group A1 but had partial interaction with group A2 candidates. 28E9 belongs in a group all to itself. 28E9 had only partial interaction with group A2 candidates.

EXAMPLE 5A

Epitope Mapping

Figure 5D:
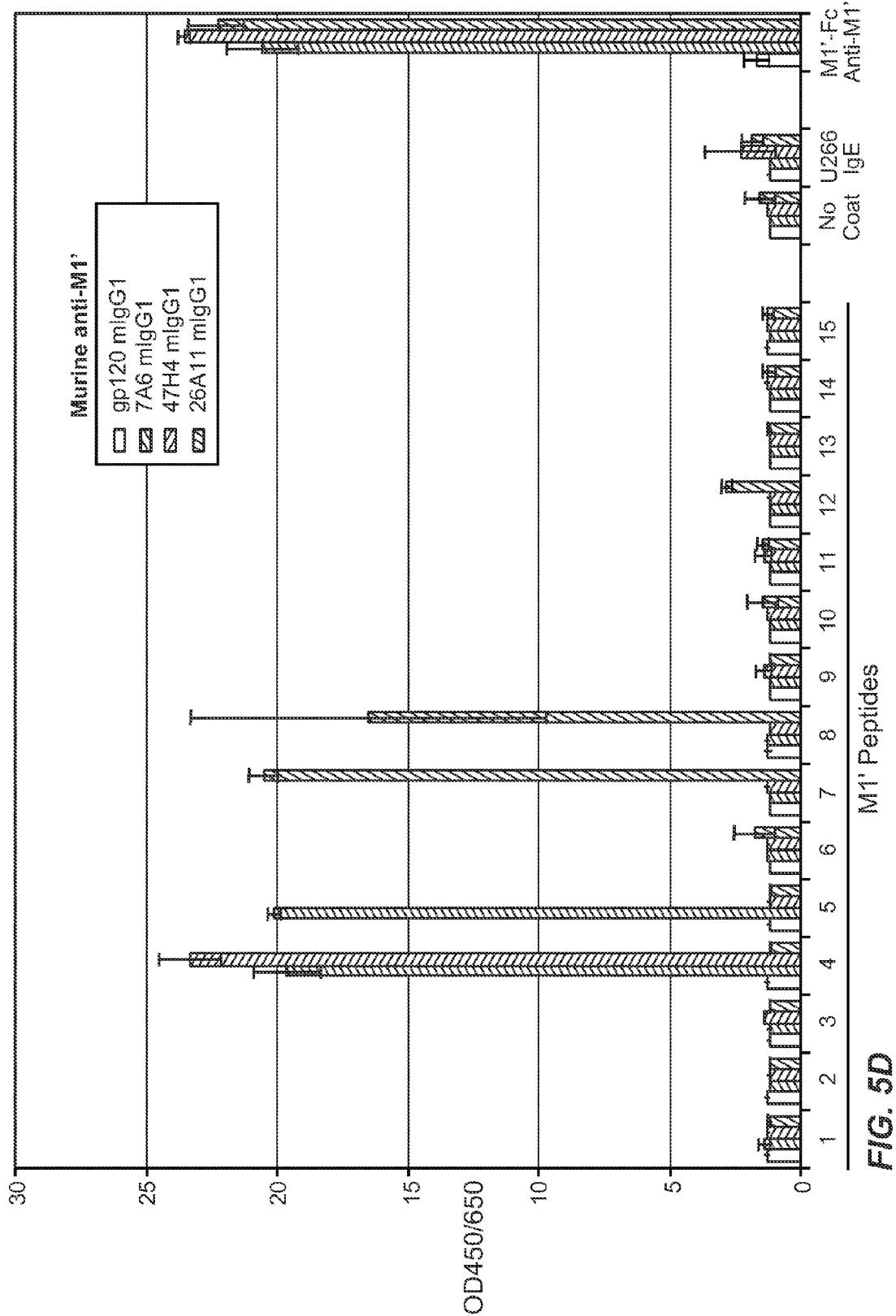
Figure 5E:
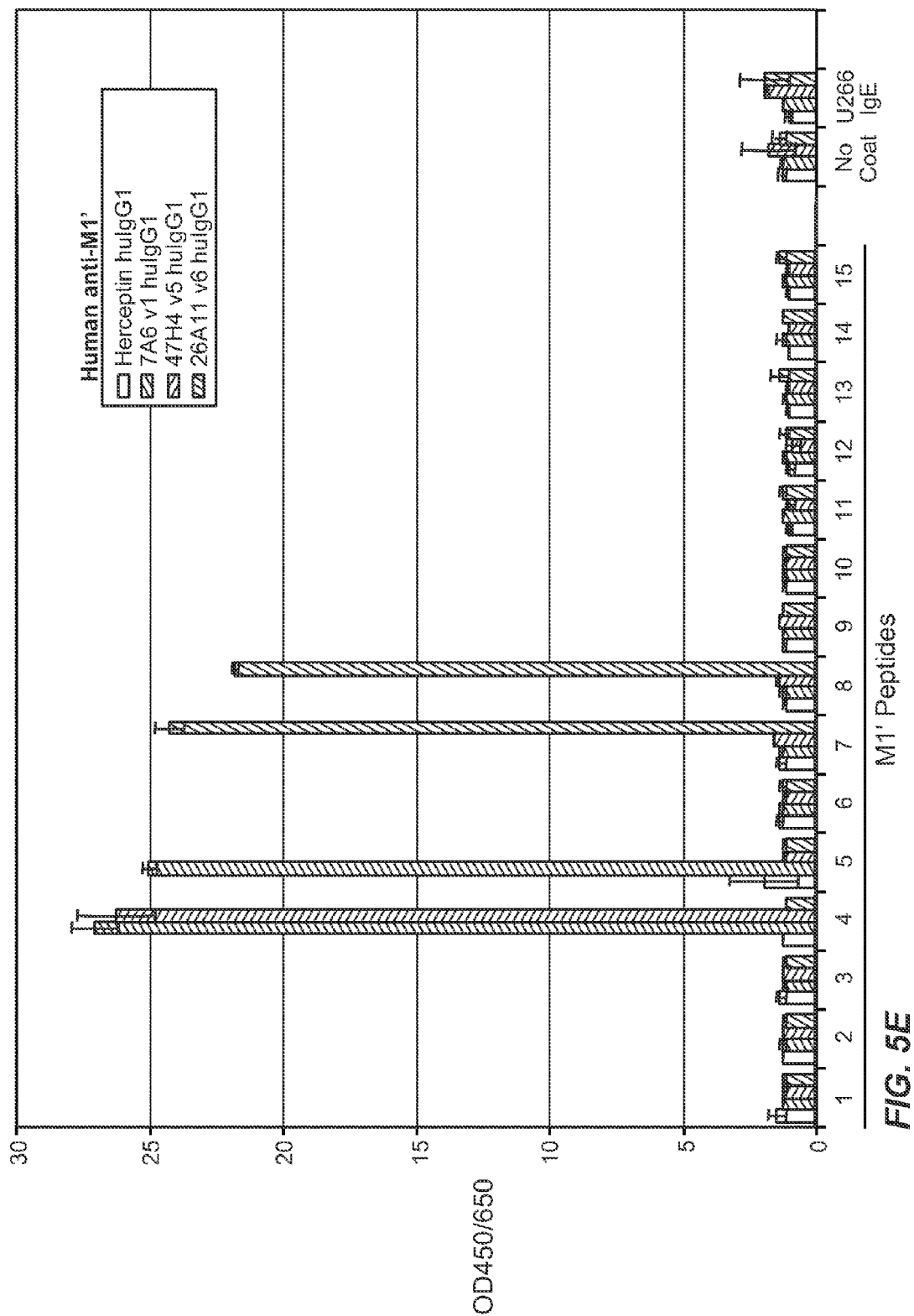
Figure 7A:
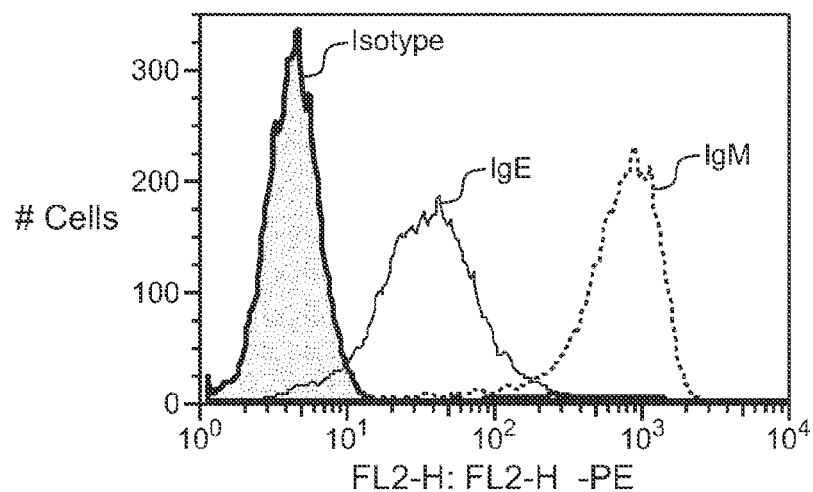
FIGS. 7A-G show the apoptotic activity of the parental anti-M1' antibodies in IgE-M1' transfected Daudi cells.
Figure 7C:
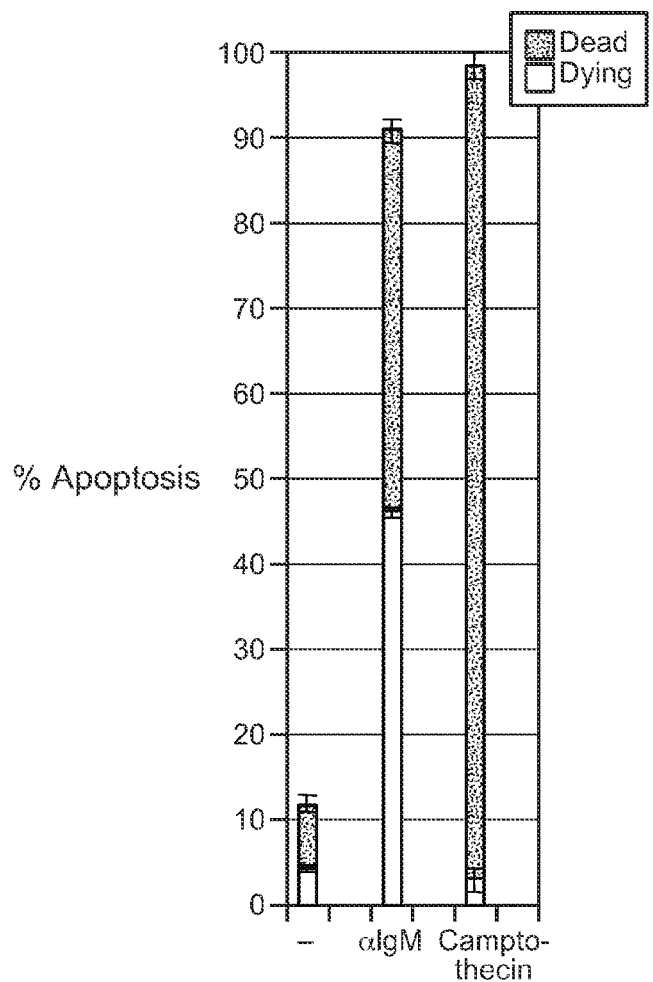
Figure 7B:
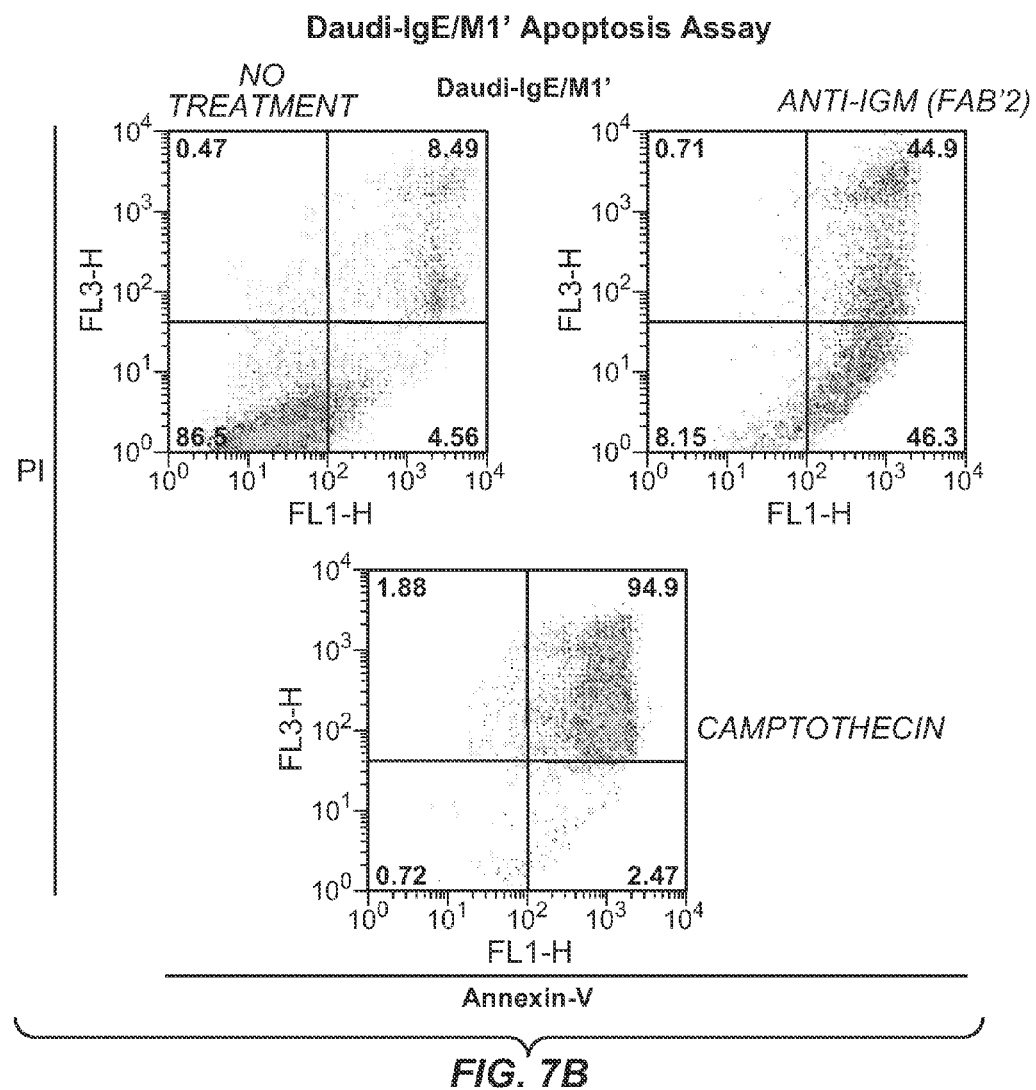
Figure 7D:
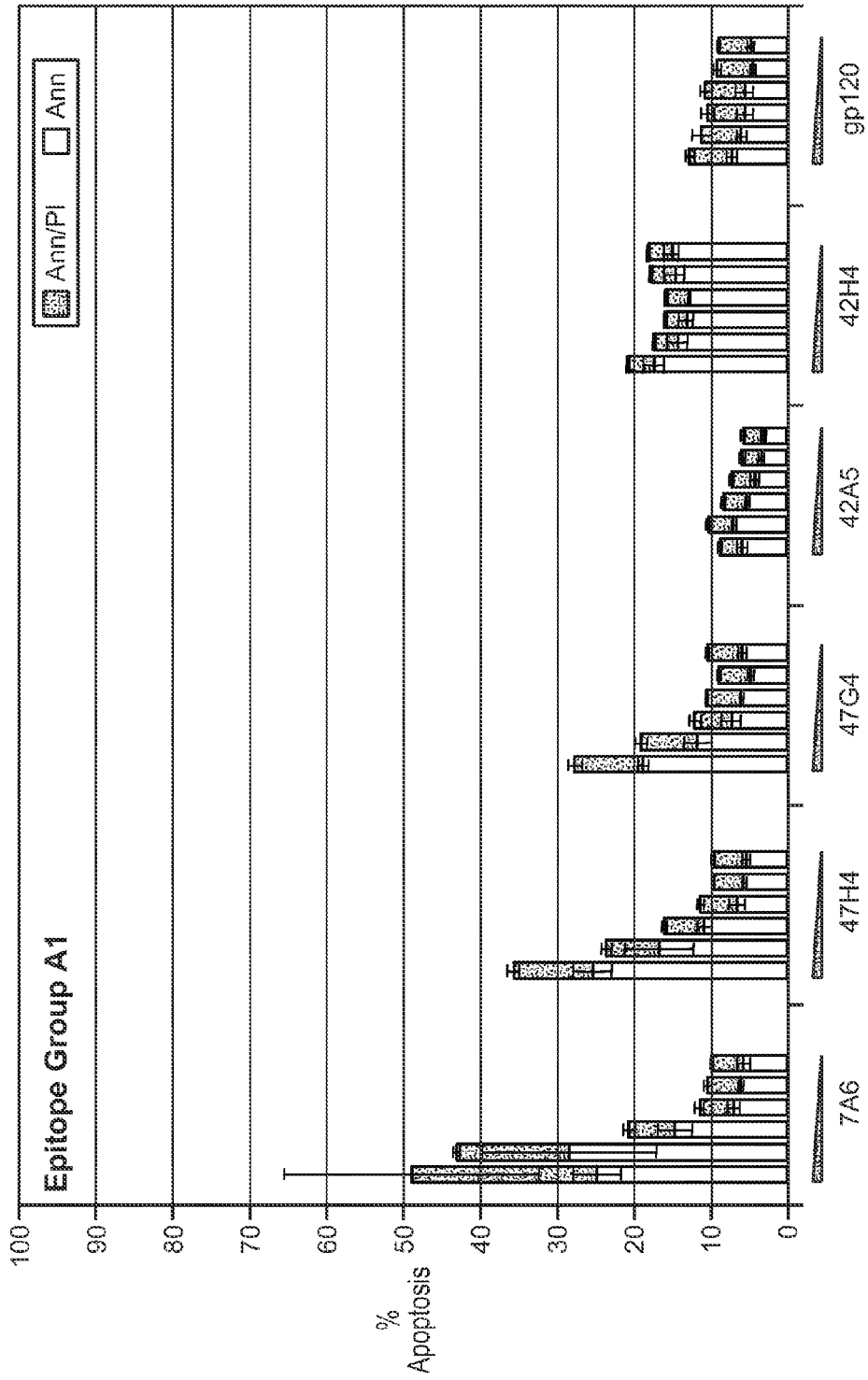
Figure 7E:
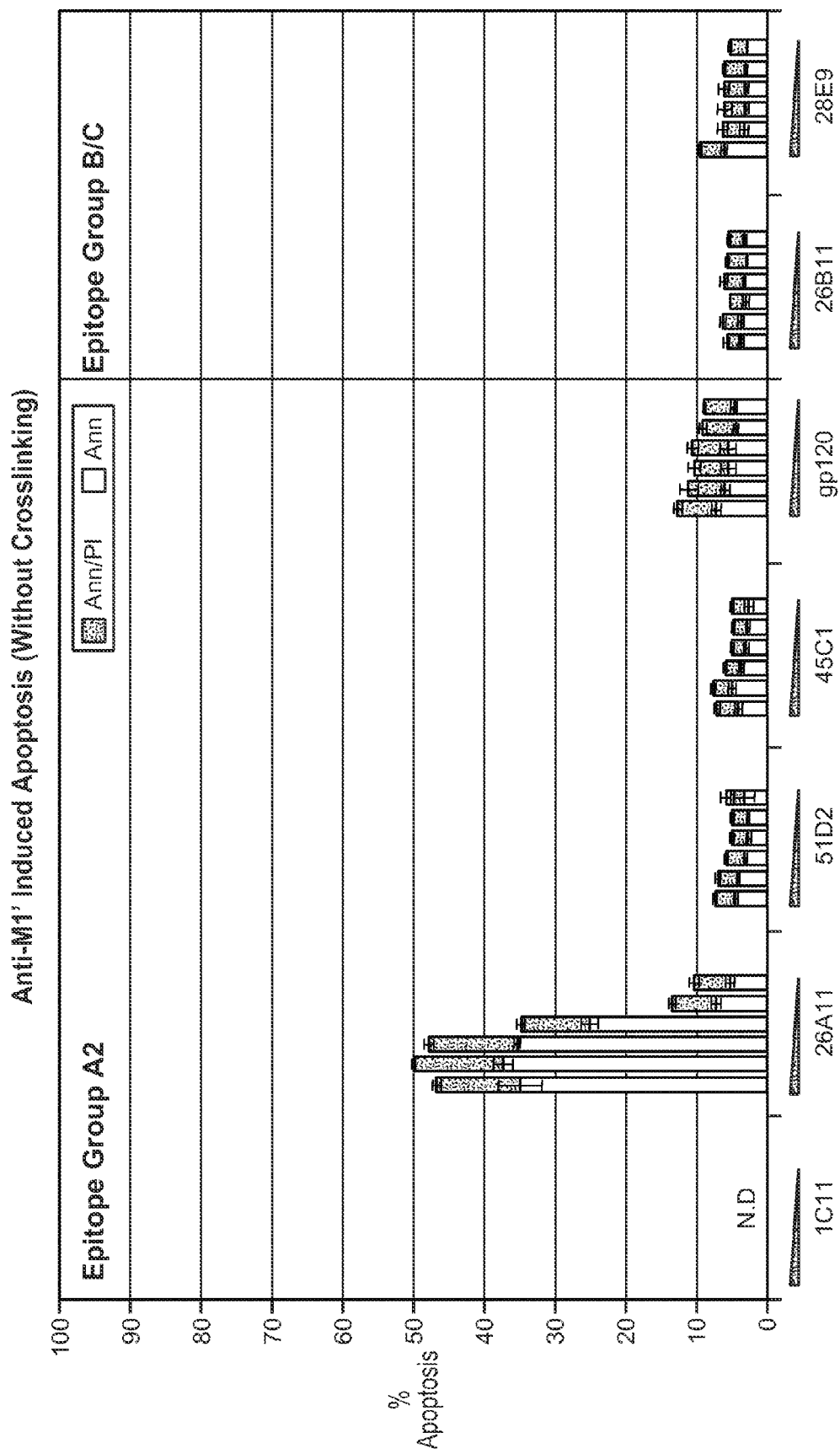
Figure 7F:
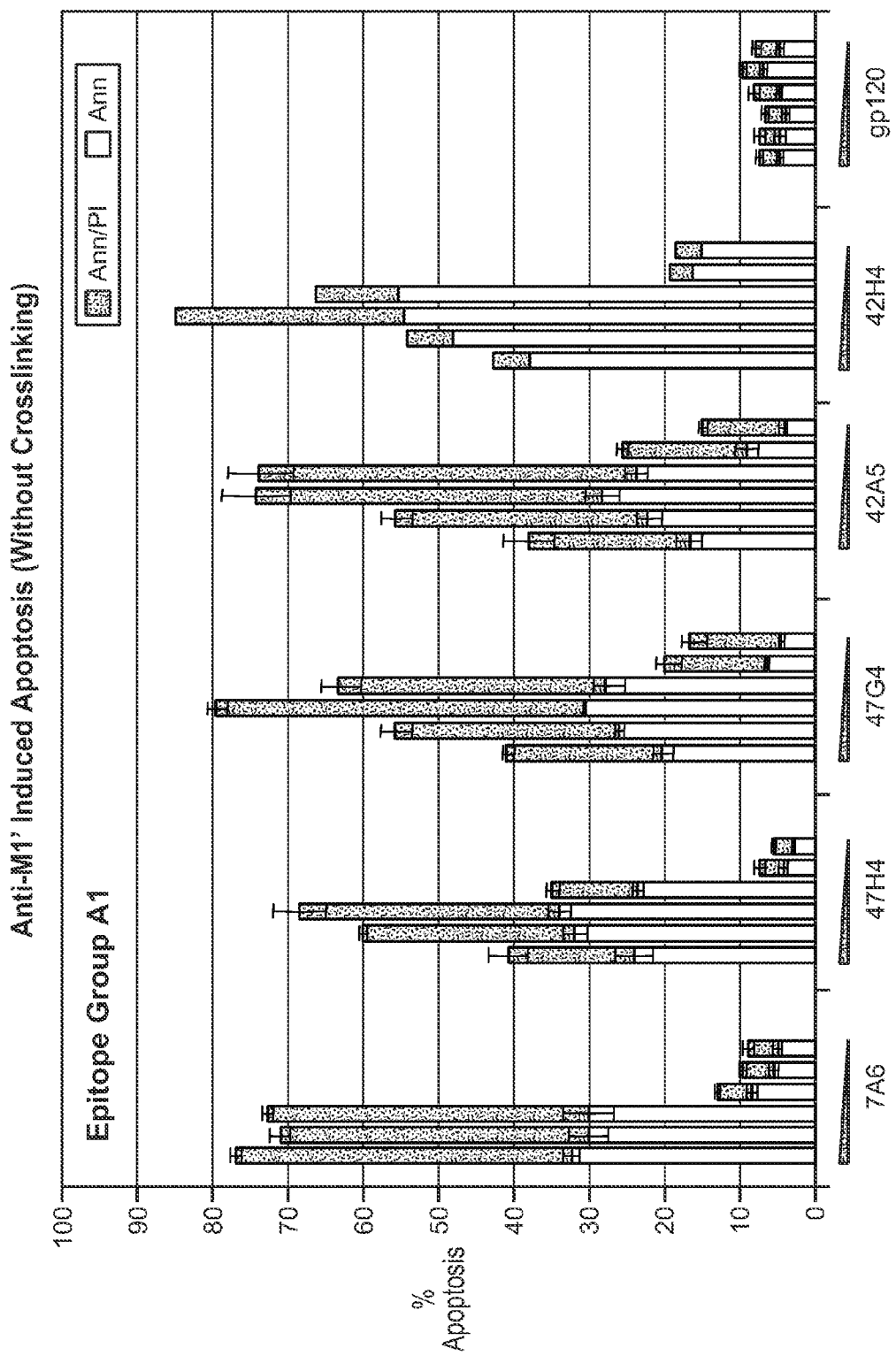
Figure 7G:
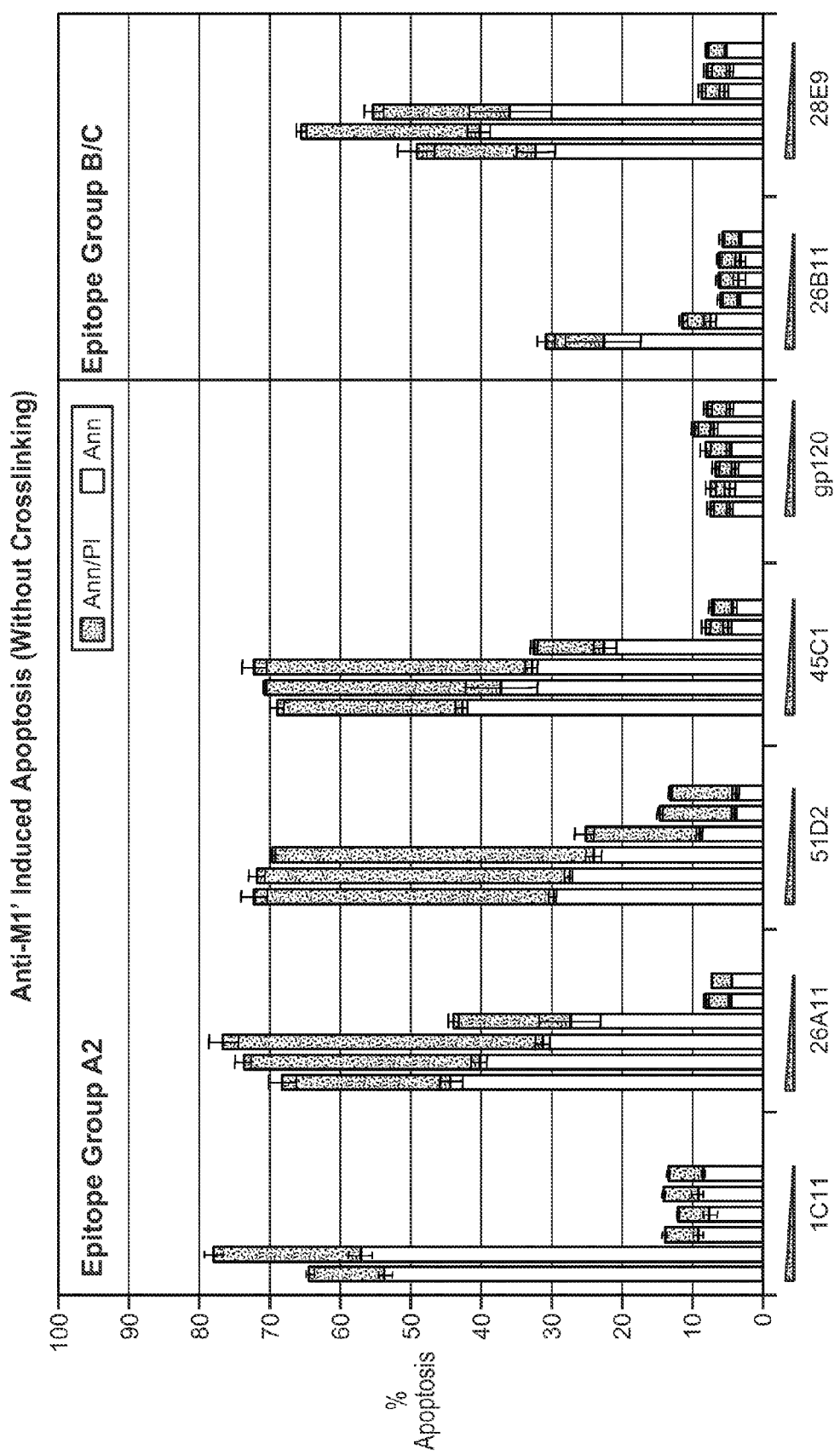

FIGS. 5A-E show epitope binding studies performed using anti-IgE/M1' antibodies. Murine antibodies 47H4, 7A6 and 26A11 are shown in FIGS. 5B and 5D, while humanized variants 47H4v5, 7A6v1 and 26A11v6 are shown in FIGS. 5C and 5E.

Epitope Mapping Studies: Murine Candidates 15 peptides were generated spanning the sequence surrounding and including human M1' (Clifford Quan) (FIG. 5A). Peptides were resuspended in either dH20 or 50% DMSO. Peptides were coated on 96 well plates (NUNC Maxisorp high protein-binding capacity ELISA plates #44-2404) at 1 μg/ml in Coating Buffer (0.05M Carbonate/bicarbonate (pH9.6) (100 μl per well). The M1'-Fc fusion protein was used as a positive control for binding. Negative controls included wells coated with human IgE (U266) and non-coated wells. Peptides were allowed to coat overnight at 4° C. The following morning Plates were washed 3 times with wash buffer (PBS/0.05% Tween-20 (pH 7.4)). Plates were then blocked in Blocking buffer (PBS, 0.5% BSA (pH 7.4)) for 1 hour with gentle agitation. Dilutions of the antibodies (40 ng/ml and 1 ng/ml) to be tested (47H4 mIgG1, 47H4v5 huIgG1, 26A11 mIgG1, 26A11v6 huIgG1, 7A6 mIgG1, 7A6v1 huIgG1) were made in Magic Buffer [PBS (pH7.4), 0.5% BSA. 0.05% Tween-20, 10 ppm Proclin., 0.2% BgG, 0.25% Chaps, 5 mM EDTA, 0.35M NaCl]. Anti-gp120 mIgG1 and HERCEPTIN® huIgG1 antibodies were used as controls for murine and human anti-IgE/M1' antibodies respectively. Once plates were sufficiently blocked (0.5% BSA/1×PBS), plates were washed 3 times, and then antibodies were added to the plate in triplicate (100 µl per well). Plates were then incubated for 2 hours at room temperature. Murine antibody plates were washed 3 times and then anti-mouse IgG1-Biotin (BD Biosciences (A85-1) #553441) was added (1:10,000, 100 µl per well) and incubated for 1 hour at RT. Following 3 washes, SA-HRP (BD Biosciences #554066) was added (1:20,000, 100 µl per well) and incubated for 1 hour. Human IgG1 antibody plates were washed as before and anti-huIgG.Fc-HRP (Jackson ImmunoResearch (#109-036-098)) was added (1:10,000, 100 µl per well) and incubated for 1 hour at RT. Once secondary incubations were complete, plates were washed 6 times and TMB substrate (BD OptEIA #555214) was added (100 µl per well). The substrate-HRP reaction was stopped with 1M H3PO4 after ~4 minutes. Plates were then read at 450/650. Data was represented as relative OD (OD450/CD650).

FIGS. 5B and 5D illustrate the binding of murine 47H4, 26A11 and 7A6 anti-IgE/M1' candidates to M1' peptides. Binding of these candidates correlate with epitope groupings defined antibody blocking studies. 47H4 mIgG1 bound peptide 4 (SAQSQRAPDRVLCHS) (SEQ ID NO:8). 7A6 mIgG1 bound peptides 4 (SAQSQRAPDRVLCHS) (SEQ ID NO:8) and 5 (RAPDRVLCHSGQQQG) (SEQ ID NO:9). 26A11 mIgG1 bound peptides 7 (GQQQGLPRAAGGSVP) (SEQ ID NO:11) and 8 (PRAAGGSVPHPRCH) (SEQ ID NO:12).

FIGS. 5C and 5E illustrate the binding of humanized anti-IgE/M1' antibodies to M1' peptides. The epitope mapping was performed as described above for the corresponding murine antibodies, except that a different secondary antibody was used. Human IgG1 antibody plates were washed as before and anti-IgG.Fc-HRP secondary antibody (Jackson ImmunoResearch (#109-036-098) was added (1:10,000, 100 µl per well) and incubated for 1 hour at RT. Epitope binding parallels that observed with the parental murine antibodies. 47H4 v5 binds peptide 4 (SAQSQRAPDRVLCHS) (SEQ ID NO:8). 7A6 v1 bound peptides 4 (SAQSQRAPDRVLCHS) (SEQ ID NO:8) and 5 (RAPDRVLCHSGQQQG) (SEQ ID NO:9). 26A11 mIgG1 bound peptides 7 (GQQQGL-PRAAGGSVP) (SEQ ID NO:11) and 8 (PRAAGGSVPH-PRCH) (SEQ ID NO:12).

EXAMPLE 6

Induction of Apoptosis by Murine Anti-IgE/M1' in Daudi-IgE/Long Cells

Daudi-Long (IgE/M1') cells were used to test the effect of crosslinking surface IgE on the induction of apoptosis. Daudi cells (ATCC, Manassas, Va., #CCL-213) are a human Burkitt Lymphoma cell line known to be susceptible to apoptosis in response to BCR crosslinking. Daudi cells expressing the long form of IgE were generated by retroviral transduction of the U266 heavy and light chains of IgE with M1', as described above for the generation of BJAB IgE long cells. Flow cytometry analysis of Daudi-IgE/Long cells using antibodies against endogenous IgM and transfected IgE B cell receptor indicate higher expression of IgM than IgE. Apoptosis of Daudi-IgE/Long cells was studied in cells cultured to a density of $0.2 \times 10^6/1.5$ ml in culture medium [RPMI, 10% FBS (Hyclone, Logun, Utah, #SH30071.03), Penicillin/Streptomycin (Gibco/Invitrogen, Carlsbad, Calif. #15140-122), 2 mM Glutamine (Genentech, Inc.), 10 mM HEPES (7.2) (Genentech, Inc.), 1 mM NaPyruvate (Gibco/Invitrogen, Carlsbad, Calif. #11360), 1.59 g/L sodium bicarbonate solution (Gibco/Invitrogen, Carlsbad, Calif. #25080-094)]. Prior to the start of the apoptosis assay, dead cells were removed over a ficoll gradient (GE Healthcare #17-1440-03) to reduce background levels of cell death in the assay. $0.2 \times 10^6$ cells were cultured in triplicate with and without anti-M1' antibodies or control antibodies in solution for 72 hours. Cells were then harvested and analyzed for levels of apoptosis using the Annexin V-FITC Apoptosis Detection Kit I (BD Biosciences, San Jose, Calif. #556547). Cells were washed twice in cold PBS (Genentech, Inc.) and then resuspended in 100 µl 1× binding buffer (0.1 M Hepes/NaOH (pH7.4), 1.4 M NaCl, 25 mM $CaCl_2$) (BD Biosciences, San Jose, Calif., #51-66121E). Cells were then stained with 2.5 µl of Annexin V-FITC antibody (BD Biosciences, San Jose, Calif. #51-65874X) and 5 µl of Propidium Iodide (PI) (BD Biosciences, San Jose, Calif. #51-66211E) in the dark. After 15 minutes, 400 µl of 1× binding buffer was added to each tube and cells were analyzed on a FACs Calibur flow cytometry machine (BD, Inc. Franklin Lakes, N.J.). Approximately 10-20,000 events were collected for each sample. Dying cells are defined as Annexin-V positive and PI negative. Dead cells are positive for both Annexin-V and PI. The percentage of each population (dead and dying) was calculated using FlowJo FACs analysis software (Tree Star, Inc., Ashland, Oreg.). Data in triplicate were averaged and standard deviations calculated. Percent Apoptosis was calculated as the sum of dead and dying cells and graphed using Excel (Microsoft, Inc.).

Camptothecin (Sigma-Aldrich, St. Louis, Mo., #C9911-100 mg) and anti-IgM antibody (JacksonImmuno Research, West Grove, Pa., #109-006-120) were used as positive controls for inducing apoptosis in the Daudi-IgE/Long cell line. Anti-gp120 mIgG1 or anti-Ragweed mIgG1 antibodies (Genentech, Inc.) were used as negative controls for this assay. Daudi-IgE/Long cells were cultured with a range of Anti-IgE/M1' or isotype control antibodies concentrations (25, 10, 1, 0.1, 0.01, 0.001 µg/ml). Anti-IgE/M1' antibodies tested were 7A6, 47H4, 47G4, 42A5, 42H4, 1C11, 26A11, 51D2, 45C1, 26B11 and 28E9 (Genentech, Inc.). Anti-human IgE antibody (Mae11-mIgG1) was also used for comparison.

Isotype control anti-gp120 and anti-ragweed antibodies did not induce apoptosis above untreated cells. Background levels of apoptosis were in the 10-15% range for each experiment. Anti-IgE/M1' antibodies 7A6 (>10 µg/ml), 47H4 (>10 µg/ml), and 47G4 (25 µg/ml) induced apoptosis of Daudi IgE long cells. 26A11 induced similar magnitudes of apoptosis (~30-50%) but at much lower concentrations (>0.1 µg/ml). 42A5, 51D2, 45C1, 26B11, and 28E9 did not induce apoptosis above background levels. Mae11 also did not induce apoptosis above background levels.

We also performed the apoptosis assay in the presence of a goat anti-mouse IgG $F(ab')_2$ secondary antibody (Jackson ImmunoResearch, West Grove, Pa. #115-006-062) to supercrosslink the IgE B-cell receptor on the Daudi cell line.

Crosslinking experiments were done in the presence of goat anti-mouse IgG F(ab')$_2$ antibody (30 µg) (Jackson ImmunoResearch, West Grove, Pa., #115-006-062). With the exception of 26B11 (30%), all antibodies induced maximum apoptotic levels of 70-80% but at different concentrations. These antibodies can be classified into two groups. 7A6, 1C11, 26A11, 51D2, 45C1, and 28E9 induced maximum apoptosis at the highest concentrations. The other group 47H4, 47G4, 42A5, and 42H4, and MAE11 exhibited decreasing apoptosis at higher concentrations.

EXAMPLE 6A

Induction of Apoptosis of Humanized Anti-IgE/M1' Antibodies in Daud/IgE-Long Cells Daudi-Long (IgE/M1') cells were used to test the effect of crosslinking surface IgE on the induction of apoptosis in this cell line. Daudi cells (ATCC, Manassas, Va., #CCL-213) are a human Burkitt Lymphoma cell line known to be susceptible to apoptosis in response to BCR crosslinking. Daudi-IgE/Long cells were cultured at a density of $0.2 \times 10^6/1.5$ ml in culture medium [RPMI, 10% FBS (Hyclone, Logun, Utah, #SH30071.03), Penicillin/Streptomycin (Gibco/Invitrogen, Carlsbad, Calif. #15140-122), 2 mM Glutamine (Genentech, Inc.), 10 mM HEPES (7.2) (Genentech, Inc.), 1 mM NaPyruvate (Gibco/Invitrogen, Carlsbad, Calif. #11360), 1.59 g/L sodium bicarbonate solution (Gibco/Invitrogen, Carlsbad, Calif. #25080-094)] the night before and then dead cells were removed over a ficoll gradient (GE Healthcare #17-1440-03) the next day. This reduced background levels of cell death in the assay. $0.2 \times 10^6$ cells were cultured in triplicate with and without anti-M1' antibodies or control antibodies in solution for 72 hours. Cells were then harvested and analyzed for levels of apoptosis using the Annexin V-FITC Apoptosis Detection Kit I (BD Biosciences, San Jose, Calif. #556547). Cells were washed twice in cold PBS (Genentech, Inc.) and then resuspended in 100 µl 1× binding buffer (0.1 M Hepes/NaOH (pH7.4), 1.4 M NaCl, 25 mM CaCl$_2$) (BD Biosciences, San Jose, Calif., #51-66121E). Cells were then stained with 2.5 µl of Annexin V-FITC antibody (BD Biosciences, San Jose, Calif. 451-65874X) and 5 µl of Propidium Iodide (PI) (BD Biosciences, San Jose, Calif. #51-66211E) in the dark. After 15 minute 400 µl of 1× binding buffer was added to each tube and cells were analyzed on a FACs Calibur flow cytometry machine (BD, Inc. Franklin Lakes, N.J.). Approximately 10-20,000 events were collected for each sample. Dying cells are defined as Annexin-V positive and PI negative. Dead cells are positive for both Annexin-V and PI. The percentage of each population (dead and dying) was calculated using FlowJo FACs analysis software (Tree Star, Inc., Ashland, Oreg.). Data in triplicate were averaged and standard deviations calculated. Percent Apoptosis was calculated as the sum of dead and dying cells and graphed using Excel (Microsoft, Inc.).

An Anti-IgM antibody (JacksonImmuno Research, West Grove, Pa., #109-006-120) was used as a positive control for inducing apoptosis in the Daudi-IgE/Long cell line. HERCEPTIN® huIgG1 (Genentech, Inc.) was used as a negative control for this assay. Daudi-IgE/Long cells were cultured with a range of Anti-IgE/M1' or isotype control antibodies concentrations (25, 10, 1, 0.1, 0.01, 0.001 µg/ml). Secondary crosslinking experiments were done in the presence of goat anti-human IgG F(ab')$_2$ antibody (50 µg) (Biosource #AHI1301). Anti-IgE/M1' antibodies tested were 47H4v5, 26A11 v6, 7A6v1 huIgG1.

Figure 8A:
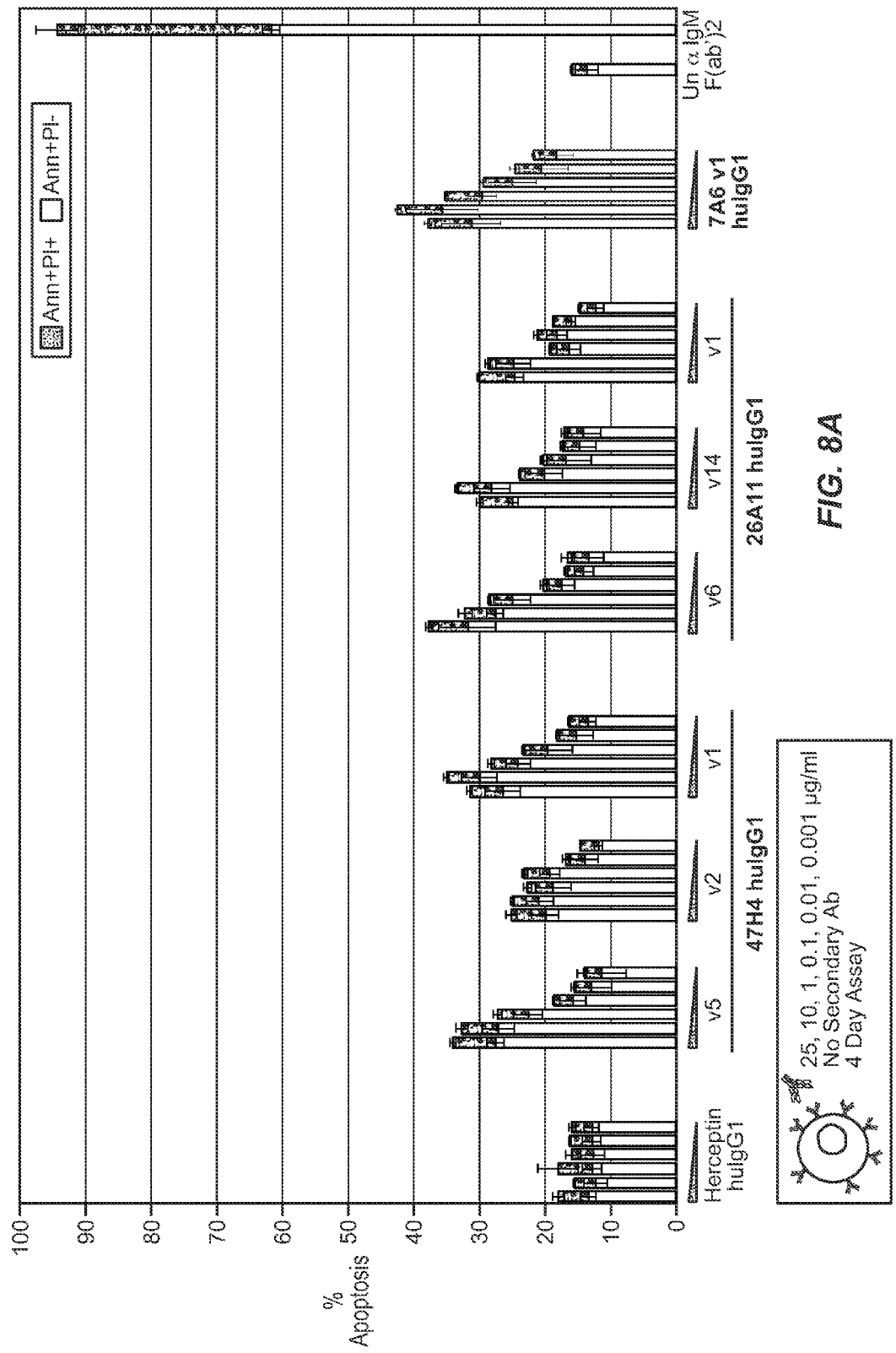
FIGS. 8A-B show the apoptotic activity of the humanized anti-M1' variants in Daudi cells transfected with IgE-M1' treated with various humanized anti-M1' antibody variants at concentrations of 25, 10, 1, 0.1, 0.01 and 0.001 µg/ml.

Isotype control HERCEPTIN® huIgG1 did not induce apoptosis above non treated cells. Background levels of apoptosis were in the 10-15% range for each experiment. Anti-IgE/M1' antibodies 47H4 v5, 26A11v6 and 7A6v1 induced apoptosis in the range of 30-40% (FIG. 8A).

Figure 8B:
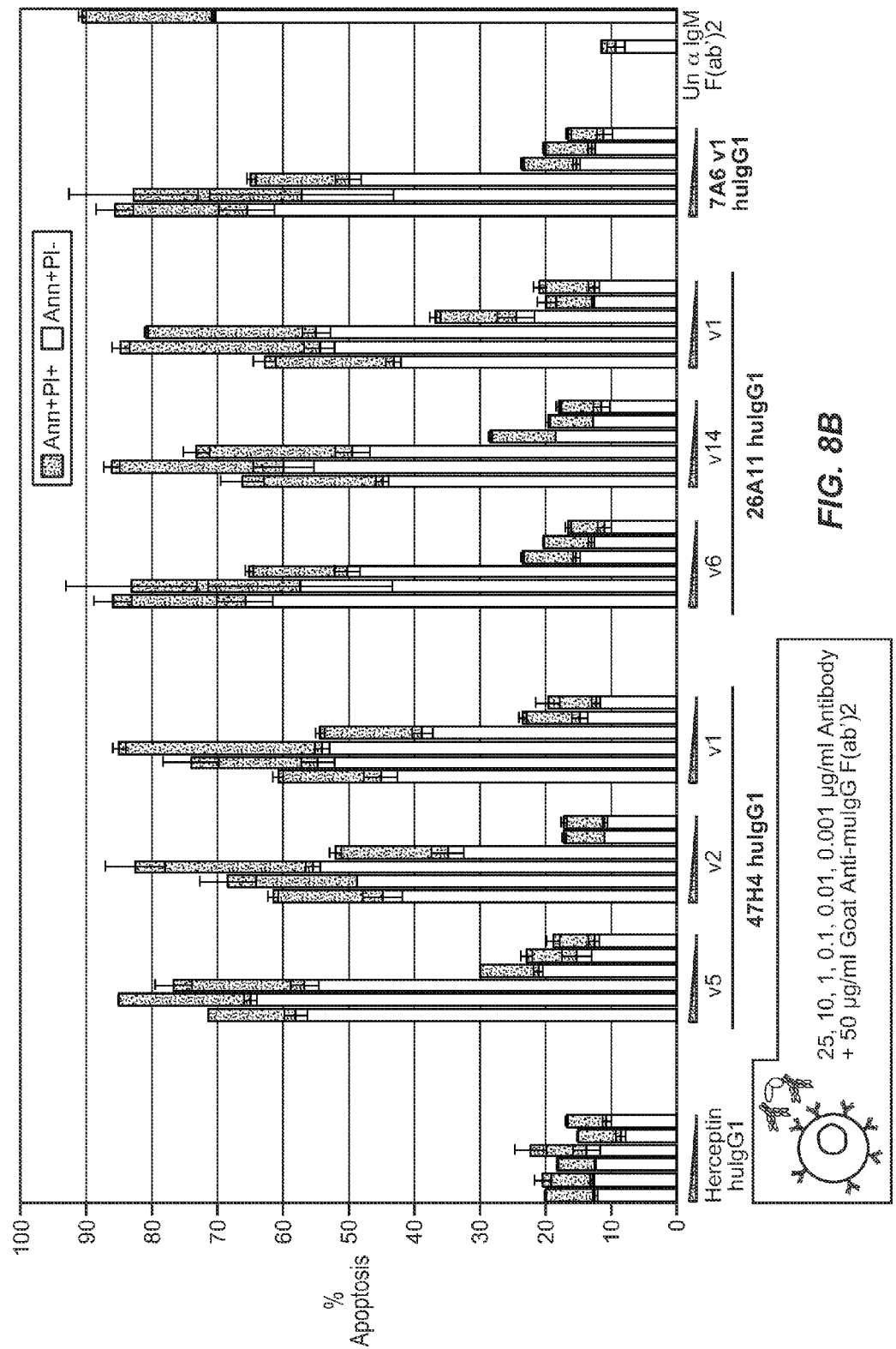

We repeated the same assays in the presence of a goat anti-human IgG F(ab')2 secondary antibody (Biosource #AHI1301) to crosslink the IgE receptor on the Daudi cell line. All antibodies induced maximum apoptotic levels of 70-90%, with some decrease in apoptotic activity at high concentrations of primary anti-IgE/M1' antibody (FIG. 8B). Wildtype vs. Afucosylated 47H4v5 in Inducing Apoptosis without Secondary Crosslinking.

Figure 8C:
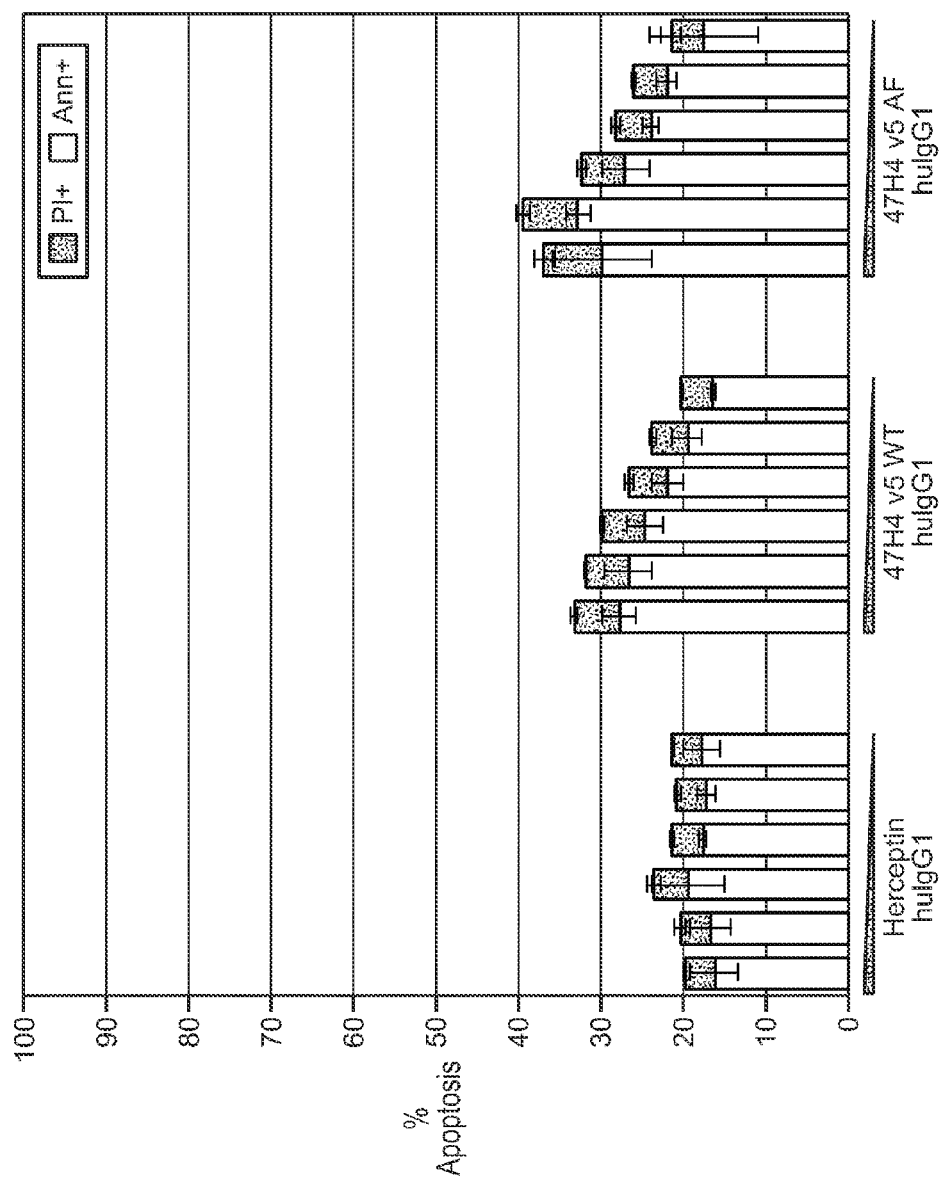
FIG. 8C shows that both wildtype and afucosylated 47H4v5 were able to induce apoptosis at similar levels.
Figure 9A:
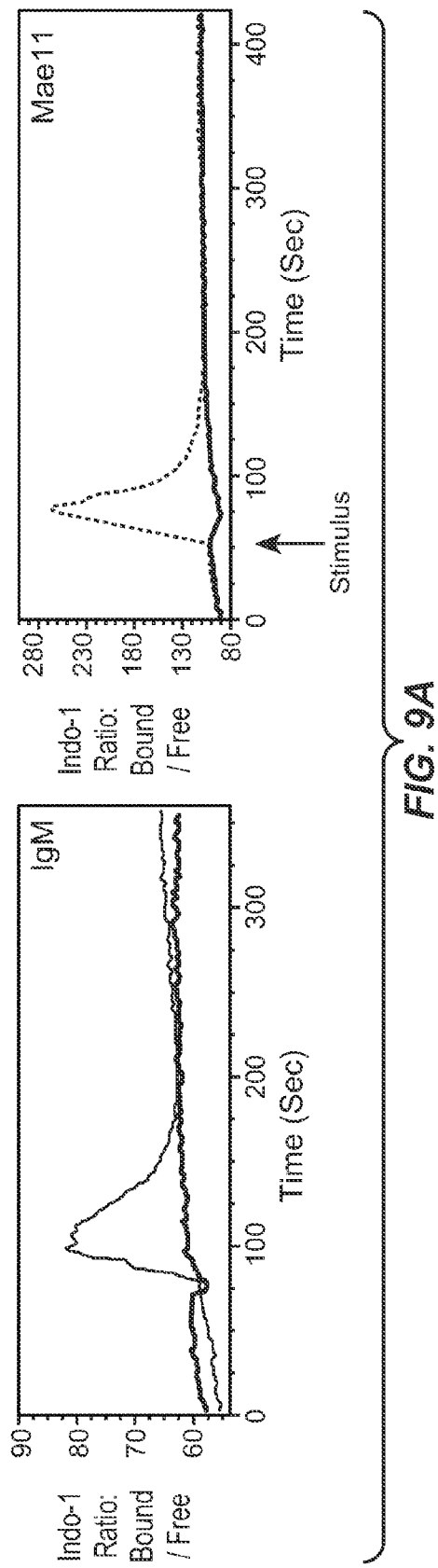
FIGS. 9A-B1-2 shows the ability of the murine anti-M1' antibodies to induce calcium flux in Daudi-IgE/M1' cells.
Figures 1, 9B:
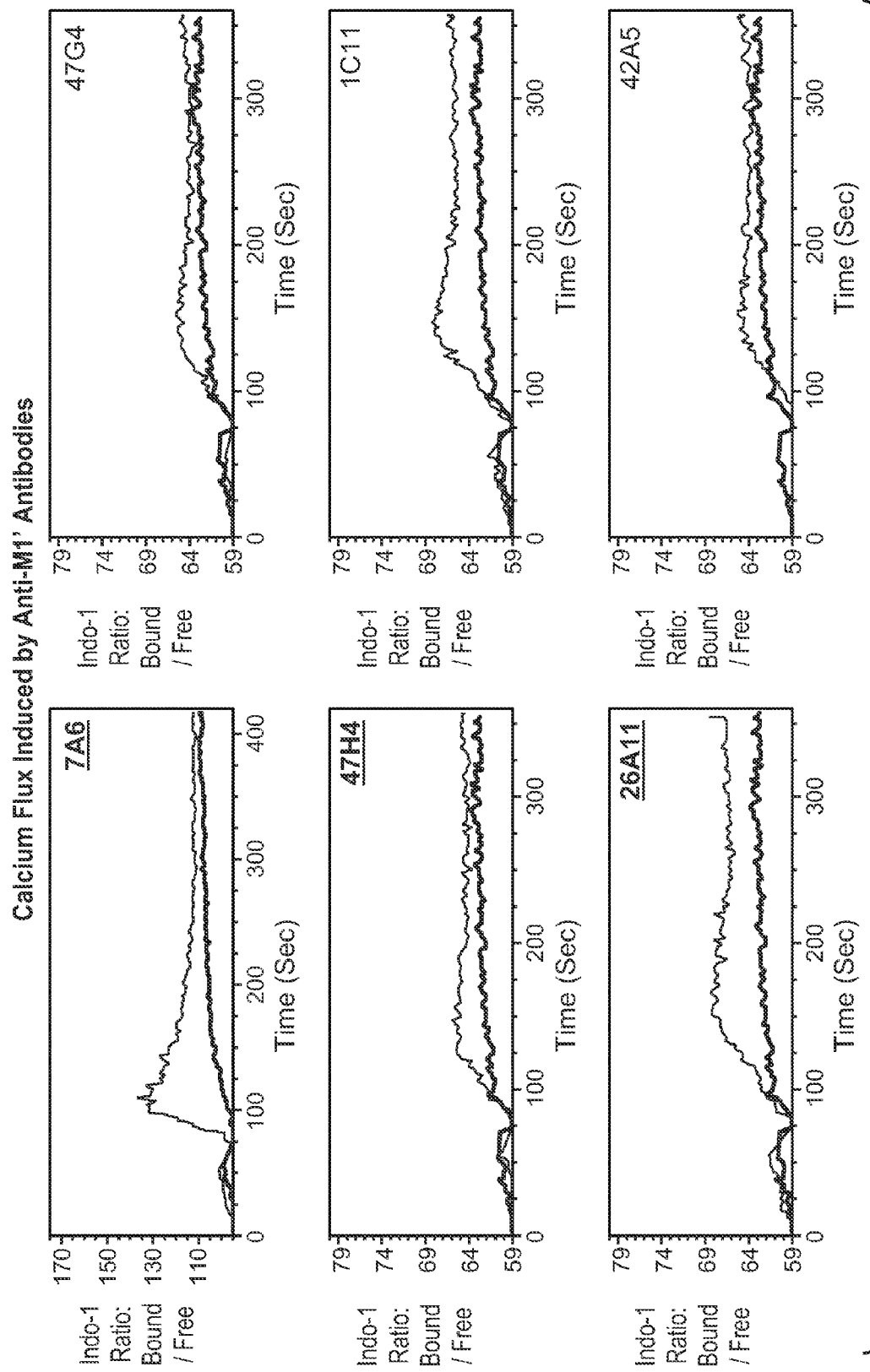
Figure 10:
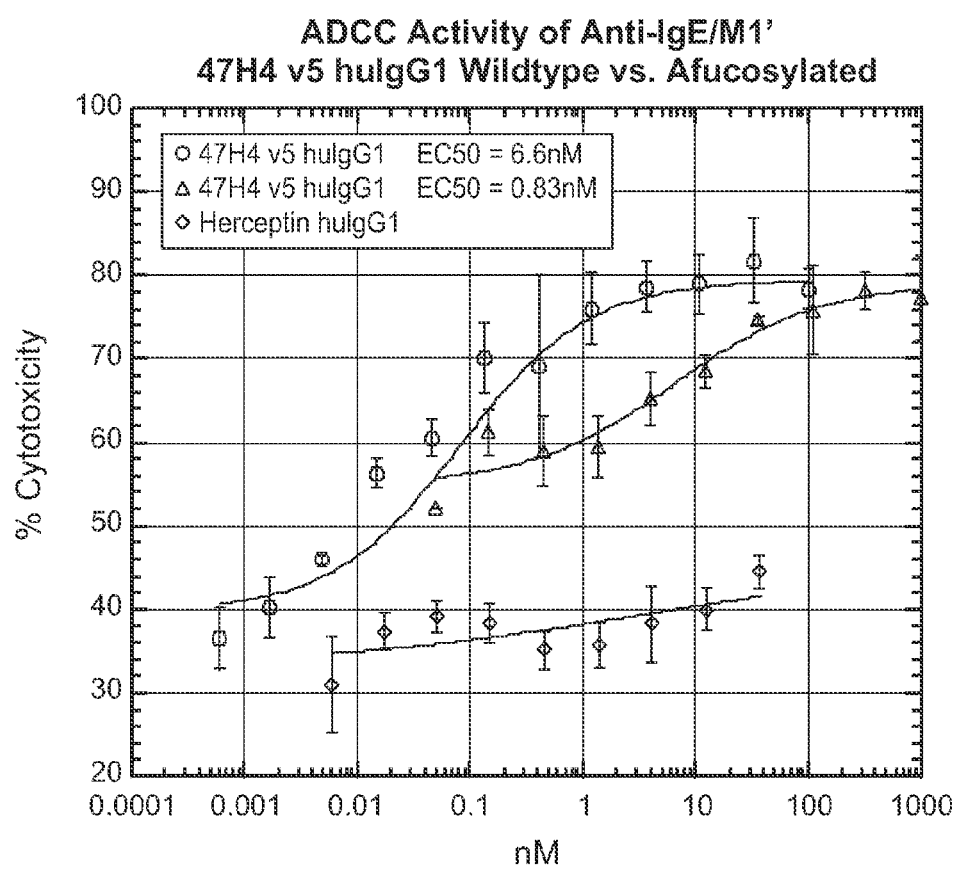

An afucosylate (AF) version of 47H4 v5 was produced using BIOWA cell lines (Genentech, Inc.). Both WT and AF versions of 47H4 v5 were able to induce apoptosis to similar levels (FIG. 8C).

TABLE 1

Humanized Anti-IgE/M1' Binding Affinities

| | Sequence Changes | | Scatchard KD (nM) | BJAB-IgE cell binding IC50 (nM) | IC50 (nM) | Biacore A100 M1' immobilized KD (nM) | Biacore 2000 M1' immobilized KD (nM) | Biacore 2000 IgG Immobilized KD (nM) |
|---|---|---|---|---|---|---|---|---|
| | L1-31/32 | H1-34/35 | | | | | | |
| mu26A11 | NS | MM | 1.6 nM | 12 | 25/26 | 0.3 | | 5.1 |
| 26A11.v1 | NS | MM | | 15 | 19 | 0.2 | 1.7 | 9.0 |
| 26A11.v2 | NA | MM | | 18 | | 0.3 | | |
| 26A11.v3 | NY | MM | | 10 | 22 | 0.0 | 2.8 | |
| 26A11.v4 | NS | IM | | 20 | 29 | 0.9 | | |
| 26A11.v5 | NA | IM | | 25 | 35 | | | |
| 26A11.v6 | NY | IM | | 11 | 23 | 2.6 | | 8.3 |
| 26A11.v7 | NS | IH | | | 890 | | very weak | |
| 26A11.v10 | NS | IN | | ~3300 | | 1064 | | |
| 26A11.v11 | NA | IN | | ~540 | | 21364 | | |
| 26A11.v12 | NY | IN | | ~1200 | | | | |
| 26A11.v13 | SS | MM | | | 19 | | 4.0 | |
| 26A11.v14 | QS | MM | | | 19 | | 3.9 | |
| 26A11.v15 | SS | IM | | | 32 | | 8.4 | |
| 26A11.v16 | QS | IM | | | 27 | | 8.8 | |

TABLE 1-continued

Humanized Anti-IgE/M1' Binding Affinities

| | Sequence Changes | | | Scatchard | BJAB-IgE cell binding | | Biacore A100 | Biacore 2000 | | |
|---|---|---|---|---|---|---|---|---|---|---|
| | | | | | | | M1' immobilized | M1' immobilized | M1' immobilized | IgG Immobilized |
| | L1-27e/28 | H1-34 | H3-100k | KD (nM) | IC50 (nM) | IC50 (nM) | KD (nM) | KD (nM) | | KD (nM) |
| mu47H4 | NG | M | M | 0.4 nM | 62 | 57 | 5.6 | 12 | | 1.5 |
| 47H4.v1 | NG | M | M | | 12 | 18 | 7.8 | | | 3.1 |
| 47H4.v2 | NA | M | M | | 38 | | 7.4 | | | 2.8 |
| 47H4.v3 | NG | I | L | | ~7600 | | 69 | | | |
| 47H4.v4 | NA | I | L | | >1300 | | 56 | | | |
| 47H4.v5 | NA | I | M | | | 60 | | 23 | | |
| 47H4.v6 | NA | M | L | | | 170 | | 54 | | |
| | H1-34 | H3-100k | | | | | | | | |
| mu7A6 | M | M | | 0.6 nM | 52 | | 4.5 | | | |
| 7A6.v1 | M | M | | | 39 | | 15 | | | |
| 7A6.v2 | I | L | | | ~370 | | 571 | | | |

EXAMPLE 7

Induced Calcium Flux

We investigated the ability of anti-M1' antibodies to induce calcium flux in Daudi-IgE/Long cells as evidence that these antibodies can induce cellular signaling downstream of the IgE B-cell receptor. Daudi cells (ATCC, Manassas, Va., #CCL-213) that overexpress the long form of IgE/M1' were cultured overnight at a light density of $0.2 \times 10^6$/ml. The next morning dead cells were removed over a ficoll gradient (GE Healthcare #17-1440-03). Cells were loaded with Indo-1 in bulk to ensure even loading among all stimuli. Cells were resuspended at $5 \times 10^6$/ml in culture medium (RPMI-10% FBS (Hyclone), penicillin/streptomycin, 2 mM L-Glutamine) and combined with the calcium detection dye Indo-1 (5 µM) (Molecular probes/Invitrogen, Carlsbad, Calif., #11223). The cells were then washed in culture media and resuspended at $10^6$/ml. $10^6$ cells were used per stimulus. Samples were warmed in a 37° C. water bath for 5 minutes prior to running on a FACs Vantage machine (BD, Inc, Franklin Lakes, N.J.). Samples were initially run for 1 minute to generate a baseline and then samples were stimulated with 20 µg of each antibody, except for anti-IgM (10 µg). Data was collected for 8-10 minutes. Kinetic analysis was performed on FlowJo FACs analysis software (Tree Star, Inc., Ashland, Oreg.). Data is reported as the ratio of Indo-1 405 Bound/Indo-1 1530 Free. All anti-M1' antibodies were compared to isotype control anti-gp120 mIgG1 (20 µg). Anti-human IgM (Jackson Immuno-Research, West Grove, Pa., #109-005-129) and anti-IgE (Mae11, Genentech, Inc.) were used as positive controls. 7A6, 47H4, 47G4, 26A11, and 1C11 induced a calcium flux in Daudi IgE long cells. 28E9 and 42A5 induced low levels of calcium flux, 45C1, 26B11, and 51D2 did not induce calcium flux.

EXAMPLE 8

Induction of ADCC by Anti-IgE/M1' 47H4 v5 wt and Afucosylated

Antibody-dependent cell-mediate toxicity enables to cytotoxic cells to bind (through the antibody) to the antigen-binding target cell and subsequently kill the target cell with cytotoxins. Anti-IgE/M1' antibodies possessing ADCC activity or enhanced ADCC activity may have enhanced therapeutic value in the treatment of IgE-mediated disorders.

It has been discovered that antibodies produced in mammalian cells that are afucosylated have enhanced ADCC activity. The following experiment described the production of afuscosylated anti-IgE/M1' antibody.

NK cells were isolated from 100 ml whole blood (RosetteSep #15065, Stem Cell Technologies). Purity of NK cells was determined by anti-human CD56 staining. >70% pure CD56+ NK cell were used in each assay. Anti-IgE/M1' antibodies and HERCEPTIN® anti-Her2 MAb huIgG1 isotype control were titrated serially. These antibodies (50 µl) were incubated with BJAB cells overexpressing human IgE/M1' on the cell surface for 30 minutes at room temperature in RPMI-1640 (no phenol red) (BioWhitaker #12-918F) with 1% FBS (Cell line was generated as outlined above). NK cells (50 µl) were then added to the cell line at a 15:1 ratio (150,000 NK cells to 10,000 targets (BJAB-Long)). Assays were done in triplicate. BJAB-huLong, antibodies, and NK cells were then incubated for 4 hours at 37° C. After culture, 96 well U bottom plates were spun down and supernatants were harvested (100 µl). Supernatants were then tested for LDH release using the LDH reaction Assay (Roche #1644793). Target alone and Target lysed were used to calculate the percent cytotoxicity. Superantants were incubated at an equeal volume with the LDH reaction mixture as outlined by the manufacturer for 30-60 minutes. Plates were then read at 490 nm. % cytotoxicity was calculated as follows: =(Exp value−Target alone)/target lysed−Target alone). Data was plotted using Kaleidagraph and best fit curves were used to generate ED50 values.

Figures 4, 4A, 5, 6, 7, 8, 9, 10:
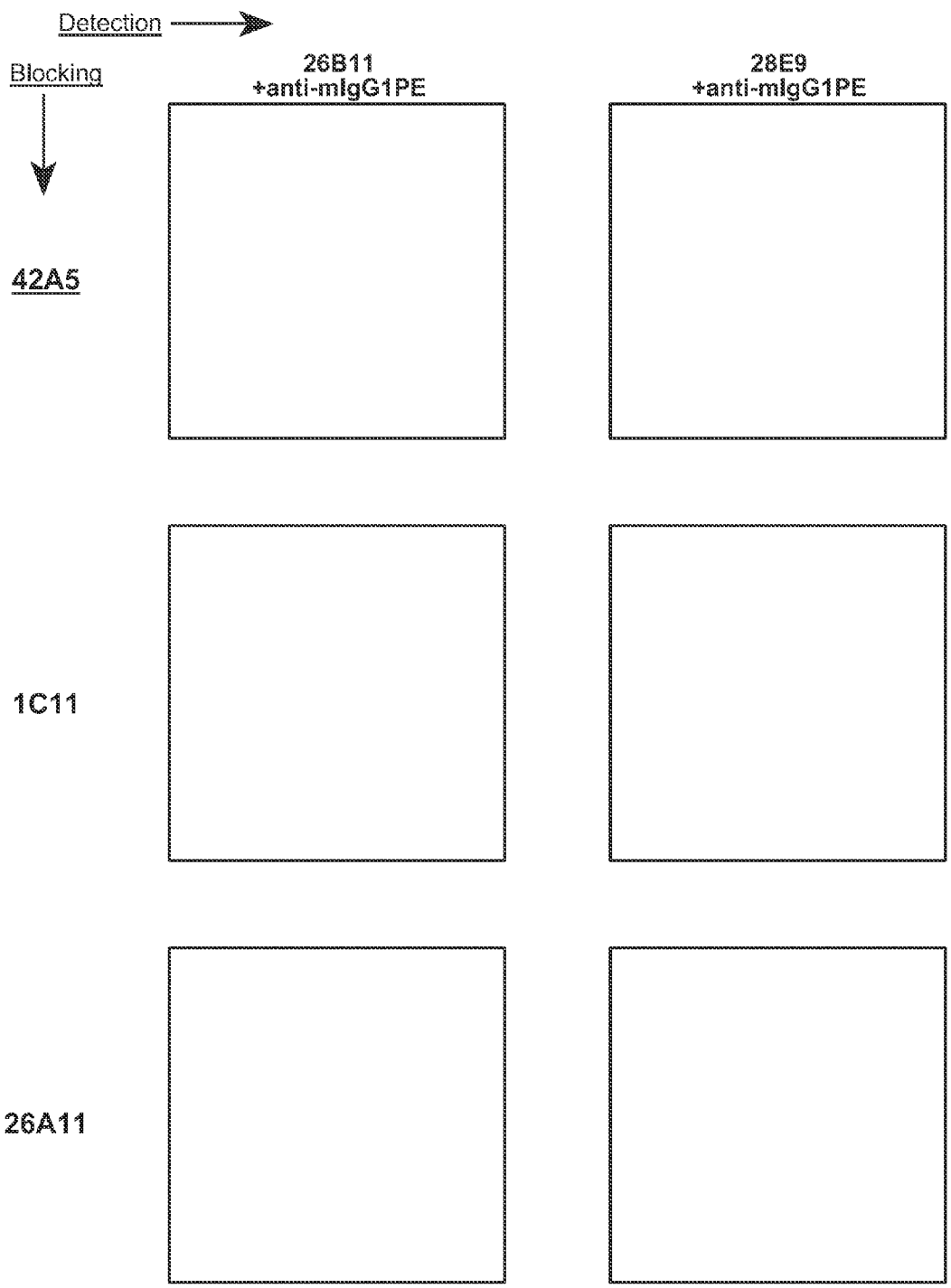
Figures 4, 4A, 5, 6, 7, 8, 9, 10, 11:
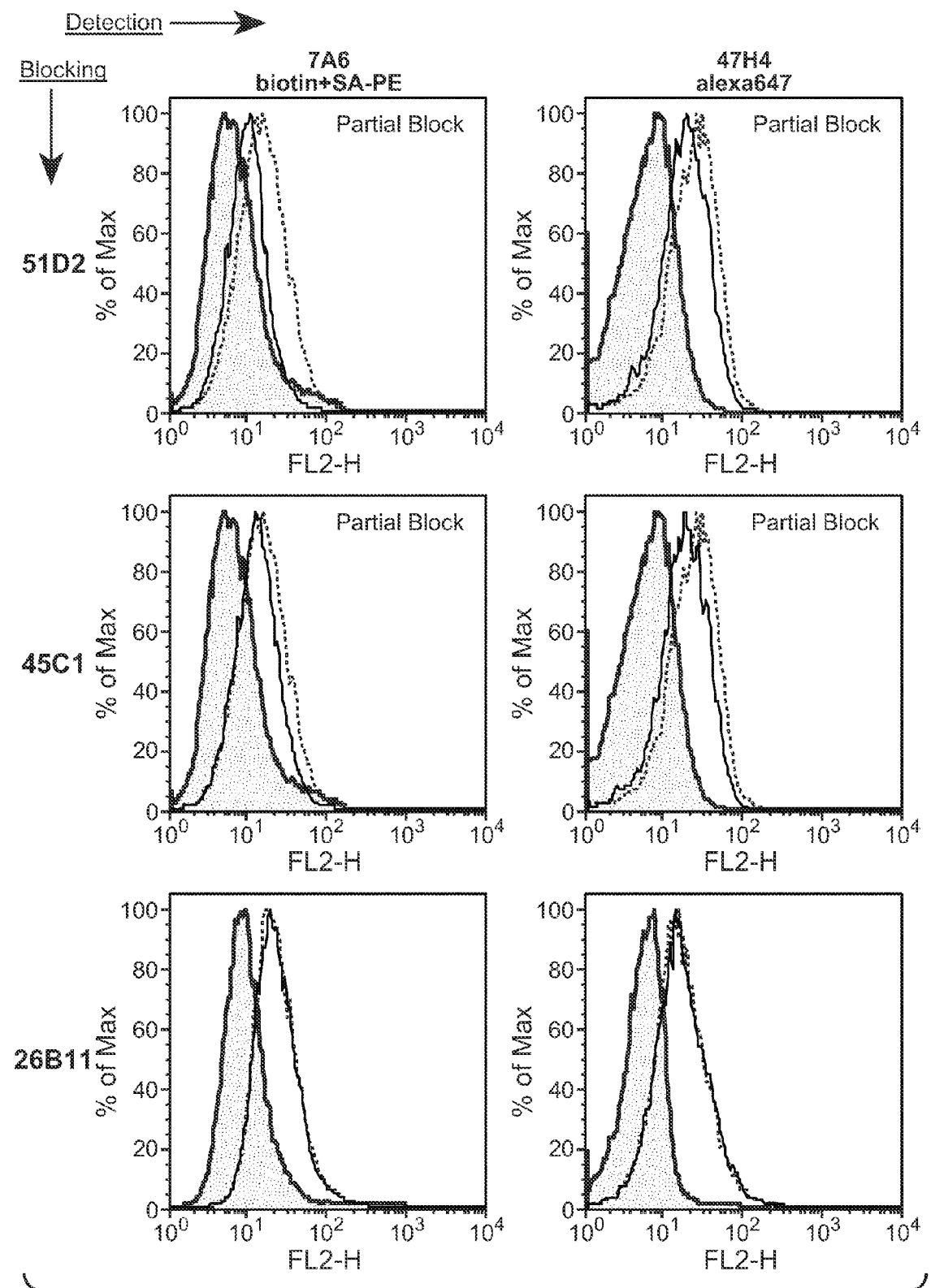

In FIG. 10, the HERCEPTIN® huIgG1 isotype control antibody induced low level cytotoxicity. Anti-IgE/M1' antibodies induced specific cytotoxicity. The wildtype and afucosylated forms of Anti-IgE/M1' 47H4v5 induced similar maximal % cytoxicity (~70-80%). The afucosylated 47H4v5 was more potent than the wildtype form (the EC50 of the afucoylated 47H4v5 was ~0.83 nM; the EC50 of the wildtype 47H4v5 was ~6.6 nM).

EXAMPLE 9

Effect of Murine Anti-IgE/M1' Antibodies in Atopic hu-SCID Mouse

Figure 12A:
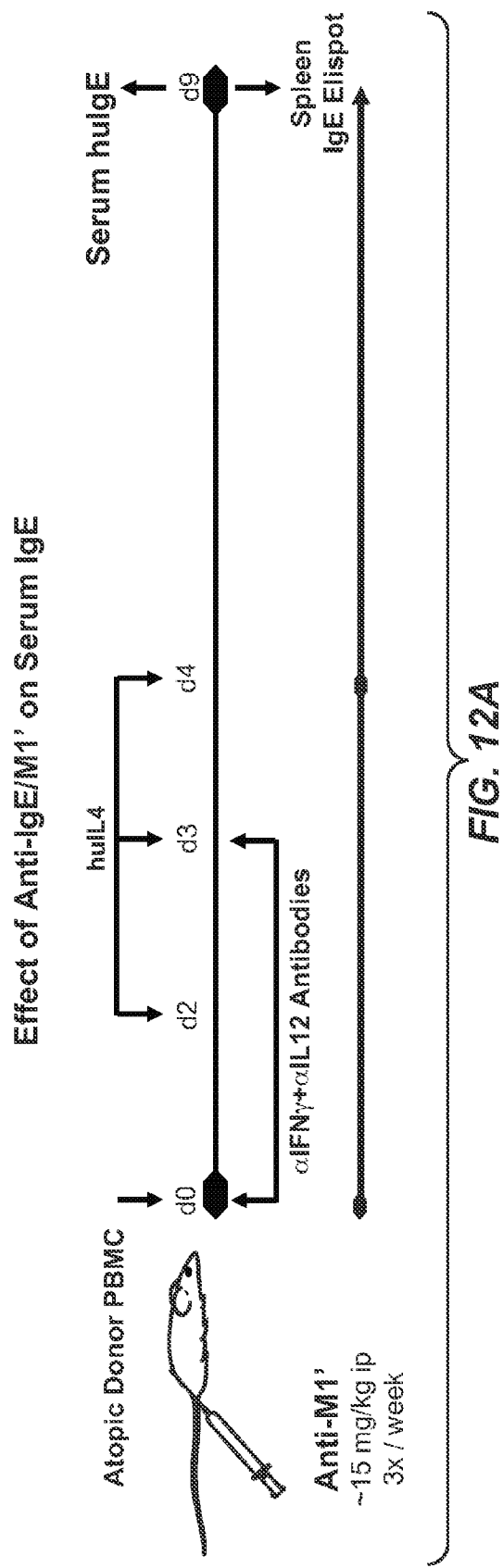
Figure 12B:
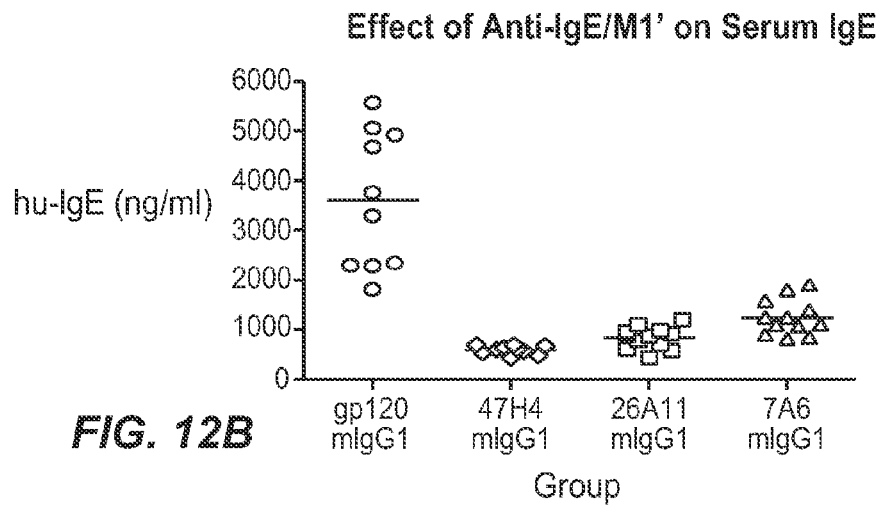
Figure 12D:
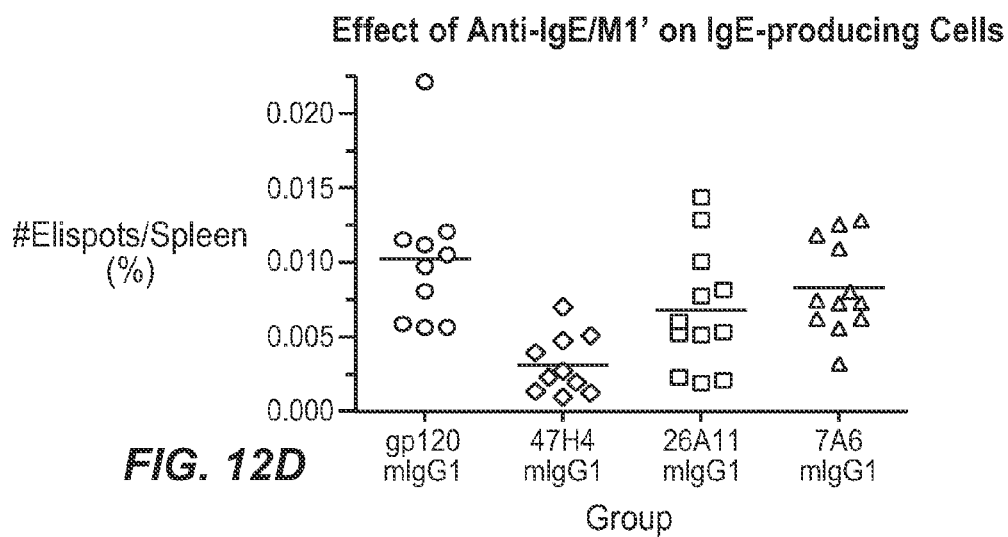
Figure 12H:
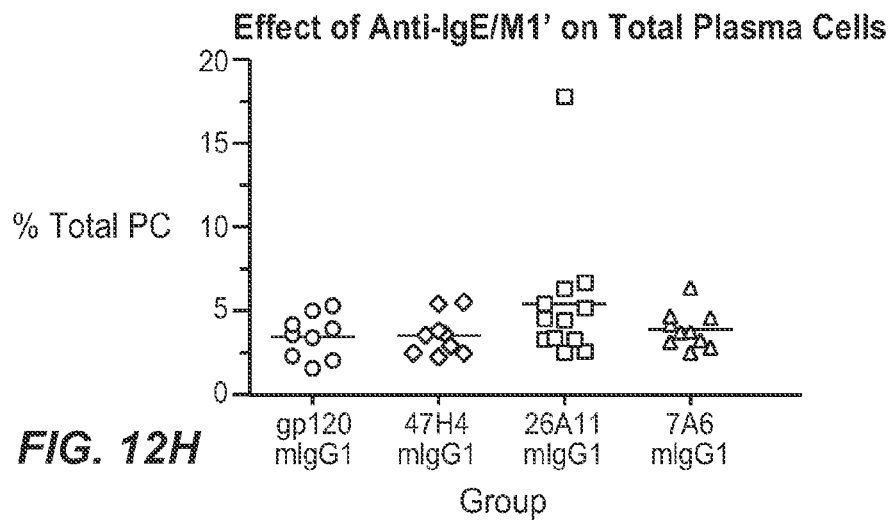
Figure 12F:
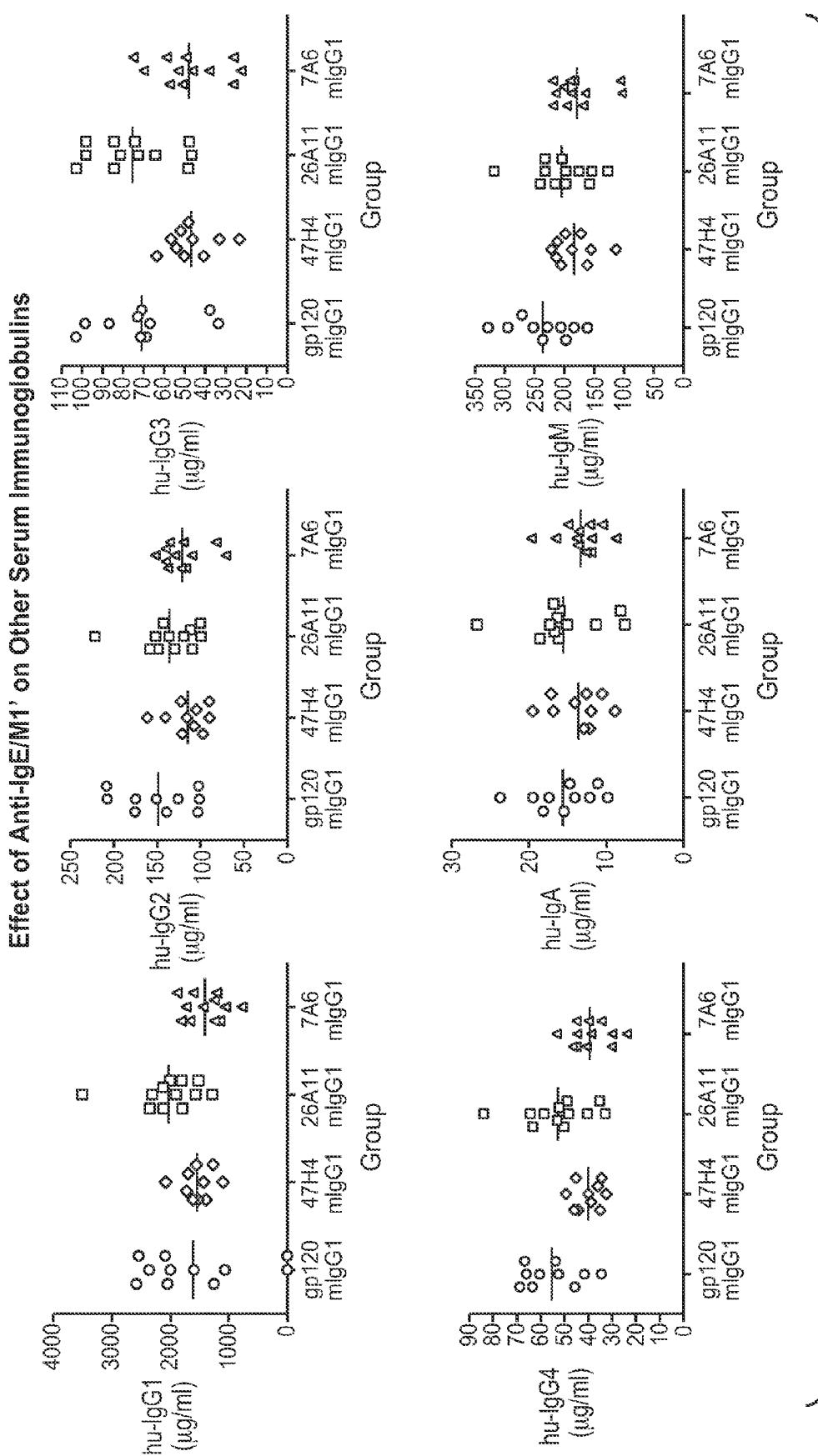
Figures 13A, 13D:
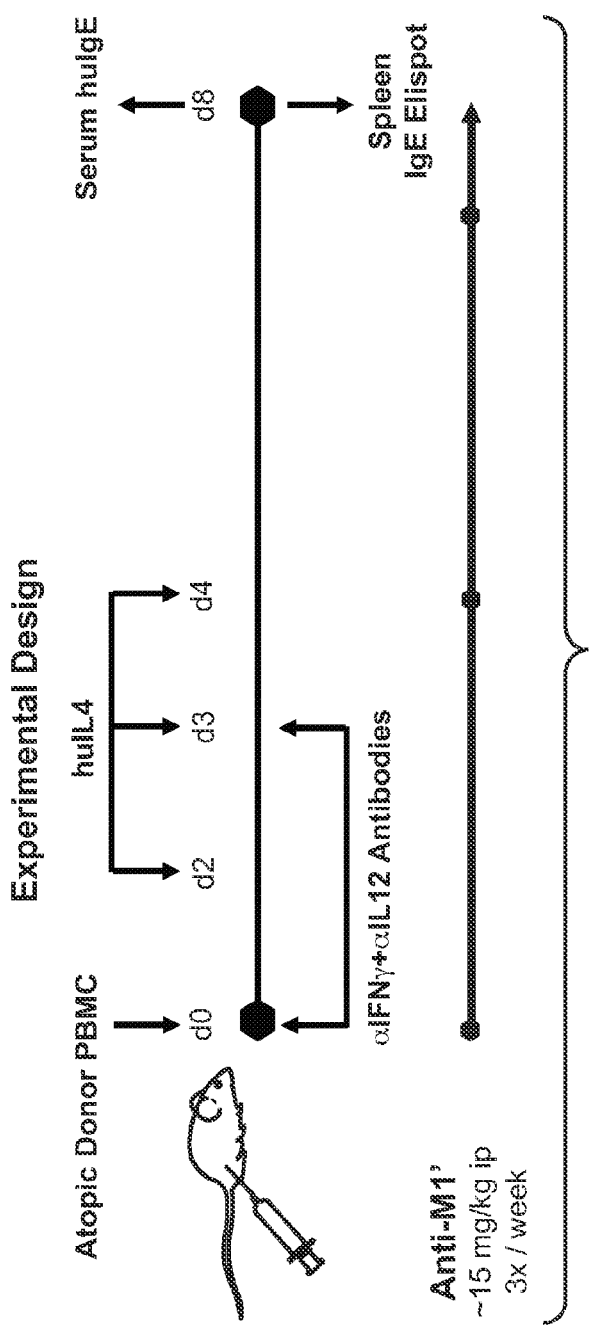
Figure 13B:
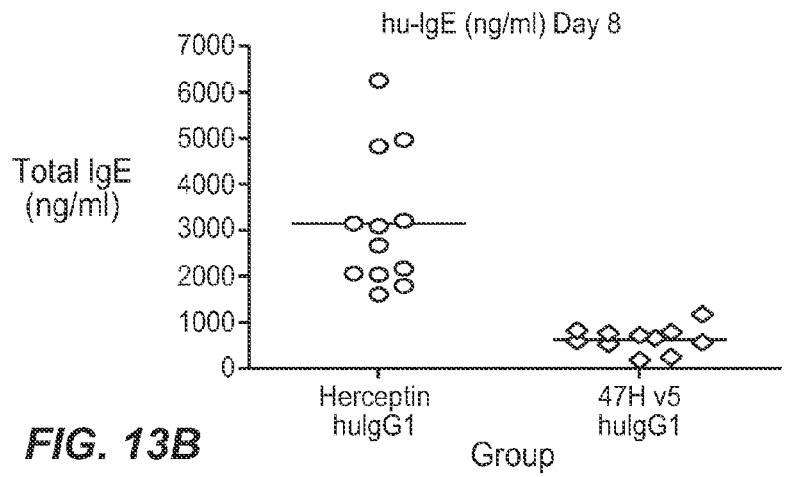
Figure 13C:
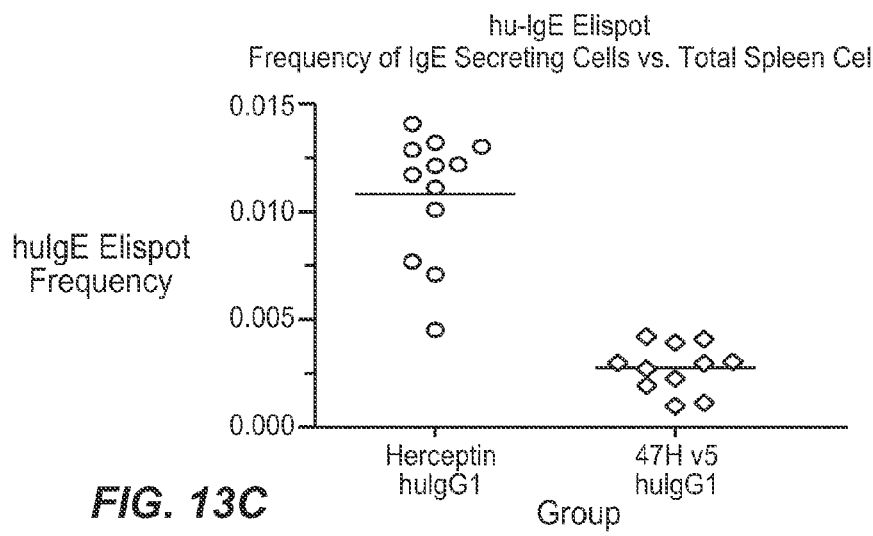
Figure 13G:
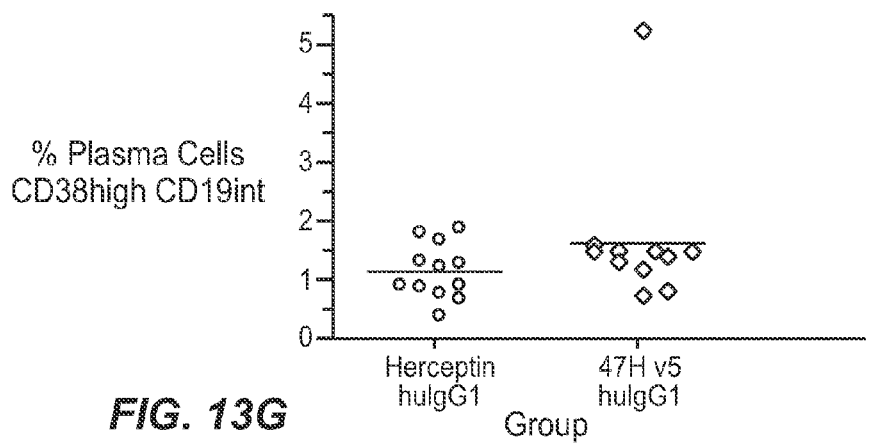
Figure 13E:
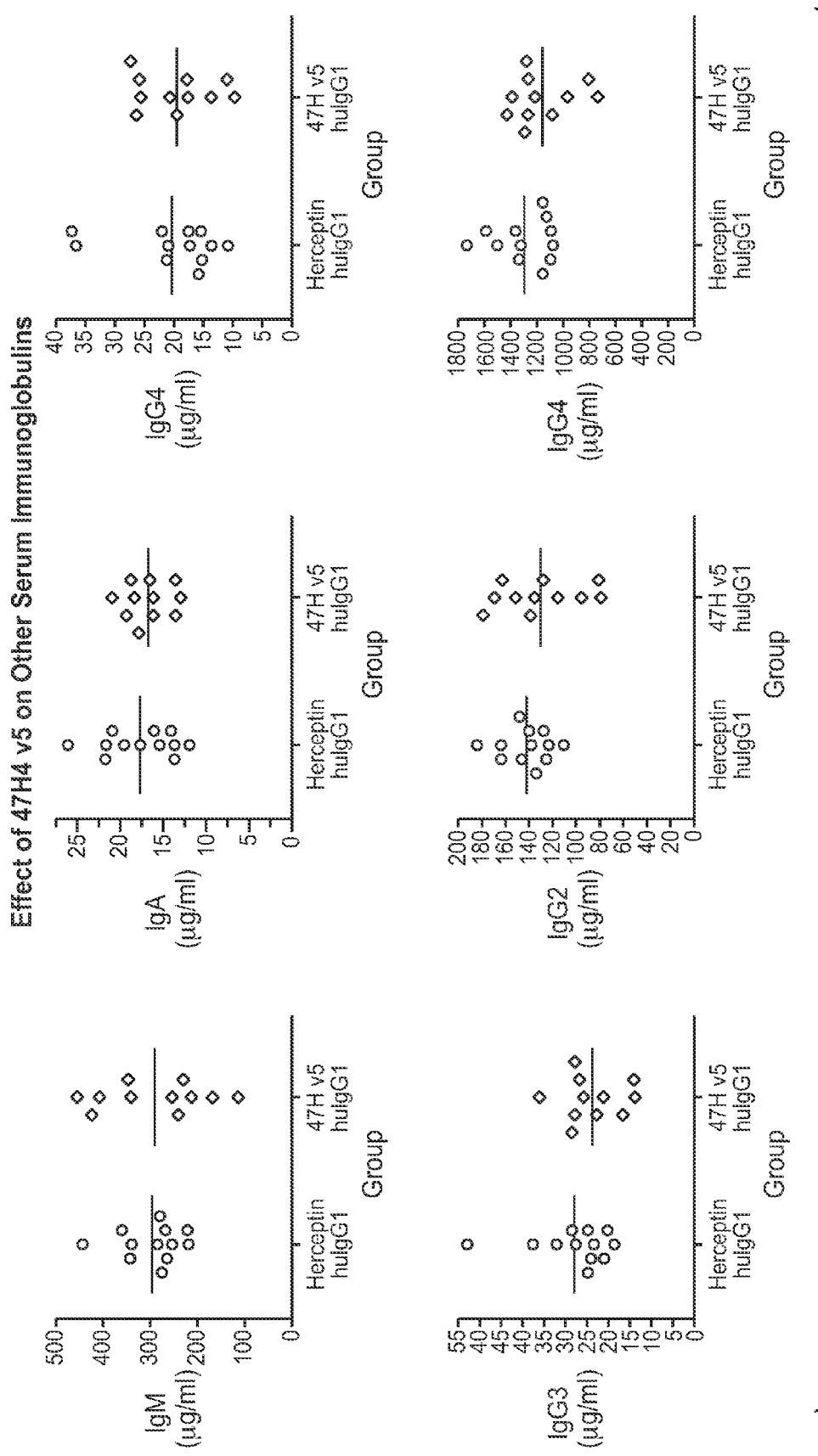

FIGS. 12A and 13A demonstrate the ability of anti-IgE/M1' antibodies (both murine and humanized, respectively) to inhibit the production of serum IgE and IgE producing plasma cells in an atopic hu-SCID model. Experiment 1 (#07-0377) tested murine anti-IgE/M1' candidates and experiment 2 (#07-1232) tested a humanized anti-IgE/M1' candidate.

Donors were screened for serum IgE levels from our in house Leukopack blood donor program. Two donors selected to provide cells for the Atopic hu-SCID model self identified as having allergies and had serum IgE levels of 1696 and 1152 ng/ml. Normal donors typically have IgE ranging from <100 to 300 ng/ml.

The hu-SCID experiments are outlined in FIGS. 12A and 13A. PBMC were isolated by Leukophoresis and ficoll density gradient (GE Healthcare #17-1440-03) and counted. $10^8$ PBMC cells ($10^8$ per 100 µl) were injected i.p. into irradiated SCID-beige mice on day zero. To skew the response towards IgE production, mice were treated with anti-IFNγ (BD Biosciences, San Jose, Calif., #554698) and anti-IL12 antibodies (100 µg/dose) (BD Biosciences, San Jose, Calif., #554659) on days 0 and 3; and rhIL-4 (100 ng/dose) (R&D Systems, Minneapolis, Minn., #204-IL-010) on days 2,3,4. Mice were treated with experimental antibodies (i.e. anti-IgE/M) three times per week (approximately every three days) starting on day 0 until the end of the study. Human cells were allowed to expand between 7 and 14 days upon which the mice were euthanized. Bleeds were taken on day 7 and at the end of the study. On the final day of the experiment, mice were euthanized and spleen cells were isolated. Single cell suspensions were used for IgE Elispot assay and FACs to determine extent of human cell reconstitution and IgE plasma cell depletion.

Data is expressed as the mean±Standard Deviation. P-values were calculated using JMP statistics software. Dunnett's test compares group means where all test groups are tested against a reference group. Each Pair Student's t compares each group pair using Student's t-test. A Bonferroni Correction is then applied to adjust the p-values of the Each Pair Student's t to safeguard against pairwise comparisons. All p-value threshold is 0.05. Percent change in the data reported in FIGS. 12A-I and 13A-H was calculated between treatment group and control group with no normalization to baseline levels.

Free IgE levels were determined using a human ELISA procedure in which Maxisorp 384-well ELISA plates (Nalge Nunc International, Rochester, N.Y.) were coated with 1 µg/ml monoclonal antibody MAE11 in 50 mM carbonate buffer, pH 9.6, at 4° C. overnight and blocked with 0.5% bovine serum albumin, in PBS at room temperature for 1 hour. Standards (0.098-12.5 ng/ml) and threefold serial dilutions of samples (minimum dilution 1:10 to avoid any serum effect) in PBS containing 0.5% bovine serum albumin, 0.05% polysorbate 20, 10 parts per million Proclin 300 (Supelco, Bellefonte, Pa.), 0.25% CHAPS (Sigma, St. Louis, Mo.), 0.2% bovine g globulins (Biocell, Rancho Dominguez, Calif.) and 5 mM EDTA were incubated on the plates at room temperature for 1 hour. Bound IgE was detected by incubating peroxidase labeled goat anti-human IgE antibody (Kirkegaard & Perry Laboratories, Gaithersburg, Md.) in the wells for 1 hour. The substrate 3,3',5,5'-tetramethyl benzidine (Kirkegaard & Perry Laboratories, Gaithersburg, Md.) was added and the reaction was stopped by adding 1 M phosphoric acid. Plates were washed between steps. Absorbance was read at 450 nm on a Titertek stacker reader (ICN, Costa Mesa, Calif.). The standard curve was fitted using a four-parameter nonlinear regression curve-fitting program (developed at Genentech). Data points which fell in the linear range of the standard curve were used for calculating the IgE concentration in samples.

The human immunoglobulin isotype panel was performed by taking mouse monoclonal antibody (mAb) to human IgG1 (clone 2C11, Abcam Inc., Cambridge, Mass.) was diluted to 4 ug/ml in 0.05M sodium carbonate buffer, pH 9.6, and coated on ELISA plates (384-well, high-bind plates, Greiner Bio One, Monroe, N.C.) during an overnight incubation at 4° C. After washing 3 times with wash buffer (PBS/0.05% Tween-20), the plates were blocked with PBS/0.5% bovine serum albumin (BSA) for 1 to 2 hours. This and all other incubations were performed at room temperature on an orbital shaker. Mouse serum samples were diluted 1:100 followed by serial 1:3 dilutions using assay buffer (PBS/0.5% BSA/0.05% Tween 20/0.25% CHAPS/5 mM EDTA/15PPM Proclin). Using the same buffer, serial dilutions of IgG1 were prepared for the standard curve (12.20-1560 ng/ml). Pre-diluted frozen controls at the high, mid, and low regions of the standard curve were thawed. After the blocking step, the plates were washed and the samples, standards, and controls were added to the 384 well plates and incubated for 2 hours. The plates were washed and biotinylated mouse mAb to human IgG1 (Zymed Laboratories, South San Francisco, Calif.) was diluted 1:500 in assay buffer and added to the washed plates for 1 hr incubation. Streptavidin-horse radish peroxidase (SA-HRP) (GE Healthcare, Piscataway, N.J.) was diluted 1:40,000 in assay buffer and added to the plates after washing. Following a 30 min incubation and a final wash step, tetramethyl benzidine (TMB) (Kirkegaard & Perry Laboratories, Gaithersburg, Md.) was added and color was developed for 10 to 15 minutes. The reaction was stopped by adding 1M phosphoric acid. The optical density was obtained using a microplate reader (450 nm, 650 nm reference wavelengths), and the sample concentrations were calculated from 4-parameter fits of the standard curves. The minimum quantifiable concentration of human IgG1 in the mouse serum samples was 1.22 ug/ml.

This overall ELISA method described above was also used for the analysis of the other Ig isotypes.

IgG2

Mouse anti-human IgG2 mAb ($\gamma_2$ chain specific) (Southern Biotech, Birmingham, Ala.) was coated on ELISA plates at 4 ug/ml. The human IgG2 standard curve range was 12.20-1560 ng/ml. Biotinylated mouse anti-human IgG2 mAb ($\gamma_2$ chain specific) (Southern Biotech) was diluted to 0.5 µg/ml and used as the detection antibody. SA-HRP was added to the 384 well plates at a 1:10,000 dilution. The minimum quantifiable concentration of human IgG2 in the mouse serum samples was 1.22 µg/ml.

IgG3

Mouse anti-human IgG3 mAb (Zymed Laboratories) was diluted to 1 µg/ml and coated onto ELISA plates. The human IgG3 standard curve range was 0.78-100 ng/ml. Biotinylated mouse anti-human IgG3 mAb ($\gamma_3$ chain specific) (Southern Biotech) was diluted to 0.1 µg/ml and used as the detection antibody. SA-HRP was added to the 384 well plates at a 1:20,000 dilution. The minimum quantifiable concentration of human IgG3 in the mouse serum samples was 78.1 ng/ml.

IgG4

Purified mouse anti-human IgG4 mAb (BD Pharmingen, San Jose, Calif.) was diluted to 0.25 ug/ml and coated onto ELISA plates. The human IgG4 standard curve range was 0.20-25 ng/ml. Biotin-conjugated mouse anti-human IgG4 mAb (BD Pharmingen) was diluted to 0.25 µg/ml and used as the detection antibody. SA-HRP was added to the 384 well plates at a 1:20,000 dilution. The minimum quantifiable concentration of human IgG4 in the mouse serum samples was 39.1 ng/ml.

IgA

Purified mouse anti-human IgA$_1$/A$_2$ mAb (BD Pharmingen) was diluted to 2 μg/ml and coated onto ELISA plates. The human IgA standard curve range was 0.20-25 ng/ml. Biotin-conjugated mouse anti-human IgA$_1$/A$_2$ mAb (BD Pharmingen) was diluted to 1 μg/ml and used as the detection antibody. SA-HRP was added to the 384 well plates at a 1:80,000 dilution. The minimum quantifiable concentration of human IgA in the mouse serum samples was 39.1 ng/ml.

IgM

Purified mouse anti-human IgM mAb (BD Pharmingen) was diluted to 0.5 ug/ml and coated onto ELISA plates. The human IgM standard curve range was 0.78-100 ng/ml. Biotin-conjugated mouse anti-human IgM mAb (BD Pharmingen) was diluted to 0.5 μg/ml and used as the detection antibody. SA-HRP was added to the 384 well plates at a 1:40,000 dilution. The minimum quantifiable concentration of human IgM in the mouse serum samples was 156 ng/ml.

Hu-SCID splenocytes, mouse splenocytes or lymph node cells were counted using Fluoresbrite YG microspheres (Polysciences, Inc. #18862) on a FACs Calibur Flow Cytometer (BD (San Jose, Calif.)).

Elispot assays were used to determine the frequency of IgE producing plasma cells in hu-SCID mice following treatment with rhuIL-4, anti-IFNγ, and anti-IL-12 antibodies for 15 days. Elispot plates (Millipore, Billerica, Mass., #MSIPS4510, clear) were coated with a 1:500 dilution of primary unconjugated anti-human IgE antibody (AXXORA, San Diego, Calif., #BET-A80-108A) in coating buffer [Genentech, Inc. (A3323)] at 100 μl/well overnight at 4° C. The primary antibody solution was then decanted and plates were washed twice with wash buffer (1×PBS, 0.05% Tween-20). Membranes were blocked with 200 μl/well of 0.5% BSA in 1×PBS for 0.5-1 hour at 37° C. Blocking solution was removed and positive control cells or hu-SCID splenocytes were added to the plate. The human Myeloma IgE producing U266 cell line (ATCC, Manassas, Va., #TIB 196) was used as a positive control for the assay. U266 cells were added to the plate starting at a concentration 3000 cells/0.1 ml (=0.032× 10$^6$/ml) of hybridoma medium [RPMI 1640, 15% Fetal bovine serum, 2 mM L-glutamine, 10 mM HEPES, 4.5 g/L glucose, 1.5 g/L bicarbonate] then seven serial dilutions (1:2) from performed. Whole spleen single cell suspensions were resuspended in 1 ml media. 100 μl was added to the first well. Seven 1:2 serial dilutions were then performed. U266 hybridoma and spleen cells were incubated overnight at 37° C. The following day plates were washed three times with wash buffer (1×PBS, 0.05% Tween-20) and then 100 μl/well of the secondary antibody, anti-human IgE-Alkaline Phosphatase conjugated (Sigma, St. Louis, Mo., A-3525), was added at 1:2000 in 0.5% BSA/1×PBS to each well and incubated at 37° C. for 2 hours. Plates were washed three times and then rinsed once with ddH$_2$0 (Genentech, Inc.). 100 μl/well of BCIP/NBT solution (R&D Systems, Minneapolis, Minn., Elispot Blue Color Module, #SEL002) was added to each well and incubated in the dark for 30 minutes. The plates were then rinsed with ddH20 once and the plate was allowed to dry at room temperature. Plates were sent to BD Biosciences for counting (BD, Inc., Franklin Lakes, N.J.). The number of plasma cells was calculated using the number of spots detected, fold dilution (cell input), and the total spleen cell count.

Human plasma cells were prepared by removing spleens on day 15 from antibody treated hu-SCID mice. Single cell suspensions were prepared and filtered. 5×10$^6$ cells were blocked with human (Sigma, St. Louis, Mo., #S-2257) and mouse sera (VWR, #RLD108-0100), and then stained with anti-human CD38 PE (BD Biosciences, San Jose, Calif., #555460) and anti-human PC FITC (Dakocytomation, Glostrup, Denmark, #K$_{2311}$) antibodies in FACs wash buffer (2% FBS, 1×PBS) on ice for 20 minutes. Cells were then washed and analyzed on a FACs Calibur machine (BD, Inc., Franklin Lakes, N.J.). Human CD38 expression was used as a positive control for successful human PBMC transfer. Plasma cells were defined as CD38 high, PC+.

Figures 4, 4A, 5, 6, 7, 8, 9, 10, 11, 12:
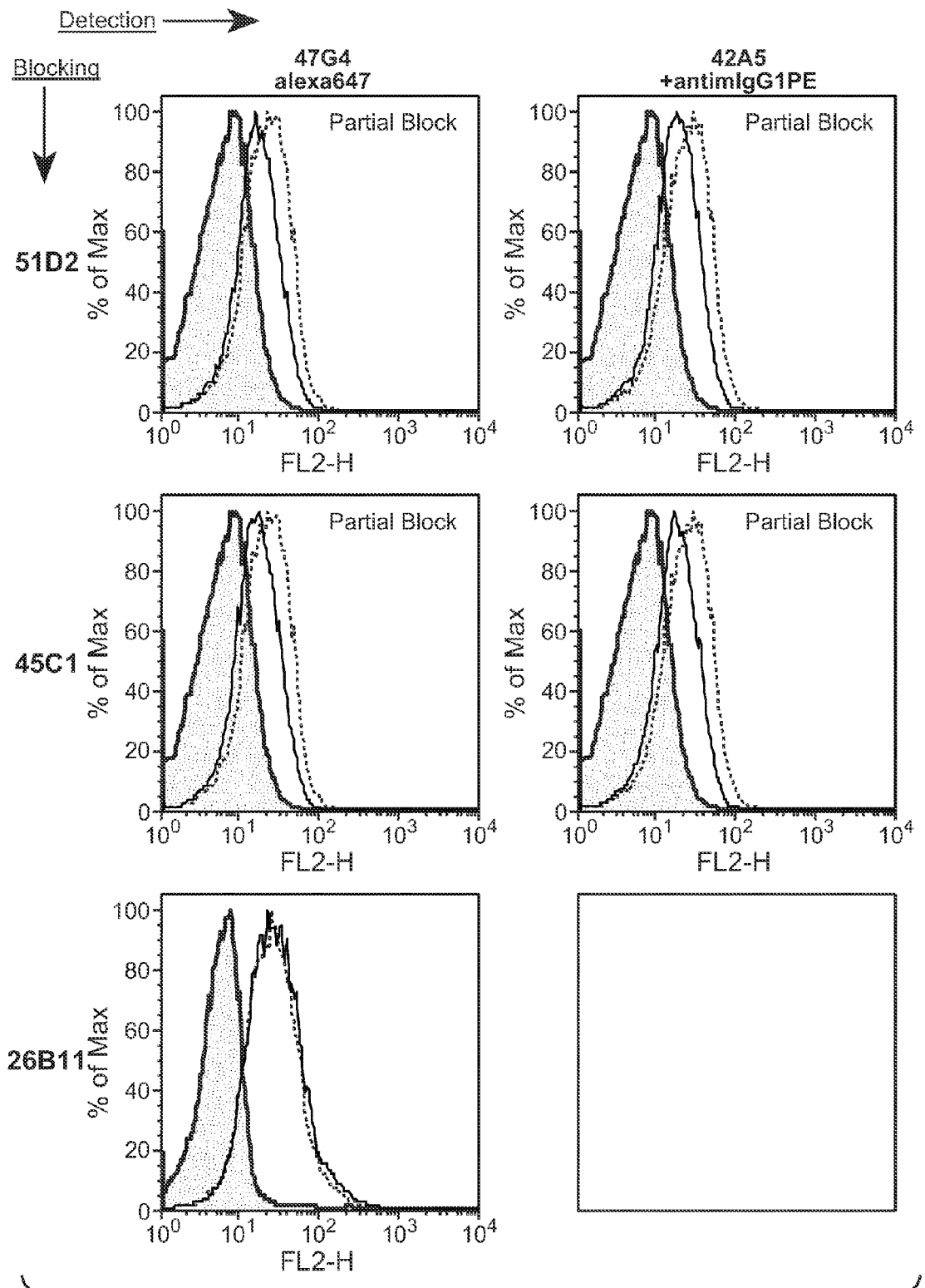

In experiment #07-0377 (FIG. 12A), three anti-IgE/M1' antibodies (47H4, 26A11, and 7A6) were tested against isotype control anti-gp120-muIgG1. Isotype control treated mice generated high levels of human IgE by day 9. Treatment with anti-IgE/M1' candidates reduced IgE levels by 65-84% (FIG. 12 B-C). Anti-IgE/M1' treatment also reduced IgE producing cells in vivo by 19-69% (FIG. 12 D-E). Other serum Igs were relatively unaffected by anti-IgE/M1' treatment (reductions of ~30% were observed with some anti-M1' antibodies for huIg1, IgG3 and IgG4 (FIG. 12 F-G). No reduction in the percentage of total plasma cells of the spleen was observed with anti-IgE/M1' treatment (FIG. 12 H-I).

Figures 4, 4A, 5, 6, 7, 8, 9, 10, 11, 12, 13:
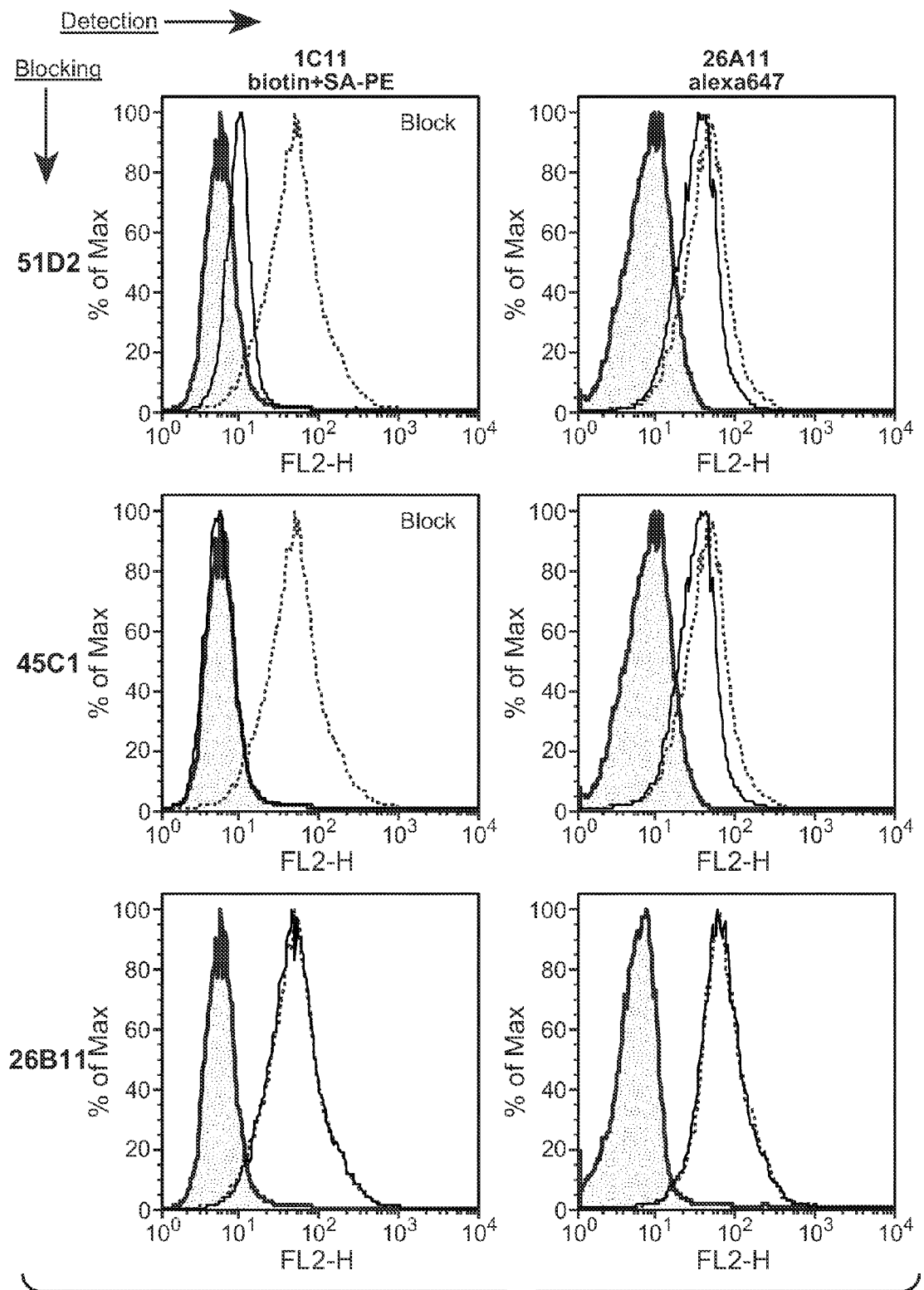

In experiment #07-1232 (FIG. 13A), a humanized anti-IgE/M1' (47H4v5) was tested against isotype control antibody HERCEPTIN®-huIgG1. Isotype control treated mice generated high levels of serum IgE by day 8. Treatment with anti-IgE/M1' huIgG1 reduced IgE levels by 79% (FIG. 13 B-D) and IgE producing plasma cells by 75% (FIG. 13 C-D). No reduction in other serum Igs (IgG1, IgG2, IgG3, IgG4, IgM, IgA) (FIG. 13 E-F) or the percentage of total plasma cells in the spleen was observed (FIG. 13 G-H). These studies demonstrate that anti-IgE/M1' antibodies specifically reduce serum IgE and IgE-producing cells, but not immunoglobulins of other isotypes.

EXAMPLE 10

Human M1' Transgenic Mice

Generation of huM1' Transgenic "Knockin" Mice

Figures 4, 4A, 5, 6, 7, 8, 9, 10, 11, 12, 13, 14:
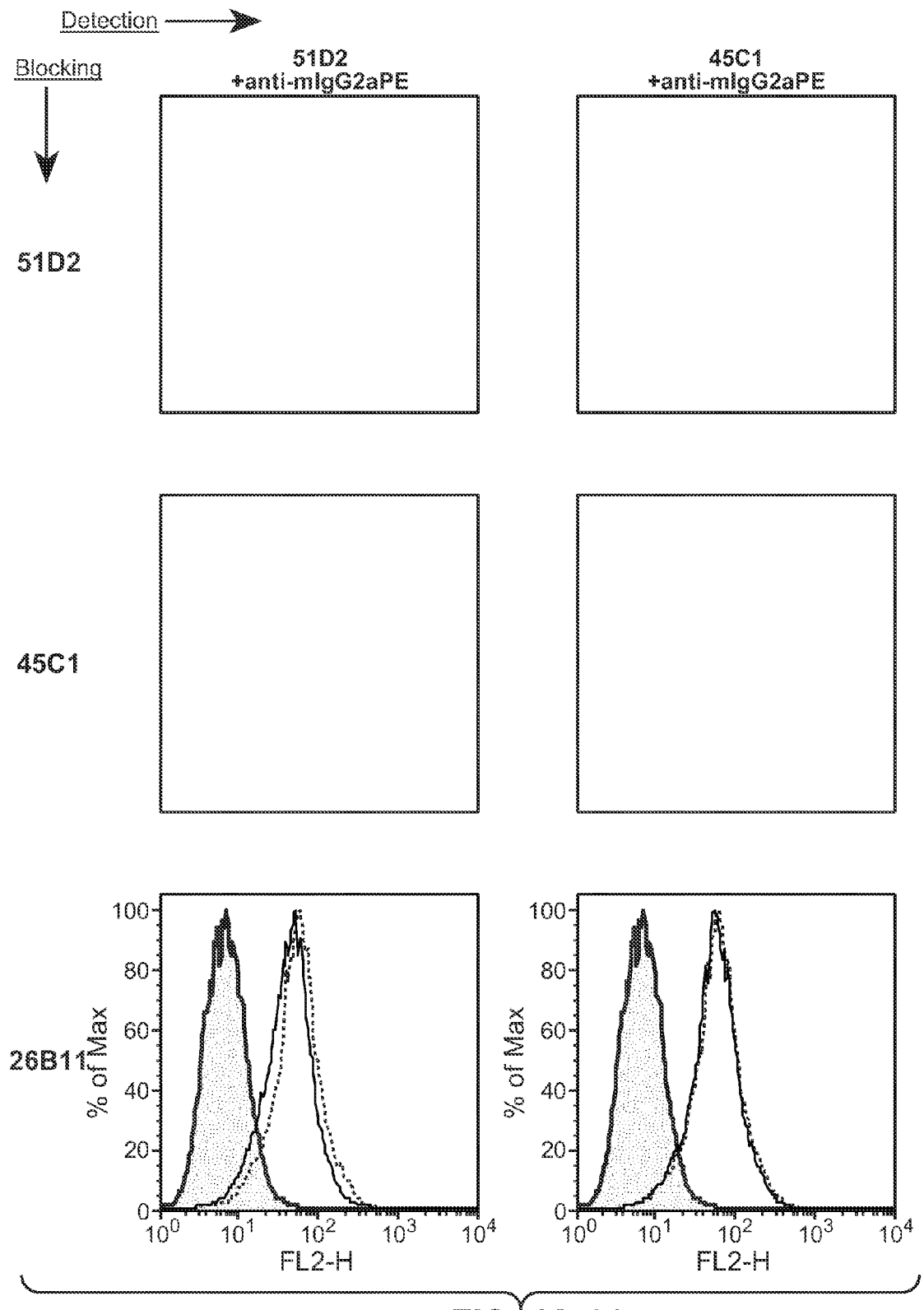

Since mice do not normally express an M1' domain similar to humans, we generated mice with the human M1' domain "knocked into" the mouse IgE locus (FIG. 14A). The human M1' sequence uses the mouse M1 splice acceptor site upstream and is then fused to the mouse M1 sequence downstream (FIG. 14B). An TRES-EGFPpA—Neo cassette was also knocked in 3' of the mouse M2 sequence. This knockin will allow for expression of mouse IgE with the human M1' domain on the surface of IgE+ B cells. The M1' sequence will not be expressed on secreted IgE.

Screening of M1' Knockin Lines (PCR)

Human M1' knockin mice were genotyped by PCR using primers specific for the mouse IgE locus and human M1' sequence. Primers used were as follows:

```
                                       (SEQ ID NO: 106)
    WT FOR     5'-GGCCAAAGACCCTAAGACAGTC (SEQ ID NO: 107)
    huM1' FOR 5'-GGGCTGGCTGGCGGCTCCGC (SEQ ID NO: 108)
    WT REV     5'-CTATGCCCTGGTCTGGAAGATG
```

Figure 14C:
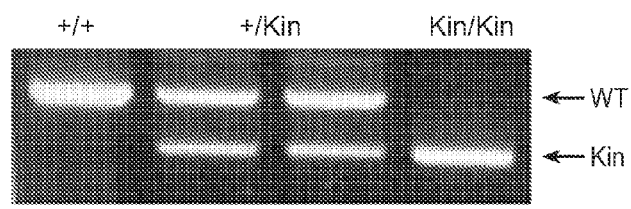

Purified genomic DNA was analyzed with the above primers using 32 cycles of the following program [94° C. 4 min; 94° C. 1 min; 60° C. 30 sec; 72° C. 1 min (30 cycles); 72° C. 10 min]. PCR products were then run out on a 2% agarose 0.5×TBE gel. Wildtype PCR genotype gave a 668 bp product and the hu-M1' knockin generated a 457 bp product (FIG. 14C).

Screening of M1' Knockin Lines (Southern)

huM1' knockin ES cells and final mouse lines were screened and verified by Southern blot. 10 μg of purified ES cell or Tail genomic DNA was digested with HindIII for the left arm or BamHI for the right arm overnight. Digested DNA was then run out on a 0.8% Agarose 1×TAE gel. DNA was then transferred to a nylon membrane (Roche #1417240) using denaturation buffer (1.5M NaCl; 0.5M NaOH) overnight. The membrane was rinsed, UV crosslinked, and then soaked in DIG Easy Hyb solution (Roche #1585762) for 4 hours with rotation at 46° C. Probes were generated by PCR using the PCR DIG probe Synthesis Kit as directed by the manufacturer (Roche #11636090910).

Primers for the left arm were:

```
                                          (SEQ ID NO: 109)
     FOR 5'-TGTCTGGTGGTGGACCTGGAAAGCG (SEQ ID NO: 110)
     Rev 5'-TCCTCGCTCTCCTCCTCTGGTGGTG
```

Primers for the right arm were:

```
                                          (SEQ ID NO: 111)
     FOR 5'-CCATGCAACCTAGTATCCTATTCTC (SEQ ID NO: 112)
     Rev 5'-CTTTATACAGGAGAACCTAGCCCAG
```

Figure 14D:
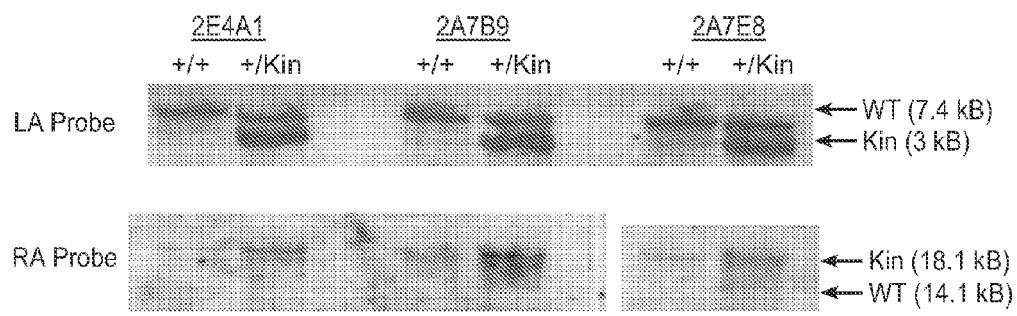

Probes were tested against unlabeled PCR product to ensure increased size and good DIG-labeling. Blots were then probes overnight with boiled probe overnight at 46° C. with rotation. The following day blots were then washed and developed with anti-DIG antibody according to manufactures directions. Blots were exposed to film for 15-20 minutes. FIG. 14D illustrates with southern results. Wildtype mice generate a left arm 7.4 kB HindIII fragment which becomes a 3 kB fragment in the hu-M1' knockin allele. Wildtype mice generate a right arm 14.1 kB BamHI fragment which becomes a 18.1 kB fragment in the hu-M1' knockin allele. Wildtype and heterozygous mice are shown (FIG. 14D).

EXAMPLE 11

Hu-M1' TransgenicModel

TNP-OVA Immunization

This Example illustrates the ability of anti-IgE/M1' candidates to prevent the generation of IgE resulting stimulated by TNP-OVA in both an immune primary response (Exp. #07-0234F; FIGS. 15A-I) or memory response (Exp. #07-0234B; FIGS. 16A-K) immune response to TNP-OVA. TNP-OVA or trinitrophenyl-ovalbumin is a high potent immunogen often used to generate potent antibody immune responses.

Data is expressed as the mean±Standard Deviation. P-values were calculated using JMP statistics software. Dunnett's test compares group means where all test groups are tested against a reference group. Each Pair Student's t compares each group pair using Student's t-test. A Bonferroni Correction is then applied to adjust the p-values of the Each Pair Student's t to safeguard against pairwise comparisons. All p-value threshold is 0.05. Percent change in the data reported for primary response (FIGS. 15A-I) and the memory immune response (Figures A-K) was calculated by subtracting the uninfected or unimmunized group mean value from each of the mouse values, group means were recalculated and percent change was then calculated against the control group for each timepoint.

TNP-OVA immunization of human IgE/M1' knockin mice (C57BL/6) induces a balanced Th1/Th2 response in vivo. Antigen specific IgE levels following primary immunization and challenge reach levels of ~10-200 ng/ml. In experiment #07-0234F, huM1' knockin mice (C57B1/6) were immunized with TNP-OVA (Biosearch Technologies, Novato, Calif.) (100 μg in 2 mg alum per mouse i.p.) on day 0 (FIG. 15A). Mice were then treated with 0.1 mg/kg antibodies three times per week between days 0 and 28 (FIG. 15A). In experiment #07-0234B, huM1' knockin mice (C57B1/6) were immunized with TNP-OVA/Alum on day 0 (as before) and then challenged with TNP-OVA (100 μg per mouse i.p.) on day 28 (FIG. 16A). Mice were treated with 10 mg/kg antibodies between days 28 and 49 (FIG. 16A). Mice were bled over the course of the immune response to monitor antigen specific serum IgE and IgG1 levels.

TNP-OVA specific IgE IgG1 was measured using ELISA plates (384 well with MaxiSorp™ surface, Nunc, Neptune, N.J.) coated for 12-18 hr at 2-8° C. with 25 μL/well TNP-OVA (TNP:OVA ratio of 13:1) (Biosearch Technologies, Novato, Calif.) diluted to 0.5 μg/mL in 50 mM sodium carbonate/bicarbonate, pH 9.6. The plates were then decanted and blotted dry. Block buffer (PBS, 0.5% BSA, pH 7.2, 50 μL/well) was added to the plates for 1-2 hr. This and all subsequent incubations were performed at room temperature with gentle agitation. Samples were diluted 1/50 in assay diluent (PBS, 0.5% BSA, 0.05% Tween-20, 0.01% Proclin 300) followed by serial 1/3 dilutions over eleven points. The standards were serially diluted two-fold in assay diluent over seven points, starting at 1 ng/ml for Anti-TNP OVA IgG1 and 3 ng/ml for Anti-TNP OVA IgE. Plates were washed three times with wash buffer (PBS, 0.05% Tween-20, pH 7.2) and standards, samples and controls were added (25 μL/well) to duplicate plates for the separate detection of IgG1 and IgE isotypes. After a 1.5-2 hr incubation, plates were washed six times with wash buffer. Biotinylated rat anti-mouse IgG1 and IgE mAb (BD Biosciences, San Diego, Calif.) were diluted to 0.5 μg/mL for IgG1 or 1.0 μg/mL for IgE in assay diluent and added to the appropriate plates (25 μL/well). Plates were incubated for 1-1.5 hr and washed six times with wash buffer. Streptavidin-horseradish peroxidase conjugate (AMDEX, GE Healthcare, Piscataway, N.J.) was diluted 1/80,000 for IgG1 or 1/5,000 for IgE and added to the plates (25 μL/well) for 30 min. After washing six times with wash buffer, plates were developed by adding 254/well tetramethyl benzidine (Kirkegaard & Perry Laboratories, Gaithersburg, Md.) and incubating for 15 min for IgG1 or 25 min for IgE. The reaction was stopped by the addition of 25 μL/well 1M $H_3PO_4$, and the absorbance was read at 450 nm with a 620 nm reference. The results of unknown samples interpolated from 4-parameter fits of the standard curves.

Mouse plasma cells from the spleen or lymph notes were first identified by separating CD138+ cells. These IgE producing plasma cells were quantified by the Elispot method. For total IgE producing cells, an anti-IgE antibody (from BD OptEIA mIgE set #555248) was coated on MultiScreen HTS plates (Millpore #MSIPS4W10) at a dilution of 1:2 using ELISA coating buffer at 50 μl per well. Coating was performed at 4° C. overnight. The following morning plates were washed 5 times with 200 μl sterile PBS-tween 20 (0.05%) using a multichannel pipet in the tissue culture hood. Plates were then blocked in 300 μl PBS/5% BSA or cell culture medium (RPMI-1640, 10% FBS) for two hours at room temperature. Single cell suspensions were prepared from the spleen or lymph node and cells counted by FACS (as outlined above). Cells were prepared for plating, starting with $10^7$ cells followed by 3-4 fold dilutions for TNP-OVA immunization models, or $4 \times 10^6$ cells followed by 2 fold dilutions for the *Nippostrongylus* infection models. The mouse A20 B cell line was used as a negative control and the TIB-141 cell line was used as a positive control. Cell dilutions were prepared in cell culture medium (RPMI-1640+10% FBS). Following the blocking step plates were washed once with cell culture medium and aspirated. Cells were plated in 100 µl per well. Plates were then incubated overnight at 37° C., 5% $CO_2$. The following day plates were washed 6 times using a Skan-Washer 300 (Molecular Devices (Sunnyvale, Calif.)) with PBS-tween 20 (0.05%). A biotinylated secondary antibody from the BD OptEIA mIgE set (#555248) was then used at the concentration noted by the manufacturer, usually between 1:250-1:500 in 100 µl/well. The secondary antibody was prepared in PBS/1% BSA. Plates were then incubated for 1 hour at room temperature and then washed 6 times using a Skan-Washer300 with PBS-tween 20 (0.05%). Streptavidin AP (R&D #SEL002) was then added at a dilution of 1:60 in 100 µl per well, again prepared in PBS/1% BSA, and incubated for 1 hour at room temperature. Plates were then washed as before 3 times and then rinsed twice with DI water. Any remaining liquid was blotted away on a paper towel. The developing reagent, BCIP/NBT (100 µl/well) was then added, and the plates incubated for 30 minutes at room temperature in the dark. The substrate was then decanted and plates rinsed twice with DI water. Plates were inverted to remove any excess water and allowed to dry. Spots were quantified using a dissection microscope.

Figures 4, 4A, 5, 6, 7, 8, 9, 10, 11, 12, 13, 14, 15:
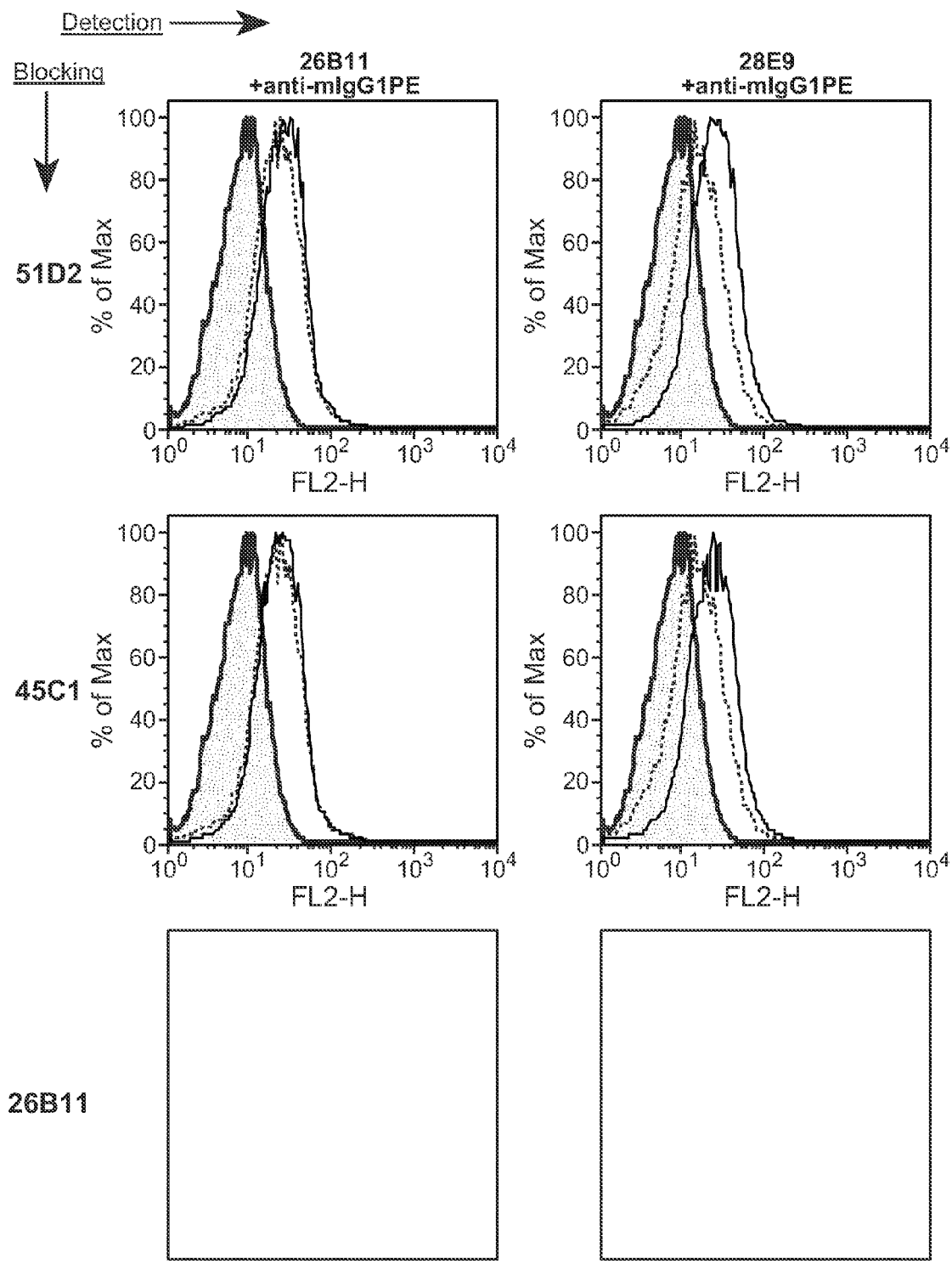
Figure 15B:
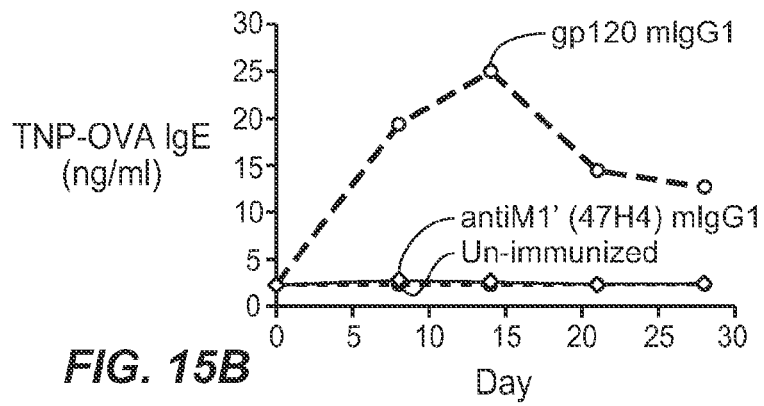
Figure 15C:
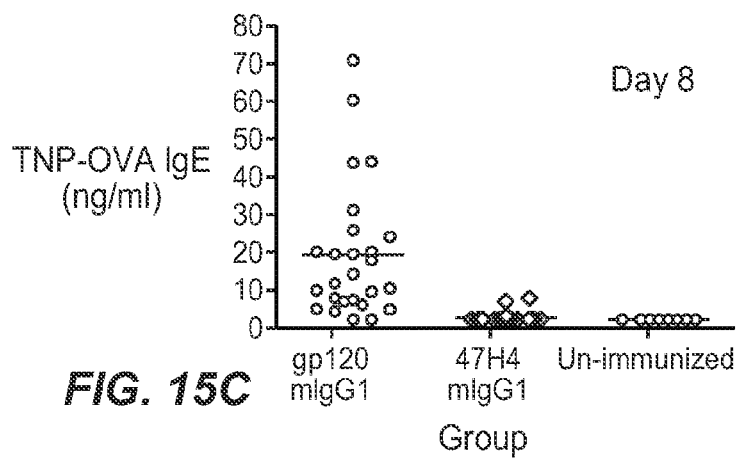
Figure 15D:
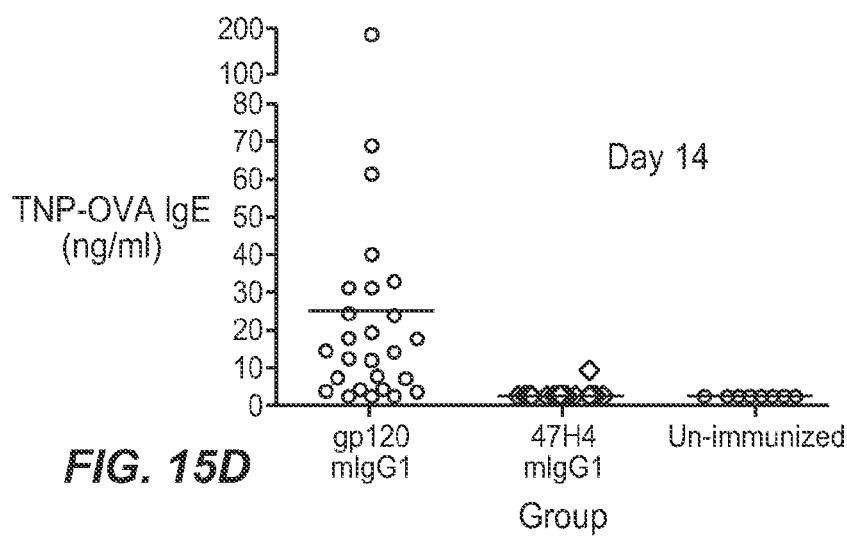
Figure 15F:
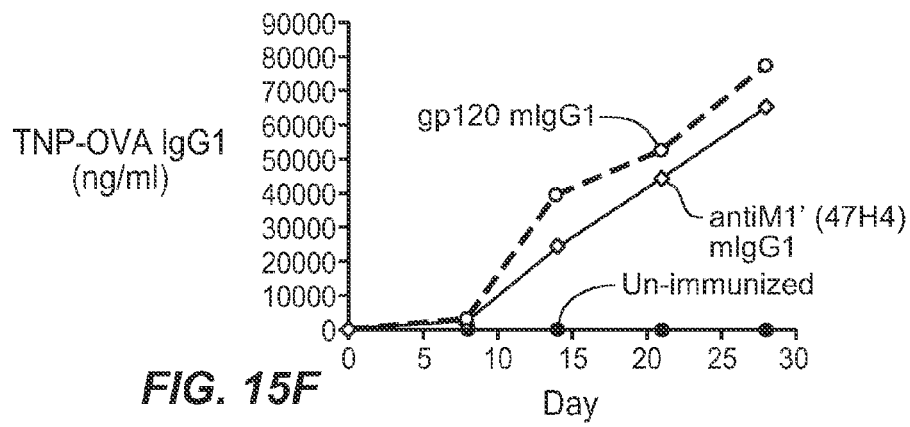
Figure 15G:
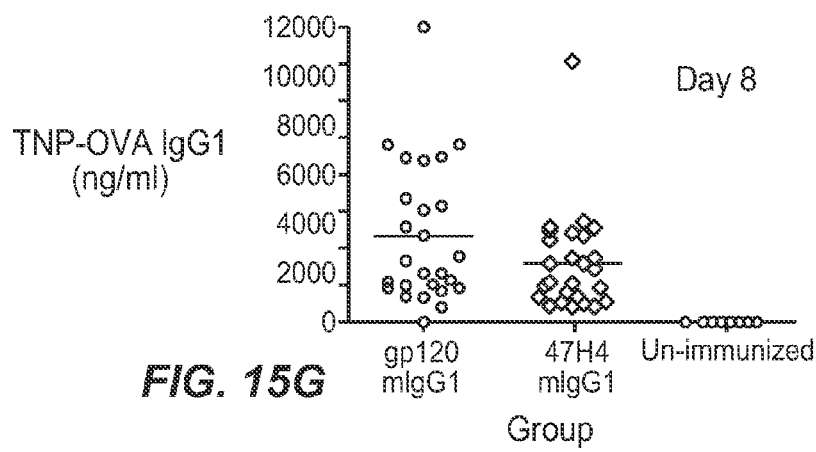
Figure 15H:
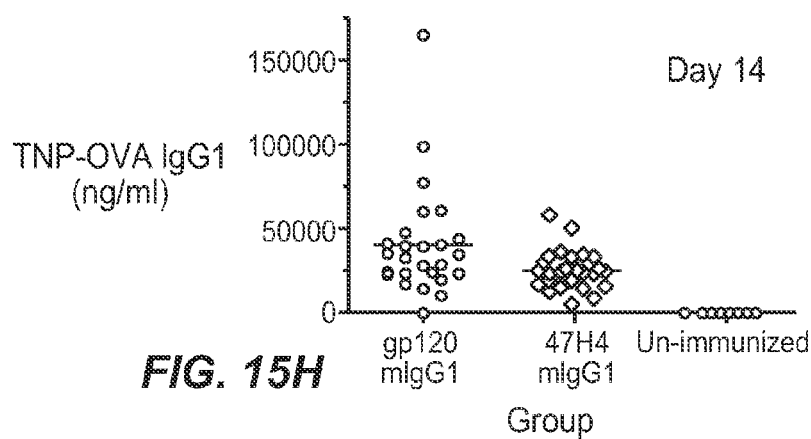

Experiment #07-0234F tested the ability of anti-IgE/M1' to prevent an IgE response to TNP-OVA primary immunization. Anti-gp120 isotype control treated mice generated serum IgE, reaching peak levels between day 8 to 14 (~25 ng/ml) (FIG. 15B). Anti-IgE/M1' treatment prevented the increase in serum IgE by day 8 (98%) and 14 (99%) (FIG. 15 C-D). This reduction was significantly different from isotype treated animals, and not significantly different from unimmunized mice (FIGS. 15 C-E). The levels of antigen specific IgG1 were only modestly affected by anti-IgE/M1' through the 28 days of the experiment (FIGS. 15 F-I).

Figures 4, 4A, 5, 6, 7, 8, 9, 10, 11, 12, 13, 14, 15, 16:
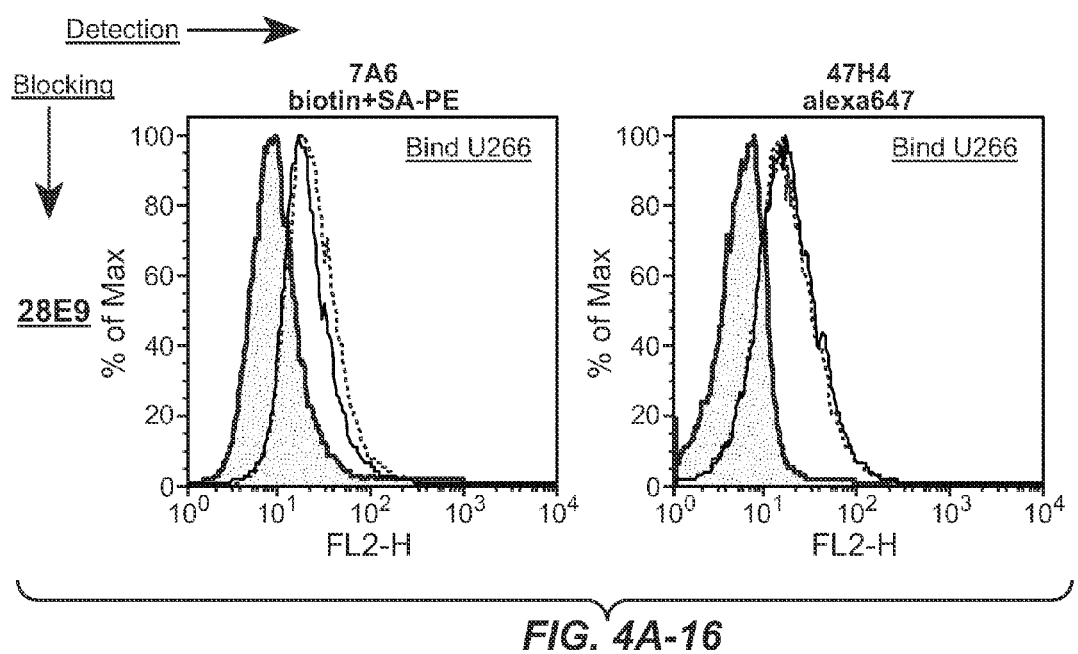
Figures 4, 4A, 5, 6, 7, 8, 9, 10, 11, 12, 13, 14, 15, 16, 17:
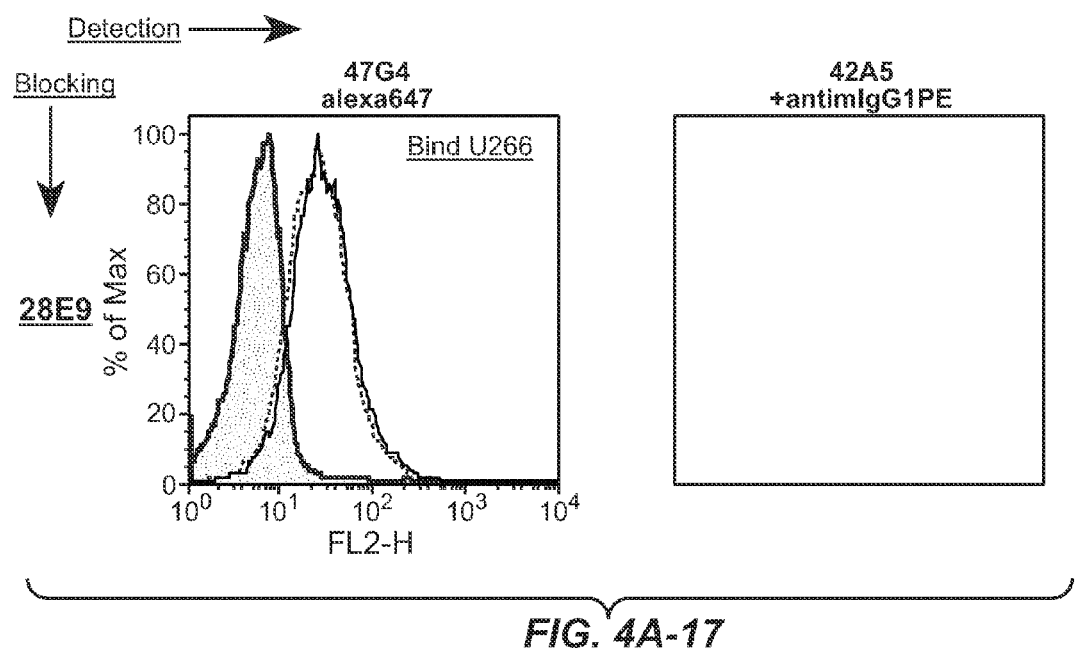
Figure 16B:
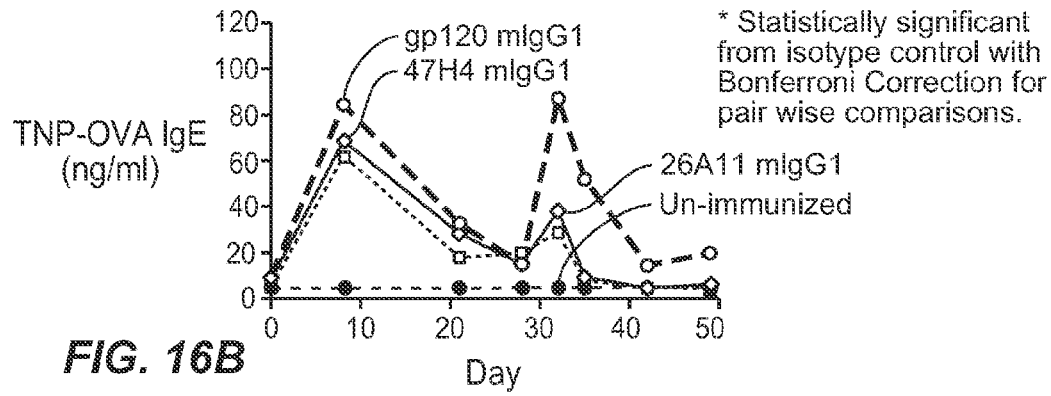
Figure 16C:
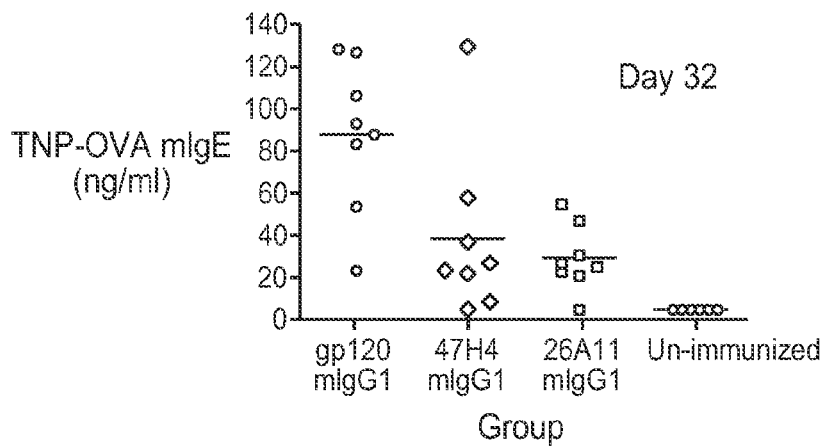
Figure 16C:
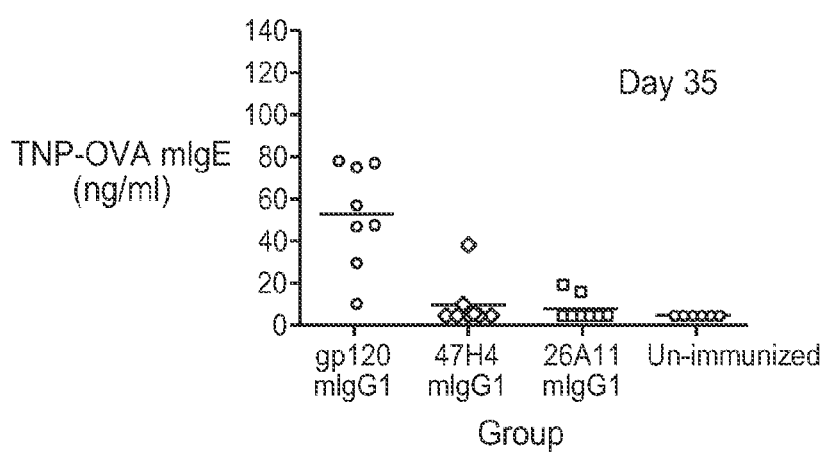
Figure 16E:
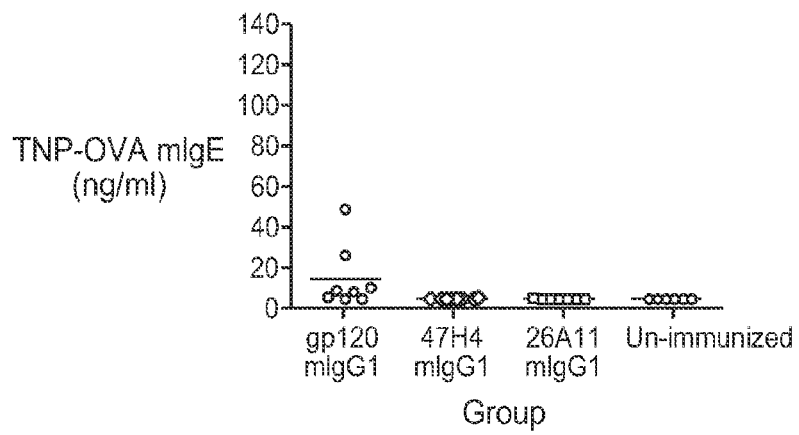
Figure 16F:
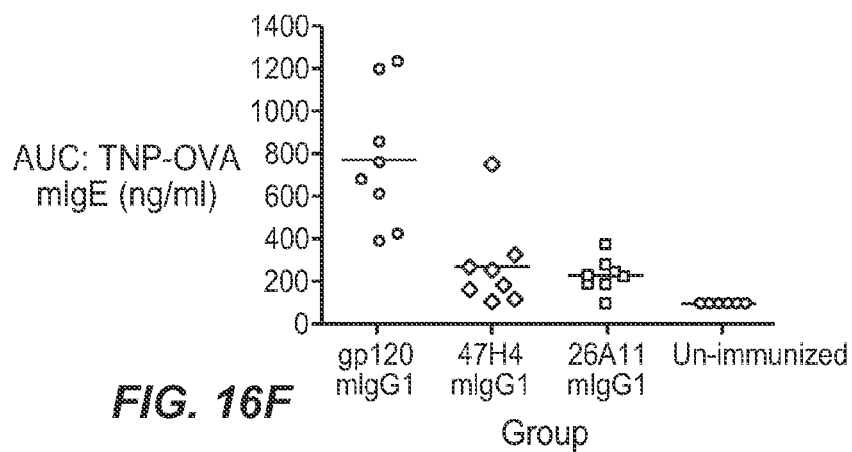
Figure 16G:
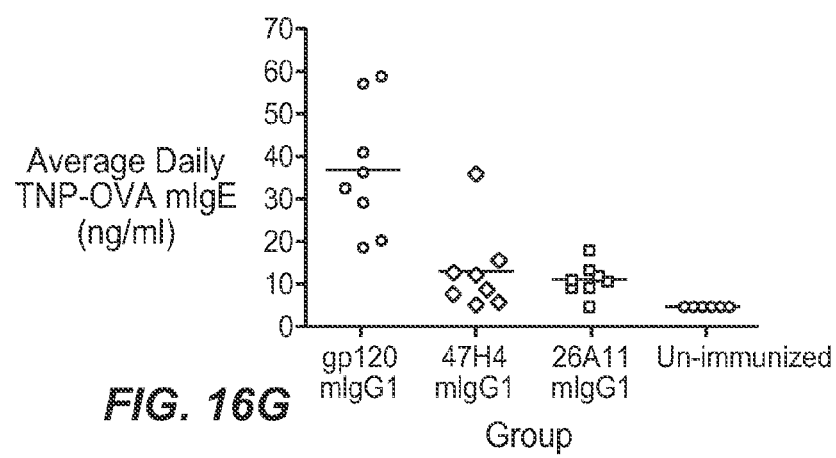
Figure 16I:
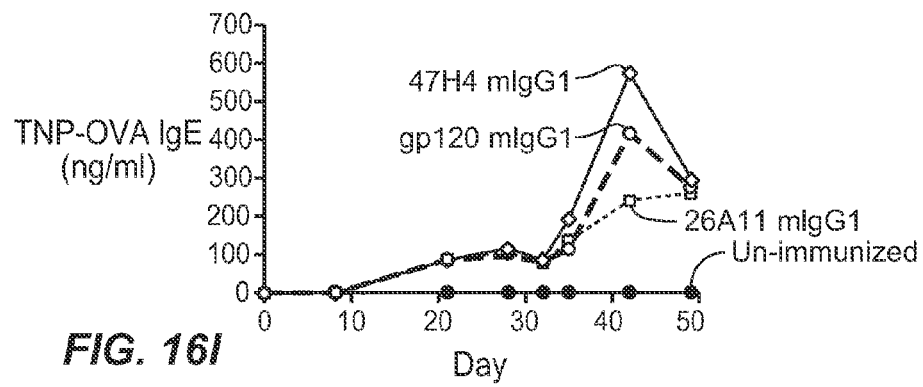
Figure 16J:
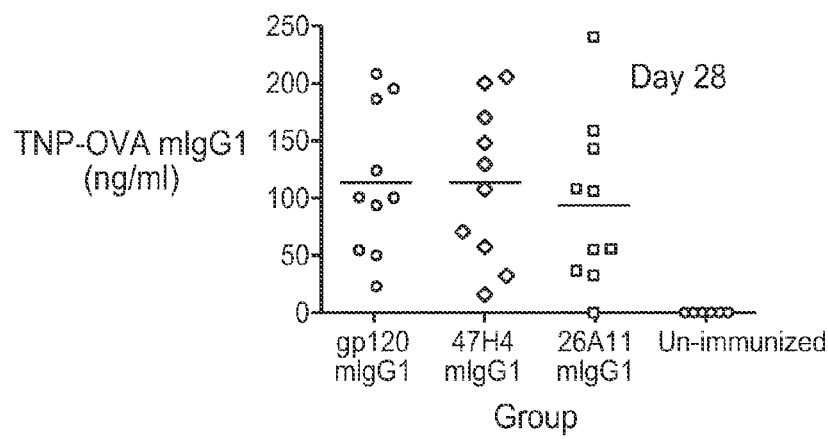
Figure 16J:
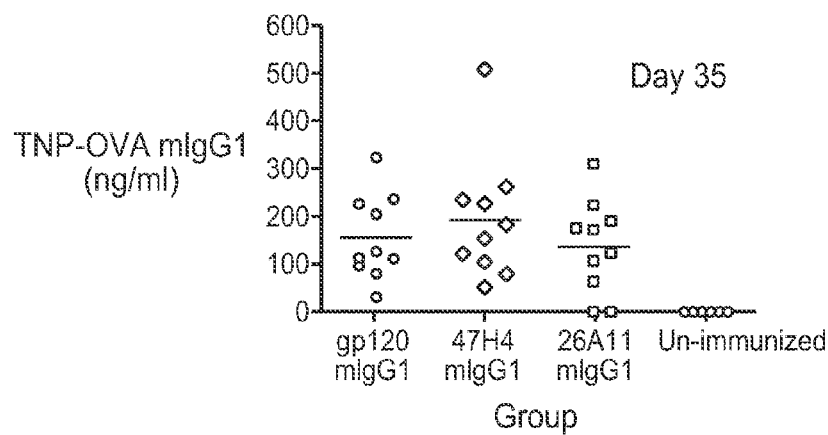

Experiment #07-0234B tested the ability of anti-IgE/M1' to prevent a secondary/memory IgE response to TNP-OVA. The secondary IgE response to TNP-OVA boost on day 28 is more rapid, peaking after 4 days rather than 8-9 days in the primary response (FIG. 16B). Treatment with anti-IgE/M1' candidates starting with the boost on day 28 diminished the increase in IgE between days 28 and 35 (FIG. 16B). Anti-IgE/M1' treated IgE levels were significantly reduced compared to isotype control, 59-75% by day 32 and 90-93% by day 35 (FIGS. 16C-D). By day 35-42 IgE levels were not significantly different from unimmunized mice (FIG. 16E). Area under the curve analysis of these treatment groups between days 28 and 49 further demonstrates that anti-IgE/M1' reduced serum IgE levels by 74-84%, and the average daily level of antigen specific IgE was also reduced by 74-83% (FIGS. 16 F-H). No significant reduction in antigen specific IgG1 was observed following treatment with anti-IgE/M1' (FIGS. 16 I-K).

EXAMPLE 12

Hu-M1' Transgenic Model

*Nippostrongylus brasiliensis* Infection Model

Figures 4, 4A, 5, 6, 7, 8, 9, 10, 11, 12, 13, 14, 15, 16, 17, 18:
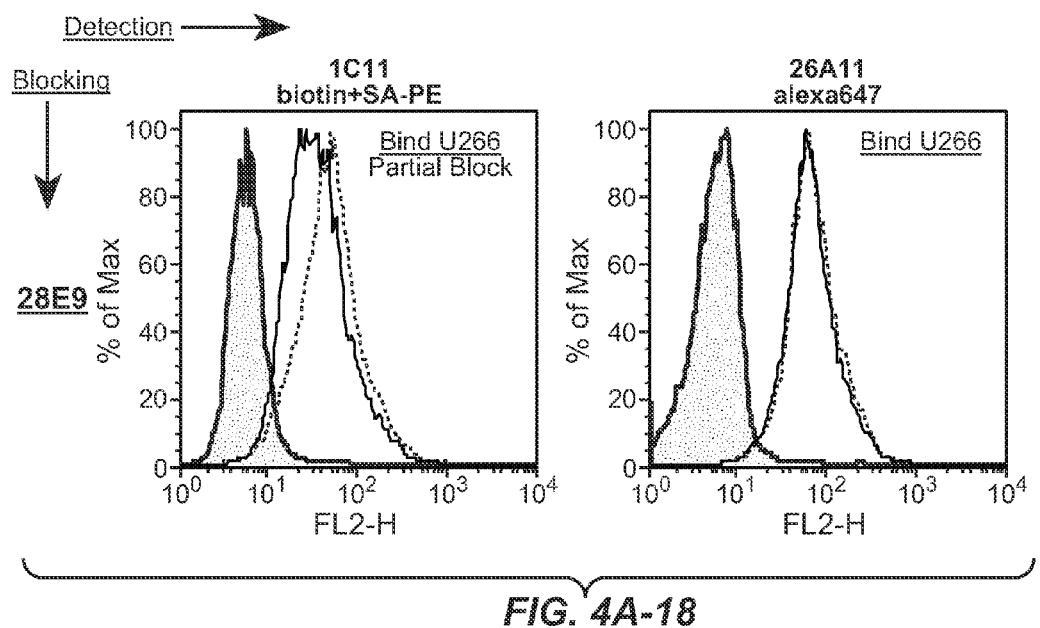
Figures 4, 4A, 5, 6, 7, 8, 9, 10, 11, 12, 13, 14, 15, 16, 17, 18, 19:
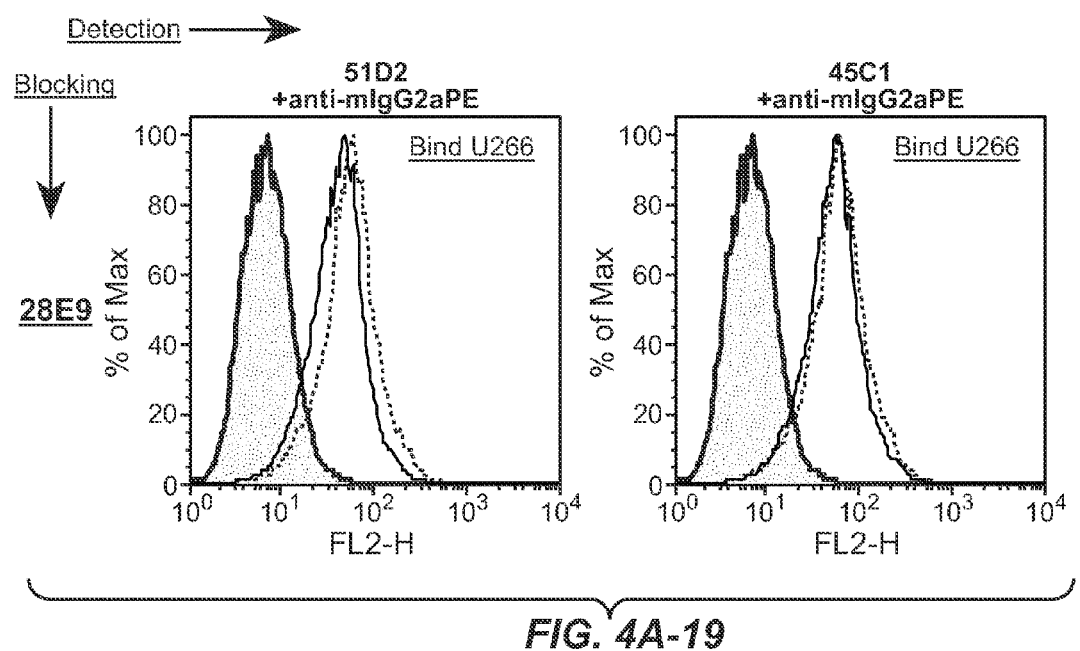
Figures 4, 4A, 5, 6, 7, 8, 9, 10, 11, 12, 13, 14, 15, 16, 17, 18, 19, 20:
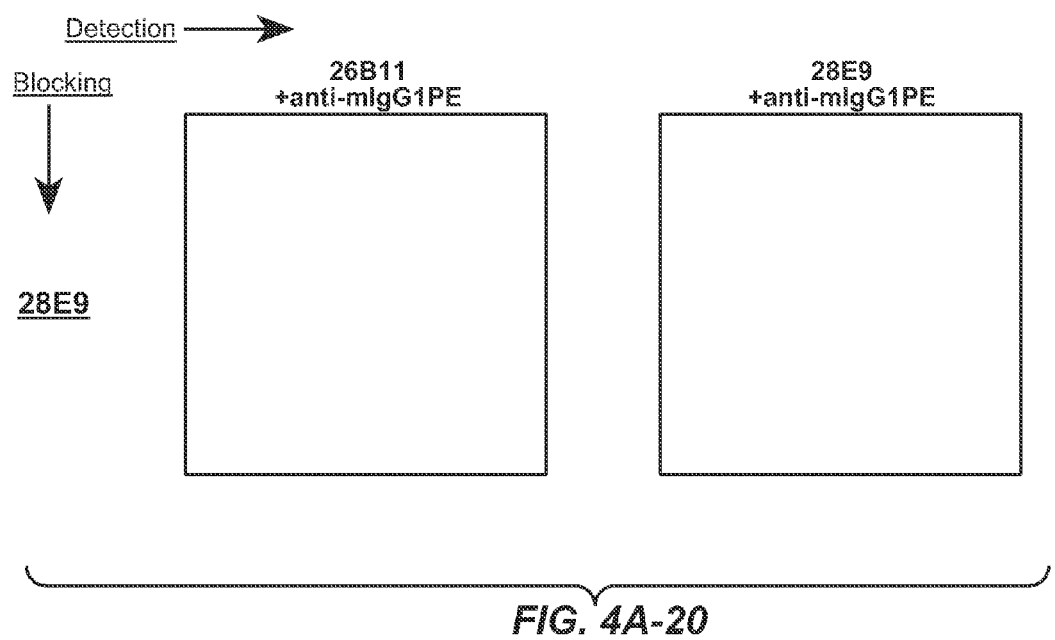
Figure 4C:
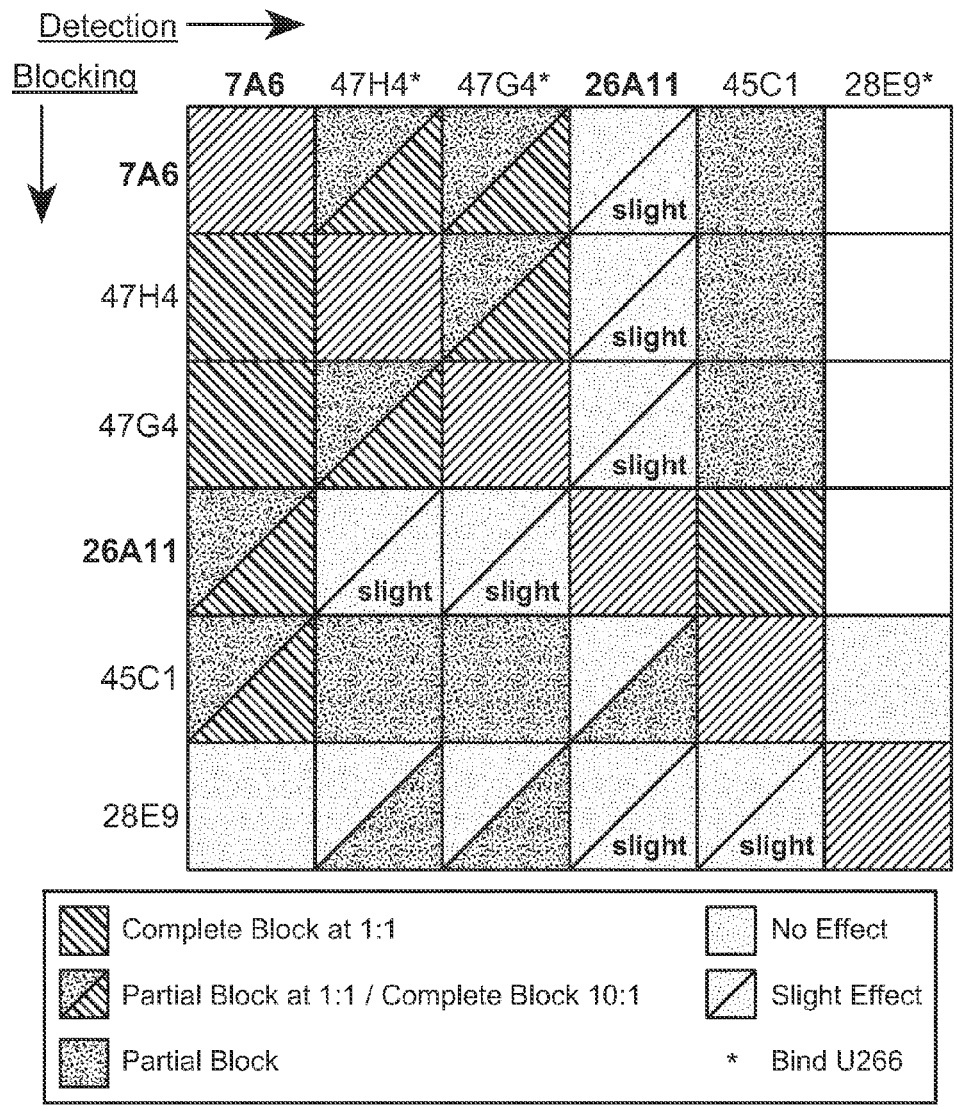
Figure 4D:
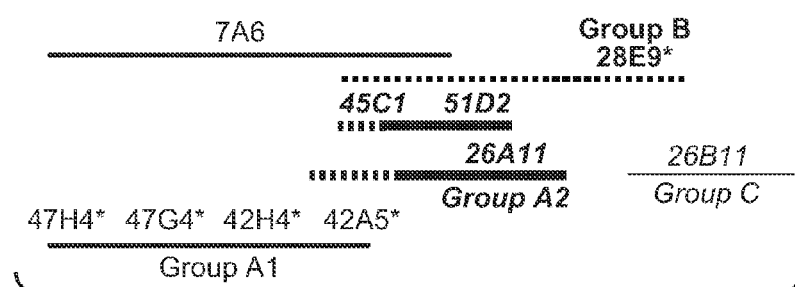

This Example illustrates the ability of anti-IgE/M1' antibodies to prevent the production of IgE (FIGS. 17A-D), as well as therapeutically reduce the production of IgE in a previously induced *Nippostrongylus brasiliensis* infection. The reduction in IgE production was evaluated by administration of anti-IgE/M1' antibodies both at peak IgE levels of the immune response (FIGS. 18 A-I), and when applied late in the immune response (FIGS. 19 A-G).

*Nippostrongylus brasiliensis* is a gastrointestinal nematode that infects rats and mice. Its eggs hatch in feces and mature into the infective stage larvae L3. L3 larvae enter host through skin and migrate to the blood vessels, and then travel to the lung after one to two days. After developing into L4 stage larvae in the lung, they travel along the host's tracheus and esophagus and reach the jejunum at day 2 to 3. The larvae mature into adult worms and mate, and produce eggs around day 5. *N. brasiliensis* eggs are excreted out of the hosts along with feces.

Mice infected with *N. brasiliensis* demonstrate an initial innate immune response, followed by strong type 2 immunity to clear the infection. Complement and fibronectin deposition are found in the earlier stage of the infection to facilitate leukocyte recruitment and adherence. Effector cells, such as eosinophils, basophils, and CD4+ Th2 cells, are recruited to the lung to fight against the infection. Th2 cytokines, IL-4 and IL-13, play essential role in sustaining the immune response in the lung, and are required for worm clearance in the intestine. Type 2 responses are characterized by high levels of antibody production, including IgE.

Figures 17A, 17D:
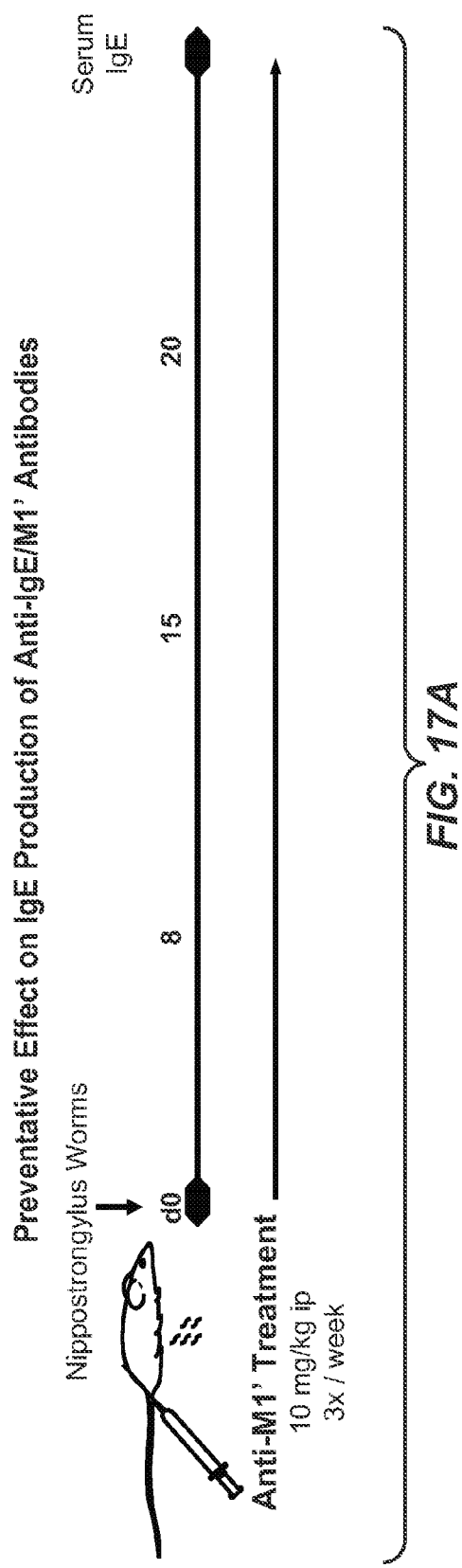
FIGS. 17A-D illustrate the ability of the anti-IgE/M1' antibodies to preventatively reduce the production of IgE in response to *Nippostrongylus brasiliensis* ("NB") infection.
Figure 17B:
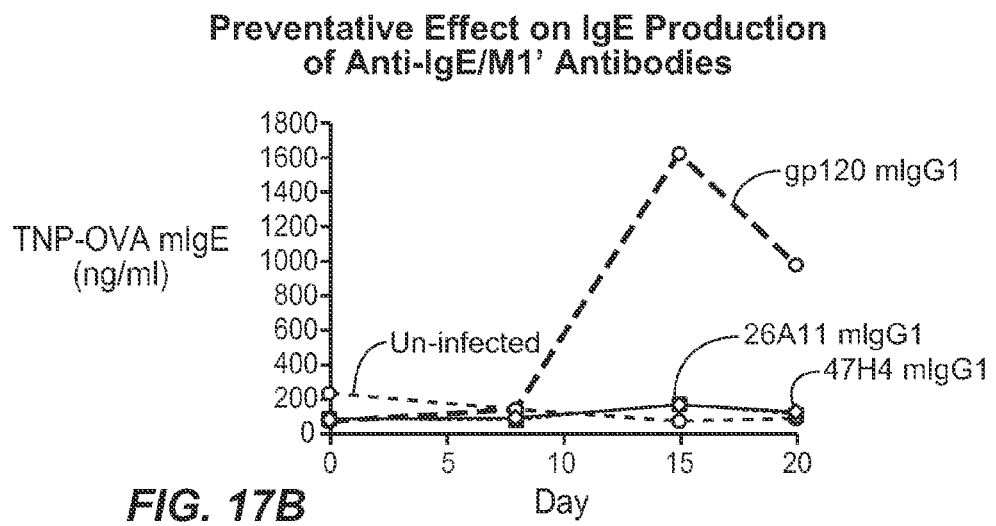
Figure 17C:
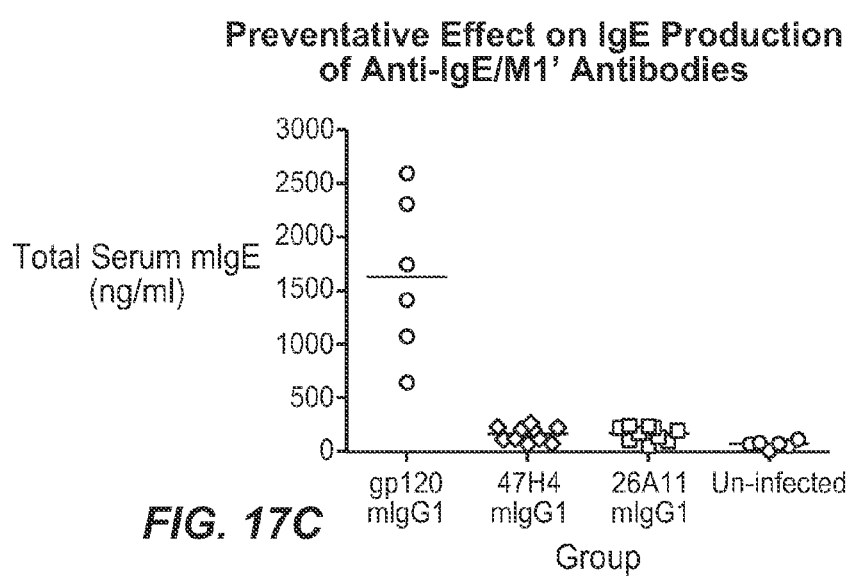
Figure 18B:
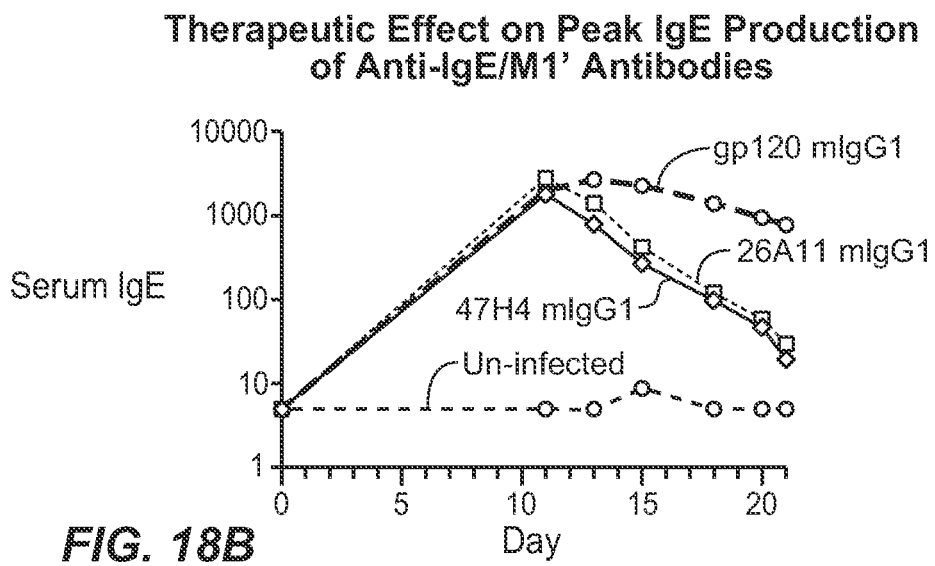
Figure 18C:
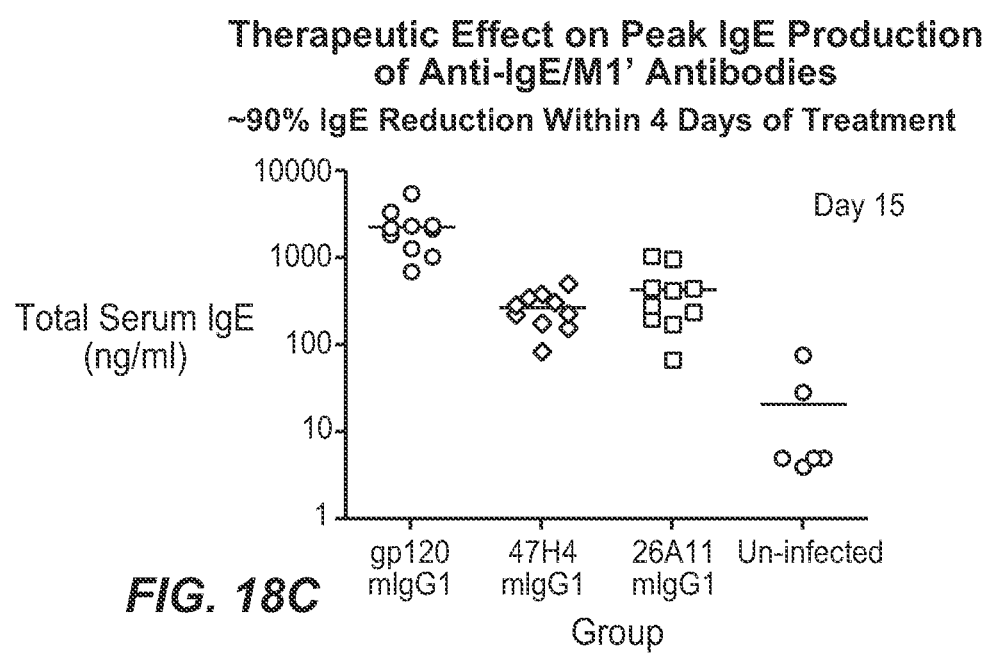
Figure 19B:
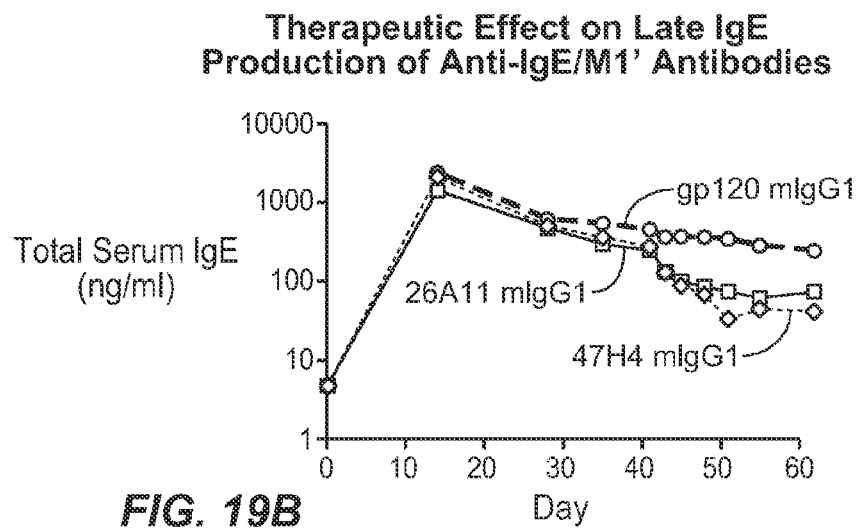
Figure 19C:
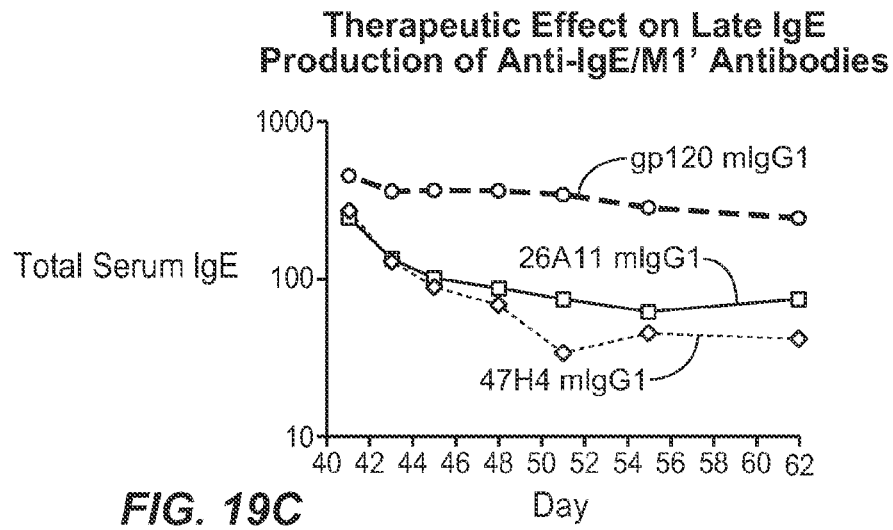

Human IgE/M1' knockin mice (C57BL/6) generate a strong IgE response to *N. brasiliensis* infection peaking at day 15-20 (FIGS. 17B, 18B, 19B). Serum IgE levels then drop to a lower, but elevated sustained level. Mice were infected with *Nippostrongylus brasiliensis* on day 0. All three *N. brasiliensis* infection experiments were treated with 10 mg/kg anti-IgE/M1' mIgG1 antibodies or anti-gp120 mIgG1 isotype control. In the preventative study (FIG. 17A), huM1' knockin mice were treated three times per week starting on day 0 through day 21. In the peak production study (FIG. 18A), huM1' knockin mice were treated three times per week between days 11 and 21. In the late intervention study (FIG. 19A), huM1' knockin mice were treated three times per week between days 41 and 62.

Data is expressed as the mean±Standard Deviation. P-values were calculated using JMP statistics software. Dunnett's test compares group means where all test groups are tested against a reference group. Each Pair Student's t compares each group pair using Student's t-test. A Bonferroni Correction is then applied to adjust the p-values of the Each Pair Student's t to safeguard against pairwise comparisons. All p-value threshold is 0.05. Percent change in the data reported in the preventative and peak production studies was calculated by subtracting the uninfected or unimmunized group mean value from each of the mouse values, group means were recalculated and percent change was then calculated against the control group for each timepoint. In the late intervention study, the percent change was calculated within each treatment group by comparing days 48 and 55 to day 41.

The IgE-producing plasma cells were defined and evaluated by Elispot as described previously in Example 12.

The preventative study tested the ability of anti-IgE/M1' to prevent the increase in IgE in response to a primary *Nippostrongylus* infection. Control (isotype treated) mice reached high levels of IgE production by day 15 following infection (3000 ng/ml). Anti-IgE/M1' treated mice had reduced IgE production following infection (reduced 93-94% compared to anti-gp120 mIgG1) that was not significantly different from uninfected mice (FIGS. 17 B-D).

Figure 18E:
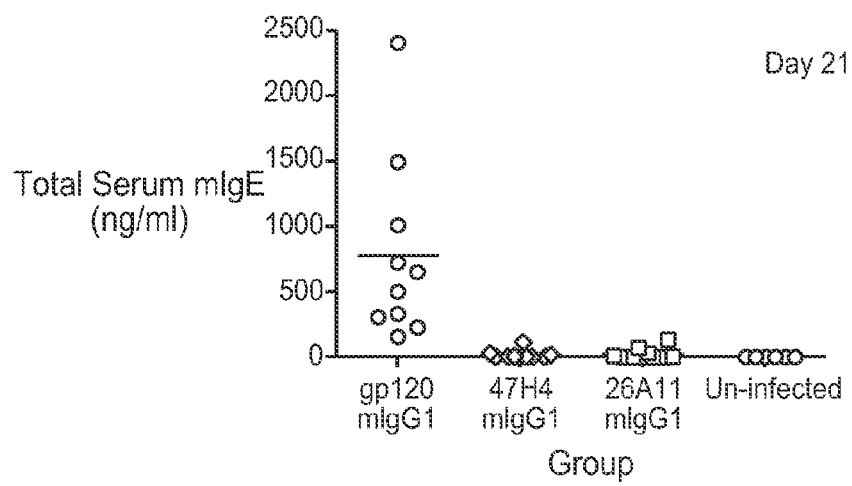
Figure 18F:
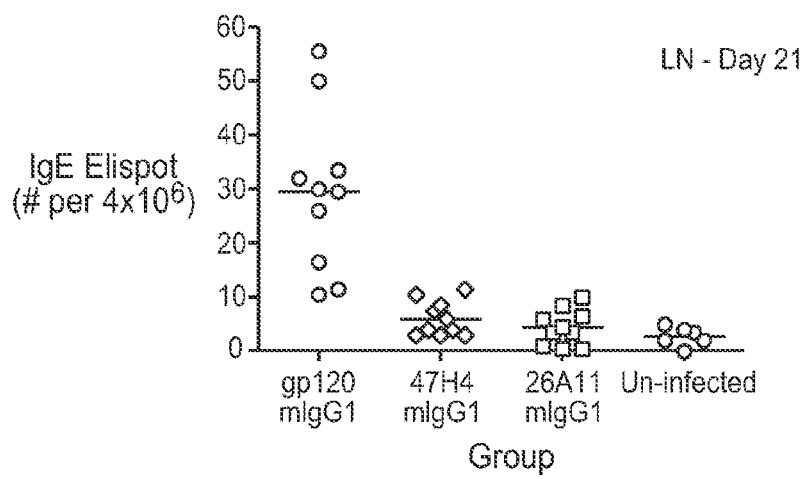
Figure 18G:
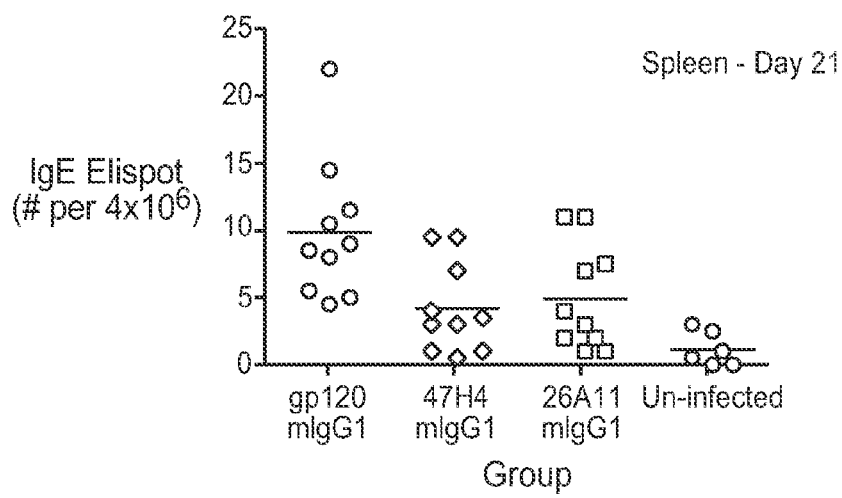
Figure 18H:
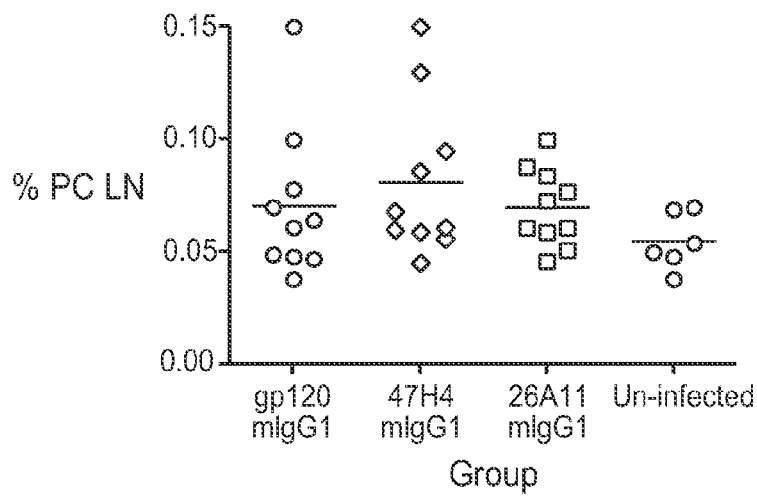
Figure 18I:
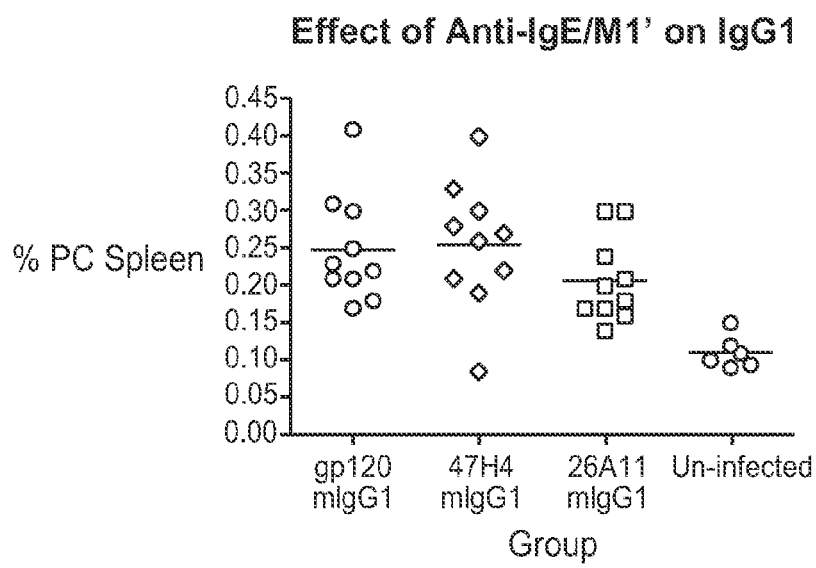

The peak production study tested the ability of anti-IgE/M1' to reduce IgE levels therapeutically at the peak of the IgE response to *N. brasiliensis* infection. All treatment groups reached high IgE levels (2000 ng/ml) by day 11 following *Nippostrongylus* infection (FIG. 18B). Anti-IgE/M1' treatment started on day 11 at the peak of this response. Anti-IgE/M1' mIgG1 candidates reduced serum IgE levels by 82-89% within four days of treatment (FIG. 18 C-D). By day 21 the IgE levels in anti-IgE/M1' treated mice were reduced by 97-98%, reaching levels that are not statistically different from the uninfected control group (FIG. 18E). IgE producing plasma cells were quantified by anti-IgE Elispot. *N. brasiliensis* infection induced significant numbers of IgE producing cells in both the mesenteric lymph node (~30 cells per $4 \times 10^6$; FIG. 18F) and spleen (~10 cells per $4 \times 10^6$; FIG. 18G). By day 21 anti-IgE/M1' treatment reduced IgE producing cells in the mesenteric lymphnode by 88-94% and in the spleen by 57-66%. The frequency of total plasma cells (CD138+ cells) in the mesenteric lymph node and spleen was increased in all treatment groups compared with uninfected mice, and there was no significant change in total plasma cell frequency in either organ due to treatment with anti-IgE/M1' (FIG. 18 H-I). These results demonstrate the ability of anti-IgE/M1' antibodies to reduce serum IgE to nominal levels by depleting IgE producing cells in vivo, even when applied at the peak level of IgE production.

Figure 19D:
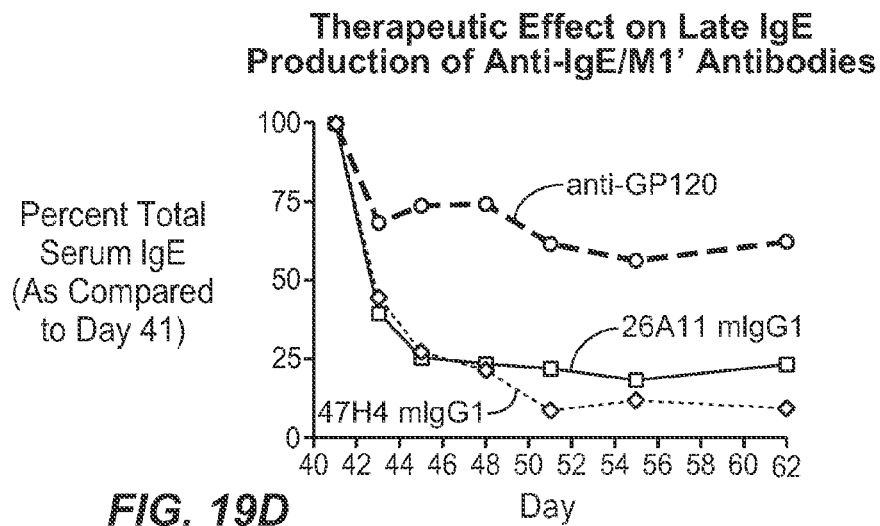
Figure 19E:
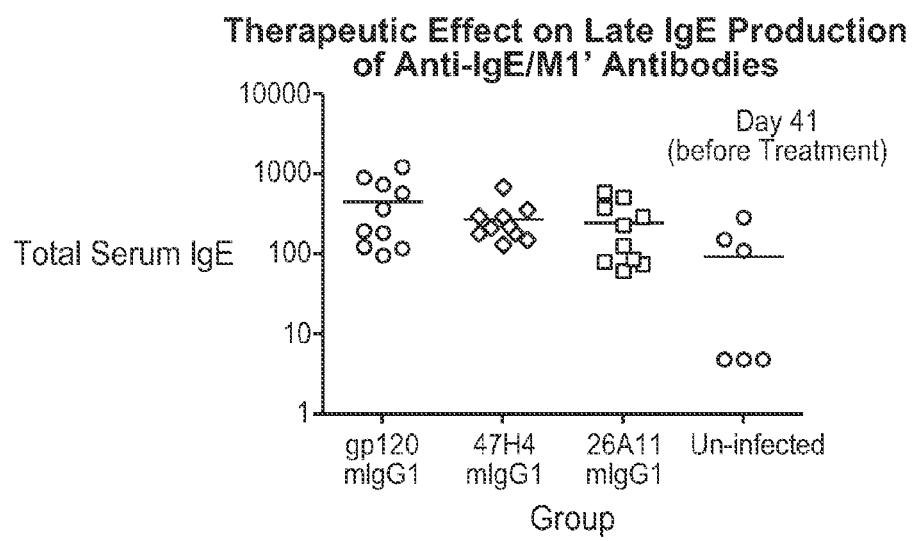
Figure 19F:
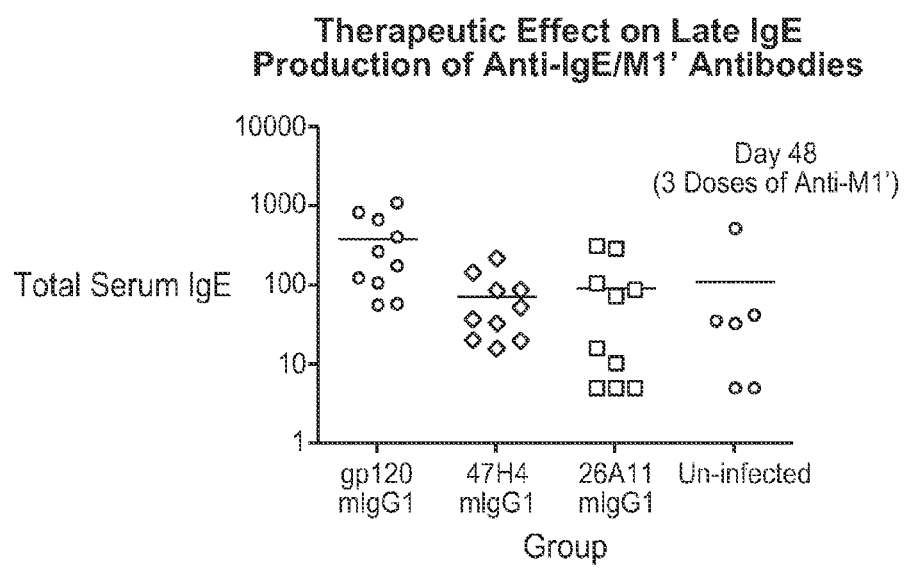
Figure 19G:
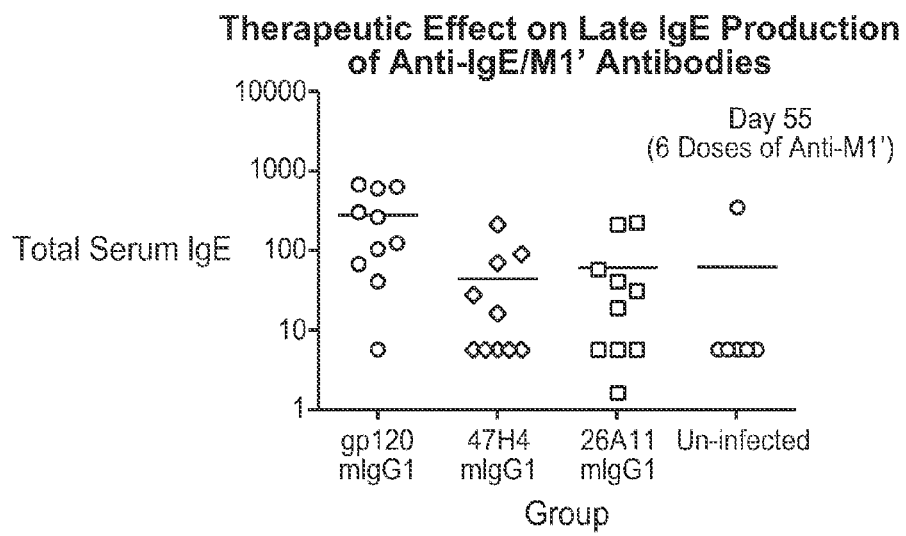

The late intervention study tested the ability of anti-IgE/M1' to reduce the low level sustained IgE that is achieved late in the infection cycle. All treatment groups reached the peak of IgE production around day 15. Upon initiation of anti-IgE/M1' treatment on day 41, there were some differences in serum IgE levels amongst treatment groups (FIGS. 19 B-C), that was normalized by referencing the day 41 levels as 100% (FIG. 19D). Anti-IgE/M1' treatment significantly reduced serum IgE levels compared to the anti-gp120 mIgG1 isotype control between days 48 and 55 (FIG. 19 E-G). By day 48 and 55 IgE levels were reduced 64-75% and 75-84%, respectively, compared with isotype control (anti-gp120 mIgG1) which decreased 20% and 37%, respectively (FIGS. 19 F-G). The difference in mean IgE levels between treatment groups was not significantly different from the isotype control group (gp120) prior to commencement of anti-IgE/M1' therapy (FIG. 19E). However, treatment with anti-IgE/M1' antibodies showed a more dramatic and significant decrease in serum IgE levels than that observed in the control group by day 48 (FIG. 19F) and Day 55 (FIG. 19G). Percent change and p-value (d41) were calculated by comparing each treatment group days 48 or 55 to the same group starting value in day 41 prior to treatment.

EXAMPLE 13

Expression of Anti-IgE/M1' Antibody in Mammalian Cells

This example illustrates preparation of potentially glycosylated forms of the desired protein or antibody by recombinant expression in mammalian cells.

The vector, pRK5 (see EP 307,247, published Mar. 15, 1989), is employed as the expression vector. Optionally, DNA encoding the light and/or heavy chain of the anti-IgE/M1' antibody is ligated into pRK5 with selected restriction enzymes to allow insertion such DNA using ligation methods such as described in Sambrook et al., supra.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg if DNA encoding the anti-IgE/M1' antibody ligated into pRK5 is mixed with about 1 µg DNA encoding the VA RNA gene [Thimmappaya et al., *Cell*, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of the anti-IgE/M1' antibody. The cultures containing transfected cells may undergo further incubation (in serum free medium) and the medium is tested in selected bioassays.

In an alternative technique, the anti-IgE/M1' antibody may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg DNA encoding the anti-IgE/M1' antibody ligated into pRK5 is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing the expressed anti-IgE/M1' antibody can then be concentrated and purified by any selected method, such as dialysis and/or column chromatography.

In another embodiment, the anti-IgE/M1' antibody can be expressed in CHO cells. The DNA encoding the anti-IgE/M1' antibody ligated into pRK5 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of the anti-IgE/M1' antibody, the culture medium may be replaced with serum free medium. Preferably, the cultures are incubated for about 6 days, and then the conditioned medium is harvested. The medium containing the expressed anti-IgE/M1' antibody can then be concentrated and purified by any selected method.

Epitope-tagged variants of the anti-IgE/M1' antibody may also be expressed in host CHO cells. The DNA encoding the anti-IgE/M1' antibody ligated into pRK5 may be subcloned out of the pRK5 vector. The subclone insert can undergo PCR to fuse in frame with a selected epitope tag such as a poly-his tag into a Baculovirus expression vector. The poly-his tagged DNA encoding the anti-IgE/M1' antibody insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged anti-IgE/M1' antibody can then be concentrated and purified by any selected method, such as by Ni$^{2+}$-chelate affinity chromatography.

The anti-IgE/M1' antibody may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECT® (Quiagen), DOSPER® or FUGENE® (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number and pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated at 4° C., in 20 mM Hepes, pH 7.4, buffer containing 0.3 M NaCl and 5 mM imidazole at a flow rate of 4-5 ml/min. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

DEPOSIT OF MATERIAL

The following materials have been deposited with the American Type Culture Collection, 10801 University Blvd., Manassas, Va. 20110-2209, USA (ATCC):

| Material | ATCC Dep. No. | Deposit Date |
|---|---|---|
| 7A6.18 | PTA-8268 | Mar. 21, 2007 |
| 1C11.10.20 | PTA-8267 | Mar. 21, 2007 |
| 47G4.6.2 | PTA-8266 | Mar. 21, 2007 |
| 47H4.12.10 | PTA-8270 | Mar. 21, 2007 |
| 42H4.6.9 | PTA-8260 | Mar. 21, 2007 |
| 42A5.20.11 | PTA-8265 | Mar. 21, 2007 |
| 26A11.6.5 | PTA-8262 | Mar. 21, 2007 |
| 51D2.22.15 | PTA-8264 | Mar. 21, 2007 |
| 45C1.6.14 | PTA-8269 | Mar. 21, 2007 |
| 26B11.3.12 | PTA-8261 | Mar. 21, 2007 |
| 28E9.12.9 | PTA-8263 | Mar. 21, 2007 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposits for thirty (30) years from the date of deposits, and at least five (5) years after the most recent request for a sample. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws. The foregoing written description is considered to be sufficient to enable one skilled in the art to practice the invention. The present invention is not to be limited in scope by the example presented herein. Indeed, various modifications of the invention in addition to those shown and described herein will become apparent to those skilled in the art from the foregoing description and fall within the scope of the appended claims.

What is claimed is:

1. A method for specifically depleting IgE-producing B-cells, comprising administering to a mammal a therapeutically effective amount of an anti-IgE/M1' antibody that specifically binds to the M1' segment of IgE defined by residues 317 to 351 of SEQ ID NO:1.

2. The method of claim 1, wherein the antibody induces apoptosis in IgE-expressing B-cells.

3. The method of claim 1, wherein the antibody comprises the heavy and light chain HVRs of the antibody selected from the group consisting of: 26A11, 26A11 v1-16, 7A6, 7A6v1, 47H4 and 47H4v1-6.

4. The method of claim 3, wherein the antibody comprises the heavy and light chain HVRs of 47H4v1-6.

5. The method of claim 4, wherein the antibody comprises the heavy and light chain HVRs of 47H4v5.

6. The method of claim 5, wherein the antibody is afucosylated.

7. The method of claim 1, wherein the antibody comprises the heavy and light chain variable regions of the antibody or antigen-binding fragment thereof selected from the group consisting of: 26A11, 26A11 v1-16, 7A6, 7A6v1, 47H4, 47H4v1-6.

8. The method of claim 7, wherein the antibody is selected from the group consisting of: 47H4v1, 47H4v2, 47H4v3, 47H4v4, 47H4v5, and 47H4v6.

9. The method of claim 7, wherein the antibody is 47H4v5.

10. The method of any of claims 1-9, further comprising the reduction of total serum IgE.

11. The method of claim 10, wherein the IgE is allergen-specific.

12. The method of any of claims 1-9, wherein the antibody has ADCC activity.

13. A method of treating an IgE-mediated disorder comprising administering a therapeutically effective amount of an anti-IgE/M1' antibody that specifically binds to the M1' segment of IgE defined by residues 317 to 351 of SEQ ID NO:1.

14. The method of claim 13, wherein the antibody induces apoptosis of IgE-expressing B-cells.

15. The method of claim 13, wherein the antibody specifically depletes IgE-expressing B-cells.

16. The method of claim 13, wherein the antibody reduces total serum IgE.

17. The method of claim 13, wherein the IgE is allergen-specific.

18. The method of claim 13, wherein the antibody has ADCC activity.

19. The method of claim 13, wherein the antibody is afucosylated.

20. A method of treating an IgE-mediated disorder comprising administering a therapeutically effective amount of an antibody comprising the heavy and light chain HVRs of an antibody selected from the group consisting of: 26A11, 26A11v1-16, 7A6, 7A6v1, 47H4 and 47H4v1-6.

21. The method of claim 20, wherein the antibody is selected from the group consisting of: 47H4 v1-6.

22. The method of claim 21, wherein the antibody is 47H4v5.

23. The method of claim 20, further comprising the reduction of total serum IgE.

24. The method of claim 20, wherein the IgE is allergen-specific.

25. The method of claim 20, wherein the antibody has ADCC activity.

26. The method of claim 20, wherein the antibody is afuscosylated.

27. A method of treating an IgE-mediated disorder comprising administering a therapeutically effective amount of an antibody comprising the heavy and light chain variable regions of the antibody or antigen-binding fragment thereof selected from the group consisting of: 26A11, 26A11v1-16, 7A6, 7A6v1, 47H4 and 47H4v1-6.

28. The method of claim 27, wherein the antibody is selected from the group consisting of 47H4v1-6.

29. The method of claim 28, wherein the antibody is 47H4v5.

30. The method of claim 27, wherein the heavy chain variable region of the antibody comprises SEQ ID NO:41, and the light chain variable region of the antibody comprises SEQ ID NO:31.

31. The method of claim 27, further comprising the reduction of total serum IgE.

32. The method of claim 27, wherein the IgE is allergen-specific.

33. The method of claim 27, wherein the antibody has ADCC activity.

34. The method of claim 27, wherein the antibody is afucosylated.

35. The method of claim 27, wherein the IgE-mediated disorder is selected from the group consisting of: allergic rhinitis, allergic asthma, non-allergic asthma, atopic dermatitis, allergic gastroenteropathy, anaphylaxis, urticaria, food allergies, allergic bronchopulmonary aspergillosis, parasitic diseases, interstitial cystitis, hyper-IgE syndrome, ataxia-telangiectasia, Wiskott-Aldrich syndrome, athymic lymphoplasia, IgE myeloma, graft-versus-host reaction and allergic purpura.

36. The method of claim 35, in combination with the administration of a therapeutically effective amount of at least one drug selected from the group consisting of: anti-IgE antibody, antihistamine, bronchodilator, glucocorticoid, NSAID, decongestant, cough suppressant, analgesic, TNF-antagonist, integrin antagonist, immunosuppressive agent, IL-4 antagonist, IL-13 antagonist, dual IL-4/IL-13 antagonist, DMARD, antibody that binds to a B-cell surface marker and BAFF antagonist.

37. The method of claim 35, wherein the drug is administered in combination with prior to, simultaneous with the antibody.

38. The method of claim 35, wherein the antibody is administered in combination with a treatment regimen of allergen densitization.

39. A method for inhibiting allergen-induced IgE production, comprising administering a therapeutically effective amount of an anti-IgE/M1' antibody that that specifically binds to the M1' segment of IgE defined by residues 317 to 351 of SEQ ID NO:1.

40. The method of claim 39, wherein the antibody induces apoptosis of IgE-expressing B-cells.

41. The method of claim 39, further comprising the reduction of total serum IgE.

42. The method of claim 41 wherein the IgE is allergen-specific.

43. The method of claim 39, wherein the antibody has ADCC activity.

44. The method of claim 39, wherein the antibody is afucosylated.

45. A method for reducing allergen-induced IgE production, comprising administering a therapeutically effectgive amount of an anti-IgE/M1' antibody that that specifically binds to the M1' segment of IgE defined by residues 317 to 351 of SEQ ID NO:1.

46. The method of claim 45, wherein the antibody induces apoptosis of IgE-expressing B-cells.

47. The method of claim 45, further comprising the reduction of total serum IgE.

48. The method of claim 47, wherein the IgE is allergen-specific.

49. The method of claim 45, wherein the antibody has ADCC activity.

50. The method of claim 45, wherein the antibody is afucosylated.

* * * * *

UNITED STATES PATENT AND TRADEMARK OFFICE
CERTIFICATE OF CORRECTION

PATENT NO.        : 8,586,040 B2                                      Page 1 of 1
APPLICATION NO.   : 13/281209
DATED             : November 19, 2013
INVENTOR(S)       : Lawren Wu et al.

It is certified that error appears in the above-identified patent and that said Letters Patent is hereby corrected as shown below:

In the claims:

Claim 39: Under Column 188, line 6, please delete "that";

Claim 45: Under Column 188, line 20, please delete "effectgive" and insert --effective--;

Claim 45: Under Column 188, line 21, please delete "that".

Signed and Sealed this
Twenty-seventh Day of May, 2014

Michelle K. Lee
*Deputy Director of the United States Patent and Trademark Office*

```
                           SEQUENCE LISTING

<160> NUMBER OF SEQ ID NOS: 112

<210> SEQ ID NO 1
<211> LENGTH: 431
<212> TYPE: PRT
<213> ORGANISM: Homo sapiens
<220> FEATURE:
<221> NAME/KEY: Misc-feature
<223> OTHER INFORMATION: human IgE

<400> SEQUENCE: 1

Ile Leu Gln Ser Ser Cys Asp Gly Gly Gly His Phe Pro Pro Thr
 1               5                  10                  15

Ile Gln Leu Leu Cys Leu Val Ser Gly Tyr Thr Pro Gly Thr Ile
                20                  25                  30

Asn Ile Thr Trp Leu Glu Asp Gly Gln Val Met Asp Val Asp Leu
                35                  40                  45

Ser Thr Ala Ser Thr Thr Gln Glu Gly Glu Leu Ala Ser Thr Gln
                50                  55                  60

Ser Glu Leu Thr Leu Ser Gln Lys His Trp Leu Ser Asp Arg Thr
                65                  70                  75

Tyr Thr Cys Gln Val Thr Tyr Gln Gly His Thr Phe Glu Asp Ser
                80                  85                  90

Thr Lys Lys Cys Ala Asp Ser Asn Pro Arg Gly Val Ser Ala Tyr
                95                  100                 105

Leu Ser Arg Pro Ser Pro Phe Asp Leu Phe Ile Arg Lys Ser Pro
                110                 115                 120

Thr Ile Thr Cys Leu Val Val Asp Leu Ala Pro Ser Lys Gly Thr
                125                 130                 135

Val Asn Leu Thr Trp Ser Arg Ala Ser Gly Lys Pro Val Asn His
                140                 145                 150

Ser Thr Arg Lys Glu Glu Lys Gln Arg Asn Gly Thr Leu Thr Val
                155                 160                 165

Thr Ser Thr Leu Pro Val Gly Thr Arg Asp Trp Ile Glu Gly Glu
                170                 175                 180

Thr Tyr Gln Cys Arg Val Thr His Pro His Leu Pro Arg Ala Leu
                185                 190                 195

Met Arg Ser Thr Thr Lys Thr Ser Gly Pro Arg Ala Ala Pro Glu
                200                 205                 210

Val Tyr Ala Phe Ala Thr Pro Glu Trp Pro Gly Ser Arg Asp Lys
                215                 220                 225

Arg Thr Leu Ala Cys Leu Ile Gln Asn Phe Met Pro Glu Asp Ile
                230                 235                 240

Ser Val Gln Trp Leu His Asn Glu Val Gln Leu Pro Asp Ala Arg
                245                 250                 255

His Ser Thr Thr Gln Pro Arg Lys Thr Lys Gly Ser Gly Phe Phe
                260                 265                 270

Val Phe Ser Arg Leu Glu Val Thr Arg Ala Glu Trp Glu Gln Lys
                275                 280                 285

Asp Glu Phe Ile Cys Arg Ala Val His Glu Ala Ala Ser Pro Ser
                290                 295                 300
```

```
Gln Thr Val Gln Arg Ala Val Ser Val Asn Pro Gly Leu Ala Gly
                305                 310                 315

Gly Ser Ala Gln Ser Gln Arg Ala Pro Asp Arg Val Leu Cys His
            320                 325                 330

Ser Gly Gln Gln Gln Gly Leu Pro Arg Ala Ala Gly Gly Ser Val
        335                 340                 345

Pro His Pro Arg Cys His Cys Gly Ala Gly Arg Ala Asp Trp Pro
    350                 355                 360

Gly Pro Pro Glu Leu Asp Val Cys Val Glu Glu Ala Glu Gly Glu
365                 370                 375

Ala Pro Trp Thr Trp Thr Gly Leu Cys Ile Phe Ala Ala Leu Phe
                380                 385                 390

Leu Leu Ser Val Ser Tyr Ser Ala Ala Leu Thr Leu Leu Met Val
            395                 400                 405

Gln Arg Phe Leu Ser Ala Thr Arg Gln Gly Arg Pro Gln Thr Ser
        410                 415                 420

Leu Asp Tyr Thr Asn Val Leu Gln Pro His Ala
    425                 430

<210> SEQ ID NO 2
<211> LENGTH: 432
<212> TYPE: PRT
<213> ORGANISM: Macaca mulatta
<220> FEATURE:
<221> NAME/KEY: Other...
<223> OTHER INFORMATION: rhesus IgE

<400> SEQUENCE: 2

Ile Leu Gln Ser Ser Cys Asp Asp Gly His Phe Pro Pro Thr
 1               5                  10                  15

Ile Gln Leu Leu Cys Leu Ile Ser Gly Tyr Thr Pro Gly Ala Ile
                 20                  25                  30

Asn Val Thr Trp Leu Glu Asn Gly Gln Val Met Lys Val Asn Ser
             35                  40                  45

Pro Thr Pro Pro Ala Thr Gln Glu Gly Glu Leu Ala Ser Thr Gln
         50                  55                  60

Ser Glu Phe Thr Leu Ala Gln Lys His Trp Leu Ser Asp Arg Thr
     65                  70                  75

Tyr Thr Cys Gln Val Thr Tyr Gln Gly Thr Thr Tyr Asn Asp Ser
                 80                  85                  90

Thr Lys Lys Cys Ala Asp Ser Asn Pro Arg Gly Val Ser Ala Tyr
                 95                 100                 105

Leu Ser Arg Pro Ser Pro Phe Asp Leu Phe Ile Ser Lys Ser Pro
             110                 115                 120

Thr Ile Thr Cys Leu Val Val Asp Leu Ala Pro Ser Lys Glu Thr
         125                 130                 135

Val Asn Leu Thr Trp Ser Arg Ala Ser Gly Lys Pro Val Pro His
                 140                 145                 150

Ile Pro Ala Thr Glu Lys Lys Gln Gln Arg Asn Gly Thr Leu Thr
                 155                 160                 165

Val Thr Ser Ile Leu Pro Val Val Thr Gln Asp Trp Ile Glu Gly
             170                 175                 180

Glu Thr Tyr Gln Cys Arg Val Thr His Pro His Leu Pro Arg Ala
                 185                 190                 195

Leu Val Arg Ser Met Thr Lys Thr Ser Gly Pro Arg Ala Ala Pro
             200                 205                 210
```

```
Glu Val Tyr Val Phe Ala Thr Pro Lys Leu Glu Ser Arg Asp
            215                 220                 225

Lys Arg Thr Leu Ala Cys Leu Ile Gln Asn Phe Met Pro Glu Asp
                230                 235                 240

Ile Ser Val Gln Trp Leu His Ser Asp Val Gln Leu Pro Asp Ala
                245                 250                 255

Arg His Ser Val Thr Gln Pro Arg Lys Thr Lys Gly Ser Gly Phe
                260                 265                 270

Phe Val Phe Ser Arg Leu Glu Val Thr Lys Ala Glu Trp Glu Gln
                275                 280                 285

Lys Asp Glu Phe Ile Cys Arg Ala Val His Glu Ala Ala Ser Pro
                290                 295                 300

Ser Trp Ile Val Gln Gln Ala Val Ser Val Asn Pro Gly Leu Ala
                305                 310                 315

Gly Gly Ser Ala Gln Ser Gln Arg Ala Pro Asp Arg Val Leu Cys
                320                 325                 330

His Ser Glu Gln Gln Gln Gly Leu Pro Arg Ala Ala Arg Gly Ser
                335                 340                 345

Val Pro Asp His His Cys His Cys Gly Ala Gly Arg Ala Asp Trp
                350                 355                 360

Pro Gly Leu Pro Glu Leu Asp Leu Cys Val Glu Glu Ala Glu Ser
                365                 370                 375

Glu Val Leu Trp Thr Trp Thr Gly Leu Cys Ile Phe Ala Thr Leu
                380                 385                 390

Phe Leu Leu Ser Val Ser Tyr Ser Ala Ala Ile Thr Leu Leu Met
                395                 400                 405

Val Gln Arg Phe Leu Ser Ala Thr Arg Gln Gly Arg Pro Gln Thr
                410                 415                 420

Ser Leu Asp Tyr Thr Asn Val Leu Gln Pro His Ala
                425                 430

<210> SEQ ID NO 3
<211> LENGTH: 431
<212> TYPE: PRT
<213> ORGANISM: Macaca fascicularis
<220> FEATURE:
<221> NAME/KEY: Other...
<223> OTHER INFORMATION: cyno IgE

<400> SEQUENCE: 3

Ile Leu Gln Ser Ser Cys Asp Asp Gly His Phe Pro Pro Thr
  1               5                  10                  15

Ile Gln Leu Leu Cys Leu Ile Ser Gly Tyr Thr Pro Gly Ala Ile
                 20                  25                  30

Asn Val Thr Trp Leu Glu Asn Gly Gln Val Met Lys Val Asn Ser
                 35                  40                  45

Pro Thr Pro Pro Ala Thr Gln Glu Gly Glu Leu Ala Ser Thr Gln
                 50                  55                  60

Ser Glu Phe Thr Leu Ala Gln Lys His Trp Leu Ser Asp Arg Thr
                 65                  70                  75

Tyr Thr Cys Gln Val Thr Tyr Gln Gly Thr Thr Tyr Asn Asp Ser
                 80                  85                  90

Thr Lys Lys Cys Ala Asn Ser Asn Pro Arg Gly Val Ser Ala Tyr
                 95                 100                 105

Leu Ser Arg Pro Ser Pro Phe Asp Leu Phe Ile Ser Lys Ser Pro
                110                 115                 120
```

```
Thr Ile Thr Cys Leu Val Val Asp Leu Ala Pro Ser Lys Glu Thr
            125                 130                 135

Val Asn Leu Thr Trp Ser Arg Ala Ser Gly Lys Pro Val Pro His
            140                 145                 150

Thr Pro Ala Thr Glu Lys Lys Gln Arg Asn Gly Thr Leu Thr Val
            155                 160                 165

Thr Ser Ile Leu Pro Val Val Thr Gln Asp Trp Ile Glu Gly Glu
            170                 175                 180

Thr Tyr Gln Cys Arg Val Thr His Pro His Leu Pro Arg Ala Leu
            185                 190                 195

Val Arg Ser Met Thr Lys Thr Ser Gly Pro Arg Ala Ala Pro Glu
            200                 205                 210

Val Tyr Val Phe Ala Thr Pro Glu Lys Leu Glu Ser Arg Asp Lys
            215                 220                 225

Arg Thr Leu Ala Cys Leu Ile Gln Asn Phe Met Pro Glu Asp Ile
            230                 235                 240

Ser Val Gln Trp Leu His Ser Asp Val Gln Leu Pro Asp Ala Arg
            245                 250                 255

His Ser Val Thr Gln Pro Arg Lys Thr Lys Gly Ser Gly Phe Phe
            260                 265                 270

Val Thr Ser Arg Leu Glu Val Thr Lys Ala Glu Trp Glu Gln Lys
            275                 280                 285

Asp Glu Phe Ile Cys Arg Ala Val His Glu Ala Ala Ser Pro Ser
            290                 295                 300

Trp Ile Val Gln Gln Ala Val Ser Val Asn Pro Gly Leu Ala Gly
            305                 310                 315

Gly Ser Ala Gln Ser Gln Arg Ala Pro Asp Arg Val Leu Cys His
            320                 325                 330

Ser Glu Gln Gln Gln Gly Leu Pro Arg Ala Ala Arg Gly Ser Val
            335                 340                 345

Pro Asp His Arg Cys His Cys Gly Ala Gly Arg Ala Asp Trp Pro
            350                 355                 360

Gly Leu Pro Glu Leu Asp Leu Cys Val Glu Glu Ala Glu Ser Glu
            365                 370                 375

Val Leu Trp Thr Trp Thr Gly Leu Cys Ile Phe Ala Thr Leu Phe
            380                 385                 390

Leu Leu Ser Val Ser Tyr Ser Ala Ala Ile Thr Leu Leu Met Val
            395                 400                 405

Gln Arg Phe Leu Ser Val Thr Arg Gln Gly Arg Pro Gln Thr Ser
            410                 415                 420

Leu Asp Tyr Thr Asn Ile Leu Gln Pro His Ala
            425                 430

<210> SEQ ID NO 4
<211> LENGTH: 104
<212> TYPE: PRT
<213> ORGANISM: Homo sapiens
<220> FEATURE:
<221> NAME/KEY: Other...
<223> OTHER INFORMATION: Human IgE fragment

<400> SEQUENCE: 4

Phe Ile Cys Arg Ala Val His Glu Ala Ala Ser Pro Ser Gln Thr
 1               5                  10                  15

Val Gln Arg Ala Val Ser Val Asn Pro Gly Leu Ala Gly Gly Ser
            20                  25                  30
```

```
Ala Gln Ser Gln Arg Ala Pro Asp Arg Val Leu Cys His Ser Gly
            35                  40                  45

Gln Gln Gln Gly Leu Pro Arg Ala Ala Gly Gly Ser Val Pro His
        50                  55                  60

Pro Arg Cys His Cys Gly Ala Gly Arg Ala Asp Trp Pro Gly Pro
            65                  70                  75

Pro Glu Leu Asp Val Cys Val Glu Glu Ala Glu Gly Glu Ala Pro
            80                  85                  90

Trp Thr Trp Thr Gly Leu Cys Ile Phe Ala Ala Leu Phe Leu
            95                 100
```

<210> SEQ ID NO 5
<211> LENGTH: 15
<212> TYPE: PRT
<213> ORGANISM: Artificial sequence
<220> FEATURE:
<223> OTHER INFORMATION: M1' pepide 1

<400> SEQUENCE: 5

```
Ala Ser Pro Ser Gln Thr Val Gln Arg Ala Val Ser Val Asn Pro
  1               5                  10                  15
```

<210> SEQ ID NO 6
<211> LENGTH: 15
<212> TYPE: PRT
<213> ORGANISM: Artificial sequence
<220> FEATURE:
<223> OTHER INFORMATION: M1' peptide 2

<400> SEQUENCE: 6

```
Thr Val Gln Arg Ala Val Ser Val Asn Pro Gly Leu Ala Gly Gly
  1               5                  10                  15
```

<210> SEQ ID NO 7
<211> LENGTH: 15
<212> TYPE: PRT
<213> ORGANISM: Artificial sequence
<220> FEATURE:
<223> OTHER INFORMATION: M1' peptide 3

<400> SEQUENCE: 7

```
Gly Leu Ala Gly Gly Ser Ala Gln Ser Gln Arg Ala Pro Asp Arg
  1               5                  10                  15
```

<210> SEQ ID NO 8
<211> LENGTH: 15
<212> TYPE: PRT
<213> ORGANISM: Artificial sequence
<220> FEATURE:
<223> OTHER INFORMATION: M1' peptide 4

<400> SEQUENCE: 8

```
Ser Ala Gln Ser Gln Arg Ala Pro Asp Arg Val Leu Cys His Ser
  1               5                  10                  15
```

<210> SEQ ID NO 9
<211> LENGTH: 15
<212> TYPE: PRT
<213> ORGANISM: Artificial sequence
<220> FEATURE:
<223> OTHER INFORMATION: M1' peptide 5

<400> SEQUENCE: 9

```
Arg Ala Pro Asp Arg Val Leu Cys His Ser Gly Gln Gln Gln Gly
  1               5                  10                  15
```

```
<210> SEQ ID NO 10
<211> LENGTH: 15
<212> TYPE: PRT
<213> ORGANISM: Artificial sequence
<220> FEATURE:
<223> OTHER INFORMATION: M1 peptide 6

<400> SEQUENCE: 10

Val Leu Cys His Ser Gly Gln Gln Gln Gly Leu Pro Arg Ala Ala
 1               5                  10                  15

<210> SEQ ID NO 11
<211> LENGTH: 15
<212> TYPE: PRT
<213> ORGANISM: Artificial sequence
<220> FEATURE:
<223> OTHER INFORMATION: M1' peptide 7

<400> SEQUENCE: 11

Gly Gln Gln Gln Gly Leu Pro Arg Ala Ala Gly Gly Ser Val Pro
 1               5                  10                  15

<210> SEQ ID NO 12
<211> LENGTH: 14
<212> TYPE: PRT
<213> ORGANISM: Artificial sequence
<220> FEATURE:
<223> OTHER INFORMATION: M1' peptide 8

<400> SEQUENCE: 12

Pro Arg Ala Ala Gly Gly Ser Val Pro His Pro Arg Cys His
                 5                  10

<210> SEQ ID NO 13
<211> LENGTH: 15
<212> TYPE: PRT
<213> ORGANISM: Artificial sequence
<220> FEATURE:
<223> OTHER INFORMATION: M1' peptide 9

<400> SEQUENCE: 13

Gly Gly Ser Val Pro His Pro Arg Cys His Cys Gly Ala Gly Arg
 1               5                  10                  15

<210> SEQ ID NO 14
<211> LENGTH: 15
<212> TYPE: PRT
<213> ORGANISM: Artificial sequence
<220> FEATURE:
<223> OTHER INFORMATION: M1' peptide 10

<400> SEQUENCE: 14

His Pro Arg Cys His Cys Gly Ala Gly Arg Ala Asp Trp Pro Gly
 1               5                  10                  15

<210> SEQ ID NO 15
<211> LENGTH: 15
<212> TYPE: PRT
<213> ORGANISM: Artificial sequence
<220> FEATURE:
<223> OTHER INFORMATION: M1' peptide 11

<400> SEQUENCE: 15

Cys Gly Ala Gly Arg Ala Asp Trp Pro Gly Pro Pro Glu Leu Asp
 1               5                  10                  15
```

```
<210> SEQ ID NO 16
<211> LENGTH: 15
<212> TYPE: PRT
<213> ORGANISM: Artificial sequence
<220> FEATURE:
<223> OTHER INFORMATION: M1' peptide 12

<400> SEQUENCE: 16

Ala Asp Trp Pro Gly Pro Pro Glu Leu Asp Val Cys Val Glu Glu
  1               5                  10                  15

<210> SEQ ID NO 17
<211> LENGTH: 15
<212> TYPE: PRT
<213> ORGANISM: Artificial sequence
<220> FEATURE:
<223> OTHER INFORMATION: M1' peptide 13

<400> SEQUENCE: 17

Pro Pro Glu Leu Asp Val Cys Val Glu Glu Ala Glu Gly Glu Ala
  1               5                  10                  15

<210> SEQ ID NO 18
<211> LENGTH: 15
<212> TYPE: PRT
<213> ORGANISM: Artificial sequence
<220> FEATURE:
<223> OTHER INFORMATION: M1' peptide 14

<400> SEQUENCE: 18

Val Cys Val Glu Glu Ala Glu Gly Glu Ala Pro Trp Thr Trp Thr
  1               5                  10                  15

<210> SEQ ID NO 19
<211> LENGTH: 15
<212> TYPE: PRT
<213> ORGANISM: Artificial sequence
<220> FEATURE:
<223> OTHER INFORMATION: M1' peptide 15

<400> SEQUENCE: 19

Ala Glu Gly Glu Ala Pro Trp Thr Trp Thr Gly Leu Cys Ile Phe
  1               5                  10                  15

<210> SEQ ID NO 20
<211> LENGTH: 108
<212> TYPE: PRT
<213> ORGANISM: Homo sapiens
<220> FEATURE:
<221> NAME/KEY: Other...
<223> OTHER INFORMATION: Human kappa I antibody light chain

<400> SEQUENCE: 20

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Ile Ser
                 20                  25                  30

Asn Tyr Leu Ala Trp Tyr Gln Gln Lys Pro Gly Lys Ala Pro Lys
                 35                  40                  45

Leu Leu Ile Tyr Ala Ala Ser Ser Leu Glu Ser Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90
```

Tyr Asn Ser Leu Pro Trp Thr Phe Gly Gln Gly Thr Lys Val Glu
                 95                  100                 105

Ile Lys Arg

<210> SEQ ID NO 21
<211> LENGTH: 108
<212> TYPE: PRT
<213> ORGANISM: Mus musculus
<220> FEATURE:
<221> NAME/KEY: Other...
<223> OTHER INFORMATION: Murine 26A11 antibody light chain

<400> SEQUENCE: 21

Asp Ile Gln Met Thr Gln Thr Thr Ser Ser Leu Ser Ala Ser Leu
 1               5                  10                  15

Gly Asp Arg Val Thr Ile Thr Cys Arg Ser Ser Gln Asp Ile Ser
                 20                  25                  30

Asn Ser Leu Asn Trp Tyr Gln Gln Lys Pro Asp Gly Pro Val Lys
                 35                  40                  45

Leu Leu Ile Tyr Ser Thr Ser Arg Leu His Ser Gly Val Pro Ser
                 50                  55                  60

Arg Phe Ser Gly Ser Gly Ser Gly Thr Asp Tyr Ser Leu Thr Ile
                 65                  70                  75

Ser Asn Leu Glu Gln Glu Asp Leu Ala Thr Tyr Phe Cys Gln Gln
                 80                  85                  90

Gly His Thr Leu Pro Trp Thr Phe Gly Gly Gly Thr Lys Val Glu
                 95                  100                 105

Ile Lys Arg

<210> SEQ ID NO 22
<211> LENGTH: 108
<212> TYPE: PRT
<213> ORGANISM: Artificial sequence
<220> FEATURE:
<223> OTHER INFORMATION: Humanized 26A11 v 1,4 antibody light chain

<400> SEQUENCE: 22

Asp Ile Gln Met Thr Gln Ser Pro Ser Ser Leu Ser Ala Ser Val
 1               5                  10                  15

Gly Asp Arg Val Thr Ile Thr Cys Arg Ser Ser Gln Asp Ile Ser
                 20                  25                  30

Asn Ser Leu Asn Trp Tyr Gln Gln Lys Pro Gly Lys Ala Pro Lys
                 35                  40                  45

Leu Leu Ile Tyr Ser Thr Ser Arg Leu His Ser Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90

Gly His Thr Leu Pro Trp Thr Phe Gly Gln Gly Thr Lys Val Glu
                 95                  100                 105

Ile Lys Arg

<210> SEQ ID NO 23
<211> LENGTH: 108
<212> TYPE: PRT
<213> ORGANISM: Artificial sequence
<220> FEATURE:
<223> OTHER INFORMATION: humanized 26A11 v2,5 antibody light chain -continued

<400> SEQUENCE: 23

Asp Ile Gln Met Thr Gln Ser Pro Ser Ser Leu Ser Ala Ser Val
1               5                   10                  15

Gly Asp Arg Val Thr Ile Thr Cys Arg Ser Ser Gln Asp Ile Ser
            20                  25                  30

Asn Ala Leu Asn Trp Tyr Gln Gln Lys Pro Gly Lys Ala Pro Lys
        35                  40                  45

Leu Leu Ile Tyr Ser Thr Ser Arg Leu His Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Gly His Thr Leu Pro Trp Thr Phe Gly Gln Gly Thr Lys Val Glu
            95                  100                 105

Ile Lys Arg

<210> SEQ ID NO 24
<211> LENGTH: 108
<212> TYPE: PRT
<213> ORGANISM: Artificial sequence
<220> FEATURE:
<223> OTHER INFORMATION: humanized 26A11 V3,6 antibody light chain

<400> SEQUENCE: 24

Asp Ile Gln Met Thr Gln Ser Pro Ser Ser Leu Ser Ala Ser Val
1               5                   10                  15

Gly Asp Arg Val Thr Ile Thr Cys Arg Ser Ser Gln Asp Ile Ser
            20                  25                  30

Asn Tyr Leu Asn Trp Tyr Gln Gln Lys Pro Gly Lys Ala Pro Lys
        35                  40                  45

Leu Leu Ile Tyr Ser Thr Ser Arg Leu His Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Gly His Thr Leu Pro Trp Thr Phe Gly Gln Gly Thr Lys Val Glu
            95                  100                 105

Ile Lys Arg

<210> SEQ ID NO 25
<211> LENGTH: 108
<212> TYPE: PRT
<213> ORGANISM: Artificial sequence
<220> FEATURE:
<223> OTHER INFORMATION: Humanized 26A11 V13,15 antibody light chain

<400> SEQUENCE: 25

Asp Ile Gln Met Thr Gln Ser Pro Ser Ser Leu Ser Ala Ser Val
1               5                   10                  15

Gly Asp Arg Val Thr Ile Thr Cys Arg Ser Ser Gln Asp Ile Ser
            20                  25                  30

Ser Ser Leu Asn Trp Tyr Gln Gln Lys Pro Gly Lys Ala Pro Lys
        35                  40                  45

Leu Leu Ile Tyr Ser Thr Ser Arg Leu His Ser Gly Val Pro Ser
    50                  55                  60

```
Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
                80                  85                  90

Gly His Thr Leu Pro Trp Thr Phe Gly Gln Gly Thr Lys Val Glu
            95                  100                 105

Ile Lys Arg

<210> SEQ ID NO 26
<211> LENGTH: 108
<212> TYPE: PRT
<213> ORGANISM: Artificial sequence
<220> FEATURE:
<223> OTHER INFORMATION: Humanized 26A11 V14,16 antibody light chain

<400> SEQUENCE: 26

Asp Ile Gln Met Thr Gln Ser Pro Ser Ser Leu Ser Ala Ser Val
  1               5                  10                  15

Gly Asp Arg Val Thr Ile Thr Cys Arg Ser Ser Gln Asp Ile Ser
            20                  25                  30

Gln Ser Leu Asn Trp Tyr Gln Gln Lys Pro Gly Lys Ala Pro Lys
            35                  40                  45

Leu Leu Ile Tyr Ser Thr Ser Arg Leu His Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
                80                  85                  90

Gly His Thr Leu Pro Trp Thr Phe Gly Gln Gly Thr Lys Val Glu
            95                  100                 105

Ile Lys Arg

<210> SEQ ID NO 27
<211> LENGTH: 114
<212> TYPE: PRT
<213> ORGANISM: Mus musculus
<220> FEATURE:
<221> NAME/KEY: Other...
<223> OTHER INFORMATION: Murine 7A6 antibody light chain

<400> SEQUENCE: 27

Asp Ile Val Met Ser Gln Ser Pro Ser Ser Leu Thr Val Ser Val
  1               5                  10                  15

Gly Glu Lys Val Thr Leu Ser Cys Lys Ser Ser Gln Thr Leu Leu
            20                  25                  30

Tyr Ser Thr Asn Gln Lys Asn Tyr Leu Ala Trp Tyr Gln Gln Lys
            35                  40                  45

Pro Gly Gln Ser Pro Lys Leu Leu Ile Tyr Trp Ala Ser Thr Arg
            50                  55                  60

Glu Ser Gly Val Pro Asp Arg Phe Thr Gly Ser Gly Ser Gly Thr
            65                  70                  75

Asp Phe Thr Leu Thr Ile Ser Ser Val Lys Ala Glu Asp Leu Ala
            80                  85                  90

Val Tyr Tyr Cys Gln Gln Tyr Tyr Ser Tyr Pro Tyr Thr Phe Gly
            95                  100                 105

Gly Gly Thr Lys Val Glu Ile Lys Arg
            110
```

```
<210> SEQ ID NO 28
<211> LENGTH: 114
<212> TYPE: PRT
<213> ORGANISM: Artificial sequence
<220> FEATURE:
<223> OTHER INFORMATION: Humanized 7A6 V.1 antibody light chain

<400> SEQUENCE: 28

Asp Ile Gln Met Thr Gln Ser Pro Ser Ser Leu Ser Ala Ser Val
 1               5                  10                  15

Gly Asp Arg Val Thr Ile Thr Cys Lys Ser Gln Thr Leu Leu
                20                  25                  30

Tyr Ser Thr Asn Gln Lys Asn Tyr Leu Ala Trp Tyr Gln Gln Lys
                35                  40                  45

Pro Gly Lys Ala Pro Lys Leu Leu Ile Tyr Trp Ala Ser Thr Arg
                50                  55                  60

Glu Ser Gly Val Pro Ser Arg Phe Ser Gly Ser Gly Ser Gly Thr
65                  70                  75

Asp Phe Thr Leu Thr Ile Ser Ser Leu Gln Pro Glu Asp Phe Ala
                80                  85                  90

Thr Tyr Tyr Cys Gln Gln Tyr Tyr Ser Tyr Pro Tyr Thr Phe Gly
                95                 100                 105

Gln Gly Thr Lys Val Glu Ile Lys Arg
                110

<210> SEQ ID NO 29
<211> LENGTH: 113
<212> TYPE: PRT
<213> ORGANISM: Mus musculus
<220> FEATURE:
<221> NAME/KEY: Other...
<223> OTHER INFORMATION: Humanized 47H4 antibody light chain

<400> SEQUENCE: 29

Asp Ile Val Leu Thr Gln Thr Pro Leu Ser Leu Pro Val Ser Leu
 1               5                  10                  15

Gly Asp Gln Ala Ser Ile Ser Cys Arg Ser Ser Gln Ser Leu Val
                20                  25                  30

His Asn Asn Gly Asn Thr Tyr Leu His Trp Tyr Leu Gln Lys Pro
                35                  40                  45

Gly Gln Ser Pro Lys Leu Leu Ile Tyr Lys Val Ser Asn Arg Phe
                50                  55                  60

Ser Gly Val Pro Asp Arg Phe Ser Gly Ser Gly Ser Gly Thr Asp
                65                  70                  75

Phe Thr Leu Lys Ile Ser Arg Leu Glu Ala Glu Asp Leu Gly Val
                80                  85                  90

Tyr Phe Cys Ser Gln Asn Thr Leu Val Pro Trp Thr Phe Gly Gly
                95                 100                 105

Gly Thr Lys Val Glu Ile Lys Arg
                110

<210> SEQ ID NO 30
<211> LENGTH: 113
<212> TYPE: PRT
<213> ORGANISM: Artificial sequence
<220> FEATURE:
<223> OTHER INFORMATION: Humanized 47H4 V.1,3 antibody light chain

<400> SEQUENCE: 30

Asp Ile Gln Met Thr Gln Ser Pro Ser Ser Leu Ser Ala Ser Val
 1               5                  10                  15
```

```
Gly Asp Arg Val Thr Ile Thr Cys Arg Ser Ser Gln Ser Leu Val
            20                  25                  30

His Asn Asn Gly Asn Thr Tyr Leu His Trp Tyr Gln Gln Lys Pro
            35                  40                  45

Gly Lys Ala Pro Lys Leu Leu Ile Tyr Lys Val Ser Asn Arg Phe
            50                  55                  60

Ser Gly Val Pro Ser Arg Phe Ser Gly Ser Gly Ser Gly Thr Asp
            65                  70                  75

Phe Thr Leu Thr Ile Ser Ser Leu Gln Pro Glu Asp Phe Ala Thr
            80                  85                  90

Tyr Tyr Cys Ser Gln Asn Thr Leu Val Pro Trp Thr Phe Gly Gln
            95                 100                 105

Gly Thr Lys Val Glu Ile Lys Arg
           110

<210> SEQ ID NO 31
<211> LENGTH: 113
<212> TYPE: PRT
<213> ORGANISM: Artificial sequence
<220> FEATURE:
<223> OTHER INFORMATION: Humanized 47H4 V.24-6 antibody light chain

<400> SEQUENCE: 31

Asp Ile Gln Met Thr Gln Ser Pro Ser Ser Leu Ser Ala Ser Val
 1               5                  10                  15

Gly Asp Arg Val Thr Ile Thr Cys Arg Ser Ser Gln Ser Leu Val
            20                  25                  30

His Asn Asn Ala Asn Thr Tyr Leu His Trp Tyr Gln Gln Lys Pro
            35                  40                  45

Gly Lys Ala Pro Lys Leu Leu Ile Tyr Lys Val Ser Asn Arg Phe
            50                  55                  60

Ser Gly Val Pro Ser Arg Phe Ser Gly Ser Gly Ser Gly Thr Asp
            65                  70                  75

Phe Thr Leu Thr Ile Ser Ser Leu Gln Pro Glu Asp Phe Ala Thr
            80                  85                  90

Tyr Tyr Cys Ser Gln Asn Thr Leu Val Pro Trp Thr Phe Gly Gln
            95                 100                 105

Gly Thr Lys Val Glu Ile Lys Arg
           110

<210> SEQ ID NO 32
<211> LENGTH: 113
<212> TYPE: PRT
<213> ORGANISM: Homo sapiens
<220> FEATURE:
<221> NAME/KEY: Other...
<223> OTHER INFORMATION: Human III antibody heavy chain

<400> SEQUENCE: 32

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu
            35                  40                  45

Glu Trp Val Ser Val Ile Ser Gly Asp Gly Gly Ser Thr Tyr Tyr
            50                  55                  60

Ala Asp Ser Val Lys Gly Arg Phe Thr Ile Ser Arg Asp Asn Ser
```

```
                        65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Phe Asp Tyr Trp Gly Gln
                95                 100                 105

Gly Thr Leu Val Thr Val Ser Ser
                       110

<210> SEQ ID NO 33
<211> LENGTH: 112
<212> TYPE: PRT
<213> ORGANISM: Mus musculus
<220> FEATURE:
<221> NAME/KEY: Other...
<223> OTHER INFORMATION: Murine 26A11 antibody heavy chain

<400> SEQUENCE: 33

Glu Val Gln Leu Gln Gln Ser Gly Pro Glu Leu Val Lys Pro Gly
  1               5                  10                  15

Ala Ser Val Lys Met Ser Cys Lys Ala Ser Gly Tyr Thr Phe Thr
                 20                  25                  30

Asp Tyr Tyr Met Met Trp Val Lys Gln Ser His Gly Lys Ser Leu
                 35                  40                  45

Glu Trp Ile Gly Asp Ile Asn Pro Asn Asn Tyr Asp Thr Ser Tyr
                 50                  55                  60

Asn Gln Lys Phe Lys Gly Lys Ala Thr Leu Thr Val Asp Lys Ser
                 65                  70                  75

Ser Ser Thr Ala Tyr Ile Gln Leu Asn Ser Leu Thr Ser Glu Asp
                 80                  85                  90

Ser Ala Val Tyr Tyr Cys Ala Ser Lys Ala Tyr Trp Gly Gln Gly
                 95                 100                 105

Thr Leu Val Thr Val Ser Ser
                       110

<210> SEQ ID NO 34
<211> LENGTH: 112
<212> TYPE: PRT
<213> ORGANISM: Artificial sequence
<220> FEATURE:
<223> OTHER INFORMATION: Humanized 26A11 V.1-3,13,14 antibody heavy
      chain

<400> SEQUENCE: 34

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                 20                  25                  30

Asp Tyr Tyr Met Met Trp Val Arg Gln Ala Pro Gly Lys Gly Leu
                 35                  40                  45

Glu Trp Val Gly Asp Ile Asn Pro Asn Asn Tyr Asp Thr Ser Tyr
                 50                  55                  60

Asn Gln Lys Phe Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ala Ser Lys Ala Tyr Trp Gly Gln Gly
                 95                 100                 105

Thr Leu Val Thr Val Ser Ser
                       110
```

<210> SEQ ID NO 35
<211> LENGTH: 112
<212> TYPE: PRT
<213> ORGANISM: Artificial sequence
<220> FEATURE:
<223> OTHER INFORMATION: Humanized 26A11 V.4-6,15,16 antibody heavy
      chain

<400> SEQUENCE: 35

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
            20                  25                  30

Asp Tyr Tyr Ile Met Trp Val Arg Gln Ala Pro Gly Lys Gly Leu
        35                  40                  45

Glu Trp Val Gly Asp Ile Asn Pro Asn Asn Tyr Asp Thr Ser Tyr
    50                  55                  60

Asn Gln Lys Phe Lys Gly Arg Phe Thr Ile Ser Ala Asp Thr Ser
65                  70                  75

Lys Asn Thr Ala Tyr Leu Gln Met Asn Ser Leu Arg Ala Glu Asp
                80                  85                  90

Thr Ala Val Tyr Tyr Cys Ala Ser Lys Ala Tyr Trp Gly Gln Gly
            95                  100                 105

Thr Leu Val Thr Val Ser Ser
                110
```

<210> SEQ ID NO 36
<211> LENGTH: 122
<212> TYPE: PRT
<213> ORGANISM: Mus musculus
<220> FEATURE:
<221> NAME/KEY: Other...
<223> OTHER INFORMATION: Murine 7A6 antibody heavy chain

<400> SEQUENCE: 36

```
Gln Val Gln Leu Gln Gln Ser Gly Ala Glu Leu Val Arg Pro Gly
 1               5                  10                  15

Ala Ser Val Thr Leu Ser Cys Lys Ala Ser Gly Tyr Thr Phe Ile
            20                  25                  30

Asp Tyr Glu Met His Trp Val Lys Gln Thr Pro Val His Gly Leu
        35                  40                  45

Glu Trp Ile Gly Ala Ile Asp Pro Glu Thr Gly Thr Thr Ala Tyr
    50                  55                  60

Asn Gln Lys Phe Lys Gly Lys Ala Thr Leu Thr Ala Ala Lys Ser
65                  70                  75

Ser Ser Thr Ala Tyr Met Glu Leu Arg Ser Leu Thr Ser Glu Asp
                80                  85                  90

Ser Ala Val Tyr Tyr Cys Thr Arg Leu Arg Pro His Tyr Asp Tyr
            95                  100                 105

Asp Asn Ala Met Asp Ser Trp Gly Gln Gly Thr Thr Leu Thr Val
                110                 115                 120

Ser Ser
```

<210> SEQ ID NO 37
<211> LENGTH: 122
<212> TYPE: PRT
<213> ORGANISM: Artificial sequence
<220> FEATURE:
<223> OTHER INFORMATION: Humanized 7A6 V.1 antibody heavy chain

<400> SEQUENCE: 37

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Ile
                20                  25                  30

Asp Tyr Glu Met His Trp Val Arg Gln Ala Pro Gly Lys Gly Leu
            35                  40                  45

Glu Trp Val Gly Ala Ile Asp Pro Glu Thr Gly Thr Thr Ala Tyr
        50                  55                  60

Asn Gln Lys Phe Lys Gly Arg Phe Thr Ile Ser Ala Asp Thr Ser
65                  70                  75

Lys Asn Thr Ala Tyr Leu Gln Met Asn Ser Leu Arg Ala Glu Asp
                80                  85                  90

Thr Ala Val Tyr Tyr Cys Thr Arg Leu Arg Pro His Tyr Asp Tyr
            95                  100                 105

Asp Asn Ala Met Asp Ser Trp Gly Gln Gly Thr Leu Val Thr Val
        110                 115                 120

Ser Ser

<210> SEQ ID NO 38
<211> LENGTH: 117
<212> TYPE: PRT
<213> ORGANISM: Mus musculus
<220> FEATURE:
<221> NAME/KEY: Other...
<223> OTHER INFORMATION: Murine 47H4 antibody heavy chain

<400> SEQUENCE: 38

Glu Val Lys Leu Val Glu Ser Gly Gly Gly Leu Val Gln Pro Gly
1               5                   10                  15

Gly Ser Arg Lys Leu Ser Cys Ala Ala Ser Gly Phe Thr Phe Ser
                20                  25                  30

Asp Tyr Gly Met Ala Trp Val Arg Gln Ala Pro Gly Lys Gly Pro
            35                  40                  45

Glu Trp Val Ala Phe Ile Ser Asp Leu Ala Tyr Thr Ile Tyr Tyr
        50                  55                  60

Ala Asp Thr Val Thr Gly Arg Phe Thr Ile Ser Arg Glu Asn Ala
65                  70                  75

Lys Asn Thr Leu Tyr Leu Glu Met Ser Ser Leu Arg Ser Glu Asp
                80                  85                  90

Thr Ala Leu Tyr Tyr Cys Ala Arg Asp Asn Trp Asp Ala Met Asp
            95                  100                 105

Tyr Trp Gly Gln Gly Thr Ser Val Thr Val Ser Ser
        110                 115

<210> SEQ ID NO 39
<211> LENGTH: 117
<212> TYPE: PRT
<213> ORGANISM: Artificial sequence
<220> FEATURE:
<223> OTHER INFORMATION: Humanized 47H4 V.1,2 antibody heavy chain

<400> SEQUENCE: 39

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

```
Asp Tyr Gly Met Ala Trp Val Arg Gln Ala Pro Gly Lys Gly Leu
                35                  40                  45

Glu Trp Val Ala Phe Ile Ser Asp Leu Ala Tyr Thr Ile Tyr Tyr
         50                  55                  60

Ala Asp Thr Val Thr Gly Arg Phe Thr Ile Ser Arg Asp Asn Ser
     65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Asp Asn Trp Asp Ala Met Asp
                 95                 100                 105

Tyr Trp Gly Gln Gly Thr Leu Val Thr Val Ser Ser
                110                 115

<210> SEQ ID NO 40
<211> LENGTH: 117
<212> TYPE: PRT
<213> ORGANISM: Artificial sequence
<220> FEATURE:
<223> OTHER INFORMATION: Humanized 47H4 V.3,4 antibody heavy chain

<400> SEQUENCE: 40

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
             20                  25                  30

Asp Tyr Gly Ile Ala Trp Val Arg Gln Ala Pro Gly Lys Gly Leu
                35                  40                  45

Glu Trp Val Ala Phe Ile Ser Asp Leu Ala Tyr Thr Ile Tyr Tyr
         50                  55                  60

Ala Asp Thr Val Thr Gly Arg Phe Thr Ile Ser Arg Asp Asn Ser
     65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Asp Asn Trp Asp Ala Leu Asp
                 95                 100                 105

Tyr Trp Gly Gln Gly Thr Leu Val Thr Val Ser Ser
                110                 115

<210> SEQ ID NO 41
<211> LENGTH: 117
<212> TYPE: PRT
<213> ORGANISM: Artificial sequence
<220> FEATURE:
<223> OTHER INFORMATION: Humanized 47H4 V.5 antibody heavy chain

<400> SEQUENCE: 41

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
             20                  25                  30

Asp Tyr Gly Ile Ala Trp Val Arg Gln Ala Pro Gly Lys Gly Leu
                35                  40                  45

Glu Trp Val Ala Phe Ile Ser Asp Leu Ala Tyr Thr Ile Tyr Tyr
         50                  55                  60

Ala Asp Thr Val Thr Gly Arg Phe Thr Ile Ser Arg Asp Asn Ser
     65                  70                  75

Lys Asn Thr Leu Tyr Leu Gln Met Asn Ser Leu Arg Ala Glu Asp
                 80                  85                  90
```

```
Thr Ala Val Tyr Tyr Cys Ala Arg Asp Asn Trp Asp Ala Met Asp
                95                 100                 105

Tyr Trp Gly Gln Gly Thr Leu Val Thr Val Ser Ser
            110                 115

<210> SEQ ID NO 42
<211> LENGTH: 117
<212> TYPE: PRT
<213> ORGANISM: Artificial sequence
<220> FEATURE:
<223> OTHER INFORMATION: Humanized 47H4 V.6 antibody heavy chain

<400> SEQUENCE: 42

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Ser
                 20                  25                  30

Asp Tyr Gly Met Ala Trp Val Arg Gln Ala Pro Gly Lys Gly Leu
                 35                  40                  45

Glu Trp Val Ala Phe Ile Ser Asp Leu Ala Tyr Thr Ile Tyr Tyr
                 50                  55                  60

Ala Asp Thr Val Thr Gly Arg Phe Thr Ile Ser Arg Asp Asn Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Asp Asn Trp Asp Ala Leu Asp
                 95                 100                 105

Tyr Trp Gly Gln Gly Thr Leu Val Thr Val Ser Ser
                110                 115

<210> SEQ ID NO 43
<211> LENGTH: 446
<212> TYPE: PRT
<213> ORGANISM: Mus musculus
<220> FEATURE:
<221> NAME/KEY: Other...
<223> OTHER INFORMATION: Murine 7A6 antibody heavy chain full length

<400> SEQUENCE: 43

Gln Val Gln Leu Gln Gln Ser Gly Ala Glu Leu Val Arg Pro Gly
  1               5                  10                  15

Ala Ser Val Thr Leu Ser Cys Lys Ala Ser Gly Tyr Thr Phe Ile
                 20                  25                  30

Asp Tyr Glu Met His Trp Val Lys Gln Thr Pro Val His Gly Leu
                 35                  40                  45

Glu Trp Ile Gly Ala Ile Asp Pro Glu Thr Gly Thr Thr Ala Tyr
                 50                  55                  60

Asn Gln Lys Phe Lys Gly Lys Ala Thr Leu Thr Ala Ala Lys Ser
                 65                  70                  75

Ser Ser Thr Ala Tyr Met Glu Leu Arg Ser Leu Thr Ser Glu Asp
                 80                  85                  90

Ser Ala Val Tyr Tyr Cys Thr Arg Leu Arg Pro His Tyr Asp Tyr
                 95                 100                 105

Asp Asn Ala Met Asp Ser Trp Gly Gln Gly Thr Thr Leu Thr Val
                110                 115                 120

Ser Ser Ala Ser Thr Lys Gly Pro Ser Val Tyr Pro Leu Ala Pro
                125                 130                 135

Gly Ser Ala Ala Gln Thr Asn Ser Met Val Thr Leu Gly Cys Leu
                140                 145                 150
```

```
Val Lys Gly Tyr Phe Pro Glu Pro Val Thr Val Thr Trp Asn Ser
            155                 160                 165

Gly Ser Leu Ser Ser Gly Val His Thr Phe Pro Ala Val Leu Gln
            170                 175                 180

Ser Asp Leu Tyr Thr Leu Ser Ser Val Thr Val Pro Ser Ser
            185                 190                 195

Thr Trp Pro Ser Glu Thr Val Thr Cys Asn Val Ala His Pro Ala
            200                 205                 210

Ser Ser Thr Lys Val Asp Lys Lys Ile Val Pro Arg Asp Cys Gly
            215                 220                 225

Cys Lys Pro Cys Ile Cys Thr Val Pro Glu Val Ser Ser Val Phe
            230                 235                 240

Ile Phe Pro Pro Lys Pro Lys Asp Val Leu Thr Ile Thr Leu Thr
            245                 250                 255

Pro Lys Val Thr Cys Val Val Val Asp Ile Ser Lys Asp Asp Pro
            260                 265                 270

Glu Val Gln Phe Ser Trp Phe Val Asp Asp Val Glu Val His Thr
            275                 280                 285

Ala Gln Thr Gln Pro Arg Glu Glu Gln Phe Asn Ser Thr Phe Arg
            290                 295                 300

Ser Val Ser Glu Leu Pro Ile Met His Gln Asp Trp Leu Asn Gly
            305                 310                 315

Lys Glu Phe Lys Cys Arg Val Asn Ser Ala Ala Phe Pro Ala Pro
            320                 325                 330

Ile Glu Lys Thr Ile Ser Lys Thr Lys Gly Arg Pro Lys Ala Pro
            335                 340                 345

Gln Val Tyr Thr Ile Pro Pro Pro Lys Glu Gln Met Ala Lys Asp
            350                 355                 360

Lys Val Ser Leu Thr Cys Met Ile Thr Asp Phe Phe Pro Glu Asp
            365                 370                 375

Ile Thr Val Glu Trp Gln Trp Asn Gly Gln Pro Ala Glu Asn Tyr
            380                 385                 390

Lys Asn Thr Gln Pro Ile Met Asp Thr Asp Gly Ser Tyr Phe Val
            395                 400                 405

Tyr Ser Lys Leu Asn Val Gln Lys Ser Asn Trp Glu Ala Gly Asn
            410                 415                 420

Thr Phe Thr Cys Ser Val Leu His Glu Gly Leu His Asn His His
            425                 430                 435

Thr Glu Lys Ser Leu Ser His Ser Pro Gly Lys
            440                 445

<210> SEQ ID NO 44
<211> LENGTH: 220
<212> TYPE: PRT
<213> ORGANISM: Mus musculus
<220> FEATURE:
<221> NAME/KEY: Other...
<223> OTHER INFORMATION: Murine 7A6 antibody light chain full length

<400> SEQUENCE: 44

Asp Ile Val Met Ser Gln Ser Pro Ser Ser Leu Thr Val Ser Val
 1               5                  10                  15

Gly Glu Lys Val Thr Leu Ser Cys Lys Ser Ser Gln Thr Leu Leu
                20                  25                  30

Tyr Ser Thr Asn Gln Lys Asn Tyr Leu Ala Trp Tyr Gln Gln Lys
                35                  40                  45
```

-continued

```
Pro Gly Gln Ser Pro Lys Leu Leu Ile Tyr Trp Ala Ser Thr Arg
            50                  55                  60

Glu Ser Gly Val Pro Asp Arg Phe Thr Gly Ser Gly Ser Gly Thr
            65                  70                  75

Asp Phe Thr Leu Thr Ile Ser Ser Val Lys Ala Glu Asp Leu Ala
            80                  85                  90

Val Tyr Tyr Cys Gln Gln Tyr Tyr Ser Tyr Pro Tyr Thr Phe Gly
            95                  100                 105

Gly Gly Thr Lys Val Glu Ile Lys Arg Ala Asp Ala Ala Pro Thr
            110                 115                 120

Val Ser Ile Phe Pro Pro Ser Ser Glu Gln Leu Thr Ser Gly Gly
            125                 130                 135

Ala Ser Val Val Cys Phe Leu Asn Asn Phe Tyr Pro Lys Asp Ile
            140                 145                 150

Asn Val Lys Trp Lys Ile Asp Gly Ser Glu Arg Gln Asn Gly Val
            155                 160                 165

Leu Asn Ser Trp Thr Asp Gln Asp Ser Lys Asp Ser Thr Tyr Ser
            170                 175                 180

Met Ser Ser Thr Leu Thr Leu Thr Lys Asp Glu Tyr Glu Arg His
            185                 190                 195

Asn Ser Tyr Thr Cys Glu Ala Thr His Lys Thr Ser Thr Ser Pro
            200                 205                 210

Ile Val Lys Ser Phe Asn Arg Asn Glu Cys
            215                 220

<210> SEQ ID NO 45
<211> LENGTH: 442
<212> TYPE: PRT
<213> ORGANISM: Mus musculus
<220> FEATURE:
<221> NAME/KEY: Other...
<223> OTHER INFORMATION: Murine 47H4 antibody heavy chain full length

<400> SEQUENCE: 45

Glu Val Lys Leu Val Glu Ser Gly Gly Gly Leu Val Gln Pro Gly
 1           5                   10                  15

Gly Ser Arg Lys Leu Ser Cys Ala Ala Ser Gly Phe Thr Phe Ser
            20                  25                  30

Asp Tyr Gly Met Ala Trp Val Arg Gln Ala Pro Gly Lys Gly Pro
            35                  40                  45

Glu Trp Val Ala Phe Ile Ser Asp Leu Ala Tyr Thr Ile Tyr Tyr
            50                  55                  60

Ala Asp Thr Val Thr Gly Arg Phe Thr Ile Ser Arg Glu Asn Ala
            65                  70                  75

Lys Asn Thr Leu Tyr Leu Glu Met Ser Ser Leu Arg Ser Glu Asp
            80                  85                  90

Thr Ala Leu Tyr Tyr Cys Ala Arg Asp Asn Trp Asp Ala Met Asp
            95                  100                 105

Tyr Trp Gly Gln Gly Thr Ser Val Thr Val Ser Ser Ala Lys Thr
            110                 115                 120

Thr Pro Pro Ser Val Tyr Pro Leu Ala Pro Gly Ser Ala Ala
            125                 130                 135

Gln Thr Asn Ser Met Val Thr Leu Gly Cys Leu Val Lys Gly Tyr
            140                 145                 150

Phe Pro Glu Pro Val Thr Val Thr Trp Asn Ser Gly Ser Leu Ser
            155                 160                 165
```

```
Ser Gly Val His Thr Phe Pro Ala Val Leu Gln Ser Asp Leu Tyr
                170                 175                 180

Thr Leu Ser Ser Ser Val Thr Val Pro Ser Ser Thr Trp Pro Ser
                185                 190                 195

Glu Thr Val Thr Cys Asn Val Ala His Pro Ala Ser Ser Thr Lys
                200                 205                 210

Val Asp Lys Lys Ile Val Pro Arg Asp Cys Gly Cys Lys Pro Cys
                215                 220                 225

Ile Cys Thr Val Pro Glu Val Ser Ser Val Phe Ile Phe Pro Pro
                230                 235                 240

Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe
                260                 265                 270

Ser Trp Phe Val Asp Asp Val Glu Val His Thr Ala Gln Thr Gln
                275                 280                 285

Pro Arg Glu Glu Gln Phe Asn Ser Thr Phe Arg Ser Val Ser Glu
                290                 295                 300

Leu Pro Ile Met His Gln Asp Trp Leu Asn Gly Lys Glu Phe Lys
                305                 310                 315

Cys Arg Val Asn Ser Ala Ala Phe Pro Ala Pro Ile Glu Lys Thr
                320                 325                 330

Ile Ser Lys Thr Lys Gly Arg Pro Lys Ala Pro Gln Val Tyr Thr
                335                 340                 345

Ile Pro Pro Pro Lys Glu Gln Met Ala Lys Asp Lys Val Ser Leu
                350                 355                 360

Thr Cys Met Ile Thr Asp Phe Phe Pro Glu Asp Ile Thr Val Glu
                365                 370                 375

Trp Gln Trp Asn Gly Gln Pro Ala Glu Asn Tyr Lys Asn Thr Gln
                380                 385                 390

Pro Ile Met Asp Thr Asp Gly Ser Tyr Phe Val Tyr Ser Lys Leu
                395                 400                 405

Asn Val Gln Lys Ser Asn Trp Glu Ala Gly Asn Thr Phe Thr Cys
                410                 415                 420

Ser Val Leu His Glu Gly Leu His Asn His His Thr Glu Lys Ser
                425                 430                 435

Leu Ser His Ser Pro Gly Lys
                440

<210> SEQ ID NO 46
<211> LENGTH: 219
<212> TYPE: PRT
<213> ORGANISM: Mus musculus
<220> FEATURE:
<221> NAME/KEY: Other...
<223> OTHER INFORMATION: Murine 47H4 light chain full length

<400> SEQUENCE: 46

Asp Ile Val Leu Thr Gln Thr Pro Leu Ser Leu Pro Val Ser Leu
  1               5                  10                  15

Gly Asp Gln Ala Ser Ile Ser Cys Arg Ser Ser Gln Ser Leu Val
                 20                  25                  30

His Asn Asn Gly Asn Thr Tyr Leu His Trp Tyr Leu Gln Lys Pro
                 35                  40                  45

Gly Gln Ser Pro Lys Leu Leu Ile Tyr Lys Val Ser Asn Arg Phe
                 50                  55                  60
```

```
Ser Gly Val Pro Asp Arg Phe Ser Gly Ser Gly Ser Gly Thr Asp
             65                  70                  75

Phe Thr Leu Lys Ile Ser Arg Leu Glu Ala Glu Asp Leu Gly Val
             80                  85                  90

Tyr Phe Cys Ser Gln Asn Thr Leu Val Pro Trp Thr Phe Gly Gly
             95                 100                 105

Gly Thr Lys Val Glu Ile Lys Arg Ala Asp Ala Ala Pro Thr Val
            110                 115                 120

Ser Ile Phe Pro Pro Ser Ser Glu Gln Leu Thr Ser Gly Gly Ala
            125                 130                 135

Ser Val Val Cys Phe Leu Asn Asn Phe Tyr Pro Lys Asp Ile Asn
            140                 145                 150

Val Lys Trp Lys Ile Asp Gly Ser Glu Arg Gln Asn Gly Val Leu
            155                 160                 165

Asn Ser Trp Thr Asp Gln Asp Ser Lys Asp Ser Thr Tyr Ser Met
            170                 175                 180

Ser Ser Thr Leu Thr Leu Thr Lys Asp Glu Tyr Glu Arg His Asn
            185                 190                 195

Ser Tyr Thr Cys Glu Ala Thr His Lys Thr Ser Thr Ser Pro Ile
            200                 205                 210

Val Lys Ser Phe Asn Arg Asn Glu Cys
            215

<210> SEQ ID NO 47
<211> LENGTH: 436
<212> TYPE: PRT
<213> ORGANISM: Mus musculus
<220> FEATURE:
<221> NAME/KEY: Other...
<223> OTHER INFORMATION: Murine 26A11 antibody heavy chain full length

<400> SEQUENCE: 47

Glu Val Gln Leu Gln Gln Ser Gly Pro Glu Leu Val Lys Pro Gly
  1               5                  10                  15

Ala Ser Val Lys Met Ser Cys Lys Ala Ser Gly Tyr Thr Phe Thr
             20                  25                  30

Asp Tyr Tyr Met Met Trp Val Lys Gln Ser His Gly Lys Ser Leu
             35                  40                  45

Glu Trp Ile Gly Asp Ile Asn Pro Asn Asn Tyr Asp Thr Ser Tyr
             50                  55                  60

Asn Gln Lys Phe Lys Gly Lys Ala Thr Leu Thr Val Asp Lys Ser
             65                  70                  75

Ser Ser Thr Ala Tyr Ile Gln Leu Asn Ser Leu Thr Ser Glu Asp
             80                  85                  90

Ser Ala Val Tyr Tyr Cys Ala Ser Lys Ala Tyr Trp Gly Gln Gly
             95                 100                 105

Thr Leu Val Thr Val Ser Ala Ala Ser Thr Thr Pro Pro Ser Val
            110                 115                 120

Tyr Pro Leu Ala Pro Gly Ser Ala Ala Gln Thr Asn Ser Met Val
            125                 130                 135

Thr Leu Gly Cys Leu Val Lys Gly Tyr Phe Pro Glu Pro Val Thr
            140                 145                 150

Val Thr Trp Asn Ser Gly Ser Leu Ser Ser Gly Val His Thr Phe
            155                 160                 165

Pro Ala Val Leu Gln Ser Asp Leu Tyr Thr Leu Ser Ser Ser Val
            170                 175                 180
```

-continued

```
Thr Val Pro Ser Ser Thr Trp Pro Ser Glu Thr Val Thr Cys Asn
                185                 190                 195

Val Ala His Pro Ala Ser Ser Thr Lys Val Asp Lys Lys Ile Val
            200                 205                 210

Pro Arg Asp Cys Gly Cys Lys Pro Cys Ile Cys Thr Val Pro Glu
        215                 220                 225

Val Ser Ser Val Phe Ile Phe Pro Pro Lys Pro Lys Asp Val Leu
    230                 235                 240

Thr Ile Thr Leu Thr Pro Lys Val Thr Cys Val Val Val Asp Ile
245                 250                 255

Ser Lys Asp Asp Pro Glu Val Gln Phe Ser Trp Phe Val Asp Asp
            260                 265                 270

Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala
305                 310                 315

Ala Phe Pro Ala Pro Ile Glu Lys Thr Ile Ser Lys Thr Lys Gly
            320                 325                 330

Arg Pro Lys Ala Pro Gln Val Tyr Thr Ile Pro Pro Pro Lys Glu
        335                 340                 345

Gln Met Ala Lys Asp Lys Val Ser Leu Thr Cys Met Ile Thr Asp
    350                 355                 360

Phe Phe Pro Glu Asp Ile Thr Val Glu Trp Gln Trp Asn Gly Gln
365                 370                 375

Pro Ala Glu Asn Tyr Lys Asn Thr Gln Pro Ile Met Asp Thr Asp
            380                 385                 390

Gly Ser Tyr Phe Val Tyr Ser Lys Leu Asn Val Gln Lys Ser Asn
        395                 400                 405

Trp Glu Ala Gly Asn Thr Phe Thr Cys Ser Val Leu His Glu Gly
    410                 415                 420

Leu His Asn His His Thr Glu Lys Ser Leu Ser His Ser Pro Gly
425                 430                 435

Lys

<210> SEQ ID NO 48
<211> LENGTH: 214
<212> TYPE: PRT
<213> ORGANISM: Mus musculus
<220> FEATURE:
<221> NAME/KEY: Other...
<223> OTHER INFORMATION: Murine 26A11 antibody light chain full length

<400> SEQUENCE: 48

Asp Ile Gln Met Thr Gln Thr Thr Ser Ser Leu Ser Ala Ser Leu
 1               5                  10                  15

Gly Asp Arg Val Thr Ile Thr Cys Arg Ser Ser Gln Asp Ile Ser
                20                  25                  30

Asn Ser Leu Asn Trp Tyr Gln Gln Lys Pro Asp Gly Pro Val Lys
            35                  40                  45

Leu Leu Ile Tyr Ser Thr Ser Arg Leu His Ser Gly Val Pro Ser
        50                  55                  60

Arg Phe Ser Gly Ser Gly Ser Gly Thr Asp Tyr Ser Leu Thr Ile
    65                  70                  75
```

-continued

Ser Asn Leu Glu Gln Glu Asp Leu Ala Thr Tyr Phe Cys Gln Gln
                80                  85                  90

Gly His Thr Leu Pro Trp Thr Phe Gly Gly Gly Thr Lys Val Glu
                95                  100                 105

Ile Lys Arg Ala Asp Ala Ala Pro Thr Val Ser Ile Phe Pro Pro
                110                 115                 120

Ser Ser Glu Gln Leu Thr Ser Gly Gly Ala Ser Val Val Cys Phe
                125                 130                 135

Leu Asn Asn Phe Tyr Pro Lys Asp Ile Asn Val Lys Trp Lys Ile
                140                 145                 150

Asp Gly Ser Glu Arg Gln Asn Gly Val Leu Asn Ser Trp Thr Asp
                155                 160                 165

Gln Asp Ser Lys Asp Ser Thr Tyr Ser Met Ser Ser Thr Leu Thr
                170                 175                 180

Leu Thr Lys Asp Glu Tyr Glu Arg His Asn Ser Tyr Thr Cys Glu
                185                 190                 195

Ala Thr His Lys Thr Ser Thr Ser Pro Ile Val Lys Ser Phe Asn
                200                 205                 210

Arg Asn Glu Cys

<210> SEQ ID NO 49
<211> LENGTH: 449
<212> TYPE: PRT
<213> ORGANISM: Mus musculus
<220> FEATURE:
<221> NAME/KEY: Other...
<223> OTHER INFORMATION: Murine 45C1 antibody heavy chain full length

<400> SEQUENCE: 49

Gln Ile Gln Leu Val Gln Ser Gly Pro Glu Leu Lys Lys Pro Gly
  1               5                   10                  15

Glu Thr Val Lys Ile Ser Cys Lys Ala Ser Gly Tyr Thr Phe Thr
                20                  25                  30

Asn Tyr Gly Met Asn Trp Val Lys Gln Ala Pro Gly Lys Gly Leu
                35                  40                  45

Lys Trp Met Gly Trp Ile Asn Thr Tyr Thr Gly Glu Pro Thr Tyr
                50                  55                  60

Val Asp Asp Phe Lys Gly Arg Phe Ala Phe Ser Leu Glu Thr Ser
                65                  70                  75

Ala Ser Thr Ala Tyr Leu Gln Ile Asn Asn Leu Lys Asn Glu Asp
                80                  85                  90

Met Ala Thr Tyr Phe Cys Ala Arg Gly Ile Tyr Tyr Asp Asn Asp
                95                  100                 105

Asp Ile Tyr Trp Gly Gln Gly Thr Ile Leu Thr Val Ser Ser Ala
                110                 115                 120

Lys Thr Thr Ala Pro Ser Val Tyr Pro Leu Ala Pro Val Cys Gly
                125                 130                 135

Asp Thr Thr Gly Ser Ser Val Thr Leu Gly Cys Leu Val Lys Gly
                140                 145                 150

Tyr Phe Pro Glu Pro Val Thr Leu Thr Trp Asn Ser Gly Ser Leu
                155                 160                 165

Ser Ser Gly Val His Thr Phe Pro Ala Val Leu Gln Ser Asp Leu
                170                 175                 180

Tyr Thr Leu Ser Ser Ser Val Thr Val Thr Ser Ser Thr Trp Pro
                185                 190                 195

Ser Gln Ser Ile Thr Cys Asn Val Ala His Pro Ala Ser Ser Thr

```
                200                 205                 210
Lys Val Asp Lys Lys Ile Glu Pro Arg Gly Pro Thr Ile Lys Pro
            215                 220                 225
Cys Pro Pro Cys Lys Cys Pro Ala Pro Asn Leu Leu Gly Gly Pro
            230                 235                 240
Ser Val Phe Ile Phe Pro Pro Lys Ile Lys Asp Val Leu Met Ile
            245                 250                 255
Ser Leu Ser Pro Ile Val Thr Cys Val Val Asp Val Ser Glu
            260                 265                 270
Asp Asp Pro Asp Val Gln Ile Ser Trp Phe Val Asn Asn Val Glu
            275                 280                 285
Val His Thr Ala Gln Thr Gln Thr His Arg Glu Asp Tyr Asn Ser
            290                 295                 300
Thr Leu Arg Val Val Ser Ala Leu Pro Ile Gln His Gln Asp Trp
            305                 310                 315
Met Ser Gly Lys Glu Phe Lys Cys Lys Val Asn Asn Lys Asp Leu
            320                 325                 330
Pro Ala Pro Ile Glu Arg Thr Ile Ser Lys Pro Lys Gly Ser Val
            335                 340                 345
Arg Ala Pro Gln Val Tyr Val Leu Pro Pro Glu Glu Met
            350                 355                 360
Thr Lys Lys Gln Val Thr Leu Thr Cys Met Val Thr Asp Phe Met
            365                 370                 375
Pro Glu Asp Ile Tyr Val Glu Trp Thr Asn Asn Gly Lys Thr Glu
            380                 385                 390
Leu Asn Tyr Lys Asn Thr Glu Pro Val Leu Asp Ser Asp Gly Ser
            395                 400                 405
Tyr Phe Met Tyr Ser Lys Leu Arg Val Glu Lys Lys Asn Trp Val
            410                 415                 420
Glu Arg Asn Ser Tyr Ser Cys Ser Val Val His Glu Gly Leu His
            425                 430                 435
Asn His His Thr Thr Lys Ser Phe Ser Arg Thr Pro Gly Lys
            440                 445

<210> SEQ ID NO 50
<211> LENGTH: 219
<212> TYPE: PRT
<213> ORGANISM: Mus musculus
<220> FEATURE:
<221> NAME/KEY: Other...
<223> OTHER INFORMATION: Murine 45C1 antibody light chain full length

<400> SEQUENCE: 50

Asp Ile Val Met Thr Gln Thr Pro Leu Thr Leu Ser Val Thr Ile
  1               5                  10                  15
Gly Gln Pro Ala Ser Ile Ser Cys Lys Ser Ser Gln Ser Leu Leu
             20                  25                  30
Asp Ser Asp Gly Lys Thr Tyr Leu Asn Trp Leu Leu Gln Arg Pro
             35                  40                  45
Gly Gln Ser Pro Lys Arg Leu Ile Tyr Leu Val Ser Lys Leu Asp
             50                  55                  60
Ser Gly Val Pro Asp Arg Phe Thr Gly Ser Gly Ser Gly Thr Asp
             65                  70                  75
Phe Thr Leu Lys Ile Ser Arg Val Glu Ala Glu Asp Leu Gly Val
             80                  85                  90
Tyr Tyr Cys Trp Gln Gly Thr His Phe Pro His Thr Phe Gly Gly
```

```
                      95                  100                 105
Gly Thr Lys Val Glu Ile Lys Arg Ala Asp Ala Ala Pro Thr Val
                 110                 115                 120

Ser Ile Phe Pro Pro Ser Ser Glu Gln Leu Thr Ser Gly Gly Ala
                 125                 130                 135

Ser Val Val Cys Phe Leu Asn Asn Phe Tyr Pro Lys Asp Ile Asn
                 140                 145                 150

Val Lys Trp Lys Ile Asp Gly Ser Glu Arg Gln Asn Gly Val Leu
                 155                 160                 165

Asn Ser Trp Thr Asp Gln Asp Ser Lys Asp Ser Thr Tyr Ser Met
                 170                 175                 180

Ser Ser Thr Leu Thr Leu Thr Lys Asp Glu Tyr Glu Arg His Asn
                 185                 190                 195

Ser Tyr Thr Cys Glu Ala Thr His Lys Thr Ser Thr Ser Pro Ile
                 200                 205                 210

Val Lys Ser Phe Asn Arg Asn Glu Cys
                 215

<210> SEQ ID NO 51
<211> LENGTH: 446
<212> TYPE: PRT
<213> ORGANISM: Mus musculus
<220> FEATURE:
<221> NAME/KEY: Other...
<223> OTHER INFORMATION: Murine 28E9 antibody heavy chain full length

<400> SEQUENCE: 51

Glu Val Lys Leu Val Glu Ser Gly Gly Leu Val Gln Pro Gly
  1               5                  10                  15

Gly Ser Leu Arg Leu Ser Cys Ala Thr Ser Gly Phe Thr Phe Thr
                 20                  25                  30

Asp Tyr Tyr Met Ser Trp Val Arg Gln Pro Pro Gly Lys Pro Leu
                 35                  40                  45

Glu Trp Leu Gly Phe Ile Ser Asn Lys Leu Asn Gly Tyr Thr Thr
                 50                  55                  60

Glu Tyr Ser Ser Ser Val Gln Gly Arg Phe Thr Ile Ser Arg Asp
                 65                  70                  75

Asp Ser Gln Ser Ile Leu Tyr Leu Gln Met Asn Thr Leu Arg Pro
                 80                  85                  90

Glu Asp Ser Ala Ala Tyr Tyr Cys Ala Arg Asp Met Val Pro Tyr
                 95                 100                 105

Tyr Tyr Ala Leu Asp Tyr Trp Gly Gln Gly Thr Ser Val Ala Val
                 110                 115                 120

Ser Ser Ala Lys Thr Thr Pro Pro Ser Val Tyr Pro Leu Ala Pro
                 125                 130                 135

Gly Ser Ala Ala Gln Thr Asn Ser Met Val Thr Leu Gly Cys Leu
                 140                 145                 150

Val Lys Gly Tyr Phe Pro Glu Pro Val Thr Val Thr Trp Asn Ser
                 155                 160                 165

Gly Ser Leu Ser Ser Gly Val His Thr Phe Pro Ala Val Leu Gln
                 170                 175                 180

Ser Asp Leu Tyr Thr Leu Ser Ser Ser Val Thr Val Pro Ser Ser
                 185                 190                 195

Thr Trp Pro Ser Glu Thr Val Thr Cys Asn Val Ala His Pro Ala
                 200                 205                 210

Ser Ser Thr Lys Val Asp Lys Lys Ile Val Pro Arg Asp Cys Gly
```

```
                215                 220                 225
Cys Lys Pro Cys Ile Cys Thr Val Pro Glu Val Ser Val Phe
            230                 235                 240

Ile Phe Pro Pro Lys Pro Lys Asp Val Leu Thr Ile Thr Leu Thr
                245                 250                 255

Pro Lys Val Thr Cys Val Val Asp Ile Ser Lys Asp Asp Pro
            260                 265                 270

Glu Val Gln Phe Ser Trp Phe Val Asp Val Glu Val His Thr
        275                 280                 285

Ala Gln Thr Gln Pro Arg Glu Glu Gln Phe Asn Ser Thr Phe Arg
            290                 295                 300

Ser Val Ser Glu Leu Pro Ile Met His Gln Asp Trp Leu Asn Gly
            305                 310                 315

Lys Glu Phe Lys Cys Arg Val Asn Ser Ala Ala Phe Pro Ala Pro
            320                 325                 330

Ile Glu Lys Thr Ile Ser Lys Thr Lys Gly Arg Pro Lys Ala Pro
            335                 340                 345

Gln Val Tyr Thr Ile Pro Pro Pro Lys Glu Gln Met Ala Lys Asp
            350                 355                 360

Lys Val Ser Leu Thr Cys Met Ile Thr Asp Phe Phe Pro Glu Asp
            365                 370                 375

Ile Thr Val Glu Trp Gln Trp Asn Gly Gln Pro Ala Glu Asn Tyr
            380                 385                 390

Lys Asn Thr Gln Pro Ile Met Asp Thr Asp Gly Ser Tyr Phe Val
            395                 400                 405

Tyr Ser Lys Leu Asn Val Gln Lys Ser Asn Trp Glu Ala Gly Asn
            410                 415                 420

Thr Phe Thr Cys Ser Val Leu His Glu Gly Leu His Asn His His
            425                 430                 435

Thr Glu Lys Ser Leu Ser His Ser Pro Gly Lys
            440                 445

<210> SEQ ID NO 52
<211> LENGTH: 214
<212> TYPE: PRT
<213> ORGANISM: Mus musculus
<220> FEATURE:
<221> NAME/KEY: Other...
<223> OTHER INFORMATION: Murine 28E9 antibody light chain full length

<400> SEQUENCE: 52

Asp Ile Gln Met Thr Gln Ser Pro Ala Ser Leu Ser Val Ser Val
 1               5                  10                  15

Gly Glu Thr Val Thr Phe Thr Cys Arg Thr Ser Glu Asn Ile Tyr
                20                  25                  30

Thr Tyr Leu Ala Trp Ile Gln Gln Lys Gln Gly Lys Ser Pro Gln
            35                  40                  45

Leu Leu Val Tyr Asn Ala Gln Ile Leu Ala Glu Gly Val Pro Ser
            50                  55                  60

Arg Phe Ser Gly Ser Gly Ser Gly Gln Phe Ser Leu Gln Ile
        65                  70                  75

Asn Ser Leu Gln Pro Glu Asp Phe Gly Tyr Tyr Tyr Cys Gln His
            80                  85                  90

His Tyr Gly Thr Pro Phe Thr Phe Gly Ser Gly Thr Lys Val Glu
            95                  100                 105

Ile Lys Arg Ala Asp Ala Ala Pro Thr Val Ser Ile Phe Pro Pro
```

```
                    110                 115                 120
Ser Ser Glu Gln Leu Thr Ser Gly Gly Ala Ser Val Val Cys Phe
                125                 130                 135

Leu Asn Asn Phe Tyr Pro Lys Asp Ile Asn Val Lys Trp Lys Ile
                140                 145                 150

Asp Gly Ser Glu Arg Gln Asn Gly Val Leu Asn Ser Trp Thr Asp
                155                 160                 165

Gln Asp Ser Lys Asp Ser Thr Tyr Ser Met Ser Ser Thr Leu Thr
                170                 175                 180

Leu Thr Lys Asp Glu Tyr Glu Arg His Asn Ser Tyr Thr Cys Glu
                185                 190                 195

Ala Thr His Lys Thr Ser Thr Ser Pro Ile Val Lys Ser Phe Asn
                200                 205                 210

Arg Asn Glu Cys

<210> SEQ ID NO 53
<211> LENGTH: 442
<212> TYPE: PRT
<213> ORGANISM: Mus musculus
<220> FEATURE:
<221> NAME/KEY: Other...
<223> OTHER INFORMATION: Murine 1C11 antibody heavy chain full length

<400> SEQUENCE: 53

Gln Val Gln Leu Gln Gln Ser Gly Ala Glu Leu Val Arg Pro Gly
  1               5                  10                  15

Ala Ser Val Thr Leu Ser Cys Lys Ala Ser Gly Tyr Thr Phe Thr
                 20                  25                  30

Asp Phe Glu Met His Trp Val Lys Gln Thr Pro Val His Gly Leu
                 35                  40                  45

Glu Trp Ile Gly Ala Ile Ala Pro Glu Thr Gly Thr Ser Ala Tyr
                 50                  55                  60

Asn Gln Lys Phe Arg Gly Lys Ala Thr Leu Thr Ala Asp Ile Ser
                 65                  70                  75

Ser Ser Thr Ala Tyr Met Asp Leu Arg Ser Leu Thr Ser Glu Asp
                 80                  85                  90

Ser Ala Val Tyr Tyr Cys Thr Ile Tyr Tyr Ala Ala Pro Trp Phe
                 95                 100                 105

Ala Tyr Trp Gly Gln Gly Thr Leu Val Thr Val Ser Ser Ala Ser
                110                 115                 120

Thr Lys Gly Pro Ser Val Tyr Pro Leu Ala Pro Gly Ser Ala Ala
                125                 130                 135

Gln Thr Asn Ser Met Val Thr Leu Gly Cys Leu Val Lys Gly Tyr
                140                 145                 150

Phe Pro Glu Pro Val Thr Val Thr Trp Asn Ser Gly Ser Leu Ser
                155                 160                 165

Ser Gly Val His Thr Phe Pro Ala Val Leu Gln Ser Asp Leu Tyr
                170                 175                 180

Thr Leu Ser Ser Ser Val Thr Val Pro Ser Ser Thr Trp Pro Ser
                185                 190                 195

Glu Thr Val Thr Cys Asn Val Ala His Pro Ala Ser Ser Thr Lys
                200                 205                 210

Val Asp Lys Lys Ile Val Pro Arg Asp Cys Gly Cys Lys Pro Cys
                215                 220                 225

Ile Cys Thr Val Pro Glu Val Ser Ser Val Phe Ile Phe Pro Pro
                230                 235                 240
```

```
Lys Pro Lys Asp Val Leu Thr Ile Thr Leu Thr Pro Lys Val Thr
                245                 250                 255

Cys Val Val Asp Ile Ser Lys Asp Pro Glu Val Gln Phe
                260                 265                 270

Ser Trp Phe Val Asp Asp Val Glu Val His Thr Ala Gln Thr Gln
                275                 280                 285

Pro Arg Glu Glu Gln Phe Asn Ser Thr Phe Arg Ser Val Ser Glu
                290                 295                 300

Leu Pro Ile Met His Gln Asp Trp Leu Asn Gly Lys Glu Phe Lys
                305                 310                 315

Cys Arg Val Asn Ser Ala Ala Phe Pro Ala Pro Ile Glu Lys Thr
                320                 325                 330

Ile Ser Lys Thr Lys Gly Arg Pro Lys Ala Pro Gln Val Tyr Thr
                335                 340                 345

Ile Pro Pro Pro Lys Glu Gln Met Ala Lys Asp Lys Val Ser Leu
                350                 355                 360

Thr Cys Met Ile Thr Asp Phe Phe Pro Glu Asp Ile Thr Val Glu
                365                 370                 375

Trp Gln Trp Asn Gly Gln Pro Ala Glu Asn Tyr Lys Asn Thr Gln
                380                 385                 390

Pro Ile Met Asp Thr Asp Gly Ser Tyr Phe Val Tyr Ser Lys Leu
                395                 400                 405

Asn Val Gln Lys Ser Asn Trp Glu Ala Gly Asn Thr Phe Thr Cys
                410                 415                 420

Ser Val Leu His Glu Gly Leu His Asn His Thr Glu Lys Ser
                425                 430                 435

Leu Ser His Ser Pro Gly Lys
                440

<210> SEQ ID NO 54
<211> LENGTH: 220
<212> TYPE: PRT
<213> ORGANISM: Mus musculus
<220> FEATURE:
<221> NAME/KEY: Other...
<223> OTHER INFORMATION: Murine 1C11 antibody light chain full length

<400> SEQUENCE: 54

Asp Ile Val Met Ser Gln Ser Pro Ser Ser Leu Ala Val Ser Val
  1               5                  10                  15

Gly Glu Lys Val Thr Met Ser Cys Lys Ser Ser Gln Ser Leu Leu
                 20                  25                  30

Tyr Ser Ser Asn Gln Lys Asn Tyr Leu Ala Trp Tyr Gln Gln Lys
                 35                  40                  45

Pro Gly Gln Ser Pro Lys Leu Leu Ile Tyr Trp Ala Ser Thr Arg
                 50                  55                  60

Glu Ser Gly Val Pro Asp Arg Phe Thr Gly Ser Gly Ser Val Thr
                 65                  70                  75

Asp Phe Pro Leu Thr Ile Ser Ser Val Lys Ala Glu Asp Leu Ala
                 80                  85                  90

Val Tyr Tyr Cys Gln Gln Tyr Tyr Ser Tyr Pro Tyr Thr Phe Gly
                 95                 100                 105

Gly Gly Thr Lys Val Glu Ile Lys Arg Ala Asp Ala Ala Pro Thr
                110                 115                 120

Val Ser Ile Phe Pro Pro Ser Ser Glu Gln Leu Thr Ser Gly Gly
                125                 130                 135
```

```
Ala Ser Val Val Cys Phe Leu Asn Asn Phe Tyr Pro Lys Asp Ile
            140                 145                 150

Asn Val Lys Trp Lys Ile Asp Gly Ser Glu Arg Gln Asn Gly Val
            155                 160                 165

Leu Asn Ser Trp Thr Asp Gln Asp Ser Lys Asp Ser Thr Tyr Ser
            170                 175                 180

Met Ser Ser Thr Leu Thr Leu Thr Lys Asp Glu Tyr Glu Arg His
            185                 190                 195

Asn Ser Tyr Thr Cys Glu Ala Thr His Lys Thr Ser Thr Ser Pro
            200                 205                 210

Ile Val Lys Ser Phe Asn Arg Asn Glu Cys
            215                 220

<210> SEQ ID NO 55
<211> LENGTH: 25
<212> TYPE: PRT
<213> ORGANISM: Homo sapiens
<220> FEATURE:
<221> NAME/KEY: Other...
<223> OTHER INFORMATION: VH Human consesus framework - H1

<400> SEQUENCE: 55

Glu Val Gln Leu Val Glu Ser Gly Gly Leu Val Gln Pro Gly
  1               5                  10                 15

Gly Ser Leu Arg Leu Ser Cys Ala Ala Ser
                 20                  25

<210> SEQ ID NO 56
<211> LENGTH: 14
<212> TYPE: PRT
<213> ORGANISM: Homo sapiens
<220> FEATURE:
<221> NAME/KEY: Other...
<223> OTHER INFORMATION: VH Human consensus framework - H2

<400> SEQUENCE: 56

Trp Val Arg Gln Ala Pro Gly Lys Gly Leu Glu Trp Val Ala
  5                              10

<210> SEQ ID NO 57
<211> LENGTH: 32
<212> TYPE: PRT
<213> ORGANISM: Homo sapiens
<220> FEATURE:
<221> NAME/KEY: Other...
<223> OTHER INFORMATION: VH Human consensus framework - H3

<400> SEQUENCE: 57

Arg Phe Thr Ile Ser Arg Asp Asp Ser Lys Asn Thr Leu Tyr Leu
  1               5                  10                 15

Gln Met Asn Ser Leu Arg Ala Glu Asp Thr Ala Val Tyr Tyr Cys
                 20                  25                 30

Ala Arg

<210> SEQ ID NO 58
<211> LENGTH: 11
<212> TYPE: PRT
<213> ORGANISM: Homo sapiens
<220> FEATURE:
<221> NAME/KEY: Other...
<223> OTHER INFORMATION: VH Human consensus framework - H4

<400> SEQUENCE: 58
```

```
Trp Gly Gln Gly Thr Leu Val Thr Val Ser Ser
  5                  10
```

<210> SEQ ID NO 59
<211> LENGTH: 23
<212> TYPE: PRT
<213> ORGANISM: Homo sapiens
<220> FEATURE:
<221> NAME/KEY: Other...
<223> OTHER INFORMATION: VL Human consensus framework - L1

<400> SEQUENCE: 59

```
Asp Ile Gln Met Thr Gln Ser Pro Ser Ser Leu Ser Ala Ser Val
  1               5                  10                  15

Gly Asp Arg Val Thr Ile Thr Cys
                 20
```

<210> SEQ ID NO 60
<211> LENGTH: 15
<212> TYPE: PRT
<213> ORGANISM: Homo sapiens
<220> FEATURE:
<221> NAME/KEY: Other...
<223> OTHER INFORMATION: VL Human consensus framework - L2

<400> SEQUENCE: 60

```
Trp Tyr Gln Gln Lys Pro Gly Lys Ala Pro Lys Leu Leu Ile Tyr
  1               5                  10                  15
```

<210> SEQ ID NO 61
<211> LENGTH: 32
<212> TYPE: PRT
<213> ORGANISM: Homo sapiens
<220> FEATURE:
<221> NAME/KEY: Other...
<223> OTHER INFORMATION: VL Human consensus framework - L3

<400> SEQUENCE: 61

```
Gly Val Pro Ser Arg Phe Ser Gly Ser Gly Ser Gly Thr Asp Phe
  1               5                  10                  15

Thr Leu Thr Ile Ser Ser Leu Gln Pro Glu Asp Phe Ala Thr Tyr
                 20                  25                  30

Tyr Cys
```

<210> SEQ ID NO 62
<211> LENGTH: 11
<212> TYPE: PRT
<213> ORGANISM: Homo sapiens
<220> FEATURE:
<221> NAME/KEY: Other...
<223> OTHER INFORMATION: VL Human consensus framework - L4

<400> SEQUENCE: 62

```
Phe Gly Gln Gly Thr Lys Val Glu Ile Lys Arg
  5                  10
```

<210> SEQ ID NO 63
<211> LENGTH: 26
<212> TYPE: DNA
<213> ORGANISM: Artificial sequence
<220> FEATURE:
<223> OTHER INFORMATION: Forward cloning primer used in example 1

<400> SEQUENCE: 63
ccgcccaccg tgaagatctt acagtc                                          26

```
<210> SEQ ID NO 64
<211> LENGTH: 35
<212> TYPE: DNA
<213> ORGANISM: Artificial sequence
<220> FEATURE:
<223> OTHER INFORMATION: Reverse cloning primer used in example 1

<400> SEQUENCE: 64
cggctcgaga ctaggcgtgg ggctggagga cgttg                               35

<210> SEQ ID NO 65
<211> LENGTH: 542
<212> TYPE: PRT
<213> ORGANISM: Artificial sequence
<220> FEATURE:
<223> OTHER INFORMATION: IgE Ch3-Ch4-M'-Fc fusion

<400> SEQUENCE: 65
```

Met Gly Trp Ser Cys Ile Ile Leu Phe Leu Val Ala Thr Ala Thr
 1               5                  10                  15

Gly Val His Ser Thr Lys Lys Cys Ala Asp Ser Asn Pro Arg Gly
                20                  25                  30

Val Ser Ala Tyr Leu Ser Arg Pro Ser Pro Phe Asp Leu Phe Ile
            35                  40                  45

Arg Lys Ser Pro Thr Ile Thr Cys Leu Val Val Asp Leu Ala Pro
        50                  55                  60

Ser Lys Gly Thr Val Asn Leu Thr Trp Ser Arg Ala Ser Gly Lys
    65                  70                  75

Pro Val Asn His Ser Thr Arg Lys Glu Glu Lys Gln Arg Asn Gly
                80                  85                  90

Thr Leu Thr Val Thr Ser Thr Leu Pro Val Gly Thr Arg Asp Trp
            95                 100                 105

Ile Glu Gly Glu Thr Tyr Gln Cys Arg Val Thr His Pro His Leu
        110                 115                 120

Pro Arg Ala Leu Met Arg Ser Thr Thr Lys Thr Ser Gly Pro Arg
    125                 130                 135

Ala Ala Pro Glu Val Tyr Ala Phe Ala Thr Pro Glu Trp Pro Gly
                140                 145                 150

Ser Arg Asp Lys Arg Thr Leu Ala Cys Leu Ile Gln Asn Phe Met
            155                 160                 165

Pro Glu Asp Ile Ser Val Gln Trp Leu His Asn Glu Val Gln Leu
        170                 175                 180

Pro Asp Ala Arg His Ser Thr Thr Gln Pro Arg Lys Thr Lys Gly
    185                 190                 195

Ser Gly Phe Phe Val Phe Ser Arg Leu Glu Val Thr Arg Ala Glu
                200                 205                 210

Trp Glu Gln Lys Asp Glu Phe Ile Cys Arg Ala Val His Glu Ala
            215                 220                 225

Ala Ser Pro Ser Gln Thr Val Gln Arg Ala Val Ser Val Asn Pro
        230                 235                 240

Gly Leu Ala Gly Gly Ser Ala Gln Ser Gln Arg Ala Pro Asp Arg
    245                 250                 255

Val Leu Cys His Ser Gly Gln Gln Gln Gly Leu Pro Arg Ala Ala
                260                 265                 270

Gly Gly Ser Val Pro His Pro Arg Cys His Cys Gly Ala Gly Arg
            275                 280                 285

Ala Asp Trp Pro Gly Pro Pro Glu Leu Asp Val Cys Val Glu Glu
        290                 295                 300

Ala Glu Gly Glu Ala Pro Trp Arg Ala Gln Val Thr Asp Lys Ala
            305                 310                 315

Ala His Tyr Thr Leu Cys Pro Pro Cys Pro Ala Pro Glu Leu Leu
            320                 325                 330

Gly Gly Pro Ser Val Phe Leu Phe Pro Pro Lys Pro Lys Asp Thr
            335                 340                 345

Leu Met Ile Ser Arg Thr Pro Glu Val Thr Cys Val Val Val Asp
            350                 355                 360

Val Ser His Glu Asp Pro Glu Val Lys Phe Asn Trp Tyr Val Asp
            365                 370                 375

Gly Val Glu Val His Asn Ala Lys Thr Lys Pro Arg Glu Glu Gln
            380                 385                 390

Tyr Asn Ser Thr Tyr Arg Val Val Ser Val Leu Thr Val Leu His
            395                 400                 405

Gln Asp Trp Leu Asn Gly Lys Glu Tyr Lys Cys Lys Val Ser Asn
            410                 415                 420

Lys Ala Leu Pro Ala Pro Ile Glu Lys Thr Ile Ser Lys Ala Lys
            425                 430                 435

Gly Gln Pro Arg Glu Pro Gln Val Tyr Thr Leu Pro Pro Ser Arg
            440                 445                 450

Glu Glu Met Thr Lys Asn Gln Val Ser Leu Thr Cys Leu Val Lys
            455                 460                 465

Gly Phe Tyr Pro Ser Asp Ile Ala Val Glu Trp Glu Ser Asn Gly
            470                 475                 480

Gln Pro Glu Asn Asn Tyr Lys Thr Thr Pro Pro Val Leu Asp Ser
            485                 490                 495

Asp Gly Ser Phe Phe Leu Tyr Ser Lys Leu Thr Val Asp Lys Ser
            500                 505                 510

Arg Trp Gln Gln Gly Asn Val Phe Ser Cys Ser Val Met His Glu
            515                 520                 525

Ala Leu His Asn His Tyr Thr Gln Lys Ser Leu Ser Leu Ser Pro
            530                 535                 540

Gly Lys

<210> SEQ ID NO 66
<211> LENGTH: 25
<212> TYPE: PRT
<213> ORGANISM: Mus musculus
<220> FEATURE:
<221> NAME/KEY: Other...
<223> OTHER INFORMATION: N-terminal sequence, heavy chain 7AG

<400> SEQUENCE: 66

Gln Val Gln Leu Gln Gln Ser Gly Ala Glu Leu Val Arg Pro Gly
 1               5                  10                  15

Ala Ser Val Thr Leu Ser Cys Lys Ala Ser
                20                  25

<210> SEQ ID NO 67
<211> LENGTH: 25
<212> TYPE: PRT
<213> ORGANISM: Mus musculus
<220> FEATURE:
<221> NAME/KEY: Other...
<223> OTHER INFORMATION: N-terminal sequence, light chain 7AG

<400> SEQUENCE: 67

Asp Ile Val Met Ser Gln Ser Pro Ser Ser Leu Thr Val Ser Val

```
                1               5                  10                 15
Gly Glu Lys Val Thr Leu Ser Cys Lys Ser
                20                  25

<210> SEQ ID NO 68
<211> LENGTH: 25
<212> TYPE: PRT
<213> ORGANISM: Mus musculus
<220> FEATURE:
<221> NAME/KEY: Other...
<223> OTHER INFORMATION: N-terminal sequence, heavy chain 1C11

<400> SEQUENCE: 68

Gln Val Gln Leu Gln Gln Ser Gly Ala Glu Leu Val Arg Pro Gly
 1               5                  10                  15
Ala Ser Val Thr Leu Ser Cys Lys Ala Ser
                20                  25

<210> SEQ ID NO 69
<211> LENGTH: 25
<212> TYPE: PRT
<213> ORGANISM: Mus musculus
<220> FEATURE:
<221> NAME/KEY: Other...
<223> OTHER INFORMATION: N-terminal sequence, light chain 1C11

<400> SEQUENCE: 69

Asp Ile Val Met Ser Gln Ser Pro Ser Leu Ala Val Ser Val
 1               5                  10                  15
Gly Glu Lys Val Thr Met Ser Cys Lys Ser
                20                  25

<210> SEQ ID NO 70
<211> LENGTH: 25
<212> TYPE: PRT
<213> ORGANISM: Mus musculus
<220> FEATURE:
<221> NAME/KEY: Other...
<223> OTHER INFORMATION: N-terminal sequence, heavy chain 47H4

<400> SEQUENCE: 70

Glu Val Lys Leu Val Glu Ser Gly Gly Gly Leu Val Gln Pro Gly
 1               5                  10                  15
Gly Ser Arg Lys Leu Ser Cys Ala Ala Ser
                20                  25

<210> SEQ ID NO 71
<211> LENGTH: 21
<212> TYPE: PRT
<213> ORGANISM: Mus musculus
<220> FEATURE:
<221> NAME/KEY: Other...
<223> OTHER INFORMATION: N-terminal sequence, light chain 47H4

<400> SEQUENCE: 71

Asp Val Val Leu Thr Gln Thr Pro Leu Ser Leu Pro Val Ser Leu
 1               5                  10                  15
Gly Asp Gln Ala Ser Ile
                20

<210> SEQ ID NO 72
<211> LENGTH: 25
<212> TYPE: PRT
<213> ORGANISM: Mus musculus
<220> FEATURE:
<221> NAME/KEY: Other...
```

```
<223> OTHER INFORMATION: N-terminal sequence, heavy chain 26A11

<400> SEQUENCE: 72

Glu Val Gln Leu Gln Gln Ser Gly Pro Glu Leu Val Lys Pro Gly
 1               5                  10                  15

Ala Ser Val Lys Met Ser Cys Lys Ala Ser
            20                  25

<210> SEQ ID NO 73
<211> LENGTH: 25
<212> TYPE: PRT
<213> ORGANISM: Mus musculus
<220> FEATURE:
<221> NAME/KEY: Other...
<223> OTHER INFORMATION: N-terminal sequence, light chain 26A11

<400> SEQUENCE: 73

Asp Ile Gln Met Thr Gln Thr Thr Ser Ser Leu Ser Ala Ser Leu
 1               5                  10                  15

Gly Asp Arg Val Thr Ile Thr Cys Arg Ser
            20                  25

<210> SEQ ID NO 74
<211> LENGTH: 19
<212> TYPE: PRT
<213> ORGANISM: Mus musculus
<220> FEATURE:
<221> NAME/KEY: Other...
<223> OTHER INFORMATION: N-terminal sequence, heavy chain 45C1

<400> SEQUENCE: 74

Gln Ile Gln Leu Val Gln Ser Gly Pro Glu Leu Lys Lys Pro Gly
 1               5                  10                  15

Glu Thr Val Lys

<210> SEQ ID NO 75
<211> LENGTH: 24
<212> TYPE: PRT
<213> ORGANISM: Mus musculus
<220> FEATURE:
<221> NAME/KEY: Other...
<223> OTHER INFORMATION: N-terminal sequence, light chain 45C1

<400> SEQUENCE: 75

Asp Val Val Met Thr Gln Thr Pro Leu Thr Leu Ser Val Thr Ile
 1               5                  10                  15

Gly Gln Pro Ala Ser Ile Ser Cys Lys
            20

<210> SEQ ID NO 76
<211> LENGTH: 25
<212> TYPE: PRT
<213> ORGANISM: Mus musculus
<220> FEATURE:
<221> NAME/KEY: Other...
<223> OTHER INFORMATION: N-terminal sequence, heavy chain 28E9

<400> SEQUENCE: 76

Glu Val Lys Leu Val Glu Ser Gly Gly Gly Leu Val Gln Pro Gly
 1               5                  10                  15

Gly Ser Leu Arg Leu Ser Cys Ala Thr Ser
            20                  25

<210> SEQ ID NO 77
<211> LENGTH: 24
```

```
<212> TYPE: PRT
<213> ORGANISM: Mus musculus
<220> FEATURE:
<221> NAME/KEY: Other...
<223> OTHER INFORMATION: N-terminal sequence, light chain 28E9

<400> SEQUENCE: 77

Asp Ile Gln Met Thr Gln Ser Pro Ala Ser Leu Ser Val Ser Val
 1               5                  10                  15

Gly Glu Thr Val Thr Phe Thr Cys Arg
                20

<210> SEQ ID NO 78
<211> LENGTH: 46
<212> TYPE: DNA
<213> ORGANISM: Artificial sequence
<220> FEATURE:
<223> OTHER INFORMATION: FOR.BsiWI 7AG HC forward primer

<400> SEQUENCE: 78
tcgacgtacg ctcaggttca gctgcagcaa tctggggctg  agctgg           46

<210> SEQ ID NO 79
<211> LENGTH: 39
<212> TYPE: DNA
<213> ORGANISM: Artificial sequence
<220> FEATURE:
<223> OTHER INFORMATION: FOR.EcoRV 7A6 LC forward primer

<400> SEQUENCE: 79
gatcgatatc gtgatgtccc agtctccctc  ctccctaac                    39

<210> SEQ ID NO 80
<211> LENGTH: 46
<212> TYPE: DNA
<213> ORGANISM: Artificial sequence
<220> FEATURE:
<223> OTHER INFORMATION: FOR.BsiWI 1C11 HC forward primer

<400> SEQUENCE: 80
tcgacgtacg ctcaggttca attgcagcag tctggggctg  agctgg           46

<210> SEQ ID NO 81
<211> LENGTH: 39
<212> TYPE: DNA
<213> ORGANISM: Artificial sequence
<220> FEATURE:
<223> OTHER INFORMATION: FOR.EcoRV 1C11 LC forward primer

<400> SEQUENCE: 81
gatcgatatc gtaatgtctc agtctccttc  ctccctagc                    39

<210> SEQ ID NO 82
<211> LENGTH: 46
<212> TYPE: DNA
<213> ORGANISM: Artificial sequence
<220> FEATURE:
<223> OTHER INFORMATION: 9.1HCF.BsiWI 47H4 HC forward primer

<400> SEQUENCE: 82
tcgacgtacg ctgaggtgaa gttggtggag tctgggggag  gcttag           46

<210> SEQ ID NO 83
<211> LENGTH: 39
<212> TYPE: DNA
<213> ORGANISM: Artificial sequence
<220> FEATURE:
```

```
<223> OTHER INFORMATION: 47H4LCF.EcoRV 47H4 LC forward primer

<400> SEQUENCE: 83
gatcgatatc gtgctgactc agactccact ctccctgcc                      39

<210> SEQ ID NO 84
<211> LENGTH: 43
<212> TYPE: DNA
<213> ORGANISM: Artificial sequence
<220> FEATURE:
<223> OTHER INFORMATION: C7F7HCF.BsiWI 26A11 HC forward primer

<400> SEQUENCE: 84
tcgacgtacg ctgaggtcca gctccagcag tctggacctg agc                 43

<210> SEQ ID NO 85
<211> LENGTH: 37
<212> TYPE: DNA
<213> ORGANISM: Artificial sequence
<220> FEATURE:
<223> OTHER INFORMATION: 2B4LCF.EcoRV 26A11 LC forward primer

<400> SEQUENCE: 85
gatcgatatc cagatgaccc aaactacatc ctccctg                        37

<210> SEQ ID NO 86
<211> LENGTH: 45
<212> TYPE: DNA
<213> ORGANISM: Artificial sequence
<220> FEATURE:
<223> OTHER INFORMATION: 2G6HCF.BsiWI 45C1 HC forward primer

<400> SEQUENCE: 86
tcgacgtacg ctcagatcca gttggtgcag tctggacctg agctg               45

<210> SEQ ID NO 87
<211> LENGTH: 41
<212> TYPE: DNA
<213> ORGANISM: Artificial sequence
<220> FEATURE:
<223> OTHER INFORMATION: 9C10LCF.EcoRV 45C1 LC forward primer

<400> SEQUENCE: 87
gatcgatatc gtgatgacgc agactccact cactttgtcg g                   41

<210> SEQ ID NO 88
<211> LENGTH: 46
<212> TYPE: DNA
<213> ORGANISM: Artificial sequence
<220> FEATURE:
<223> OTHER INFORMATION: 9.1HCFBsiWI 28E9 HC forward primer

<400> SEQUENCE: 88
tcgacgtacg ctgaggtgaa gctggtggag tctgaaggag gcttgg              46

<210> SEQ ID NO 89
<211> LENGTH: 39
<212> TYPE: DNA
<213> ORGANISM: Artificial sequence
<220> FEATURE:
<223> OTHER INFORMATION: 5E10.LCF.EcoRV 28E9 LC forward primer

<400> SEQUENCE: 89
gatcgatatc cagatgaccc agtctccagc ctccctatc                      39

<210> SEQ ID NO 90
```

```
<211> LENGTH: 45
<212> TYPE: DNA
<213> ORGANISM: Artificial sequence
<220> FEATURE:
<223> OTHER INFORMATION: Heavy Chain Primer (HCR)

<400> SEQUENCE: 90
ctggacaggg atccagagtt ccaggtcact gtcactggct   caggg            45

<210> SEQ ID NO 91
<211> LENGTH: 39
<212> TYPE: DNA
<213> ORGANISM: Artificial sequence
<220> FEATURE:
<223> OTHER INFORMATION: Light Chain Primer (LCR)

<400> SEQUENCE: 91
ctgtaggtgc tgtctttgct gtcctgatca   gtccaactg                    39

<210> SEQ ID NO 92
<211> LENGTH: 38
<212> TYPE: DNA
<213> ORGANISM: Artificial sequence
<220> FEATURE:
<223> OTHER INFORMATION: REV.ApaI 7A6 HC reverse primer

<400> SEQUENCE: 92
accgatgggc ccttggtgga ggctgaagag   actgtgag                     38

<210> SEQ ID NO 93
<211> LENGTH: 43
<212> TYPE: DNA
<213> ORGANISM: Artificial sequence
<220> FEATURE:
<223> OTHER INFORMATION: REV.KpnI 7A6 LC reverse primer

<400> SEQUENCE: 93
ccttggtacc ccctccgaac gtgtacggat agctataata   ttg               43

<210> SEQ ID NO 94
<211> LENGTH: 37
<212> TYPE: DNA
<213> ORGANISM: Artificial sequence
<220> FEATURE:
<223> OTHER INFORMATION: REV.ApaI 1C11 HC reverse primer

<400> SEQUENCE: 94
gaccgatggg cccttggtgg aggctgagga   gactgtg                      37

<210> SEQ ID NO 95
<211> LENGTH: 38
<212> TYPE: DNA
<213> ORGANISM: Artificial sequence
<220> FEATURE:
<223> OTHER INFORMATION: REV.KpnI 1C11 LC reverse primer

<400> SEQUENCE: 95
ccttggtacc ccctccgaac gtgtacggat   agctataa                     38

<210> SEQ ID NO 96
<211> LENGTH: 37
<212> TYPE: DNA
<213> ORGANISM: Artificial sequence
<220> FEATURE:
<223> OTHER INFORMATION: 47H4HCR.ApaI 47H4 HC reverse primer

<400> SEQUENCE: 96
```

```
tgggcccttg gtggaggctg aggagacggt   gactgag                              37
```

<210> SEQ ID NO 97
<211> LENGTH: 21
<212> TYPE: DNA
<213> ORGANISM: Artificial sequence
<220> FEATURE:
<223> OTHER INFORMATION: 47H4LCR.KpnI 47H4 LC reverse primer

<400> SEQUENCE: 97

```
ttccaacttg gtacctccac  c                                                21
```

<210> SEQ ID NO 98
<211> LENGTH: 44
<212> TYPE: DNA
<213> ORGANISM: Artificial sequence
<220> FEATURE:
<223> OTHER INFORMATION: 7G8HCR.ApaI 26A11 HC reverse primer

<400> SEQUENCE: 98

```
gaccgatggg cccttggtgg argctgcaga gacagtgacc   agag                      44
```

<210> SEQ ID NO 99
<211> LENGTH: 21
<212> TYPE: DNA
<213> ORGANISM: Artificial sequence
<220> FEATURE:
<223> OTHER INFORMATION: 47H4LCR.KpnI 26A11 LC reverse primer

<400> SEQUENCE: 99

```
ttccaacttg gtacctccac  c                                                21
```

<210> SEQ ID NO 100
<211> LENGTH: 40
<212> TYPE: DNA
<213> ORGANISM: Artificial sequence
<220> FEATURE:
<223> OTHER INFORMATION: 45C1HCR.ApaI 45C1 HC reverse primer

<400> SEQUENCE: 100

```
cgatgggccc ttggtggarg ckgaggagac ggtgagaatg                             40
```

<210> SEQ ID NO 101
<211> LENGTH: 18
<212> TYPE: DNA
<213> ORGANISM: Artificial sequence
<220> FEATURE:
<223> OTHER INFORMATION: 5C2LCR.KpnI 45C1 LC reverse primer

<400> SEQUENCE: 101

```
agcttggtac  ccctccg                                                     18
```

<210> SEQ ID NO 102
<211> LENGTH: 40
<212> TYPE: DNA
<213> ORGANISM: Artificial sequence
<220> FEATURE:
<223> OTHER INFORMATION: 28E9.HC.REV.ApaI 28E9 HC reverse primer

<400> SEQUENCE: 102

```
cgatgggccc ttggtggagg ctgaggagac ggcgactgag                             40
```

<210> SEQ ID NO 103
<211> LENGTH: 22
<212> TYPE: DNA
<213> ORGANISM: Artificial sequence
<220> FEATURE:

<223> OTHER INFORMATION: 1D5.2LCR,KpnI 28E9 LC reverse primer

<400> SEQUENCE: 103
ttccaacttg gtacccgagc cg 22

<210> SEQ ID NO 104
<211> LENGTH: 33
<212> TYPE: DNA
<213> ORGANISM: Mus musculus

<400> SEQUENCE: 104
cctatttaca ttggtatctg cagaagccag gcc 33

<210> SEQ ID NO 105
<211> LENGTH: 33
<212> TYPE: DNA
<213> ORGANISM: Artificial sequence
<220> FEATURE:
<223> OTHER INFORMATION: Reverse mutagenesis primer

<400> SEQUENCE: 105
ggcctggctt ctgcagatac caatgtaaat agg 33

<210> SEQ ID NO 106
<211> LENGTH: 22
<212> TYPE: DNA
<213> ORGANISM: Artificial sequence
<220> FEATURE:
<223> OTHER INFORMATION: M1' screening WT forward primer

<400> SEQUENCE: 106
ggccaaagac cctaagacag tc 22

<210> SEQ ID NO 107
<211> LENGTH: 20
<212> TYPE: DNA
<213> ORGANISM: Artificial sequence
<220> FEATURE:
<223> OTHER INFORMATION: M1' screening huM1' forward primer

<400> SEQUENCE: 107
gggctggctg gcggctccgc 20

<210> SEQ ID NO 108
<211> LENGTH: 22
<212> TYPE: DNA
<213> ORGANISM: Artificial sequence
<220> FEATURE:
<223> OTHER INFORMATION: M1' screening WT reverse primer

<400> SEQUENCE: 108
ctatgccctg gtctggaaga tg 22

<210> SEQ ID NO 109
<211> LENGTH: 25
<212> TYPE: DNA
<213> ORGANISM: Artificial sequence
<220> FEATURE:
<223> OTHER INFORMATION: Left arm forward primer

<400> SEQUENCE: 109
tgtctggtgg tggacctgga aagcg 25

<210> SEQ ID NO 110
<211> LENGTH: 25
<212> TYPE: DNA

-continued

```
<213> ORGANISM: Artificial sequence
<220> FEATURE:
<223> OTHER INFORMATION: Left arm reverse primer

<400> SEQUENCE: 110
tcctcgctct cctcctctgg tggtg                                          25

<210> SEQ ID NO 111
<211> LENGTH: 25
<212> TYPE: DNA
<213> ORGANISM: Artificial sequence
<220> FEATURE:
<223> OTHER INFORMATION: Right arm forward primer

<400> SEQUENCE: 111
ccatgcaacc tagtatccta ttctc                                          25

<210> SEQ ID NO 112
<211> LENGTH: 25
<212> TYPE: DNA
<213> ORGANISM: Artificial sequence
<220> FEATURE:
<223> OTHER INFORMATION: Right arm reverse primer

<400> SEQUENCE: 112
ctttatacag gagaacctag cccag                                          25
```